(12) United States Patent
Westwick

(10) Patent No.: US 11,140,305 B2
(45) Date of Patent: Oct. 5, 2021

(54) OPEN-FIELD HANDHELD FLUORESCENCE IMAGING SYSTEMS AND METHODS

(71) Applicant: Stryker European Operations Limited, Carrigtwohill (IE)

(72) Inventor: Paul Roald Westwick, Vancouver (CA)

(73) Assignee: Stryker European Operations Limited, Carrigtwohill (IE)

( * ) Notice: Subject to any disclaimer, the term of this patent is extended or adjusted under 35 U.S.C. 154(b) by 495 days.

(21) Appl. No.: 15/591,909

(22) Filed: May 10, 2017

(65) Prior Publication Data

US 2018/0234603 A1    Aug. 16, 2018

Related U.S. Application Data

(60) Provisional application No. 62/457,690, filed on Feb. 10, 2017.

(51) Int. Cl.
*H04N 5/00*    (2011.01)
*H04N 5/225*    (2006.01)
(Continued)

(52) U.S. Cl.
CPC ............. *H04N 5/2259* (2013.01); *A61B 1/06* (2013.01); *A61B 5/0071* (2013.01);
(Continued)

(58) Field of Classification Search
CPC ............. H04N 5/2259; H04N 9/04551; H04N 5/2251; H04N 5/2254; H04N 5/2256; H04N 5/23245; H04N 5/2351; H04N 5/2352; H04N 5/2354; H04N 5/332; A61B 1/06; A61B 5/0075; A61B 1/043; G01N 21/6456
See application file for complete search history.

(56) References Cited

U.S. PATENT DOCUMENTS 1,290,744 A    1/1919    Hollander
2,453,336 A    11/1948   Orser
(Continued)

FOREIGN PATENT DOCUMENTS

AT    409451 B    8/2002
CA    2212257 A1   8/1996
(Continued)

OTHER PUBLICATIONS

US 6,692,429 B1, 02/2004, Imaizumi et al. (withdrawn)
(Continued)

*Primary Examiner* — Frank F Huang
(74) *Attorney, Agent, or Firm* — Morrison & Foerster LLP

(57) ABSTRACT

An imaging device having an imaging field of view, the imaging device including at least one illumination port configured to output light for illuminating a target; an imaging sensor to detect light traveling along an optical path to the imaging sensor; and a first movable window positioned upstream of the sensor with respect to a direction of travel of light along the optical path, wherein the first movable window is configured to move into the optical path in a deployed position for modifying light received from the target.

12 Claims, 40 Drawing Sheets
(2 of 40 Drawing Sheet(s) Filed in Color)

(51) Int. Cl.
    *G01N 21/64*     (2006.01)
    *H04N 9/04*     (2006.01)
    *H04N 5/235*     (2006.01)
    *A61B 5/00*     (2006.01)
    *A61B 1/06*     (2006.01)
    *H04N 5/232*     (2006.01)
    *H04N 5/33*     (2006.01)
    *A61B 1/04*     (2006.01)

(52) U.S. Cl.
    CPC ....... *A61B 5/0075* (2013.01); *G01N 21/6456* (2013.01); *H04N 5/2251* (2013.01); *H04N 5/2254* (2013.01); *H04N 5/2256* (2013.01); *H04N 5/2351* (2013.01); *H04N 5/2352* (2013.01); *H04N 5/2354* (2013.01); *H04N 5/23245* (2013.01); *H04N 5/332* (2013.01); *H04N 9/04551* (2018.08); *A61B 1/043* (2013.01)

(56) References Cited

U.S. PATENT DOCUMENTS

| | | |
|---|---|---|
| 2,857,523 A | 10/1958 | Corso |
| 3,215,029 A | 11/1965 | Woodcock |
| 3,582,178 A | 6/1971 | Boughton et al. |
| 3,671,098 A | 6/1972 | Rotter |
| 3,749,494 A | 7/1973 | Hodges |
| 3,790,248 A | 2/1974 | Kel Low |
| 3,931,593 A | 1/1976 | Marshall |
| 3,970,373 A | 7/1976 | Pledger |
| 3,971,068 A | 7/1976 | Gerhardt et al. |
| 4,037,866 A | 7/1977 | Price |
| 4,066,330 A | 1/1978 | Jones |
| 4,109,647 A | 8/1978 | Stern et al. |
| 4,115,812 A | 9/1978 | Akatsu |
| 4,149,190 A | 4/1979 | Wessler et al. |
| 4,158,504 A | 6/1979 | de Ponteves et al. |
| 4,162,405 A | 7/1979 | Chance et al. |
| 4,200,801 A | 4/1980 | Schuresko |
| 4,260,217 A | 4/1981 | Traeger et al. |
| 4,263,916 A | 4/1981 | Brooks et al. |
| 4,318,395 A | 3/1982 | Tawara |
| 4,355,325 A | 10/1982 | Nakamura et al. |
| 4,378,571 A | 3/1983 | Handy |
| 4,394,199 A | 7/1983 | Barnhard, IV et al. |
| 4,449,535 A | 5/1984 | Renault |
| 4,471,766 A | 9/1984 | Terayama |
| 4,473,841 A | 9/1984 | Murakoshi et al. |
| 4,532,918 A | 8/1985 | Wheeler |
| 4,541,438 A | 9/1985 | Parker et al. |
| 4,556,057 A | 12/1985 | Hiruma et al. |
| 4,575,632 A | 3/1986 | Lange |
| 4,597,630 A | 7/1986 | Brandstetter et al. |
| 4,611,888 A | 9/1986 | Prenovitz et al. |
| 4,619,249 A | 10/1986 | Landry |
| 4,638,365 A | 1/1987 | Kato |
| 4,656,508 A | 4/1987 | Yokota |
| 4,660,982 A | 4/1987 | Okada |
| 4,688,905 A | 8/1987 | Okamura |
| 4,717,952 A | 1/1988 | Kohayakawa et al. |
| 4,718,417 A | 1/1988 | Kittrell et al. |
| 4,719,508 A | 1/1988 | Sasaki et al. |
| 4,742,388 A | 5/1988 | Cooper et al. |
| 4,768,513 A | 9/1988 | Suzuki |
| 4,773,097 A | 9/1988 | Suzaki et al. |
| 4,774,568 A | 9/1988 | Matsuo |
| 4,786,813 A | 11/1988 | Svanberg et al. |
| 4,799,104 A | 1/1989 | Hosoya et al. |
| 4,805,597 A | 2/1989 | Iwakoshi |
| 4,806,005 A | 2/1989 | Schneider et al. |
| 4,815,848 A | 3/1989 | Hadeishi |
| 4,821,117 A | 4/1989 | Sekiguchi |
| 4,827,908 A | 5/1989 | Matsuo |
| 4,837,625 A | 6/1989 | Douziech et al. |
| 4,852,579 A | 8/1989 | Gilstad et al. |
| 4,852,985 A | 8/1989 | Fujihara et al. |
| 4,856,495 A | 8/1989 | Tohjoh et al. |
| 4,858,001 A | 8/1989 | Milbank et al. |
| 4,860,731 A | 8/1989 | Matsuura |
| 4,867,137 A | 9/1989 | Takahashi |
| 4,868,647 A | 9/1989 | Uehara et al. |
| 4,885,634 A | 12/1989 | Yabe |
| 4,895,145 A | 1/1990 | Joffe et al. |
| 4,900,934 A | 2/1990 | Peeters et al. |
| 4,930,516 A | 6/1990 | Alfano et al. |
| 4,930,883 A | 6/1990 | Salzman |
| 4,938,205 A | 6/1990 | Nudelman |
| 4,951,135 A | 8/1990 | Sasagawa et al. |
| 4,953,539 A | 9/1990 | Nakamura et al. |
| 4,954,897 A | 9/1990 | Ejima et al. |
| 4,957,114 A | 9/1990 | Zeng et al. |
| 4,974,936 A | 12/1990 | Ams et al. |
| 4,993,404 A | 2/1991 | Lane |
| 4,995,396 A | 2/1991 | Inaba et al. |
| 4,995,398 A | 2/1991 | Turnidge |
| 4,998,972 A | 3/1991 | Chin et al. |
| 5,001,556 A | 3/1991 | Nakamura et al. |
| 5,003,977 A | 4/1991 | Suzuki et al. |
| 5,007,408 A | 4/1991 | Ieoka |
| 5,028,128 A | 7/1991 | Onuki |
| 5,034,888 A | 7/1991 | Uehara et al. |
| 5,041,852 A | 8/1991 | Misawa et al. |
| 5,042,494 A | 8/1991 | Alfano |
| 5,071,417 A | 12/1991 | Sinofsky |
| 5,078,150 A | 1/1992 | Nara et al. |
| 5,090,400 A | 2/1992 | Saito |
| 5,091,652 A | 2/1992 | Mathies et al. |
| 5,115,137 A | 5/1992 | Andersson-Engels et al. |
| 5,115,308 A | 5/1992 | Onuki |
| 5,117,466 A | 5/1992 | Buican et al. |
| 5,121,220 A | 6/1992 | Nakamoto |
| 5,125,404 A | 6/1992 | Kittrell et al. |
| 5,128,803 A | 7/1992 | Sprafke |
| 5,131,398 A | 7/1992 | Alfano et al. |
| 5,132,837 A | 7/1992 | Kitajima |
| 5,134,662 A | 7/1992 | Bacus et al. |
| 5,150,292 A | 9/1992 | Hoffmann et al. |
| 5,159,398 A | 10/1992 | Maekewa et al. |
| 5,165,079 A | 11/1992 | Schulz-Hennig |
| 5,178,616 A | 1/1993 | Uemiya et al. |
| 5,196,928 A | 3/1993 | Karasawa et al. |
| 5,205,280 A | 4/1993 | Dennison, Jr. et al. |
| 5,208,651 A | 5/1993 | Buican |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,279,298 A | 1/1994 | Flower |
| 5,282,082 A | 1/1994 | Espie et al. |
| 5,295,017 A | 3/1994 | Brown |
| RE34,622 E | 5/1994 | Ledley |
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,379,756 A | 1/1995 | Pileski et al. |
| 5,394,199 A | 2/1995 | Flower |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,426,530 A | 6/1995 | Copenhaver et al. |
| 5,430,476 A | 7/1995 | Hafele et al. |
| 5,437,274 A | 8/1995 | Khoobehi et al. |

(56) References Cited

U.S. PATENT DOCUMENTS

| | | |
|---|---|---|
| 5,438,989 A | 8/1995 | Hochman et al. |
| D362,435 S | 9/1995 | Charych et al. |
| 5,453,448 A | 9/1995 | Narciso, Jr. |
| 5,465,718 A | 11/1995 | Hochman et al. |
| 5,481,401 A | 1/1996 | Kita et al. |
| 5,485,203 A | 1/1996 | Nakamura et al. |
| 5,490,015 A | 2/1996 | Umeyama et al. |
| 5,491,343 A | 2/1996 | Brooker |
| 5,496,369 A | 3/1996 | Howard, III |
| 5,507,287 A | 4/1996 | Palcic et al. |
| 5,514,127 A | 5/1996 | Shanks |
| 5,515,449 A | 5/1996 | Tsuruoka et al. |
| 5,519,534 A | 5/1996 | Smith et al. |
| 5,535,052 A | 7/1996 | Jörgens |
| 5,536,236 A | 7/1996 | Yabe et al. |
| 5,557,451 A | 9/1996 | Copenhaver et al. |
| 5,576,013 A | 11/1996 | Williams et al. |
| 5,585,846 A | 12/1996 | Kim |
| 5,590,660 A | 1/1997 | MacAulay et al. |
| 5,596,654 A | 1/1997 | Tanaka |
| 5,623,930 A | 4/1997 | Wright et al. |
| 5,627,907 A | 5/1997 | Gur et al. |
| 5,646,680 A | 7/1997 | Yajima |
| 5,647,368 A | 7/1997 | Zeng et al. |
| 5,647,840 A | 7/1997 | D'Amelio et al. |
| 5,656,498 A | 8/1997 | Iijima et al. |
| 5,662,644 A | 9/1997 | Swor |
| 5,664,574 A | 9/1997 | Chance |
| 5,667,472 A | 9/1997 | Finn et al. |
| 5,673,701 A | 10/1997 | Chance |
| 5,677,724 A | 10/1997 | Takizawa et al. |
| 5,682,567 A | 10/1997 | Spruck et al. |
| 5,689,241 A | 11/1997 | Clarke, Sr. et al. |
| 5,689,354 A | 11/1997 | Orino |
| 5,695,049 A | 12/1997 | Bauman |
| 5,697,373 A | 12/1997 | Richards-Kortum et al. |
| 5,699,798 A | 12/1997 | Hochman et al. |
| 5,707,986 A | 1/1998 | Miller et al. |
| 5,713,364 A | 2/1998 | DeBarysche et al. |
| 5,729,382 A | 3/1998 | Morita et al. |
| 5,732,707 A | 3/1998 | Widder et al. |
| 5,741,648 A | 4/1998 | Hemstreet, III et al. |
| 5,743,266 A | 4/1998 | Levene et al. |
| 5,749,830 A | 5/1998 | Kaneko et al. |
| 5,756,541 A | 5/1998 | Strong et al. |
| 5,769,792 A | 6/1998 | Palcic et al. |
| 5,772,355 A | 6/1998 | Ross et al. |
| 5,772,580 A | 6/1998 | Utsui et al. |
| 5,785,965 A | 7/1998 | Pratt et al. |
| 5,803,914 A | 9/1998 | Ryals et al. |
| 5,827,190 A | 10/1998 | Palcic et al. |
| 5,833,617 A | 11/1998 | Hayashi |
| 5,838,001 A | 11/1998 | Minakuchi et al. |
| 5,840,017 A | 11/1998 | Furuswaba et al. |
| 5,845,639 A | 12/1998 | Hochman et al. |
| 5,851,181 A | 12/1998 | Talmor |
| 5,852,498 A | 12/1998 | Youvan et al. |
| 5,865,754 A | 2/1999 | Sevick-Muraca et al. |
| 5,891,016 A | 4/1999 | Utsui et al. |
| 5,897,269 A | 4/1999 | Ross et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Collen |
| 5,956,435 A | 9/1999 | Buzug et al. |
| 5,965,356 A | 10/1999 | Aurelian et al. |
| 5,971,918 A | 10/1999 | Zanger |
| 5,973,315 A | 10/1999 | Saldana et al. |
| 5,984,861 A | 11/1999 | Crowley |
| 5,986,271 A | 11/1999 | Lazarev et al. |
| 5,986,642 A | 11/1999 | Ueda et al. |
| 5,990,996 A | 11/1999 | Sharp |
| 5,999,240 A | 12/1999 | Sharp et al. |
| 5,999,841 A | 12/1999 | Aoyagi et al. |
| 6,002,137 A | 12/1999 | Hayashi |
| 6,004,263 A | 12/1999 | Nakaichi et al. |
| 6,008,889 A | 12/1999 | Zeng et al. |
| 6,013,265 A | 1/2000 | Aurelian |
| 6,021,344 A | 2/2000 | Lui et al. |
| 6,028,622 A | 2/2000 | Suzuki |
| 6,030,339 A | 2/2000 | Tatsuno et al. |
| 6,032,070 A | 2/2000 | Flock et al. |
| 6,054,131 A | 4/2000 | Aurelian |
| 6,059,719 A | 5/2000 | Yamamoto et al. |
| 6,059,720 A | 5/2000 | Furusawa et al. |
| 6,061,591 A | 5/2000 | Freitag et al. |
| 6,069,689 A | 5/2000 | Zeng et al. |
| 6,070,096 A | 5/2000 | Hayashi |
| 6,074,627 A | 6/2000 | Dean et al. |
| 6,081,612 A | 6/2000 | Gutkowicz-Krusin et al. |
| 6,093,149 A | 7/2000 | Guracar et al. |
| 6,095,982 A | 8/2000 | Richards-Kortum et al. |
| 6,099,466 A | 8/2000 | Sano et al. |
| 6,110,106 A | 8/2000 | MacKinnon et al. |
| 6,120,435 A | 9/2000 | Eino |
| 6,122,042 A | 9/2000 | Wunderman et al. |
| 6,140,314 A | 10/2000 | Zeimer |
| 6,147,705 A | 11/2000 | Krauter et al. |
| 6,148,227 A | 11/2000 | Wagnieres et al. |
| 6,149,671 A | 11/2000 | Nordquist et al. |
| 6,161,035 A | 12/2000 | Furusawa |
| 6,162,242 A | 12/2000 | Peyman |
| 6,178,340 B1 | 1/2001 | Svetliza |
| 6,179,421 B1 | 1/2001 | Pang |
| 6,181,414 B1 | 1/2001 | Raz et al. |
| 6,186,628 B1 | 2/2001 | Van de Velde |
| 6,192,267 B1 | 2/2001 | Scherninski et al. |
| 6,196,226 B1 | 3/2001 | Hochman et al. |
| 6,207,168 B1 | 3/2001 | Aurelian |
| 6,211,953 B1 | 4/2001 | Niino et al. |
| 6,212,425 B1 | 4/2001 | Irion et al. |
| 6,217,848 B1 | 4/2001 | Achilefu et al. |
| 6,223,069 B1 | 4/2001 | Pfeiffer et al. |
| 6,226,126 B1 | 5/2001 | Conemac |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,258,576 B1 | 7/2001 | Richards-Kortum et al. |
| 6,263,227 B1 | 7/2001 | Boggett et al. |
| D446,524 S | 8/2001 | Bontly et al. |
| 6,272,374 B1 | 8/2001 | Flock et al. |
| 6,280,378 B1 | 8/2001 | Kazuhiro et al. |
| 6,280,386 B1 | 8/2001 | Alfano et al. |
| 6,293,911 B1 | 9/2001 | Imaizumi et al. |
| 6,315,712 B1 | 11/2001 | Rovegno |
| 6,319,273 B1 | 11/2001 | Cheen et al. |
| 6,331,703 B1 | 12/2001 | Yarnall et al. |
| 6,332,092 B1 | 12/2001 | Deckert et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,364,829 B1 | 4/2002 | Fulghum |
| 6,364,831 B1 | 4/2002 | Crowley |
| D456,809 S | 5/2002 | Schieffers |
| 6,399,354 B1 | 6/2002 | Knipe et al. |
| 6,419,628 B1 | 7/2002 | Rudischhauser et al. |
| 6,422,994 B1 | 7/2002 | Kaneko et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,462,770 B1 | 10/2002 | Cline et al. |
| 6,485,413 B1 | 11/2002 | Boppart et al. |
| 6,498,945 B1 | 12/2002 | Alfheim et al. |
| 6,510,338 B1 | 1/2003 | Irion et al. |
| 6,526,213 B1 | 2/2003 | Ilenda et al. |
| 6,529,239 B1 | 3/2003 | Dyck et al. |
| 6,529,768 B1 | 3/2003 | Hakamata |
| 6,537,211 B1 | 3/2003 | Wang et al. |
| 6,544,102 B2 | 4/2003 | Schafer et al. |
| 6,544,183 B2 | 4/2003 | Thorn Leeson et al. |
| 6,566,641 B1 | 5/2003 | Suda |

(56) References Cited

U.S. PATENT DOCUMENTS

| | | |
|---|---|---|
| 6,571,119 B2 | 5/2003 | Hayashi |
| 6,577,884 B1 | 6/2003 | Boas |
| 6,596,996 B1 | 7/2003 | Stone et al. |
| 6,603,552 B1 | 8/2003 | Cline et al. |
| 6,621,917 B1 | 9/2003 | Vilser |
| 6,631,286 B2 | 10/2003 | Pfeiffer et al. |
| 6,639,664 B2 | 10/2003 | Haan et al. |
| 6,652,452 B1 | 11/2003 | Seifert et al. |
| D483,668 S | 12/2003 | Le Roux |
| 6,671,540 B1 | 12/2003 | Hochman |
| 6,750,971 B2 | 6/2004 | Overbeck et al. |
| 6,757,554 B2 | 6/2004 | Rubinstein et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,804,549 B2 | 10/2004 | Hayashi |
| 6,821,245 B2 | 11/2004 | Cline et al. |
| 6,821,946 B2 | 11/2004 | Goldspink et al. |
| 6,826,424 B1 | 11/2004 | Zeng et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,898,458 B2 | 5/2005 | Zeng et al. |
| 6,899,675 B2 | 5/2005 | Cline et al. |
| 6,915,154 B1 | 7/2005 | Docherty et al. |
| 6,922,583 B1 | 7/2005 | Perelman et al. |
| 6,936,043 B2 | 8/2005 | Peyman |
| 6,944,493 B2 | 9/2005 | Alam et al. |
| 6,958,862 B1 | 10/2005 | Joseph |
| 6,960,165 B2 | 11/2005 | Ueno et al. |
| 7,043,291 B2 | 5/2006 | Sendai |
| D524,985 S | 7/2006 | Lukan et al. |
| D524,987 S | 7/2006 | Lukan et al. |
| 7,113,817 B1 | 9/2006 | Winchester, Jr. et al. |
| 7,150,552 B2 | 12/2006 | Weidel |
| 7,179,222 B2 | 2/2007 | Imaizumi et al. |
| 7,235,045 B2 | 6/2007 | Wang et al. |
| 7,236,815 B2 | 6/2007 | Richards-Kortum et al. |
| 7,253,894 B2 | 8/2007 | Zeng et al. |
| 7,317,554 B2 | 1/2008 | Ueda et al. |
| 7,324,674 B2 | 1/2008 | Ozawa et al. |
| 7,333,270 B1 | 2/2008 | Pochapsky et al. |
| 7,341,557 B2 | 3/2008 | Cline et al. |
| D567,649 S | 4/2008 | Borkowski et al. |
| 7,364,574 B2 | 4/2008 | Flower |
| 7,381,400 B2 | 6/2008 | Woltering |
| 7,385,772 B2 | 6/2008 | Forkey et al. |
| 7,400,753 B2 | 7/2008 | Seino et al. |
| 7,400,755 B2 | 7/2008 | West et al. |
| 7,420,151 B2 | 9/2008 | Fengler et al. |
| 7,474,906 B2 | 1/2009 | Rubinstein et al. |
| 7,479,990 B2 | 1/2009 | Imaizumi et al. |
| 7,482,318 B2 | 1/2009 | Aurelian et al. |
| 7,581,191 B2 | 8/2009 | Rice et al. |
| D599,799 S | 9/2009 | Di Bari et al. |
| D603,408 S | 11/2009 | Fitch |
| D606,544 S | 12/2009 | Di Bari et al. |
| 7,697,975 B2 | 4/2010 | Zeng |
| 7,704,206 B2 | 4/2010 | Suzuki et al. |
| 7,722,534 B2 | 5/2010 | Cline et al. |
| 7,729,750 B2 | 6/2010 | Tromberg et al. |
| 7,774,048 B2 | 8/2010 | Nakaoka et al. |
| 7,777,191 B2 | 8/2010 | Olcott et al. |
| 7,798,955 B2 | 9/2010 | Ishihara et al. |
| 7,811,229 B2 | 10/2010 | Sugimoto |
| 7,881,777 B2 | 2/2011 | Docherty et al. |
| 7,885,438 B2 | 2/2011 | Uppaluri et al. |
| 7,928,352 B2 | 4/2011 | Toda |
| D646,315 S | 10/2011 | Orf |
| 8,035,067 B2 | 10/2011 | Toda |
| 8,036,437 B2 | 10/2011 | Arditi et al. |
| 8,073,224 B2 | 12/2011 | Strobel et al. |
| D653,811 S | 2/2012 | BenZion |
| 8,140,147 B2 | 3/2012 | Maynard et al. |
| 8,144,958 B2 | 3/2012 | Nahm et al. |
| 8,185,176 B2 | 5/2012 | Mangat et al. |
| 8,194,981 B2 | 6/2012 | Suzuki |
| 8,285,015 B2 | 10/2012 | Demos |
| 8,285,353 B2 | 10/2012 | Choi et al. |
| 8,337,400 B2 | 12/2012 | Mizuyoshi |
| 8,361,775 B2 | 1/2013 | Flower |
| D677,258 S | 3/2013 | Mistkawi |
| 8,406,860 B2 | 3/2013 | Dvorsky et al. |
| 8,408,269 B2 | 4/2013 | Fengler et al. |
| 8,408,772 B2 | 4/2013 | Li |
| D682,277 S | 5/2013 | Tasselli et al. |
| 8,448,867 B2 | 5/2013 | Liu et al. |
| 8,473,035 B2 | 6/2013 | Frangioni |
| 8,480,579 B2 | 7/2013 | Serov et al. |
| 8,498,695 B2 | 7/2013 | Westwick et al. |
| 8,521,260 B2 | 8/2013 | Grinvald et al. |
| 8,538,107 B2 | 9/2013 | Röttger |
| D692,004 S | 10/2013 | Man |
| D692,576 S | 10/2013 | Steinman et al. |
| D692,892 S | 11/2013 | Mistkawi |
| D693,802 S | 11/2013 | Wikel |
| 8,630,698 B2 | 1/2014 | Fengler et al. |
| 8,647,605 B2 | 2/2014 | Mangat et al. |
| 8,718,747 B2 | 5/2014 | Bjornerud et al. |
| 8,721,532 B2 | 5/2014 | Takei et al. |
| 8,725,225 B2 | 5/2014 | Golijanin et al. |
| 8,736,748 B2 | 5/2014 | Takita |
| 8,759,243 B2 | 6/2014 | Coffy et al. |
| 8,773,756 B2 | 7/2014 | Tesar et al. |
| 8,790,253 B2 | 7/2014 | Sunagawa et al. |
| 8,830,339 B2 | 9/2014 | Velarde et al. |
| 8,892,190 B2 | 11/2014 | Docherty et al. |
| D719,574 S | 12/2014 | Alegiani et al. |
| 8,929,974 B2 | 1/2015 | Hauger et al. |
| 8,961,403 B2 | 2/2015 | Cline et al. |
| 8,965,488 B2 | 2/2015 | Dvorsky et al. |
| D723,563 S | 3/2015 | Alegiani |
| 8,979,301 B2 | 3/2015 | Moore |
| D726,186 S | 4/2015 | Jenkins et al. |
| D734,339 S | 7/2015 | Zhou et al. |
| 9,089,601 B2 | 7/2015 | Golijanin et al. |
| 9,125,552 B2 | 9/2015 | Dunki-Jacobs et al. |
| 9,129,366 B2 | 9/2015 | Nahm et al. |
| 9,143,746 B2 | 9/2015 | Westwick et al. |
| D742,509 S | 11/2015 | Anderson |
| 9,173,554 B2 | 11/2015 | Fengler et al. |
| 9,241,636 B2 | 1/2016 | Koizumi et al. |
| D749,598 S | 2/2016 | Ray et al. |
| RE45,916 E | 3/2016 | Golijanin et al. |
| 9,282,305 B2 | 3/2016 | Kikuchi |
| 9,294,691 B2 | 3/2016 | Ooki |
| 9,295,392 B2 | 3/2016 | Douplik et al. |
| 9,351,644 B2 | 5/2016 | Nahm et al. |
| 9,357,931 B2 | 6/2016 | Nahm et al. |
| 9,386,909 B2 | 7/2016 | Fengler et al. |
| D764,565 S | 8/2016 | Tekunoff et al. |
| 9,407,838 B2 | 8/2016 | Butte et al. |
| 9,421,280 B2 | 8/2016 | Mangat et al. |
| 9,435,496 B2 | 9/2016 | Moore |
| 9,451,903 B2 | 9/2016 | Feinberg |
| 9,554,738 B1 | 1/2017 | Gulati et al. |
| 9,577,012 B2 | 2/2017 | Ooki |
| D782,901 S | 4/2017 | Richter |
| 9,610,021 B2 | 4/2017 | Dvorsky et al. |
| 9,642,532 B2 | 5/2017 | Fengler et al. |
| D791,137 S | 7/2017 | Wang et al. |
| 9,814,378 B2 | 11/2017 | Moore |
| 9,816,930 B2 | 11/2017 | Moriyama et al. |
| D815,928 S | 4/2018 | Rummel et al. |
| 9,936,887 B2 | 4/2018 | Dvorsky et al. |
| D826,234 S | 8/2018 | Zhou et al. |
| 10,041,042 B2 | 8/2018 | Flower |
| D834,583 S | 11/2018 | Janzen et al. |
| D835,284 S | 12/2018 | Barker et al. |
| D835,285 S | 12/2018 | Barker et al. |
| 10,219,742 B2 | 3/2019 | Dvorsky et al. |
| 10,231,624 B2 | 3/2019 | Mangat et al. |
| 10,265,419 B2 | 4/2019 | Golijanin |
| 10,278,585 B2 | 5/2019 | Ferguson, Jr. et al. |

(56) References Cited

U.S. PATENT DOCUMENTS

| | | |
|---|---|---|
| 10,356,334 B2 | 7/2019 | Moore et al. |
| 10,721,410 B2 | 7/2020 | Moore et al. |
| 10,779,734 B2 | 9/2020 | Fengler et al. |
| 10,869,645 B2 | 12/2020 | Fengler et al. |
| D916,294 S | 4/2021 | Murray et al. |
| 10,980,420 B2 | 4/2021 | Fengler et al. |
| 10,992,848 B2 | 4/2021 | Murray et al. |
| D919,810 S | 5/2021 | Murray et al. |
| D919,811 S | 5/2021 | Murray et al. |
| D919,812 S | 5/2021 | Murray et al. |
| 2001/0016679 A1 | 8/2001 | Futatsugi et al. |
| 2001/0028458 A1 | 10/2001 | Xiao |
| 2001/0049473 A1 | 12/2001 | Hayashi |
| 2002/0007123 A1 | 1/2002 | Balas |
| 2002/0013937 A1 | 1/2002 | Ostanevich et al. |
| 2002/0016533 A1 | 2/2002 | Marchitto et al. |
| 2002/0021355 A1 | 2/2002 | Utsui et al. |
| 2002/0025541 A1 | 2/2002 | Nelson et al. |
| 2002/0035330 A1 | 3/2002 | Cline et al. |
| 2002/0038120 A1 | 3/2002 | Duhaylongsod et al. |
| 2002/0076480 A1 | 6/2002 | Hsieh et al. |
| 2002/0099279 A1 | 7/2002 | Pfeiffer et al. |
| 2002/0099295 A1 | 7/2002 | Gil et al. |
| 2002/0138008 A1 | 9/2002 | Tsujita et al. |
| 2002/0143243 A1 | 10/2002 | Geordakoudi et al. |
| 2002/0146369 A1 | 10/2002 | Goldenberg |
| 2002/0148902 A1 | 10/2002 | Schlieffers |
| 2002/0155619 A1 | 10/2002 | Kurihara et al. |
| 2002/0156380 A1 | 10/2002 | Feld et al. |
| 2002/0161282 A1 | 10/2002 | Fulghum |
| 2002/0161283 A1 | 10/2002 | Sendai |
| 2002/0161284 A1 | 10/2002 | Tanaka |
| 2002/0168096 A1 | 11/2002 | Hakamata et al. |
| 2002/0175993 A1 | 11/2002 | Ueno et al. |
| 2002/0177778 A1 | 11/2002 | Averback et al. |
| 2002/0181752 A1 | 12/2002 | Wallo et al. |
| 2002/0183621 A1 | 12/2002 | Pfeiffer et al. |
| 2002/0186478 A1 | 12/2002 | Watanabe et al. |
| 2002/0196335 A1 | 12/2002 | Ozawa |
| 2003/0002036 A1 | 1/2003 | Haan et al. |
| 2003/0032885 A1 | 2/2003 | Rubinstein et al. |
| 2003/0042493 A1 | 3/2003 | Kazakevich |
| 2003/0050543 A1 | 3/2003 | Hartmann |
| 2003/0060718 A1 | 3/2003 | Alam et al. |
| 2003/0060722 A1 | 3/2003 | Pfeiffer et al. |
| 2003/0063398 A1 | 4/2003 | Abe et al. |
| 2003/0064025 A1 | 4/2003 | Yang et al. |
| 2003/0080193 A1 | 5/2003 | Ryan et al. |
| 2003/0093064 A1 | 5/2003 | Peyman |
| 2003/0093065 A1 | 5/2003 | Peyman |
| 2003/0117491 A1 | 6/2003 | Avni et al. |
| 2003/0127609 A1 | 7/2003 | El-Hage et al. |
| 2003/0135092 A1 | 7/2003 | Cline et al. |
| 2003/0139667 A1 | 7/2003 | Hewko et al. |
| 2003/0153811 A1 | 8/2003 | Muckner |
| 2003/0156252 A1 | 8/2003 | Morris et al. |
| 2003/0158470 A1 | 8/2003 | Wolters et al. |
| 2003/0187349 A1 | 10/2003 | Kaneko et al. |
| 2003/0191368 A1 | 10/2003 | Wang et al. |
| 2003/0229270 A1 | 12/2003 | Suzuki et al. |
| 2003/0232016 A1 | 12/2003 | Heinrich |
| 2003/0236458 A1 | 12/2003 | Hochman |
| 2004/0002660 A1 | 1/2004 | Mielekamp |
| 2004/0006276 A1 | 1/2004 | Demos et al. |
| 2004/0010183 A1 | 1/2004 | Dhindsa |
| 2004/0020990 A1 | 2/2004 | Haven et al. |
| 2004/0021859 A1 | 2/2004 | Cunningham |
| 2004/0037454 A1 | 2/2004 | Ozawa et al. |
| 2004/0044275 A1 | 3/2004 | Hakamata |
| 2004/0046865 A1 | 3/2004 | Ueno et al. |
| 2004/0066961 A1 | 4/2004 | Spreeuwers et al. |
| 2004/0077952 A1 | 4/2004 | Rafter et al. |
| 2004/0109231 A1 | 6/2004 | Haisch et al. |
| 2004/0133073 A1 | 7/2004 | Berci et al. |
| 2004/0134990 A1 | 7/2004 | Fitch et al. |
| 2004/0143162 A1 | 7/2004 | Krattiger et al. |
| 2004/0148141 A1 | 7/2004 | Tsujita et al. |
| 2004/0149998 A1 | 8/2004 | Henson et al. |
| 2004/0156124 A1 | 8/2004 | Okada |
| 2004/0156782 A1 | 8/2004 | Alam et al. |
| 2004/0162489 A1 | 8/2004 | Richards-Kortum et al. |
| 2004/0171827 A1 | 9/2004 | Peng et al. |
| 2004/0174495 A1 | 9/2004 | Levine |
| 2004/0186351 A1 | 9/2004 | Imaizumi et al. |
| 2004/0218115 A1 | 11/2004 | Kawana et al. |
| 2004/0225222 A1 | 11/2004 | Zeng et al. |
| 2004/0245350 A1 | 12/2004 | Zeng |
| 2004/0263643 A1 | 12/2004 | Imaizumi et al. |
| 2005/0011954 A1 | 1/2005 | Hennick et al. |
| 2005/0019744 A1 | 1/2005 | Bertuglia |
| 2005/0020891 A1 | 1/2005 | Rubinstein et al. |
| 2005/0027166 A1 | 2/2005 | Matsumoto et al. |
| 2005/0033145 A1 | 2/2005 | Graham et al. |
| 2005/0065432 A1 | 3/2005 | Kimura |
| 2005/0069525 A1 | 3/2005 | Mikael |
| 2005/0089866 A1 | 4/2005 | Hinuma et al. |
| 2005/0096505 A1 | 5/2005 | Imaizumi et al. |
| 2005/0107380 A1 | 5/2005 | Nimmo et al. |
| 2005/0140270 A1 | 6/2005 | Henson et al. |
| 2005/0142556 A1 | 6/2005 | Hoon et al. |
| 2005/0143627 A1 | 6/2005 | Cline et al. |
| 2005/0154319 A1 | 7/2005 | Cline et al. |
| 2005/0171440 A1 | 8/2005 | Maki et al. |
| 2005/0182291 A1 | 8/2005 | Hirata |
| 2005/0182321 A1 | 8/2005 | Frangioni |
| 2005/0182327 A1 | 8/2005 | Petty et al. |
| 2005/0182431 A1 | 8/2005 | Hausen et al. |
| 2005/0182434 A1 | 8/2005 | Docherty et al. |
| 2005/0187477 A1 | 8/2005 | Serov et al. |
| 2005/0197583 A1 | 9/2005 | Chance |
| 2005/0203421 A1 | 9/2005 | Zeng et al. |
| 2005/0225656 A1 | 10/2005 | Ihama |
| 2005/0254008 A1 | 11/2005 | Ferguson et al. |
| 2005/0256373 A1 | 11/2005 | Bar-Or et al. |
| 2005/0273011 A1 | 12/2005 | Hattery et al. |
| 2005/0280783 A1 | 12/2005 | Yamasaki et al. |
| 2005/0288593 A1 | 12/2005 | Geordakoudi et al. |
| 2006/0002141 A1 | 1/2006 | Ouderkirk et al. |
| 2006/0004292 A1 | 1/2006 | Beylin |
| 2006/0011853 A1 | 1/2006 | Spartiotis et al. |
| 2006/0013768 A1 | 1/2006 | Woltering |
| 2006/0017913 A1 | 1/2006 | Kawamata et al. |
| 2006/0079750 A1 | 4/2006 | Fauci et al. |
| 2006/0089554 A1 | 4/2006 | Ishihara et al. |
| 2006/0094109 A1 | 5/2006 | Trainer |
| 2006/0108509 A1 | 5/2006 | Franigioni et al. |
| 2006/0118742 A1 | 6/2006 | Levenson et al. |
| 2006/0146322 A1 | 7/2006 | Komachi et al. |
| 2006/0147897 A1 | 7/2006 | Grinvald et al. |
| 2006/0149133 A1 | 7/2006 | Sugimoto et al. |
| 2006/0155166 A1 | 7/2006 | Takahashi et al. |
| 2006/0211915 A1 | 9/2006 | Takeuchi et al. |
| 2006/0215406 A1 | 9/2006 | Thrailkill |
| 2006/0217594 A1 | 9/2006 | Ferguson |
| 2006/0239921 A1 | 10/2006 | Mangat et al. |
| 2006/0241496 A1 | 10/2006 | Fengler et al. |
| 2006/0241499 A1 | 10/2006 | Irion et al. |
| 2006/0247537 A1 | 11/2006 | Matsumoto |
| 2006/0250696 A1 | 11/2006 | McGuire |
| 2006/0258910 A1 | 11/2006 | Stefanchik et al. |
| 2007/0041195 A1 | 2/2007 | Chen |
| 2007/0091634 A1 | 4/2007 | Sakurada |
| 2007/0121099 A1 | 5/2007 | Matsumoto et al. |
| 2007/0122344 A1 | 5/2007 | Golijanin |
| 2007/0122345 A1 | 5/2007 | Golijanin |
| 2007/0152161 A1 | 7/2007 | Olcott et al. |
| 2007/0177152 A1 | 8/2007 | Tearney et al. |
| 2007/0203413 A1 | 8/2007 | Frangioni |
| 2007/0213593 A1 | 9/2007 | Nakaoka |
| 2007/0229309 A1 | 10/2007 | Tomita et al. |
| 2007/0254276 A1 | 11/2007 | Deutsch et al. |
| 2008/0007733 A1 | 1/2008 | Marks et al. |
| 2008/0015446 A1 | 1/2008 | Mahmood et al. |
| 2008/0019615 A1 | 1/2008 | Schnee et al. |

(56) References Cited

U.S. PATENT DOCUMENTS

| | | |
|---|---|---|
| 2008/0021274 A1 | 1/2008 | Bayer et al. |
| 2008/0024868 A1 | 1/2008 | Okamura |
| 2008/0025918 A1 | 1/2008 | Frangioni et al. |
| 2008/0027280 A1 | 1/2008 | Fengler et al. |
| 2008/0039697 A1 | 2/2008 | Morishita |
| 2008/0044073 A1 | 2/2008 | Bernhardt et al. |
| 2008/0064925 A1 | 3/2008 | Gill et al. |
| 2008/0074752 A1 | 3/2008 | Chaves et al. |
| 2008/0081990 A1 | 4/2008 | Berenfeld et al. |
| 2008/0161744 A1 | 7/2008 | Golijanin et al. |
| 2008/0177140 A1 | 7/2008 | Cline et al. |
| 2008/0188728 A1 | 8/2008 | Neumann et al. |
| 2008/0208006 A1 | 8/2008 | Farr |
| 2008/0217411 A1 | 9/2008 | Ledwith et al. |
| 2008/0221421 A1 | 9/2008 | Choi et al. |
| 2008/0221648 A1 | 9/2008 | Flower |
| 2008/0239070 A1 | 10/2008 | Westwick et al. |
| 2008/0246920 A1 | 10/2008 | Buczek et al. |
| 2008/0319309 A1 | 12/2008 | Bredno et al. |
| 2009/0005693 A1 | 1/2009 | Brauner et al. |
| 2009/0012361 A1 | 1/2009 | MacKinnon et al. |
| 2009/0021739 A1 | 1/2009 | Tsujita et al. |
| 2009/0036734 A1 | 2/2009 | Dunki-Jacobs et al. |
| 2009/0040754 A1 | 2/2009 | Brukilacchio et al. |
| 2009/0042179 A1 | 2/2009 | Peltie et al. |
| 2009/0048516 A1 | 2/2009 | Yoshikawa et al. |
| 2009/0052185 A1 | 2/2009 | Toriyama et al. |
| 2009/0054788 A1 | 2/2009 | Hauger et al. |
| 2009/0112097 A1 | 4/2009 | Kato et al. |
| 2009/0114799 A1 | 5/2009 | Maeda |
| 2009/0114803 A1 | 5/2009 | Yamaguchi |
| 2009/0118623 A1 | 5/2009 | Serov et al. |
| 2009/0122135 A1 | 5/2009 | Matsui |
| 2009/0122152 A1 | 5/2009 | Yamaguchi et al. |
| 2009/0124854 A1 | 5/2009 | Yamaguchi et al. |
| 2009/0137902 A1 | 5/2009 | Frangioni et al. |
| 2009/0153797 A1 | 6/2009 | Allon et al. |
| 2009/0181339 A1 | 7/2009 | Liang et al. |
| 2009/0201577 A1 | 8/2009 | LaPlante et al. |
| 2009/0218405 A1 | 9/2009 | Joseph et al. |
| 2009/0236541 A1 | 9/2009 | Lommes et al. |
| 2009/0252682 A1 | 10/2009 | Hillman |
| 2009/0285762 A1 | 11/2009 | Flower |
| 2009/0290149 A1 | 11/2009 | Roth |
| 2009/0297004 A1 | 12/2009 | Baumgart |
| 2010/0016669 A1 | 1/2010 | Takaoka et al. |
| 2010/0022898 A1 | 1/2010 | Rubinstein et al. |
| 2010/0036217 A1 | 2/2010 | Choi et al. |
| 2010/0041999 A1 | 2/2010 | Schuhrke et al. |
| 2010/0061604 A1 | 3/2010 | Nahm et al. |
| 2010/0065641 A1 | 3/2010 | Liu et al. |
| 2010/0069759 A1 | 3/2010 | Schuhrke et al. |
| 2010/0080757 A1 | 4/2010 | Haaga et al. |
| 2010/0087741 A1 | 4/2010 | Douplik et al. |
| 2010/0094136 A1 | 4/2010 | Nakaoka et al. |
| 2010/0099961 A1 | 4/2010 | Hubner et al. |
| 2010/0110168 A1 | 5/2010 | Avni et al. |
| 2010/0110393 A1 | 5/2010 | Chen et al. |
| 2010/0121146 A1 | 5/2010 | Sugimoto |
| 2010/0125164 A1 | 5/2010 | LaBombard |
| 2010/0155487 A1 | 6/2010 | Liu et al. |
| 2010/0157039 A1 | 6/2010 | Sugai |
| 2010/0168588 A1 | 7/2010 | Matsumoto et al. |
| 2010/0198010 A1 | 8/2010 | Cline et al. |
| 2010/0208487 A1 | 8/2010 | Li |
| 2010/0222673 A1 | 9/2010 | Mangat et al. |
| 2010/0277817 A1 | 11/2010 | Durell |
| 2010/0286529 A1 | 11/2010 | Carroll et al. |
| 2010/0308116 A1 | 12/2010 | Sani et al. |
| 2011/0001061 A1 | 1/2011 | Ishihara |
| 2011/0013002 A1 | 1/2011 | Thompson et al. |
| 2011/0019992 A1 | 1/2011 | Orf |
| 2011/0032350 A1 | 2/2011 | Kikuchi et al. |
| 2011/0063427 A1 | 3/2011 | Fengler et al. |
| 2011/0071403 A1* | 3/2011 | Sevick-Muraca .... A61B 5/0059 600/476 |
| 2011/0073658 A1 | 3/2011 | Vassura et al. |
| 2011/0098685 A1 | 4/2011 | Flower |
| 2011/0158914 A1 | 6/2011 | Yamada et al. |
| 2011/0235017 A1 | 9/2011 | Iwasaki |
| 2011/0244506 A1 | 10/2011 | Sutter et al. |
| 2011/0270092 A1 | 11/2011 | Kang et al. |
| 2011/0279679 A1 | 11/2011 | Samuel et al. |
| 2011/0290889 A1 | 12/2011 | Tamburini et al. |
| 2011/0306877 A1 | 12/2011 | Dvorsky et al. |
| 2011/0309275 A1* | 12/2011 | Azimi ................... B01L 3/5027 251/129.01 |
| 2012/0006897 A1 | 1/2012 | Barkan et al. |
| 2012/0026325 A1 | 2/2012 | Bunker et al. |
| 2012/0044462 A1 | 2/2012 | Kaji |
| 2012/0078093 A1 | 3/2012 | Flower |
| 2012/0252699 A1 | 4/2012 | Jaffrey et al. |
| 2012/0150046 A1 | 6/2012 | Watson et al. |
| 2012/0165627 A1 | 6/2012 | Yamamoto |
| 2012/0165662 A1 | 6/2012 | Nahm et al. |
| 2012/0256002 A1 | 10/2012 | O'Donnell et al. |
| 2012/0271176 A1 | 10/2012 | Moghaddam et al. |
| 2012/0319645 A1 | 12/2012 | O'Donnell et al. |
| 2012/0323118 A1 | 12/2012 | Gopalakrishna et al. |
| 2013/0008964 A1 | 1/2013 | Hawley et al. |
| 2013/0203082 A1 | 8/2013 | Gonda et al. |
| 2013/0230866 A1 | 9/2013 | Miyashita et al. |
| 2013/0237762 A1 | 9/2013 | Fengler et al. |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0342674 A1 | 12/2013 | Dixon |
| 2013/0345560 A1 | 12/2013 | Ferguson, Jr. et al. |
| 2014/0071328 A1 | 3/2014 | Miesak |
| 2014/0078378 A1 | 3/2014 | Demers et al. |
| 2014/0099007 A1 | 4/2014 | Sarkar et al. |
| 2014/0139893 A1 | 5/2014 | Sugiyama et al. |
| 2014/0186351 A1 | 7/2014 | Britta et al. |
| 2014/0187967 A1 | 7/2014 | Wood et al. |
| 2014/0192258 A1 | 7/2014 | Yang et al. |
| 2014/0194687 A1 | 7/2014 | Fengler et al. |
| 2014/0254909 A1 | 9/2014 | Carmi et al. |
| 2014/0308656 A1 | 10/2014 | Flower |
| 2014/0316262 A1 | 10/2014 | Havens |
| 2014/0371583 A1 | 12/2014 | Flower |
| 2015/0083932 A1 | 3/2015 | Rizo et al. |
| 2015/0112192 A1 | 4/2015 | Docherty et al. |
| 2015/0112193 A1 | 4/2015 | Docherty et al. |
| 2015/0164396 A1 | 6/2015 | Acharya et al. |
| 2015/0182137 A1 | 7/2015 | Flower et al. |
| 2015/0184811 A1 | 7/2015 | Moore |
| 2015/0196208 A1 | 7/2015 | Dvorsky et al. |
| 2015/0230698 A1 | 8/2015 | Cline et al. |
| 2015/0230710 A1 | 8/2015 | Nahm et al. |
| 2015/0230715 A1 | 8/2015 | Nahm et al. |
| 2015/0248758 A1 | 9/2015 | Pautot |
| 2015/0320296 A1 | 11/2015 | Morita |
| 2015/0341551 A1 | 11/2015 | Perrin et al. |
| 2015/0381909 A1* | 12/2015 | Butte ..................... H04N 5/332 348/68 |
| 2016/0038027 A1 | 2/2016 | Brzozowski et al. |
| 2016/0041098 A1 | 2/2016 | Hirawake et al. |
| 2016/0044253 A1 | 2/2016 | Dainty et al. |
| 2016/0097716 A1 | 4/2016 | Gulati et al. |
| 2016/0100763 A1 | 4/2016 | Fengler et al. |
| 2016/0173802 A1 | 6/2016 | Matsuo et al. |
| 2016/0199515 A1 | 7/2016 | Flower |
| 2016/0249019 A1 | 8/2016 | Westwick et al. |
| 2016/0253800 A1 | 9/2016 | Gurevich et al. |
| 2016/0360956 A1 | 12/2016 | Moore |
| 2016/0371834 A1 | 12/2016 | Watanabe et al. |
| 2017/0039710 A1 | 2/2017 | Minai et al. |
| 2017/0064257 A1 | 3/2017 | Westwick et al. |
| 2017/0064258 A1 | 3/2017 | Westwick et al. |
| 2017/0084024 A1 | 3/2017 | Gurevich |
| 2017/0167980 A1 | 6/2017 | Dimitriadis et al. |
| 2017/0245766 A1 | 8/2017 | Flower et al. |
| 2017/0245803 A1* | 8/2017 | Ahmed ................ A61B 5/7203 |

(56) References Cited

U.S. PATENT DOCUMENTS

| | | | |
|---|---|---|---|
| 2017/0303800 A1 | 10/2017 | Flower et al. | |
| 2017/0354392 A1 | 12/2017 | Fengler et al. | |
| 2018/0020933 A1 | 1/2018 | Dvorsky et al. | |
| 2018/0104362 A1 | 4/2018 | Golijanin et al. | |
| 2018/0120230 A1 | 5/2018 | Moriyama et al. | |
| 2018/0220907 A1 | 8/2018 | Dvorsky et al. | |
| 2018/0369426 A1 | 12/2018 | Flower et al. | |
| 2021/0105393 A1 | 4/2021 | Moore et al. | |

FOREIGN PATENT DOCUMENTS

| | | |
|---|---|---|
| CA | 2413033 A1 | 3/2000 |
| CA | 2711560 A1 | 7/2009 |
| CA | 2913692 A1 | 1/2015 |
| CN | 1049781 A | 3/1991 |
| CN | 2076516 U | 5/1991 |
| CN | 1200174 A | 11/1998 |
| CN | 1399528 A | 2/2003 |
| CN | 101264014 A | 9/2008 |
| CN | 101451953 A | 6/2009 |
| CN | 101726980 A | 6/2010 |
| CN | 101828139 A | 9/2010 |
| CN | 102026668 A | 4/2011 |
| CN | 201974160 U | 9/2011 |
| CN | 102257510 A | 11/2011 |
| CN | 102288589 A | 12/2011 |
| CN | 102405212 A | 4/2012 |
| CN | 102436648 A | 5/2012 |
| CN | 103543609 A | 1/2014 |
| CN | 103608662 A | 2/2014 |
| DE | 3906860 A1 | 9/1989 |
| DE | 19535114 A1 | 3/1996 |
| DE | 19608027 A1 | 9/1996 |
| DE | 10028233 A1 | 1/2002 |
| DE | 10120980 A1 | 11/2002 |
| DE | 69727220 T2 | 12/2004 |
| DE | 102005044531 A1 | 3/2007 |
| EP | 0091805 A2 | 10/1983 |
| EP | 0215772 A2 | 3/1987 |
| EP | 0512965 A1 | 11/1992 |
| EP | 0672379 A1 | 9/1995 |
| EP | 0774865 A2 | 5/1997 |
| EP | 0792618 A1 | 9/1997 |
| EP | 0807402 A1 | 11/1997 |
| EP | 0826335 A1 | 3/1998 |
| EP | 0671706 B1 | 6/1999 |
| EP | 1374755 A1 | 1/2004 |
| EP | 1 496 690 A2 | 1/2005 |
| EP | 1677097 A1 | 7/2006 |
| EP | 1761171 | 3/2007 |
| EP | 1874181 | 1/2008 |
| EP | 1883337 A1 | 2/2008 |
| EP | 2051603 A1 | 4/2009 |
| EP | 2859837 A1 | 4/2015 |
| EP | 2 988 654 B1 | 6/2020 |
| FR | 2671405 A1 | 7/1992 |
| FR | 2944104 A1 | 10/2010 |
| GB | 2203831 A | 10/1988 |
| JP | S52-34584 A | 3/1977 |
| JP | S58-222331 A | 12/1983 |
| JP | S59-069721 A | 4/1984 |
| JP | S59-070903 A | 4/1984 |
| JP | S60-246733 A | 12/1985 |
| JP | S61-159936 A | 7/1986 |
| JP | H01-135349 A | 5/1989 |
| JP | H01-236879 A | 9/1989 |
| JP | 02-200237 A | 8/1990 |
| JP | 03-97439 A | 4/1991 |
| JP | 03-97441 A | 4/1991 |
| JP | 03-97442 A | 4/1991 |
| JP | H03-115958 A | 5/1991 |
| JP | 04-297236 A | 10/1992 |
| JP | 05-115435 A | 5/1993 |
| JP | H05-264232 A | 10/1993 |
| JP | H06-007353 A | 1/1994 |
| JP | 06-125911 A | 5/1994 |
| JP | 06-335451 A | 12/1994 |
| JP | H07-043303 A | 2/1995 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222712 A | 8/1995 |
| JP | H07-222723 A | 8/1995 |
| JP | H07-250804 A | 10/1995 |
| JP | H07-250812 A | 10/1995 |
| JP | H07-327913 A | 12/1995 |
| JP | 08-024227 A | 1/1996 |
| JP | H08-126605 A | 5/1996 |
| JP | 08-140928 A | 6/1996 |
| JP | 08-140929 A | 6/1996 |
| JP | H08-224208 A | 9/1996 |
| JP | H08-224209 A | 9/1996 |
| JP | H08-224210 A | 9/1996 |
| JP | H08-224240 A | 9/1996 |
| JP | H08-252218 A | 10/1996 |
| JP | H09-19408 A | 1/1997 |
| JP | 09-066023 A2 | 3/1997 |
| JP | 09-070384 A2 | 3/1997 |
| JP | H09-120033 A | 5/1997 |
| JP | H09-305845 A | 11/1997 |
| JP | H09-308609 A | 12/1997 |
| JP | H09-309845 A | 12/1997 |
| JP | H10-500479 A | 1/1998 |
| JP | H10-503480 A | 3/1998 |
| JP | H10-085222 A | 4/1998 |
| JP | H10-104070 A | 4/1998 |
| JP | H10-127563 A | 5/1998 |
| JP | H10-151104 A | 6/1998 |
| JP | H10-506440 A | 6/1998 |
| JP | H10-506550 A | 6/1998 |
| JP | 10-225427 A2 | 8/1998 |
| JP | H10-201700 A | 8/1998 |
| JP | H10-201707 A | 8/1998 |
| JP | H10-225426 A | 8/1998 |
| JP | H10-243915 A | 9/1998 |
| JP | H10-243920 A | 9/1998 |
| JP | H10-308114 A | 11/1998 |
| JP | H10-309281 A | 11/1998 |
| JP | H10-309282 A | 11/1998 |
| JP | H10-321005 A | 12/1998 |
| JP | H10-328129 A | 12/1998 |
| JP | H11-47079 A | 2/1999 |
| JP | 11-089789 A2 | 4/1999 |
| JP | H11-104059 A | 4/1999 |
| JP | H11-104060 A | 4/1999 |
| JP | H11-104061 A | 4/1999 |
| JP | H11-104070 A | 4/1999 |
| JP | H11-113839 A | 4/1999 |
| JP | H11-137517 A | 5/1999 |
| JP | H11-155812 A | 6/1999 |
| JP | H11-509748 A | 8/1999 |
| JP | H11-244220 A | 9/1999 |
| JP | H11-332819 A | 12/1999 |
| JP | 2000-504968 A | 4/2000 |
| JP | 2000-230903 | 8/2000 |
| JP | 2000-245693 A | 9/2000 |
| JP | 2000-354583 A | 12/2000 |
| JP | 2001-78205 A | 3/2001 |
| JP | 2001-198079 A | 7/2001 |
| JP | 2002-000560 A | 1/2002 |
| JP | 2002-049302 A | 2/2002 |
| JP | 2002-219129 A | 8/2002 |
| JP | 2002-244122 A | 8/2002 |
| JP | 2003-045210 A | 2/2003 |
| JP | 2003-510121 A | 3/2003 |
| JP | 2003-144401 A | 5/2003 |
| JP | 2003-187226 A | 7/2003 |
| JP | 2003-329589 A | 11/2003 |

(56) References Cited

FOREIGN PATENT DOCUMENTS

| | | |
|---|---|---|
| JP | 2004-024611 A | 1/2004 |
| JP | 2004-094043 A | 3/2004 |
| JP | 2004-163902 A | 6/2004 |
| JP | 2004-520105 A | 7/2004 |
| JP | 2004-247156 A | 9/2004 |
| JP | 2004-528917 A | 9/2004 |
| JP | 2004-289545 A | 10/2004 |
| JP | 2004-292722 A | 10/2004 |
| JP | 2004-325200 A | 11/2004 |
| JP | 2005-010315 A | 1/2005 |
| JP | 2005-058618 A2 | 3/2005 |
| JP | 2005-058619 A2 | 3/2005 |
| JP | 2005-058620 A2 | 3/2005 |
| JP | 2005-080819 A2 | 3/2005 |
| JP | 2005-081079 A2 | 3/2005 |
| JP | 2005-149996 A | 6/2005 |
| JP | 2005-292404 A | 10/2005 |
| JP | 2006-003103 A | 1/2006 |
| JP | 2006-503620 A | 2/2006 |
| JP | 2006-073767 A | 3/2006 |
| JP | 2006-087764 A | 4/2006 |
| JP | 2006-192280 A | 7/2006 |
| JP | 2006-525494 A | 11/2006 |
| JP | 2007-021006 A | 2/2007 |
| JP | 2007-029453 A | 2/2007 |
| JP | 2007-072392 A | 3/2007 |
| JP | 3896176 B2 | 3/2007 |
| JP | 2007-089840 A | 4/2007 |
| JP | 2008-231113 A | 2/2008 |
| JP | 2008-525126 A | 7/2008 |
| JP | 2008-220926 A | 9/2008 |
| JP | 2008-535600 A | 9/2008 |
| JP | 2008-231113 A | 10/2008 |
| JP | 2009-095683 A | 5/2009 |
| JP | 2009-519082 A | 5/2009 |
| JP | 2009-259703 A | 11/2009 |
| JP | 2009-291554 A | 12/2009 |
| JP | 2010-505582 A | 2/2010 |
| JP | 2010-107751 A | 5/2010 |
| JP | 2010-117442 A | 5/2010 |
| JP | 2010-521267 A | 6/2010 |
| JP | 2010-524194 A | 7/2010 |
| JP | 2011-500921 A | 1/2011 |
| JP | 2011-509768 A | 3/2011 |
| JP | 2011-072424 A | 4/2011 |
| JP | 2011-519589 A | 7/2011 |
| JP | 2011-169819 A | 9/2011 |
| JP | 2011-528918 A | 12/2011 |
| JP | 5231625 B2 | 7/2013 |
| JP | 2014-123941 A | 7/2014 |
| JP | 5859578 B2 | 2/2016 |
| JP | 5918532 B2 | 5/2016 |
| JP | 2016-521612 A | 7/2016 |
| KR | 90-0005434 B1 | 7/1990 |
| KR | 2002-0064287 A | 8/2002 |
| RU | 2288633 C1 | 12/2006 |
| RU | 99592 U1 | 11/2010 |
| WO | WO-1986/02730 A1 | 5/1986 |
| WO | WO-1990/10219 A1 | 9/1990 |
| WO | WO-1990/12536 A1 | 11/1990 |
| WO | WO-1993/04648 A1 | 3/1993 |
| WO | WO-1993/25141 A1 | 12/1993 |
| WO | WO-1994/12092 A1 | 6/1994 |
| WO | WO-1994/13191 A1 | 6/1994 |
| WO | WO-1995/00171 A1 | 1/1995 |
| WO | WO-1995/26673 A2 | 10/1995 |
| WO | WO-1996/09435 A1 | 3/1996 |
| WO | WO-1996/09792 A1 | 4/1996 |
| WO | WO-1996/18415 A1 | 6/1996 |
| WO | WO-1996/23524 A1 | 8/1996 |
| WO | WO-1996/39925 A1 | 12/1996 |
| WO | WO-1997/08538 A1 | 3/1997 |
| WO | WO-1998/24360 A1 | 6/1998 |
| WO | WO-1998/30144 A1 | 7/1998 |
| WO | WO-1998/46122 A1 | 10/1998 |
| WO | WO-1999/00053 A1 | 1/1999 |
| WO | WO-1999/01749 A1 | 1/1999 |
| WO | WO-1999/47940 A1 | 9/1999 |
| WO | WO-1999/53832 A1 | 10/1999 |
| WO | WO-2000/42910 A1 | 7/2000 |
| WO | WO-2000/47107 A1 | 8/2000 |
| WO | WO-2000/54652 A1 | 9/2000 |
| WO | WO-2001/08552 A1 | 2/2001 |
| WO | WO-2001/17561 A1 | 3/2001 |
| WO | WO-2001/22870 A1 | 4/2001 |
| WO | WO-2001/39764 A2 | 6/2001 |
| WO | WO-2001/69244 A2 | 9/2001 |
| WO | WO-2001/80734 A1 | 11/2001 |
| WO | WO-2001/82786 A2 | 11/2001 |
| WO | WO-2002/007587 A2 | 1/2002 |
| WO | WO-2002/50518 A2 | 6/2002 |
| WO | WO-2002/061390 A2 | 8/2002 |
| WO | WO-2003/006658 A1 | 1/2003 |
| WO | WO-2003/059159 A2 | 7/2003 |
| WO | WO-2003/059159 A8 | 7/2003 |
| WO | WO-2004/006963 A1 | 1/2004 |
| WO | WO-2004/052195 A1 | 6/2004 |
| WO | WO-2005/026319 A2 | 3/2005 |
| WO | WO-2005/034747 A1 | 4/2005 |
| WO | WO-2005/036143 A1 | 4/2005 |
| WO | WO-2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/116847 A1 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO-2006/123742 A1 | 11/2006 |
| WO | WO-2007/028032 A2 | 3/2007 |
| WO | WO-2007/081707 A2 | 7/2007 |
| WO | WO-2008/011722 A1 | 1/2008 |
| WO | WO-2008/039968 A2 | 4/2008 |
| WO | WO-2008/044822 A1 | 4/2008 |
| WO | WO-2008/070269 A2 | 6/2008 |
| WO | WO-2008/070269 A3 | 6/2008 |
| WO | WO-2008/071240 A1 | 6/2008 |
| WO | WO-2008/087869 A1 | 7/2008 |
| WO | WO-2009/033021 A2 | 3/2009 |
| WO | WO-2009/046985 A2 | 4/2009 |
| WO | WO-2009/046985 A3 | 4/2009 |
| WO | WO-2009/048660 A2 | 4/2009 |
| WO | WO-2009/092162 A1 | 7/2009 |
| WO | WO-2009/127972 A2 | 10/2009 |
| WO | WO-2012/038824 A1 | 3/2012 |
| WO | WO-2012/096878 A2 | 7/2012 |
| WO | WO-2013/160279 A1 | 10/2013 |
| WO | WO-2013/190391 A2 | 12/2013 |
| WO | WO-2014/176375 A2 | 10/2014 |
| WO | WO-2015/001427 A2 | 1/2015 |
| WO | WO-2013/002350 A1 | 2/2015 |
| WO | WO-2015/164774 A1 | 10/2015 |
| WO | WO-2016/055837 A1 | 4/2016 |

OTHER PUBLICATIONS

Amplitude Modulated Video Camera—Light Separation in Dynamic Scenes, 2016 IEEE Conference on Computer Vision and Pattern Recognition (CVPR) Kolaman et al. hereinafter "Kolaman".*

Akintunde, A. et al. (Oct.-Nov. 1992). "Quadruple Labeling of Brain-Stem Neurons: a Multiple Retrograde Fluorescent Tracer Study of Axonal Collateralization," *Journal of Neuroscience Methods* 45(1-2):15-22.

Alander, J.T. et al. (Jan. 1, 2012). "A Review of Indocyanine Green Fluorescent Imaging in Surgery," *International Journal of Biomedical Imaging* 2012:1-26, article ID 940585.

Alfano et al. (Oct. 1987). "Fluorescence Spectra from Cancerous and Normal Human Breast and Lung Tissues," *IEEE Journal of Quantum Electronics* QE-23(10):1806-1811.

Alm, A. et al. (Jan. 1, 1973). "Ocular and Optic Nerve Blood Flow at Normal and Increased Intraocular Pressures in Monkeys (*Macaca irus*): A Study with Radioactively Labelled Microspheres Including

(56) References Cited

OTHER PUBLICATIONS

Flow Determinations in Brain and Some Other Tissues," *Experimental Eye Research* 15(1):15-29.

Alonso-Burgos, A. et al. (2006). "Preoperative planning of deep inferior epigastric artery perforator flap reconstruction with multi-slice-CT angiography: imaging findings and initial experience," *Journal of Plastic, Reconstructive & Aesthetic Surgery* 59:585-593.

Alvarez, F. J. et al. (Apr. 1996). "Behaviour of Isolated Rat and Human Red Blood Cells Upon Hypotonic-Dialysis Encapsulation of Carbonic Anhydrase and Dextran," *Biotechnology and Applied Biochemistry* 23(2):173-179.

Ancalmo, N. et al. (1997). "Minimally invasive coronary artery bypass surgery: really minimal?" *Ann. Thorac. Surg.* 64:928-929.

Andersson-Engels, S. et al. (1991). "Fluorescence Characteristics of Atherosclorotic Plaque and Malignant Tumors," in *Optical Methods for Tumor Treatment and Early Diagnosis:. Mechanisms and Techniques,* T. J. Dougherty (Ed.), The Society of Photo-optical. Instrumentation Engineers (SPIE) 1426:31-43, fourteen pages.

Andersson-Engels, S. et al. (Mar. 1989). "Tissue Diagnostics Using Laser-Induced Fluorescence," *Berichte der Bunsengesellschaft für physikalische Chemie* 93(3):335-342.

Angelov, D.N. et al. (Apr. 1999). "Contralateral Trigeminal Nerve Lesion Reduces Polyneuronal Muscle Innervation after Facial Nerve Repair in Rats," *European Journal of Neuroscience* 11(4):1369-1378.

Annese, V. et al. (2005). "Erthrocytes-Mediated Delivery of Dexamethasone in Steroid-Dependent IBD Patients—a Pilot Uncontrolled Study," *American Journal of Gastroenterology* 100:1370-1375.

Argus-50/CA, Inter cellular CA2+ (calcium ion) Image Analysis system (Feb. 1992). "Observation and 2-dimensional analysis of Ca2+ concentration distribution. Fura-2 and Indo-1 compatible. Ca2+ concentrations are calculated from the fluorescence ratio," pp. 1-10.

Author Unknown. (Jun. 4, 2008)."Invitrogen," Material Safety Data Sheet, p. 1-4.

Awano, T. et al. (Jun. 2010). "Intraoperative EC-IC Bypass Blood Flow Assessment with Indocyanine Green Angiography in Moyamoya and Non-moyamoya Ischemic Stroke," *World Neurosurg.* 73(6):668-674.

Azuma, R. et al. (2008, presented in part Jun. 2007). "Detection of Skin Perforators by Indocyanine Green Fluorescence Nearly Infrared Angiography," *PRS Journal* 122(4):1062-1067.

Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.

Barton, J.K. et al. (1999) "Simultaneous irradiation and imaging of blood vessels during pulsed laser delivery," *Lasers in Surgery and Medicine* 24(3):236-243.

Bassingthwaighte, J.B. et al. (Apr. 1974). "Organ Blood Flow, Wash-in, Washout, and Clearance of Nutrients and Metabolites," *Mayo Clin. Proc.* 49(4):248-255.

Batliwala, H. et al. (Apr. 15, 1995). "Methane-Induced Haemolysis of Human Erythrocytes," *Biochemical J.* 307(2):433-438.

Baumgartner, R. et al. (1987). "Section V—In vivo Localization and Photodynamic Therapy: A Fluorescence Imaging Device for Endoscopic Detection of Early Stage Cancer—Instrumental and Experimental Studies," *Photochemistry and Photobiology* 46(5):759-763.

Baumgartner, R. et al. (Jan. 1, 1990). "A Fluorescence Imaging Device for Endoscopic Detection of Early Stage Cancer Instrumental and Experimental Studies," Section Five in *SPIE.* Press, ed. Abraham Katzir, pp. 513-517, eight pages. Reprinted by Permission by Spie. Press from Photochemistry and Photobiology 46(5):759-763, (1987).

Bek, T. (1999). "Diabetic Maculopathy Caused by Disturbances in Retinal Vasomotion: A New Hypothesis," *Acta Ophthalmologica Scandinavica* 77:376-380.

Benson, R.C. et al. (1978). "Fluorescence Properties of Indocyanine Green as Related to Angiography," *Phys. Med. Biol.* 23(1):159-163.

Black's Medical Dictionary, "Perfusion," 42nd Edition (2009), two pages.

Boer, F.et al. (1994). "Effect of Ventilation on First-Pass Pulmonary Retention of Alfentaril and Sufentanil in Patients Undergoing Coronary Artery Surgery," *British Journal Anesthesia* 73:458-463.

Boldt, .J. et al. (Feb. 1990). "Lung management during cardiopulmonary bypass: influence on extravascular lung water," *Journal of Cardiothoracic Anesthesia* 4(1):73-79.

Boldt, J. et al. (1991). "Does the technique of cardiopulmonary bypass affect lung water content?" *European Journal of Cardio-Thoracic Surgery* 5:22-26.

Bütter, A. et al. (May 2005). "Melanoma in Children and the Use of Sentinel Lymph Node Biopsy," *Journal of Pediatric Surgery* 40(5):797-800.

C2741, Compact High Performance video camera for industrial applications with Built-in contrast enhancement circuit, Jun. 1998, six pgs.

Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.

Coffey, J.H. et al. (1984). "Evaluation of Visual Acuity During Laser Photoradiation Therapy of Cancer," *Lasers in Surgery and Medicine* 4(1):65-71.

Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.

Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.

Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.

Dail, W.G. et al. (Oct. 1999). "Multiple Vasodilator Pathways from the Pelvic Plexus to the Penis of the Rat," *International Journal of Impotence Research* 11(5):277-285.

Dan, A.G. et al. (Nov. 2004). "1% Lymphazurin vs 10% Fluorescein for Sentinel Node Mapping in Colorectal Tumors," *Arch Surg.* 139(11):1180-1184.

Daniels, G. et al. (Apr. 2007). "Towards Universal Red Blood Cell," *Nature Biotechnology* 25(4):427-428.

De Flora, A. (Sep. 1986). "Encapsulation of Adriamycin in human erythrocytes," *Proc. Natl. Acad. Sci., USA* 83(18):7029-7033.

Declaration of Brian Wilson dated Aug. 22, 2017 for Inter Partes Review No. IPR2017-01426, twelve pages.

Definition of "Expose," Excerpt of Merriam Webster's Medical Desk Dictionary (1993), four pages.

Definition of "Graft," Excerpt of Stedman's Medical Dictionary for the Health Professions and Nursing; 6th Ed. (2008), three pages.

De-Grand, A.M. et al. (Dec. 2003). "An Operational Near Infrared Fluorescence Imaging System Prototype for Large Animal Surgery," *Technology in Cancer Research & Treatment* 2(6):1-10.

Deloach, J.R. (ed.) et al. (1985). *Red Blood Cells as Carriers for Drugs. A Method for Disseminating Chemotherapeutics, Hormones, Enzymes and Other Therapeutic Agents via the Circulatory System,* Karger, Basel, CH, pp. v-vii, (Table of Contents), seven pages.

Deloach, J.R. (Jun. 1983). "Encapsulation of Exogenous Agents in Erythrocytes and the Circulating Survival of Carrier Erythrocytes," *Journal of Applied Biochemistry* 5(3):149-157.

Demos (May/Jun. 2004). "Near-Infrared Autofluorescence Imaging for Detection of Cancer," *Journal of Biomedical Optics* 9(3):587-592.

Desai, N.D. et al. (Oct. 18, 2005, e-published on Sep. 28, 2005) "Improving the Quality of Coronary Bypass Surgery with lntraoperative Angiography," *Journal of the American College of Cardiology* 46(8):1521-1525.

Detter, C. et al. (Aug. 28, 2007). "Fluorescent Cardiac Imaging: A Novel lntraoperative Method for Quantitative Assessment of Myocardial Perfusion During Graded Coronary Artery Stenosis," *Circulation* 116(9):1007-1014.

(56) References Cited

OTHER PUBLICATIONS

Detter, C. et al. (Jun. 2002). "Near-Infrared Fluorescence Coronary Angiography: A New Noninvasive Technology for Intraoperative Graft Patency Control." *The Heart Surgery Forum* #2001-6973 5(4):364-369.

Dietz, F.B. et al. (Feb. 2003). "Indocyanine Green: Evidence of Neurotoxicity in Spinal Root Axons," *Anesthesiology* 98(2):516-520.

Digital CCD Microscopy (date unknown). Chapter 14, pp. 259-282.

Dougherty, T.J. et al. (1990). "Cutaneous Phototoxic Occurrences in Patients Receiving Photofrin," *Lasers in Surgery and Medicine* 10(5):485-488.

Draijer, M.J. et al. (Jun. 17-19, 2007). "Laser Doppler Perfusion Imaging with a High-Speed Cmos-Camera," in *Novel Optical Instrumentation for Biomedical Applications III*, C. Depeursinge, ed., Proceedings of SPIE-OSA Biomedical Optics (Optical Society of America, 2007), SPIE-OSA, 6631:0N1-0N7, eight pages.

Dünne, A. et al. (Nov. 2001)."Value of Sentinel lymphonodectomy in Head and Neck Cancer Patients without Evidence of Lymphogenic Metastatic Disease," *Auris Nasus Larynx* 28(4):339-344.

Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.

Emery R.W. et al. (Aug. 1996). "Revascularization Using Angioplasty and Minimally Invasive Techniques Documented by Thermal Imaging," *The Annals of Thoracic Surgery* 62(2):591-593.

Enquist, L.W. et al. (2002). "Directional Spread of an a-Herpesvirus in the Nervous System," *Veterinary Microbiology* 86:5-16.

Eren, S. et al. (Dec. 1995). "Assessment of Microcirculation of an Axial Skin Flap Using Indocyanine Green Fluorescence Angiography," *Plast. Reconstr. Surg.* 96(7):1636-1649.

Falk, T. et al. (Apr. 15, 2001). "A Herpes Simplex Viral Vector Expressing Green Fluorescent Protein can be Used to Visualize Morphological Changes in High-density Neuronal Culture," *Electronic Journal of Biotechnology* 4(1):34-45.

Flower, R. et al. (Apr.-Jun. 1999). "Effects of free and liposome-encapsulated hemoglobin on choroidal vascular plexus blood flow, using the rabbit eye as a model system," *European Journal of Ophthalmology* 9(2):103-114.

Flower, R.W. (1992). "Choroidal Angiography Today and Tomorrow," *Retina* 12(3):189-190.

Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.

Flower, R.W. (Aug. 2002). "Optimizing Treatment of Choroidal Neovascularization Feeder Vessels Associated with Age-Related Macular Degeneration," *American Journal of Ophthalmology* 134(2):228-239.

Flower, R.W. (Dec. 1973). "Injection Technique for Indocyanine Green and Sodium Fluorescein Dye Angiography of the Eye," *Investigative Opthamology* 12(12):881-895.

Flower, R.W. (Sep. 1, 1994). "Does Preinjection Binding of Indocyanine Green to Serum Actually Improve Angiograms?," *Arch Ophthalmol.* 112(9):1137-1139.

Flower, R.W. et al. (Aug. 1977). "Quantification of Indicator Dye Concentration in Ocular Blood Vessels," *Exp. Eye Res.* 25(2):103-111.

Flower, R.W. et al. (Dec. 1, 2008, e-published Aug. 15, 2008). "Observation of Erythrocyte Dynamics in the Retinal Capillaries and Choriocapillaris Using Icg-Loaded Erythrocyte Ghost Cells," *Investigative Ophthalmology, & Visual Science* 49(12):5510-5516.

Flower, R.W. et al. (Mar. 26, 2008-Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).

Forrester et al. (Nov. 1, 2002). "Comparison of Laser Speckle and Laser Doppler Perfusion Imaging: Measurement in Human Skin and Rabbit Articular Tissue," *Medical and Biological Engineering and Computing* 40(6):687-697.

Frangioni, J.V. (Oct. 2003). "In Vivo Near-Infrared Fluorescence Imaging," *Current Opinion in Chemical Biology* 7(5):626-634.

Frenzel H. et al. (Apr. 18, 2008). "In Vivo Perfusion Analysis of Normal and Dysplastic Ears and its Implication on Total Auricular Reconstruction," *Journal of Plastic, Reconstructive and Aesthetic Surgery* 61(Supplement1):S21-S28.

Fritzsch, B. et al. (Aug. 1991)."Sequential Double Labeling With Different Fluorescent Dyes Coupled to Dextran Amines as a Tool to Estimate the Accuracy of Tracer Application and of Regeneration," *Journal of Neuroscience Methods* 39(1):9-17.

Gagnon, A.R. et al. (2006). "Deep and Superficial Inferior Epigastric Artery Perforator Flaps," *Cirugia Plástica Ibero-Latinoamericana* 32(4):7-13.

Gardner, T.J. (1993). "Coronary Artery Disease and Ventricular Aneurysms," in *Surgery, Scientific Principles and Practice,* Greenfield, L.J. (ed.) et al., J.B. Lippincott Co., Philadelphia, PA, pp. 1391-1411, twenty three pages.

Garrett, W.T. et al. (Jul. 8, 1991). "Fluoro-Gold's Toxicity makes it Inferior to True Blue for Long-Term Studies of Dorsal Root Ganglion Neurons and Motoneurons," *Neuroscience Letters* 128(1):137-139.

Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal of Physical Chemistry A* 107(18):3443-3449.

Gipponi, M. et al. (Mar. 1, 2004). "New Fields of Application of the Sentinel Lymph Node Biopsy in the Pathologic Staging of Solid Neoplasms: Review of Literature and Surgical Perspectives," *Journal of Surgical Oncology* 85(3):171-179.

Giunta, R.E. et al. (Jul. 2005). "Prediction of Flap Necrosis with Laser Induced Indocyanine Green Fluorescence in a Rat Model," *British Journal of Plastic Surgery* 58(5):695-701.

Giunta, R.E. et al. (Jun. 2000). "The Value of Preoperative Doppler Sonography for Planning Free Perforator Flaps," *Plastic and Reconstructive Surgery* 105(7):2381-2386.

Glossary, Nature, downloaded from the internet <http://www.nature.com/nrg/journal/v4/nl0/glossary/nrgl 183_glossary.html>> HTML on Jun. 30, 2014, three pages.

Glover, J.C. et al. (Nov. 1986). "Fluorescent Dextran-Amines Used as Axonal Tracers in the Nervous System of the Chicken Embryo," *Journal of Neuroscience Methods* 18(3):243-254.

Goldstein, J.A. et al. (Dec. 1998). "Intraoperative Angiography to Assess Graft Patency After Minimally Invasive Coronary Bypass," *Ann. Thorac. Surg.* 66(6):1978-1982.

Gothoskar A.V. (Mar. 2004). "Resealed Erythrocytes: A Review," *Pharmaceutical Technology* pp. 140, 142, 144, 146, 148, 150, 152 and 154-158, twelve pages.

Granzow, J.W. et al. (Jul. 2007)."Breast Reconstruction with Perforator Flaps" *Plastic and Reconstructive Surgery* 120(1):1-12.

Green, H.A. et al. (Jan. 1992). "Burn Depth Estimation Using Indocyanine Green Fluorescence," *Arch Dermatol* 128(1):43-49.

Haglund, M. et al. (Feb. 1996). "Enhanced Optical Imaging of Human Gliomas and Tumor Margins," *Neurosurgery* 38(2):308-317.

Haglund, M.M. et al. (Nov. 1994). "Enhanced Optical Imaging of Rat Gliomas and Tumor Margins," *Neurosurgery* 35(5):930-941.

Hallock, G.G. (Jul. 2003). "Doppler Sonography and Color Duplex Imaging for Planning a Perforator Flap," *Clinics in Plastic Surgery* 30(3):347-357.

Hamamatsu Brochure. (May 1997). Specifications for Real-time Microscope Image Processing System: ARGUS-20 with C2400-75i, four pages.

Hamamatsu. (Date unknown). Microscope Video Camera, for Fluorescent Observation, Easy Fluorescent Image Analysis C2400-73I, -75I Series a CCD Camera, seven pages.

Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.

(56) References Cited

OTHER PUBLICATIONS

Hayata, Y. et al. (Jul. 1982). "Fiberoptic Bronchoscopic Laser Photoradiation for Tumor Localization in Lung Cancer," *Chest* 82(1):10-14.
He, Z. (Feb. 2009). "Fluorogold Induces Persistent Neurological Deficits and Circling Behavior in Mice Over-Expressing Human Mutant Tau," *Current Neurovascular Research* 6(1):54-61.
Herts, B.R. (May 2003). "Imaging for Renal Tumors," *Current Opin.. Urol.* 13(3):181-186.
Hirano, T. et al. (1989). "Photodynamic Cancer Diagnosis and Treatment System Consisting of Pulse Lasers and an Endoscopic Spectro-Image Analyzer," *Laser in Life Sciences* 3(2):99-116.
Holm, C. et al. (2002). "Monitoring Free Flaps Using Laser-Induced Fluorescence of Indocyanine Green: A Preliminary Experience," *Microsurgery* 22(7):278-287.
Holm, C. et al. (Apr. 2003, e-published on Feb. 25, 2003). "Laser-Induced Fluorescence of Indocyanine Green: Plastic Surgical Applications," *European Journal of Plastic Surgery* 26(1):19-25.
Holm, C. et al. (Dec. 1, 2002). "Intraoperative Evaluation of Skin-Flap Viability Using Laser-Induced Fluorescence of Indocyanine Green," *British Journal of Plastic Surgery* 55(8):635-644.
Humblet, V. et al. (Oct. 2005). "High-Affinity Near-Infrared Fluorescent Small-Molecule Contrast Agents for In Vivo Imaging of Prostate-Specific Membrane Antigen," *Molecular Imaging* 4(4):448-462.
Hung, J. J et al.(1991). "Autofluorescence of Normal and Malignant Bronchial Tissue," *Lasers in Surgery and Medicine* 11(2):99-105.
Hyvärinen, L. et al. (1980). "Indocyanine Green Fluorescence Angiography." *Acta ophthalmologica* 58(4):528-538.
Ikeda, S. (Jul. 1989). "Bronichial Telivision Endoscopy," *Chest* 96(1):41S-42S.
Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.
Jagoe, J.R. et al. (1989). "Quantification of retinal damage during cardiopulmonary bypass," Third International Conference on Image Processing and its Applications (Conf. Publ. No. 307), IEE, pp. 319-323.
Jamis-Dow, C.A. et al. (Mar. 1996). "Small (< or = 3-cm) Renal Masses: Detection with CT versus US and Pathologic Correlation," *Radiology* 198(3):785-788.
Jolion, J. et al. (Aug. 1991). "Robust Clustering with Applications in Computer Vision," *IEEE Transactions on Pattern Analysis and Machine Intelligence* 13(8):791-802.
Kamolz, L.-P. et al. (Dec. 2003). "Indocyanine Green Video Angiographies Help to Identify Burns Requiring Operation," *Burns* 29(8):785-791.
Kapadia, C. R. et al. (Jul. 1990). "Laser-Induced Fluorescence Spectroscopy of Human Colonic Mucosa. Detection of Adenomatous Transformation," *Gastroenterology* 99(1):150-157.
Kato, H. et al. (Jun. 1985). "Early Detection of Lung Cancer by Means of Hematoporphyrin Derivative Fluorescence and Laser Photoradiation," *Clinics in Chest Medicine* 6(2):237-253.
Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.
Keon, W.J. et al. (Dec. 1979). "Coronary Endarterectomy: an Adjunct to Coronary Artery Bypass Grafting," *Surgery* 86(6):859-867.
Kim, S. et al. (Jan. 2004, e-published Dec. 7, 2003). "Near-Infrared Fluorescent Type II Quantum Dots for Sentinel Lymph Node Mapping," *Nature Biotechnology* 22(1):93-97.
Kiryu, J. et al. (Sep. 1994). "Noninvasive Visualization of the Choriocapillaris and its Dynamic Filling," *Investigative Ophthalmology & Visual Science* 35(10):3724-3731.
Kitai, T. et al. (Jul. 2005). "Fluorescence Navigation with Indocyanine Green for Detecting Sentinel Lymph Nodes in Breast Cancer," *Breast Cancer* 12(3):211-215.

Kleszcyńska, H. et al. (Mar. 2005). "Hemolysis of Erythrocytes and Erythrocyte Membrane Fluidity Changes by New Lysosomotropic Compounds," *Journal of Fluorescence* 15(2):137-141.
Köbbert, C. et al. (Nov. 2000). "Current Concepts in Neuroanatomical Tracing," *Progress in Neurobiology* 62(4):327-351.
Kokaji, K. et al. (Date Unknown). "Intraoperative Quality Assessment by Using Fluorescent Imaging in Off-pump Coronary Artery Bypass Grafting," *The Department of Cardiovascular Surgery*, University of Keio, Tokyo, Japan, one page (Abstract only).
Kömürcü, F. et al. (Feb. 2005). "Management Strategies for Peripheral Iatrogenic Nerve Lesions," *Annals of Plastic Surgery* 54(2):135-139.
Krishnan, K. G. et al. (Apr. 1, 2005). "The Role of Near-Infrared Angiography in the Assessment of Post-Operative Venous Congestion in Random Pattern, Pedicled Island and Free Flaps", *British Journal of Plastic Surgery* 58(3):330-338.
Kuipers, J.A. et al. (1999). "Recirculatory and Compartmental Pharmacokinetic Modeling of Alfentanil Pigs, the Influence of Cardiac Output," *Anesthesiology* 90(4)1146-1157.
Kupriyanov, V.V. et al. (Nov. 2004; , e-publication Sep. 28, 2004). "Mapping Regional Oxygenation and Flow in Pig Hearts In Vivo Using Near-infrared Spectroscopic Imaging," *Journal of Molecular and Cellular Cardiology* 37(5):947-957.
Kurihara, K. et al. (Jun. 1984). "Nerve Staining with Leucomethylene Blue: An Experimental Study," Plastic and Reconstruction Surgery 73(6):960-964.
Kyo, S. (Date Unknown). "Use of Ultrasound Cardiology during Coronary Artery Bypass Surgery," *Heart and Blood Vessel Imaging II*, three pages.
Lam, S. et al. (1991). "Mechanism of Detection of Early Lung Cancer by Ratio Fluorometry," *Lasers in Life Sciences* 4(2):67-73.
Lam, S. et al. (Feb. 1990). "Detection of Early Lung Cancer Using Low Dose Photofrin II," *Chest* 97(2):333-337.
Lam, S. et al. (Jul. 1, 1990). "Detection of Lung Cancer by Ratio Fluorometry With and Without Photofrin II," *Proc. SPIE—Optical Fibers in Medicine V* 1201:561-568.
Lam, S. et al. (Nov. 1-4, 1990). "Fluorescence Imaging of Early Lung Cancer," *Annual International Conference of the IEEE Engineering in Medicine and Biology Society* 12(3):1142-1143.
Lam, S.C. et al. (1993). "Fluorescence Detection," Chapter 20 in *Lung Cancer*, Roth, J.A. (ed.), et al., Blackwell Scientific Publications Inc., 238 Main Street, Cambridge, Massachusetts, 02142, pp. 325-338, sixteen pages.
Lanciego, J.L. et al. (Jun. 1998). "Multiple Neuroanatomical Tracing in Primates," *Brain Research Protocols* 2(4):323-332.
Lanciego, J.L. et al. (Oct. 1998). "Multiple Axonal Tracing: Simultaneous Detection of Three Tracers in the Same Section," *Histochemistry and Cell Biology* 110(5):509-515.
Laub, G.W. et al.(Nov. /Dec. 1989). "Experimental Use of Fluorescein for Visualization of Coronary Arteries," *Vascular and Endovascular Surgery* 23(6):454-457.
Lee, E.T. et al. (Mar. 1997). "A New Method for Assessment of Changes in Retinal Blood Flow," *Medical Engineering & Physics* 19(2):125-130.
Leissner, J. et al. (Jan. 2004). "Extended Radical Lymphadenectomy in Patients with Urothelial Bladder Cancer: Results of a Prospective Multicenter Study," *The Journal of Urology* 171(1):139-144.
Leithner, C. (Jul. 14, 2003). "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/d issertationen/leith nerch ristoph-2003-07-14/>, two hundred and eight pages, (English Abstract and Machine Translation).
Liedberg, F. et al. (2003). "Sentinel-Node-Diagnostik Beim Invasiven (Bladder Cancer and the Sentinel Node Concept)," *Aktuel Urol.* 34:115-118, (English Abstract Only).
Liedberg, F. et al. (Jan. 2006). "Intraoperative Sentinel Node Detection Improves Nodal Staging in Invasive Bladder Cancer," *The Journal of Urology* 175(1):84-89.
Lippincott's New Medical Dictionary. "Perfusion," p. 707 (1897), three pages.

(56) References Cited

OTHER PUBLICATIONS

Liptay, M.J. (Mar. 2004). "Sentinel Node Mapping in Lung Cancer," *Annals of Surgical Oncology* 11(Supplement 3):271S-274S.

Little, J.R. et al. (May 1979). "Superficial Temporal Artery to Middle Cerebral Artery Anastomosis: Intraoperative Evaluation by Fluorescein Angiography and Xenon-133 Clearance," *Journal of Neurosurgery* 50(5):560-569.

Liu, Q.P. et al. (Apr. 2007). "Bacterial Glycosidases for the Production of Universal Red Blood Cells" *Nature Biotechnology* 25(7):454-464.

Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.

Mack, M.J. et al. (Sep. 1998). "Arterial Graft Patency in Coronary Artery Bypass Grafting: What Do We Really Know?," *Ann. Thorac. Surg.* 66(3):1055-1059.

Magnani, M. et al. (1998). "Erythrocyte Engineering for Drug Delivery and Targeting," *Biotechnol. Appl. Biochem.* 28:1-6.

Magnani, M. et al. (Jul. 15, 1992). "Targeting Antiretroviral Nucleoside Analogues in Phosphorylated Form to Macrophasges: In Vitro and In Vivo Studies," *Proc. Natl. Acad. Sci. USA* 89(14):6477-6481.

Malmstrom et al. (Nov. 2002). "Early Metastatic Progression of Bladder Carcinoma: Molecular Profile of Primary Tumor and Sentinel Lymph Node," *The Journal of Urology* 168(5):2240-2244.

Malmström, P.U. et al. (Jul. 2004). "RE: Extended Radical Lymphadenectomy in Patients With Urothelial Bladder Cancer: Results of a Prospective Multicenter Study," *J. of Urol.* 172(1):386, one page.

Marangos, N. et al. (Dec. 2001). "In Vivo Visualization of the Cochlear Nerve and Nuclei with Fluorescent Axonal Tracers," *Hearing Research* 162(1-2):48-52.

Martinez-Pérez, M. et al. (Sep. 19, 1996). "Unsupervised Segmentation Based on Robust Estimation and Cooccurrence Data," *Proceedings of the International Conference on Miage Processing (ICIP) Lausanne* 3:943-945.

May, S. (May/Jun. 1995). "Photonic Approaches to Burn Diagnostics," *Biophotonics International* pp. 44-50.

McKee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.

Merriam Webster Medline Plus Medical Dictionary. "Perfusion," located at http://www.merriam-webster.com/medlineplus/perfusion, last visited on Apr. 15, 2015, one page.

Minciacchi, D. et al. (Jul. 1991). "A Procedure for the Simultaneous Visualization of Two Anterograde and Different Retrograde Fluorescent Tracers—Application to the Study of the Afferent-Efferent Organization of Thalamic Anterior Intralaminar Nuclei" *Journal of Neuroscience Methods* 38(2-3):183-191.

Mitaka USA, Inc. (2015). "PDE Breast Free Flap Evaluation," located at <http://mitakausa.com/category/pde_education/flaps/>, last visited on Oct. 7, 2016, four pages.

Mitaka USA, Inc. (2015). "PDE-Neo" located at <http://mitakausa.com/pde-neo/>, last visited on Oct. 7, 2016, two pages.

Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.

Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.

Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-1024.

Motomura, K. et al. (1999). "Sentinel Node Biopsy Guided by Indocyanine Green Dye in Breast Cancer Patients," *Japan J. Clin. Oncol.* 29(12):604-607.

Mullooly, V.M. et al. (1990). "Dihematoporphyrin Ether-Induced Photosensitivity in Laryngeal Papilloma Patients," *Lasers in Surgery and Medicine* 10(4):349-356.

Murphy (2001). "Digital CCD Microscopy," Chapter 14 in *Fundamentals of Light Microscopy and Electronic lmaaing*, John Wiley and Sons, pp. i-xi and 259-281.

Nahlieli, O. et al. (Mar. 2001). "Intravital Staining with Methylene Blue as an Aid to Facial Nerve Identification in Parotid Gland Surgery" J. Oral Maxillofac. Surgery 59(3):355-356.

Nakamura, T. et al. (1964). "Use of Novel Dyes, Coomassie Blue and Indocyanine Green in Dye Dilution Method," Tohoka University, Nakamura Internal Department, the Tuberculosis Prevention Society, Tuberculosis Research Laboratory, 17(2):1361-1366, seventeen pages.

Nakayama, A. et al. (Oct. 2002). "Functional Near-Infrared Fluorescence Imaging for Cardiac Surgery and Targeted Gene Therapy," *Molecular Imaging* 1(4):365-377.

Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," *Journal of Neuroscience Methods* 103 (1):11-21.

Newman et al. (Oct. 31, 2008). "Update on the Application of Laser-Assisted Indocyanine Green Fluorescent Dye Angiography in Microsurgical Breast Reconstruction," American Society of Plastic Surgeons, Plastic Surgery 2008, 2 pp.

Nimura, H. et al. (May 2004, e-published on Mar. 22, 2004). "Infrared Ray Electronic Endoscopy Combined with Indocyanine Green Injection for Detection of Sentinel Nodes of Patients with Gastric Cancer," *British Journal of Surgery* 91(5):575-579.

Novadaq Technologies Inc. (Jan. 29, 2007). "Novadaq Imaging System Receives FDA Clearance for use During Plastic Reconstructive Surgery," *PR Newswire* three pages.

Novadaq Technologies Inc. (Jan. 19, 2005). 510(k) Summary-Showing X-Ray Fluoroscopy as Predicate Device, Fluorescent Angiographic System, six pages.

Oddi, A. et al. (Jun. 1996). "Intraoperative Biliary Tree Imaging with Cholyl-Lysyl-Fluorescein: An Experimental Study in the Rabbit" *Surgical Laparoscopy & Endoscopy* 6(3):198-200.

Ogata, F. et al. (Jun. 2007). "Novel Lymphography Using Indocyanine Green Dye for Near-Infrared Fluorescence Labeling," *Annals of Plastic Surgery* 58(6):652-655.

Ohnishi, S. et al. (Jul.-Sep. 2005). "Organic Alternatives to Quantum Dots for Intraoperative Near-Infrared Fluorescent Lymph Node Mapping" *Molecular Imaging* 4(3):172-181.

Ooyama, M. (Oct. 12-15, 1994). The 8th Congress of International YAG Laser Symposium, The 15th Annual Meeting of Japan Society for Laser Medicine, Sun Royal Hotel, Japan, eight pages.

Ott, P. (1998). "Hepatic Elimination of Indocyanine Green with Special Reference to Distribution Kinetics and the Influence of Plasma Protein Binding," *Pharmacology & Toxicology* 83(Supp. II):5-48.

Oxford Concise Medical Dictionary. "Perfusion," p. 571 (1980), three pages.

Pagni, S. et al. (Jun. 1997). "Anastomotic Complications in Minimally Invasive Coronary Bypass Grafting," *Ann. Thorac. Surg.* 63(6 Suppl):S64-S67.

Palcic et al. (1991). "Lung Imaging Fluorescence Endoscope: A Device for Detection of Occult Lung Cancer," *Medical Design and Material*, thirteen pages.

Palcic, B. et al. (1990). "Development of a Lung Imaging Fluorescence Endoscope," *Annual International Conference of the IEEE Engineering in Medicine and Biology Society* 12(1):0196-0197.

Palcic, B. et al. (Aug. 1, 1990). "The Importance of Image Quality for Computing Texture Features in Biomedical Specimens," *Proc. SPIE* 1205:155-162.

Palcic, B. et al. (Jun. 1, 1991). "Lung Imaging Fluorescence Endoscope: Development and Experimental Prototype," *Proc. SPIE* 1448:113-117.

Palcic, B. et al. (Mar. 1991). "Detection and Localization of Early Lung Cancer by Imaging Techniques," *Chest* 99(3):742-743.

(56) References Cited

OTHER PUBLICATIONS

Pandharlpande, P.V. et al. (Mar. 2005). "Perfusion Imaging of the Liver: Current Challenges and Future Goals," *Radiology* 234(3):661-673.

Paques, M. et al. (Mar. 2003). "Axon-Tracing Properties of Indocyanine Green," *Arch Ophthalmol.* 121(3):367-370.

Parungo, C.P. et al. (Apr. 2005). "Intraoperative Identification of Esophageal Sentinel Lymph Nodes with Near-Infrared Fluorescence Imaging," *The Journal of Thoracic and Cardiovascular Surgery* 129(4):844-850.

Parungo, C.P. et al. (Dec. 2004, e-published on Nov. 15, 2004). "In Vivo Optical Imaging of Pleural Space Drainage to Lymph Nodes of Prognostic Significance," *Annals of Surgical Oncology* 11(12):1085-1092.

Peak, M.J. et al. (1986). "DNA-to-Protein Crosslinks and Backbone Breaks Caused by Far-and Near-Ultraviolet and Visible Light Radiations in Mammalian Cells," in *Mechanism of DNA Damage and Repair, Implications for Carcinogenesis and Risk Assessment*, Simic, M.G. (ed.). et al., Plenum Press, 233 Spring Street, New York, N.Y. 10013, pp. 193-202.

Peiretti et al. (2005). "Human erythrocyte-ghost-mediated choroidal angiography and photocoagulation." Database Biosis [online] Biosciences Information Service, Philadelphia, PA, US, XP002725023, Database accession No. Prev200600056121 (abstract), three pages.

Peiretti, E. et al. (May 2005). "Human Erythrocyte-Ghost-Mediated Choroidal Angiography and Photocoagulation," *Investigative Ophthalmology & Visual Science*, ARVO Annual Meeting Abstract 46(13):4282, located at <http://iovs.arvojournals.org/article.aspx?articleid=2403707>, last visited on Oct. 7, 2016, two pages.

Perez, M.T. et al. (Sep. 2002). "In Vivo Studies on Mouse Erythrocytes Linked to Transferrin," *IUBMB Life* 54(3):115-121.

Pfister, A.J. et al. (Dec. 1992). "Coronary Artery Bypass Without Cardiopulmonary Bypass," *Ann. Thorac. Surg.* 54(6):1085-1092, (Discussion by S.R. Gundry).

Phillips, R.P. et al. (1991). "Quantification of Diabetic Maculopathy by Digital Imaging of the Fundus," *Eye* 5(1):130-137.

Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.

Profio, A.E. et al. (Jul.-Aug. 1984). "Fluorometer for Endoscopic Diagnosis of Tumors," *Medical Physics* 11(4):516-520.

Profio, A.E. et al. (Jun. 1, 1991). "Endoscopic Fluorescence Detection of Early Lung Cancer," *Proc. SPIE* 1426:44-46.

Profio, A.E. et al. (Nov./Dec. 1979). "Laser Fluorescence Bronchoscope for Localization of Occult Lung Tumors," *Medical Physics* 6:523-525.

Profio, A.E. et al. (Sep.-Oct. 1986). "Digital Background Subtraction for Fluorescence Imaging," *Medical Physics* 13(5):717-721.

Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," *Journal of Neuroscience Methods* 115(2):115-127.

Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.

Raabe et al. (2009, e-published on Nov. 12, 2008). "Laser Doppler Imaging for Intraoperative Human Brain Mapping", *NeuroImage* 44:1284-1289.

Raabe, A. et al. (Jan. 2003). "Near-Infrared Indocyanine Green Video Angiography: A New Method for Intraoperative Assessment of Vascular Flow," *Neurosurgery* 52(1):132-139.

Rava, R.P. et al. (Jun. 1, 1991). "Early Detection of Dysplasia in Colon and Bladder Tissue Using Laser-Induced Fluorescence," *Proc. SPIE* 1426:68-78.

Razum, N. et al. (Nov. 1987). "Skin Photosensitivity: Duration and Intensity Following Intravenous Hematoporphyrin Derivatives, HpD and DHE," *Photochemistry and Photobiology* 46(5):925-928.

Report on Observation by C2400-75i and ARGUS20 Under Low illumination conditions, Jan. 17, 2008, six pages.

Request for Invalidation dated Jun. 29, 2007 for Japanese Patent No. JP-3881550, filed by Hamamatsu Photonics, Inc., eighty five pages, (with English Translation).

Reuthebuch, O et al. (Feb. 2004). "Novadaq SPY: Intraoperative Quality Assessment in Off Pump Coronary Artery Bypass Grafting," *Chest* 125(2):418-424.

Reuthebuch, O.T. et al. (May 2003). "Graft Occlusion After Deployment of the Symmetry Bypass System," *Ann. Thorac. Surg.* 75(5):1626-1629.

Richards-Kortum, R. et al. (Jun. 1991). "Spectroscopic Diagnosis of Colonic Dysplasia: Spectroscopic Analysis," *Biochemistry and Photobiology* 53(6):777-786.

Roberts, W.W. et al. (Dec. 1997). "Laparoscopic Infrared Imaging," *Surg. Endoscopy* 11(12):1221-1223.

Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.

Ropars, C. (ed.) et al. (1987). *Red Blood Cells as Carriers for Drugs. Potential therapeutic. Applications*, Pergamon Press, Oxford, New York, pp. v-vii, (Table of Contents only), four pages.

Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.

Ross, G.L. et al. (Jul. 2004, e-published on Jun. 14, 2000). "Sentinel Node Biopsy in Head and Neck Cancer: Preliminary Results of a Multicenter Trial," *Annals of Surgical Oncology* 11(7):690-696.

Rossi, L. et al. (2001). "Erthrocyte-Mediated Delivery of Dexamethasone in Patients with Chronic Obstructive Pulmonary Disease," *BiotechnoL AppL Biochem.* 33:85-89.

Rossi, L. et al. (1999). "Heterodimer-Loaded Erthrocytes as Bioreactors for Slow Delivery of the Antiviral Drug Azidothymidine and the Antimycobacterial Drug Ethambutol," *Aids Research and Human Retroviruses* 15(4):345-353.

Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.

Rozen, W.M. et al. (Jan. 2008). "Preoperative Imaging for DIEA Perforator Flaps: A Comparative Study of Computed Tomographic Angiography and Doppler Ultrasound," *Plastic and Reconstructive Surgery* 121(1):9-16.

Rübben, A. et al. (Mar. 1994). "Infrared Videoangiofluorography of the Skin with Indocyanine Green—Rat Random Cutaneous Flap Model and Results in Man," *Microvascular Research* 47(2):240-251.

Rubens, F.D. et al. (2002). "A New and Simplified Method for Coronary and Graft Imaging During CABG," *The Heart Surgery Forum* 5(2):141-144.

Sakatani, K. et al. (Nov. 1997). "Noninvasive Optical Imaging of the Subarchnoid Space and Cerebrospinal Fluid Pathways Based on Near Infrared Fluorescence," *J. Neurosurg.* 87(5):738-745.

Salmon, E.D. et al. (Oct. 1994). "High Resolution Multimode Digital Imaging System for Mitosis Studies In Vivo and In Vitro," *Biol. Bull* 187(2):231-232.

Sato, M. et al., (1991). "Development of a Visualization Method for the Microcirculation of Deep Viscera Using an Infrared Intravital Microscope System," *Research on ME Devices and ME Technology,* five pages, (with English Translation).

Satpathy G.R. et al. (Oct. 2004; , e-publication Aug. 7, 2004). "Loading Red Blood Cells with Trehalose: A Step Towards Biostabilization," *Cryobiology* 49(2):123-136.

Schaff, H.V. et al. (Oct. 15, 1996). "Minimal Thoracotomy for Coronary Artery Bypass: Value of Immediate Postprocedure Graft Angiography," *Supplement to Circulation* 94(8):I-51, (Abstract No. 0289), two pages.

Schellingerhout, D. et al. (Oct. 2000). "Quantitation of Hsv Mass Distribution in a Rodent Brain Tumor Model," *Gene Therapy* 7(19):1648-1655.

(56) References Cited

OTHER PUBLICATIONS

Schmued, L. et al. (Aug. 27, 1990). "In Vivo Anterograde and Retrograde Axonal Transport of the Fluorescent Rhodamine-Dextran-Amine, Fluoro-Ruby, Within the CNS," *Brain Research* 526(1):127-134.

Schmued, L.C. et al. (Oct. 29, 1993). "Intracranial Injection of Fluoro-Gold Results in the Degeneration of Local but not Retrogradely Labeled Neurons," *Brain Research* 626(1-2):71-77.

Schneider Jr., H.C. et al. (Jan. 1975). "Fluorescence of Testicle, An Indication of Viability of Spermatic Cord After Torsion," *Urology* V(1):133-136.

Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.

Sekijima, M. et al. (Sep. 2004). "An Intraoperative Fluorescent Imaging System in Organ Transplantation," *Transplantation Proceedings* 36(7):2188-2190.

Serov, A. et al. (Mar. 1, 2002). "Laser Doppler Perfusion Imaging with a Complimentary Metal Oxide Semiconductor Image Sensor," *Optics Letters* 27(5):300-302.

Serov, A.N. et al. (Sep. 23, 2003). "Quasi-Parallel Laser Doppler Perfusion Imaging Using a CMOS Image Sensor," *Proc. SPIE* 5067:73-84.

Sezgin, M. et al. (Jan. 2004). "Survey Over Image Thresholding Techniques and Quantitative Performance Evaluation," *Journal of Electronic Imaging* 13(1):146-165.

Sherif, A. et al. (Sep. 2001). "Lymphatic Mapping and Detection of Sentinel Nodes in Patients with Bladder Cancer," *The Journal of Urology* 166(3):812-815.

Sheth, S.A. et al. (Apr. 22, 2004). "Linear and Nonlinear Relationships between Neuronal Activity, Oxygen Metabolism, and Hemodynamic Responses," *Neuron* 42(2):347-355.

Shoaib, T. et al. (Jun. 1, 2001). "The Accuracy of Head and Neck Carcinoma Sentinel Lymph Node Biopsy in the Clinically No Neck," *Cancer* 91(11):2077-2083.

Siemers, B.M. et al. (Nov. 2001). "The Acoustic Advantage of Hunting at Low Heights Above Water: Behaviorual Experiments on the European 'Trawling' Bats *Myotis capaccinii, M Dasycneme* and *M. Daubentonii,*" *J. Experimental Biol.* 204(Pt. 22):3843-3854.

Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.

Slakter, J.S. et al. (Jun. 1995). "Indocyanine-Green Angiography," *Current Opinion in Ophthalmology* 6(III):25-32.

Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.

Soltesz, E.G. et al. (Jan. 2005). "Intraoperative Sentinel Lymph Node Mapping of the Lung Using Near-Infrared Fluorescent Quantum Dots," *Ann. Thorac. Surg.* 79(1):269-277.

Sony Corporation. The Sony U-Matic Videocassette Recorder, VO-9800, ten pages.

Staurenghi, G. et al. (Dec. 2001)."Combining Photodynamic Therapy and Feeder Vessel Photocoagulation: A Pilot Study," *Seminars in Ophthalmology* 16(4):233-236.

Stern, M.D. (Mar. 6, 1975). "In Vivo Evaluation of Microcirculation by Coherent Light Scattering," *Nature* 254(5495):56-58.

Still, J. et al. (Mar. 1999). "Evaluation of the Circulation of Reconstructive Flaps Using Laser-Induced Fluorescence of Indocyanine Green," *Ann. Plast. Surg.* 42(3):266-274.

Still, J.M. et al. (Jun. 2001). "Diagnosis of Burn Depth Using Laser-Induced Indocyanine Green Fluorescence: A Preliminary Clinical Trial," *Burns* 27(4):364-371.

Stoeckli, S.J. et al. (Sep. 2001). "Sentinel Lymph Node Evaluation in Squamous Cell Carcinoma of the Head and Neck," *Otolaryngol Head Neck Surg.* 125(3):221-226.

Subramanian, V.A. et al. (Oct. 15, 1995). "Minimally Invasive Coronary Bypass Surgery: A Multi-Center Report of Preliminary Clinical Experience," *Supplement to Circulation* 92(8):I645, (Abstract No. 3093), two pages.

Sugi, K. et al. (Jan. 2003). "Comparison of Three Tracers for Detecting Sentinel Lymph Nodes in Patients with Clinical N0 Lung Cancer," *Lung Cancer* 39(1):37-40.

Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.

Suma, H. et al. (2000). "Coronary Artery Bypass Grafting Without Cardiopulmonary Bypass in 200 Patients," *J. Cardiol.* 36(2):85-90, (English Abstract only).

Summary of Invention Submitted to EPO, "Development of Novadaq SPY™ Cardiac Imaging Invention," five pages.

Taggart, D.P. et al. (Mar. 2003). "Preliminary Experiences with a Novel Intraoperative Fluorescence Imaging Technique to Evaluate the Patency of Bypass Grafts in Total Arterial Revascularization," *Ann Thorac Surg.* 75(3):870-873.

Taichman, G.C. et al. (Jun. 1987). "The Use of Cardio-Green for Intraoperative Visualization of the Coronary Circulation: Evaluation of Myocardial Toxicity," *Texas Heart Institute Journal* 14(2):133-138.

Takahashi, M. et al. (Sep. 2004). "SPY™: An Innovative Intra-Operative Imaging System to Evaluate Graft Patency During Off-Pump Coronary Artery Bypass Grafting," *Interactive Cardio Vascular and Thoracic Surgery* 3(3):479-483.

Takayama, T. et al. (Apr. 1992). "Intraoperative Coronary Angiography Using Fluorescein Basic Studies and Clinical Application," *Vascular and Endovascular Surgery* 26(3):193-199.

Takayama, T. et al. (Jan. 1991). "Intraoperative Coronary Angiography Using Fluorescein" *The Annals of Thoracic Surgery* 51(1):140-143.

Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.

Tang, G.C. et al. (1989). "Spectroscopic Differences between Human Cancer and Normal Lung and Breast Tissues," *Lasers in Surgery and Medicine* 9(3):290-295.

Taylor, K.M. (Apr. 1998). "Brain Damage During Cardiopulmonary Bypass," *Annals of Thoracic Surgery* 65(4):S20-S26.

The American Heritage Medical Dictionary. "Perfuse." p. 401 (2008), three pages.

Thelwall, P.E. et al. (Oct. 2002). "Human Erythrocyte Ghosts: Exploring the Origins of Multiexponential Water Diffusion in a Model Biological Tissue with Magnetic Resonance," *Magnetic Resonance in Medicine* 48(4):649-657.

Torok, B. et al. (May 1996). "Simultaneous Digital Indocyanine Green and Fluorescein Angiography," *Klinische Monatsblatter Fur Augenheilkunde* 208(5):333-336, (Abstract only), two pages.

Tsutsumi, D. et al. "Moisture Detection of road surface using infrared camera," Reports of the Hokkaido Industrial Research Institute (No. 297), Issued on Nov. 30, 1998, two pages.

Tubbs, R.S. et al. (Apr. 2005). "Anatomic Landmarks for Nerves of the Neck: A Vade Mecum for Neurosurgeons," *Neurosurgery* 56(2 Suppl.):ONS256-ONS260.

Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.

Uren, R.F. (Jan. 2004). "Cancer Surgery Joins the Dots," *Nature Biotechnology* 22(1):38-39.

Valero-Cabré, A. et al. (Jan. 15, 2001). "Superior Muscle Reinnervation after Autologous Nerve Graft or Poly-L-Lactide-ϵ-Caprolactone (PLC) Tube Implantation in Comparison to Silicone Tube Repair," *Journal of Neuroscience Research* 63(2):214-223.

Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.

(56) References Cited

OTHER PUBLICATIONS

Verbeek, X. et al. (2001). "High-Resolution Functional Imaging With Ultrasound Contrast Agents Based on Rf Processing in an In Vivo Kidney Experiment", *Ultrasound in Med. & Biol.* 27(2):223-233.
Wachi, A. et al. (Apr. 1995). "Characteristics of Cerebrospinal Fluid Circulation in Infants as Detected With MR Velocity Imaging," *Child's Nerv Syst* 11(4):227-230.
Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.
Weinbeer, M. et al. (Nov. 25, 2013). "Behavioral Flexibility of the Trawling Long-Legged Bat, *Macrophyllum macrophyllum* (Phyllostomidae)," *Frontiers in Physiology* 4(Article 342):1-11.
What is Perfusion? A Summary of Different Typed of Perfusion. (Sep. 1, 2004). Located at, <http://www.perfusion.com/cgi-bin/absolutenm/templates/articledisplay.asp?articleid=1548#.Vo8Hv02FPGj>, last visited on Jan. 7, 2016, two pages.
Wise, R.G. et al. (Nov. 2005). "Simultaneous Measurement of Blood and Myocardial Velocity in the Rat Heart by Phase Contrast MRI Using Sparse q-Space Sampling" *Journal of Magnetic Resonance Imaging* 22(5):614-627.
Woitzik, J. et al. (Apr. 2005). "Intraoperative Control of Extracranial-Intracranial Bypass Patency by Near-Infrared Indocyanine Green Videoangiography," *J. Neurosurg.* 102(4):692-698.
Wollert, H.G. et al. (Dec. 1989). "Intraoperative Visualization of Coronary Artery Fistula Using Medical Dye," *The Thoracic and Cardiovascular Surg.* 46(6):382-383.
Wu, C. et al. (Apr. 15, 2005). "cGMP (Guanosine 3',5'-Cyclic Monophosphate) Transport Across Human Erythrocyte Membranes," *Biochemical Pharmacology* 69(8):1257-1262.
Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.
Yamaguchi, S. et al. (Apr. 2005). "Evaluation of Skin Perfusion After Nipple-Sparing Mastectomy by Indocyanine Green Dye" *Journal of Saitama Medical University,* Japan, 32(2):45-50, (with English Abstract).
Yoneya, S. et al. (Jun. 1998). "Binding Properties of Indocyanine Green in Human Blood," *IOVS* 39(7):1286-1290.
Yoneya, S. et al. (Sep. 1993). "Improved Visualization of the Choroidal Circulation with Indocyanine Green Angiography," *Arch Opthalmol.* 111(9):1165-1166.
Young. I.T. et al. (1993). "Depth of Focus in Microscopy," SCIA '93, Proc. of the 8th Scandinavian Conference on Image Analysis, Tromso, Norway, pp. 493-498, six pages.
Australian Examination Report No. 1 dated Jun. 26, 2018 for Australian Patent Application No. 2014408488, filed on Mar. 31, 2017, nine pages.
Australian Notice of Allowance dated Sep. 17, 2018 for Australian Patent Application No. 2015327665, filed on Mar. 23, 2017, three pages.
Canadian Notice of Allowance dated Jan. 4, 2018 for Canadian Application No. 2,750,760, filed on Jul. 25, 2008, one page.
Canadian Notice of Allowance dated Sep. 27, 2017 for Canadian Application No. 2,811,847, filed on Mar. 20, 2013, one page.
Canadian Office Action dated Feb. 27, 2017 for Canadian Application No. 2,750,760, filed on Jul. 25, 2011, three pages.
Canadian Office Action dated Dec. 12, 2018 for CA Application No. 2,963,987 filed on Mar. 27, 2017, four pages.
Canadian Office Action dated Dec. 28, 2018 for CA Application No. 2,963,450 filed on Apr. 3, 2017, four pages.
Canadian Office Action dated Feb. 13, 2018 for CA Application No. 2,963,450 filed on Apr. 3, 2017, three pages.
Canadian Office Action dated Feb. 28, 2018 for CA Application No. 2,963,987 filed on Mar. 27, 2017, five pages.
Canadian Office Action dated Jan. 19, 2017 for Canadian Application No. 2,914,778 filed on Dec. 8, 2015, four pages.
Canadian Office Action dated Mar. 16, 2016 for CA Application No. 2,750,760 filed on Jan. 23, 2009, five pages.
Canadian Office Action dated Nov. 28, 2017 for Canadian Application No. 2,914,778 filed on Dec. 8, 2015, six pages.
Canadian Office Action dated Nov. 28, 2018 for CA Application No. 2,750,760 filed on Jan. 23, 2009, three pages.
Canadian Office Action dated Oct. 25, 2016 for Canadian Patent Application No. 2,811,847, filed on Sep. 20, 2011, three pages.
Canadian Office Action dated Sep. 30, 2015 for CA Application No. 2,811,847, filed on Sep. 20, 2011, four pages.
Chinese Fifth Office Action dated Dec. 19, 2017 for Chinese Application No. 201180057244.8 filed on Sep. 20, 2011, eleven pages.
Chinese First Office Action dated Apr. 6, 2017 for Chinese Application No. 201510214021.8, filed on May 14, 2009, fifteen pages.
Chinese Fourth Office Action dated Mar. 13, 2017 for Chinese Application No. 201180057244.8 filed on Sep. 20, 2011, twenty pages.
Chinese Office Action dated Jul. 3, 2012, issued in counterpart Chinese Application No. 200980123414.0, eight pages.
Chinese Office Action dated May 23, 2013, issued in counterpart Chinese Application No. 200980123414.0, nineteen pages.
Chinese Office Action dated Apr. 17, 2019 for Chinese Application No. 201510214021.8 filed on May 14, 2009, sixteen pages.
Chinese Office Action dated Nov. 12, 2015 for Chinese Patent Application No. 201180057244.8, filed on Sep. 20, 2010, five pages.
Chinese Second Office Action dated Feb. 8, 2018 for Chinese Application No. 201510214021.8, filed on May 14, 2009, seventeen pages.
Chinese Third Office Action dated Aug. 8, 2016 for Chinese Application No. 201180057244.8 filed on Sep. 20, 2011, eighteen pages.
Chinese Third Office Action dated Sep. 27, 2018 for Chinese Application No. 201510214021.8, filed on May 14, 2009, seventeen pages.
European Decision in Opposition Proceeding Revoking (dated Jun. 10, 2010). European Patent No. 1 143 852, thirty pages.
European Decision of European Patent Office Technical Board of Appeal Revoking Counterpart Patent No. 1143852, dated Oct. 23, 2013.
European Decision to Grant dated Apr. 21, 2017 for EP Application No. 09732993.2, filed on Nov. 8, 2010, two pages.
European Decision to Grant dated Mar. 15, 2018 for EP Application No. 09739980.2 filed on Nov. 30, 2010, two pages.
European Extended Search Report dated Apr. 28, 2014 for EP Application No. 09 732 993.2, filed on Apr. 14, 2008, eight pages.
European Extended Search Report dated Feb. 22, 2012 for EP Application No. 09 704 642.9, filed on Jan. 25, 2008, fifteen pages.
European Extended Search Report dated Jan. 28, 2014 for EP Application No. 11 826 475.3, filed on Sep. 20, 2010, six pages.
European Extended Search Report dated Jul. 16, 2018 for EP Application No. 15846111.1, filed on Apr. 25, 2017, thirteen pages.
European Extended Search Report dated Jun. 6, 2018 for EP Application No. 18166591.0 filed on Apr. 10, 2018, six pages.
European Extended Search Report dated May 23, 2018 for EP Application No. 14903635.2 filed on May 2, 2017, nine pages.
European Extended Search Report dated Oct. 14, 2015 for EP Application No. 13806313.6 filed on Jun. 20, 2013, nine pages.
European Extended Search Report dated Sep. 16, 2016 for EP Application No. 16183434.6 filed on Aug. 9, 2016, ten pages.
European Notice of Allowance dated Oct. 29, 2015 for EP Application No. 09 704 642.9, filed on Jan. 25, 2008, two pages.
European Office Action—Communication in pursuant to Article 94(3) EPC dated Mar. 9, 2016 for European Patent Application No. 09739980.2 filed May 1, 2009, five pages.
European Office Action—Communication Pursuant to Article 94(3) EPC dated Apr. 6, 2018 for EP Application No. 15188378.2 filed on Oct. 5, 2015, four pages.
European Office Action—Communication Pursuant to Article 94(3) EPC dated Aug. 31, 2017 for EP Application No. 09739980.2 filed on Nov. 30, 2010, four pages.

(56) References Cited

OTHER PUBLICATIONS

European Office Action—Communication pursuant to Article 94(3) dated May 27, 2016 for EP Application No. 15160177.0 filed on Aug. 11, 2000, five pages.
European Office Action—Communication Pursuant to Article 94(3) dated Sep. 21, 2017 for European Application No. 16163909.1 filed on Apr. 5, 2016, three pages.
European Office Action—Communication pursuant to Rules 70(2) and 70a(2) EPC dated May 15, 2014 in EP Application No. 09732993.2 , one page.
European Office Action—Communication pursuant to Rules 70(2) and 70a(2) EPC dated Nov. 14, 2016 in EP Application No. 16163909.1, two pages.
European Office Action—Communication Under Rule 71(3) EPC (Intention to Grant) dated Dec. 1, 2017 for European patent Application No. 09739980.2, filed on Nov. 30, 2010, seven pages.
European Office Action—Communication under Rule 71(3) EPC (Intention to Grant) dated Nov. 21, 2017 for European Patent Application No. 15160177.0, filed on Aug. 11, 2000, seven pages.
European Office Action dated Mar. 27, 2015 for EP Application No. 09 732 993.2, filed on Apr. 14, 2008, six pages.
European Office Action dated May 28, 2018 for EP Application No. 16183434.6 filed on Aug. 9, 2016, four pages.
European Opposition of European Patent No. EP1143852 lodged by Hamamatsu Photonics, Inc., Jul. 30, 2008.
European Partial Search Report dated Dec. 16, 2010 for European Application No. 10186218.3 filed on Aug. 11, 2000, seven pages.
European Partial Search Report dated Jan. 10, 2018 for Ep Application No. 17171383.7 filed on May 16, 2017, eleven pages.
European Partial Search Report dated Jun. 11, 2014 for European Application No. 13178642.8, filed on May 1, 2009, five pages.
European Partial Search Report dated Jun. 28, 2016 for European Application No. 16163909.1 filed on Apr. 5, 2016, six pages.
European Summons to attend the Oral Proceedings mailed on Oct. 24, 2018 for European Application No. 16163909.1 filed on Apr. 5, 2016, four pages.
European Summons to attend Oral Proceedings pursuant to Rule 115(1) EPC issued on Apr. 25, 2016 for European patent application No. 09732993.2, filed on Apr. 14, 2009, 5 pages.
European Summons to attend Oral Proceedings pursuant to Rule 115(1) EPC dated Dec. 16, 2016 for European patent application No. 15160177.0, filed on Aug. 11, 2000, seven pages.
European Supplemental Search Report dated Jul. 6, 2004 for EP Application No. 00955472.6 filed on Aug. 11, 2000, five pages.
Indian Examination Report dated Jan. 16, 2018 for Indian Application No. 2993/DELNP/2011, filed on Apr. 25, 2011, eleven pages.
Indian Examination Report dated Jul. 28, 2017 for Indian Application No. 1983/MUMNP/2007, filed on Nov. 27, 2007, seven pages.
Indian Examination Report dated Sep. 22, 2016 for Indian Application No. 7566/DELNP/2010, filed on Oct. 27, 2010, nine pages.
International Preliminary Examination Report completed on Jul. 1, 2001 for PCT/US00/22088, filed on Aug. 11, 2000, three pages.
International Preliminary Report on Patentability mailed Apr. 4, 2017 for PCT Application No. PCT/CA2015/050973 filed on Sep. 28, 2015, six pages.
International Search Report and the Written Opinion of the International Searching Authority, or the Declaration dated Apr. 3, 2008 for PCT/US07/77892, filed on Sep. 7, 2007, ten pages.
International Search Report and Written Opinion dated Jul. 29, 2009 for PCT/US2009/043975 filed on May 14, 2009, eleven pages.
International Search Report and Written Opinion dated Oct. 24, 2017 for PCT Application No. PCT/CA2017/050564 filed on May 10, 2017, fourteen pages.
International Search Report dated Dec. 3, 2015 for PCT Application No. PCT/CA2015/050973 filed on Sep. 28, 2015, three pages.
International Search Report dated Jul. 4, 2008 for PCT Patent Application No. PCT/US2007/080847, filed on Oct. 9, 2007, three pages.
International Search Report dated Dec. 3, 2009 for PCT Patent Application No. PCT/IB2009/005700, filed on Apr. 14, 2009, three pages.
International Search Report dated Feb. 1, 2012 for PCT Patent Application No. PCT/IB2011/002381, filed on Sep. 20, 2011, five pages.
International Search Report dated Jan. 22, 2014 for PCT Application No. PCT/IB2013/001934, filed on Jun. 20, 2013, four pages.
International Search Report dated Jun. 2, 2009 for PCT Application No. PCT/EP2008/008547, filed on Oct. 9, 2008, five pages.
International Search Report dated Jun. 8, 2009 for PCT Patent Application No. PCT/CA2009/000073, filed on Jan. 23, 2009, three pages.
International Search Report dated Oct. 18, 2000 for PCT Application No. PCT/US2000/22088, filed on Aug. 11, 2000, one page.
International Search Report dated Sep. 11, 2009 for Application No. PCT/US2009/042606 filed on May 1, 2009, five pages.
Invitation to Pay Additional Fees and, Where Applicable, Protest Fee dated Jul. 4, 2017 for PCT/CA2017/050564, filed on May 10, 2017, two pages.
Japanese Final Office Action dated Feb. 5, 2018 for Japanese Patent Application No. 2016-014503, filed on Jan. 28, 2016, six pages.
Japanese Final Office Action dated Jan. 28, 2019 for Japanese Patent Application No. 2016-014503, filed on Jan. 28, 2016, 3 pages.
Japanese Final Office Action dated Sep. 25, 2018 for Japanese Application No. 2017-518785 filed on Apr. 7, 2017, six pages.
Japanese First Office Action dated Feb. 1, 2016 for Japanese Patent Application No. 2015-517876 filed Jun. 20, 2013, eight pages.
Japanese First Office Action dated Jul. 28, 2017 for Japanese Patent Application No. 2016-203798 filed Oct. 17, 2016, four pages.
Japanese Notice of Allowance dated Jan. 25, 2019 for Japanese Application No. 2017-518785 filed on Apr. 7, 2017, six pages.
Japanese Notice of Allowance dated Jun. 8, 2018 for Japanese Patent Application No. 2016-203798 filed Oct. 17, 2016, six pages.
Japanese Notice of Allowance dated May 10, 2019 for Japanese Patent Application No. 2017-205499, filed on Nov. 24, 2017, six pages.
Japanese Notice of Allowance dated Sep. 16, 2016 for Japanese Patient Application No. 2015-517876 filed on Jun. 20, 2013, six pages, (with English Translation).
Japanese Notice of Allowance dated Sep. 25, 2017 for Japanese Patent Application No. 2013-529729, filed on Mar. 21, 2013, six pages.
Japanese Office Action dated Apr. 1, 2016 for Japanese Patent Application No. 2013-529729, filed on Mar. 21, 2013, seven pages.
Japanese Office Action dated Aug. 20, 2018 for Japanese Patent Application no. 2017-205499, filed on Nov. 24, 2017, six pages.
Japanese Office Action dated Jul. 30, 2013, issued in counterpart Japanese Application No. 2011-504574, filed Apr. 14, 2009, six pages.
Japanese Office Action dated Mar. 3, 2017 for Japanese Patent Application No. 2016-014503, filed on Jan. 28, 2016, ten pages.
Japanese Office Action dated Mar. 19, 2018 for Japanese Application No. 2017-518785 filed on Apr. 7, 2017, eight pages.
Japanese Office Action dated Mar. 31, 2017 for Japanese Patent Application No. 2013-529729, filed on Mar. 21, 2013, eleven pages.
Japanese Office Action dated May 7, 2018 for Japanese Patent Application No. 2017-516925 filed on Mar. 28, 2017, four pages.
Japanese Office Action dated Nov. 19, 2018 for Japanese Patent Application No. 2017-516925 filed on Mar. 28, 2017, four pages.
Japanese Office Action dated Sep. 14, 2015 for Japanese Patent Application No. 2011-504574, filed on Apr. 14, 2009, three pages.
Korean Notice of Allowance dated Apr. 27, 2017 for Korean Patent Application No. 10-2016-7007994, filed on Mar. 25, 2016, three pages.
Korean Notice of Allowance dated Apr. 29, 2016 for Korean Patent Application No. 10-2010-7024977, filed on Apr. 14, 2009, three pages, (with English Translation).
Korean Notice of Allowance dated Nov. 30, 2018 for Korean Patent Application No. 10-2017-7012463, filed on May 8, 2017, three pages.
Korean Office Action dated Apr. 17, 2018 for Korean Patent Application No. 10-2017-7012463, filed on May 8, 2017, six pages.

(56) References Cited

OTHER PUBLICATIONS

Korean Office Action dated Dec. 4, 2018 for Korean Patent Application No. 2017-7011565, filed on Apr. 4, 2017, nine pages.
Korean Office Action dated Nov. 30, 2015 for Korean Patent Application No. 10-2010-7024977, filed on Apr. 14, 2009, two pages.
Korean Patent Office Action dated Jun. 25, 2014 in Korean Patent Application No. 10-2013-7035027, filed on May 14, 2009, fifteen pages.
Mexican Office Action dated May 30, 2013, issued in counterpart Mexican Application No. MX/a/2010/011249.
Novadaq Technologies Inc.'s Preliminary Response filed on Aug. 23, 2017 to Petition for Inter Partes Review of U.S. Pat. No. 8,892,190 sixty one pages.
Petition for Inter Partes Review of U.S. Pat. No. 8,892,190 (May 11, 2017), filed by Visionsense Corp., fifty four pages.
Russian Decision on Grant dated Jul. 29, 2013, issued in counterpart Russian Application No. 2011111078.14, five pages.
Russian Office Action dated Mar. 29, 2013, issued in counterpart Russian Application No. 2011111078.14, three pages.
Translation of Decision of Japanese Patent Office Trial Board revoking Counterpart Patent No. U.S. Pat. No. 3,881,550, twenty six pages.
U.S. Final Office Action dated Apr. 2, 2013 for U.S. Appl. No. 13/419,368, filed Mar. 13, 2012, five pages.
U.S. Final Office Action dated Apr. 4, 2017 for U.S. Appl. No. 12/933,477, filed Sep. 20, 2010, twelve pages.
U.S. Final Office Action dated Apr. 10, 2008 for U.S. Appl. No. 11/106,154, filed Apr. 14, 2005, six pages.
U.S. Final Office Action dated Apr. 12, 2017 for U.S. Appl. No. 14/543,429, filed Nov. 17, 2014, nine pages.
U.S. Final Office Action dated Apr. 20, 2016 for U.S. Appl. No. 14/543,429, filed Nov. 17, 2014, seven pages.
U.S. Final Office Action dated Apr. 27, 2011 for U.S. Appl. No. 11/515,419, filed Sep. 1, 2006, nine pages.
U.S. Final Office Action dated Aug. 10, 2012 for U.S. Appl. No. 11/912,877, filed Aug. 13, 2008, ten pages.
U.S. Final Office Action dated Dec. 4, 2014 for U.S. Appl. No. 12/776,835, filed May 10, 2010, thirteen pages.
U.S. Final Office Action dated Dec. 31, 2015 for U.S. Appl. No. 14/177,050, filed Feb. 10, 2014, eighteen pages.
U.S. Final Office Action dated Feb. 1, 2013 for U.S. Appl. No. 12/776,835, filed May 10, 2010, thirteen page.
U.S. Final Office Action dated Feb. 4, 2015 for U.S. Appl. No. 13/314,418, filed Dec. 8, 2011, six pages.
U.S. Final Office Action dated Feb. 13, 2015 for U.S. Appl. No. 14/543,429, filed Nov. 17, 2014, six pages.
U.S. Final Office Action dated Feb. 18, 2010 for U.S. Appl. No. 11/106,154, filed Apr. 14, 2005, six pages.
U.S. Final Office Action dated Jul. 9, 2015 for U.S. Appl. No. 14/543,356, filed Nov. 17, 2014, eight pages.
U.S. Final Office Action dated Jul. 21, 2016 for U.S. Appl. No. 14/543,356, filed Nov. 17, 2014, seven pages.
U.S. Final Office Action dated Jun. 1, 2015 for U.S. Appl. No. 14/543,429, filed Nov. 17, 2014, nine pages.
U.S. Final Office Action dated Jun. 13, 2014 for U.S. Appl. No. 12/776,835, filed May 10, 2010, thirteen pages.
U.S. Final Office Action dated Jun. 25, 2014 for U.S. Appl. No. 12/933,477, filed Sep. 20, 2010, fifteen pages.
U.S. Final Office Action dated Mar. 20, 2017 for U.S. Appl. No. 14/177,050, filed Feb. 10, 2014, twenty three pages.
U.S. Final Office Action dated Mar. 28, 2013 for U.S. Appl. No. 12/063,349, filed May 12, 2010, twenty pages.
U.S. Final Office Action dated May 29, 2013 for U.S. Appl. No. 12/933,477, filed Sep. 20, 2010, twelve pages.
U.S. Final Office Action dated Nov. 6, 2013 for U.S. Appl. No. 13/419,368, filed Mar. 13, 2012, five pages.
U.S. Final Office Action dated Oct. 7, 2011 for U.S. Appl. No. 11/851,312, filed Sep. 6, 2007, ten pages.
U.S. Final Office Action dated Sep. 13, 2011 for U.S. Appl. No. 11/106,154, filed Apr. 14, 2005, five pages.
U.S. Final Office Action dated Sep. 17, 2014 for U.S. Appl. No. 11/515,419, filed Sep. 1, 2006, eleven pages.
U.S. Final Office Action dated Sep. 17, 2015 for U.S. Appl. No. 12/933,477, filed Sep. 20, 2010, six pages.
U.S. Final Office Action dated Sep. 23, 2004 for U.S. Appl. No. 09/744,034, filed Apr. 27, 2001, seven pages.
U.S. Final Office Action dated Sep. 29, 2016 for U.S. Appl. No. 13/922,996, filed Jun. 20, 2013, fourteen pages.
U.S. Non-Final Office Action dated Apr. 1, 2015 for U.S. Appl. No. 12/933,477, filed Sep. 20, 2010, fourteen pages.
U.S. Non-Final Office Action dated Apr. 26, 2012 for U.S. Appl. No. 12/776,835, filed May 10, 2010, nine pages.
U.S. Non-Final Office Action dated Apr. 28, 2010 for U.S. Appl. No. 11/946,672, filed Nov. 28, 2007, nine pages.
U.S. Non-Final Office Action dated Aug. 10, 2016 for U.S. Appl. No. 14/177,050, filed Feb. 10, 2014, twenty pages.
U.S. Non-Final Office Action dated Aug. 29, 2014 for U.S. Appl. No. 12/063,349, filed May 12, 2010, nineteen pages.
U.S. Non-Final Office Action dated Dec. 16, 2016 for U.S. Appl. No. 14/868,369, filed Sep. 28, 2015, seven pages.
U.S. Non-Final Office Action dated Dec. 20, 2013 for U.S. Appl. No. 12/933,477, filed Sep. 20, 2010, thirteen pages.
U.S. Non-Final Office Action dated Dec. 30, 2010 for U.S. Appl. No. 11/106,154, filed Apr. 14, 2005, six pages.
U.S. Non-Final Office Action dated Feb. 1, 2011 for U.S. Appl. No. 11/851,312, filed Sep. 6, 2007, seven pages.
U.S. Non-Final Office Action dated Feb. 5, 2016 for U.S. Appl. No. 14/543,356, filed Nov. 17, 2014, seven pages.
U.S. Non-Final Office Action dated Jan. 8, 2018 for U.S. Appl. No. 15/077,677, filed Mar. 22, 2016, nine pages.
U.S. Non-Final Office Action dated Jan. 9, 2009 for U.S. Appl. No. 11/106,154, filed Apr. 14, 2005, six pages.
U.S. Non-Final Office Action dated Jan. 22, 2014 for U.S. Appl. No. 11/851,312, filed Sep. 6, 2007, ten pages.
U.S. Non-Final Office Action dated Jan. 27, 2012 for U.S. Appl. No. 11/912,877, filed Aug. 13, 2008, eleven pages.
U.S. Non-Final Office Action dated Jan. 31, 2018 for U.S. Appl. No. 15/799,727, filed Oct. 31, 2017, seven pages.
U.S. Non-Final Office Action dated Jul. 2, 2015 for U.S. Appl. No. 14/177,050, filed Feb. 10, 2014, nineteen pages.
U.S. Non-Final Office Action dated Jul. 8, 2014 for U.S. Appl. No. 13/314,418, filed Dec. 8, 2011, seven pages.
U.S. Non-Final Office Action dated Jul. 22, 2015 for U.S. Appl. No. 13/314,418, filed Dec. 8, 2011, six pages.
U.S. Non-Final Office Action dated Jun. 11, 2013 for U.S. Appl. No. 11/515,419, filed Sep. 1, 2006, eleven pages.
U.S. Non-Final Office Action dated Jun. 28, 2012 for U.S. Appl. No. 12/063,349, filed May 12, 2010, seventeen pages.
U.S. Non-Final Office Action dated Mar. 6, 2007 for U.S. Appl. No. 11/106,154, filed Apr. 14, 2005, eight pages.
U.S. Non-Final Office Action dated Mar. 10, 2004 for U.S. Appl. No. 09/744,034, filed Apr. 27, 2001, seven pages.
U.S. Non-Final Office Action dated Mar. 13, 2015 for U.S. Appl. No. 14/543,356, filed Nov. 17, 2014, eight pages.
U.S. Non-Final Office Action dated Mar. 22, 2018 for U.S. Appl. No. 15/610,102, filed May 31, 2017, eleven pages.
U.S. Non-Final Office Action dated Mar. 22, 2019 for U.S. Appl. No. 15/799,727, filed Oct. 31, 2017, eight pages.
U.S. Non-Final Office Action dated May 6, 2015 for U.S. Appl. No. 12/063,349, filed May 12, 2010, seventeen pages.
U.S. Non-Final Office Action dated May 21, 2015 for U.S. Appl. No. 13/922,996, filed Jun. 20, 2013, fourteen pages.
U.S. Non-Final Office Action dated Nov. 9, 2015 for U.S. Appl. No. 14/177,045, filed Feb. 10, 2014, seven pages.
U.S. Non-Final Office Action dated Nov. 18, 2016 for U.S. Appl. No. 12/933,477, filed Sep. 20, 2010, six pages.
U.S. Non-Final Office Action dated Nov. 27, 2015 for U.S. Appl. No. 14/543,429, filed Nov. 17, 2014, six pages.
U.S. Non-Final Office Action dated Oct. 3, 2013 for U.S. Appl. No. 12/776,835, filed May 10, 2010, twelve pages.

(56) References Cited

OTHER PUBLICATIONS

U.S. Non-Final Office Action dated Oct. 12, 2016 for U.S. Appl. No. 14/543,429, filed Nov. 17, 2014, nine pages.
U.S. Non-Final Office Action dated Oct. 13, 2017 for U.S. Appl. No. 13/922,996, filed Jun. 20, 2013, seventeen pages.
U.S. Non-Final Office Action dated Oct. 26, 2017 for U.S. Appl. No. 14/543,429, filed Nov. 17, 2014, nine pages.
U.S. Non-Final Office Action dated Oct. 28, 2016 for U.S. Appl. No. 14/543,356, filed Nov. 17, 2014, eight pages.
U.S. Non-Final Office Action dated Sep. 5, 2012 for U.S. Appl. No. 12/933,477, filed Sep. 20, 2010, seven pages.
U.S. Non-Final Office Action dated Sep. 15, 2010 for U.S. Appl. No. 11/106,154, filed Apr. 14, 2005, six pages.
U.S. Non-Final Office Action dated Sep. 27, 2017 for U.S. Appl. No. 14/177,050, filed Feb. 10, 2014, twenty two pages.
U.S. Non-Final Office Action dated Sep. 30, 2010 for U.S. Appl. No. 11/515,419, filed Sep. 1, 2006, eleven pages.
U.S. Notice of Allowance dated Apr. 17, 2014 for U.S. Appl. No. 13/419,368, filed Mar. 13, 2012, five pages.
U.S. Notice of Allowance dated Aug. 7, 2014 for U.S. Appl. No. 13/850,063, filed Mar. 25, 2013, nine pages.
U.S. Notice of Allowance dated Dec. 2, 2016 for U.S. Appl. No. 14/598,832, filed Jan. 16, 2015, seven pages.
U.S. Notice of Allowance dated Dec. 6, 2017 for U.S. Appl. No. 15/476,290, filed Mar. 31, 2017, nine pages.
U.S. Notice of Allowance dated Dec. 18, 2018 for U.S. Appl. No. 13/922,996, filed Jun. 20, 2013, six pages.
U.S. Notice of Allowance dated Dec. 4, 2018 for U.S. Appl. No. 11/515,419, filed Sep. 1, 2006, seven pages.
U.S. Notice of Allowance dated Jan. 10, 2019 for U.S. Appl. No. 15/610,102, filed May 31, 2017, five pages.
U.S. Notice of Allowance dated Jul. 12, 2017 for U.S. Appl. No. 14/868,369, filed Sep. 28, 2015, nine pages.
U.S. Notice of Allowance dated Jul. 13, 2016 for U.S. Appl. No. 14/598,832, filed Jan. 16, 2015, seven pages.
U.S. Notice of Allowance dated Jun. 15, 2018 for U.S. Appl. No. 11/515,419, filed Sep. 1, 2006, five pages.
U.S. Notice of Allowance dated Mar. 7, 2005 for U.S. Appl. No. 09/744,034, filed Apr. 27, 2001, five pages.
U.S. Notice of Allowance dated Mar. 15, 2016 for U.S. Appl. No. 14/598,832, filed Jan. 16, 2015, seven pages.
U.S. Notice of Allowance dated Mar. 29, 2018 for U.S. Appl. No. 14/177,050, filed Feb. 10, 2014, ten pages.
U.S. Notice of Allowance dated May 15, 2019 for U.S. Appl. No. 15/610,102, filed May 31, 2017, eight pages.
U.S. Notice of Allowance dated May 26, 2016 for U.S. Appl. No. 14/177,045, filed Feb. 10, 2014, eight pages.
U.S. Notice of Allowance dated Nov. 25, 2015 for U.S. Appl. No. 14/598,832, filed Jan. 16, 2015, seven pages.
U.S. Notice of Allowance dated Nov. 30, 2010 for U.S. Appl. No. 11/946,672, filed Nov. 28, 2007, six pages.
U.S. Notice of Allowance dated Oct. 4, 2013 for U.S. Appl. No. 11/912,877, filed Aug. 13, 2008, nine pages.
U.S. Notice of Allowance dated Oct. 6, 2014 for U.S. Appl. No. 13/419,368, filed Mar. 13, 2012, five pages.
U.S. Notice of Allowance dated Oct. 16, 2014 for U.S. Appl. No. 13/850,063, filed Mar. 25, 2013, eight pages.
U.S. Notice of Allowance dated Oct. 17, 2018 for U.S. Appl. No. 12/933,477, filed Sep. 20, 2010, seven pages.
U.S. Notice of Allowance dated Oct. 18, 2012 for U.S. Appl. No. 12/841,659, filed Jul. 22, 2010, seven pages.
U.S. Notice of Allowance dated Oct. 29, 2018 for U.S. Appl. No. 12/063,349, filed May 12, 2010, eight pages.
U.S. Notice of Allowance dated Sep. 6, 2018 for U.S. Appl. No. 12/776,835, filed May 10, 2010, five pages.
U.S. Notice of Allowance dated Sep. 6, 2018 for U.S. Appl. No. 13/922,996, filed Jun. 20, 2013, nine pages.
U.S. Notice of Allowance dated Sep. 11, 2018 for U.S. Appl. No. 15/799,727, filed Oct. 31, 2017, eight pages.
U.S. Notice of Allowance dated Sep. 26, 2018 for U.S. Appl. No. 15/610,102, filed May 31, 2017, eight pages.
U.S. Appl. No. 16/291,930, filed Mar. 4, 2019. (herewith pursuant to the waiver of 37 C.F.R. § 1.98(a)(2)(iii) issued by the Office dated Sep. 21, 2004).
U.S. Restriction Requirement dated Jun. 26, 2017 for U.S. Appl. No. 15/077,677, filed Mar. 22, 2016, seven pages.
Written Opinion of the International Searching Authority dated Jul. 4, 2008 for PCT Patent Application No. PCT/US2007/080847, filed on Oct. 9, 2007, six pages.
Written Opinion of the International Searching Authority dated Dec. 3, 2009 for PCT Patent Application No. PCT/IB2009/005700, filed on Apr. 14, 2009, six pages.
Written Opinion of the International Searching Authority dated Dec. 3, 2015 for PCT Patent Application No. PCT/CA2015/050973 filed on Sep. 28, 2015, five pages.
Written Opinion of the International Searching Authority dated Feb. 1, 2012 for PCT Patent Application No. PCT/IB2011/002381, filed on Sep. 20, 2011, four pages.
Written Opinion of the International Searching Authority dated Jan. 22, 2014 for PCT Patent Application No. PCT/IB2013/001934, filed on Jun. 20, 2013, six pages.
Written Opinion of the International Searching Authority dated Jun. 2, 2009 for PCT Patent Application No. PCT/EP2008/008547, filed on Oct. 9, 2008, eleven pages.
Written Opinion of the International Searching Authority dated Jun. 8, 2009 for PCT Patent Application No. PCT/CA2009/000073, filed on Jan. 23, 2009, four pages.
Alfano, R.R. et al. (Oct. 1987). "Fluorescence Spectra From Cancerous and Normal Human Breast and Lung Tissues," IEEE Journal of Quantum Electronics QE-23(10):1806-1811.
Andersson-Engels, S. et al. (Mar. 1989). "Tissue Diagnostics Using Laser Induced Fluorescence," Ber. Bunsenges Physical Chemistry 93(3):335-342.
Australian Notice of Acceptance for Patent Application dated Jun. 26, 2019 for Patent Application No. 2016351730 filed on Nov. 10, 2016, three pages.
Australian Office Action dated Jun. 28, 2018 for Australian Patent Application No. 2016351730 filed on Nov. 10, 2016, five pages.
Australian Office Action dated May 10, 2019 for Australian Patent Application No. 2016351730 filed on Nov. 10, 2016, ten pages.
Bhunchet, E. et al. (Apr. 2002). "Fluorescein Electronic Endoscopy: A Novel Method for Detection of Early Stage Gastric Cancer Not Evident to Routine Endoscopy," Gastrointestinal. Endoscopy 55(4):562-571.
Brazilian Office Action dated Aug. 5, 2019, for Patent Application No. BR112013022997-7, filed Mar. 8, 2012, 4 pages.
Brazilian Office Action dated Mar. 16, 2020 for Patent Application No. 112013022997-7, filed Mar. 8, 2012, six pages.
Canadian Notice of Allowance dated Oct. 29, 2019, for Patent Application No. 2998920, filed Nov. 10, 2016, one page.
Canadian Office Action dated Feb. 1, 2017 for Canadian Patent Application No. 171282, filed on Oct. 27, 2016, two pages.
Canadian Office Action dated Feb. 19, 2019 for CA Patent Application No. 2,998,920 filed on Mar. 16, 2018, four pages.
Canadian Office Action dated Nov. 5, 2019, for Canadian Patent Application No. 3027592, filed on Jun. 14, 2017, four pages.
Chinese Notice of Allowance dated Jan. 13, 2020, for Patent Application No. 2017-10785223.7, filed Mar. 8, 2012, six pages.
Chinese Notice of Allowance dated Jun. 19, 2017 for Chinese Patent Application No. 201280022284.3, filed on Nov. 7, 2013, four pages.
Chinese Office Action dated Jul. 29, 2016 for Chinese Patent Application No. 2012800222843 filed on Mar. 8, 2012, eight pages.
Chinese Office Action dated Mar. 14, 2017 for Chinese Patent Application No. 201280022284.3, filed on Nov. 7, 2013, seven pages.
Chinese Office Action dated Nov. 24, 2015 for Chinese Patent Application No. 2012800222843 filed on Mar. 8, 2012, sixteen pages.
Chinese Office Action dated Sep. 26, 2018 for Chinese Patent Application No. 2018092001857100, filed on Sep. 4, 2017, nineteen pages.

(56) References Cited

OTHER PUBLICATIONS

Chinese Office Action, Notification to Pay Restoration Fee for Unity, dated Apr. 7, 2020, for Patent Application No. 2016800660600, filed Nov. 10, 2016, 2 pages.
Dawson, J.B. et al. (Jul. 1980). "A Theoretical and Experimental Study of Light Absorption and Scattering by In Vivo Skin," Phys. Med. Biol. 25(4):695-709.
European Extended Search Report dated Jan. 14, 2020, for Appl. No. 17812362.6, filed Jun. 14, 2017, 8 pages.
European Extended Search Report dated May 7, 2019, for Patent Application No. 16863277.6, filed Nov. 10, 2016, seven pages.
European Extended Search Report dated Oct. 16, 2019, for Patent Application No. 17743524.5, filed Jan. 26, 2017, four pages.
European Notice of Allowance dated Feb. 28, 2018 for EP Patent Application No. 12754208.2 filed Oct. 4, 2013, six pages.
European Notice of Allowance dated Jul. 12, 2018 for EP Patent Application No. 12754208.2 filed Oct. 4, 2013, two pages.
European Notice of Allowance dated Jun. 22, 2017 for EP Patent Application No. 08706262.6 filed on Aug. 21, 2009, two pages.
European Notice of Allowance dated Mar. 18, 2019 for EP Patent Application No. 09819758.5, filed on May 4, 2011, seven pages.
European Notice of Allowance dated Mar. 6, 2018 for EP Patent Application No. 13180297.7 filed Aug. 13, 2013, seven pages.
European Notice of Allowance dated May 25, 2018 for EP Patent Application No. 13180297.7 filed Aug. 13, 2013, two pages.
European Notice of Allowance dated Nov. 25, 2016 for EP Patent Application No. 08706262.6 filed on Aug. 21, 2009, eight pages.
European Office Action dadted Apr. 13, 2017, for EP Patent Application No. 12754208.2 filed on Oct. 4, 2013, five pages.
European Office Action dated Apr. 6, 2017, for EP Patent Application No. 09819758.5, filed on May 4, 2011, five pages.
European Office Action dated Dec. 3, 2015 for EP Patent Application No. 08706262.6 filed on Jan. 23, 2008, fifteen pages.
European Office Action dated Jan. 23, 2017 for EP Patent Application No. 16186321.2 filed on Aug. 30, 2016, two pages.
European Office Action dated Nov. 19, 2015 for EP Patent Application No. 07 785 001.4, filed on Jul. 30, 2007, four pages.
European Office Action dated Nov. 3, 2015 for EP Patent Application No. 12754208.2 filed Oct. 4, 2013, four pages.
European Office Action dated Sep. 29, 2015, for EP Patent Application No. 09721252.6 filed Mar. 18, 2009; five pages.
European Search Report dated Dec. 21, 2016 for EP Patent Application No. 16186321.2 filed on Aug. 30, 2016, nine pages.
European Search Report dated Feb. 18, 2019 for EP Patent Application No. 18178620.3 filed on Jun. 19, 2018, eight pages.
European Search Report dated Jan. 24, 2012 for EP Patent Application No. 07785001.4 filed on Jul. 30, 2007, seven pages.
European Search Report dated Jul. 17, 2014 for EP Patent Application No. 09721252.6 filed Mar. 18, 2009, eleven pages.
European Search Report dated Oct. 1, 2014 for EP Patent Application No. 12754208.2 filed on Mar. 8, 2012, five pages.
European Search Report dated Oct. 9, 2013, for European Patent Application No. 06721854.5, filed on May 4, 2005, seven pages.
European Search Report dated Sep. 20, 2013 for EP Patent Application No. 08706262.6 filed on Jan. 23, 2008, five pages.
Georgakoudi, I et al. (2003). "Quantitative Characterization of Biological Tissue Using Optical Spectroscopy," in Chapter 31 of *Biomedical Photonics Handbook,* Tuan Vo-Dinh (ed.), CRC Press, New York, thirty three pages.
Georgakoudi, I et al. (Apr. 2005). "Characterization of Dysplastic Tissue Morphology and Biochemistry in Barrett's Esophagus using Diffuse Reflectance and Light Scattering Spectroscopy," Techniques in Gastrointestinal Endoscopy 7(2):100-105.
Hubel, P.M. et al. (2004). "Spatial Frequency Response of Color Image Sensors: Bayer Color Filters and Foveon X3," Proceedings of SPIE 5301:402-406.
Hung, J. et al. (1991). "Autofluorescence of Normal and Malignant Bronchial Tissue," Lasers in Surgery and Medicine 11(2):99-105.
Indian Office Action dated Jan. 31, 2018 for Indian Patent Application No. 6532/DELNP/2010 filed on Sep. 16, 2010, six pages.
Indian Office Action dated Jun. 26, 2018 for Indian Patent Application No. 8678/DELNP/2013 filed on Mar. 8, 2012, five pages.
International Preliminary Report on Patentability dated Aug. 22, 2019, for Patent Application No. PCT/CA2017/050564, dated May 10, 2017, nine pages.
International Preliminary Report on Patentability dated Dec. 27, 2018 for International Patent Application No. PCT/CA2017/050734 filed on Jun. 14, 2017, six pages.
International Preliminary Report on Patentability dated Feb. 3, 2009 for International Patent Application No. PCT/CA2007/001335 filed on Jul. 30, 2007, five pages.
International Preliminary Report on Patentability dated May 24, 2018 for International Patent Application No. PCT/CA2016/051315 filed on Nov. 10, 2016, nine pages.
International Preliminary Report on Patentability dated Nov. 6, 2007 for International Patent Application No. PCT/CA2006/000669, filed on Apr. 27, 2006, nine pages.
International Preliminary Report on Patentability dated Sep. 21, 2010 for International Patent Application No. PCT/US2009/037506, filed on Mar. 18, 2009, seven pages.
International Search Report and written Opinion dated Apr. 24, 2017 for International Patent Application No. PCT/CA2017/050083, filed on Jan. 26, 2017, seven pages.
International Search Report and written Opinion dated Feb. 10, 2017 for International Patent Application No. PCT/CA2016/051315 filed on Nov. 10, 2016, thirteen pages.
International Search Report and Written Opinion dated Sep. 18, 2017 for International Patent Application No. PCT/CA2017/050734, filed on Jun. 14, 2017, eight pages.
International Search Report dated Oct. 24, 2017, for Patent Application No. PCT/CA2017/050564, dated May 10, 2017, six pages.
International Search Report dated Aug. 3, 2006, for International Patent Application No. PCT/CA2006/000669, filed on Apr. 27, 2006, three pages.
International Search Report dated Aug. 3, 2012, for International Patent Application No. PCT/162012/000601, filed on Mar. 8, 2012, three pages.
International Search Report dated Dec. 7, 2007, for International Patent Application No. PCT/CA2007/001335, filed on Jul. 30, 2007, two pages.
International Search Report dated Jan. 21, 2002 for International Patent Application No. PCT/US2001/022198, filed on Jul. 13, 2001, three pages.
International Search Report dated Jul. 22, 2009 for International Patent Application No. PCT/US09/37506, filed on Mar. 18, 2009, two pages.
International Search Report dated May 13, 2008 for Intentional Patent Application No. PCT/CA2008/00015, filed on Jan. 8, 2008, one page.
Invitation to Pay additional Fees and, where Applicable, Protest Fee, dated Jul. 4, 2017, for Patent Application No. PCT/CA2017/050564, filed May 10, 2017, two pages.
Invitation to Pay additional Fees and, where Applicable, Protest Fee, dated Dec. 22, 2016 for International Patent Application No. PCT/CA2016/051315, filed on Nov. 10, 2016, two pages.
Japanese Final Office Action dated Aug. 2, 2013 for Japanese Application No. 2008-509275, filed on Apr. 27, 2006, four pages.
Japanese Notice of Allowance dated Apr. 2, 2018 for Japanese Patent Application No. 2017-018858 filed on Feb. 3, 2017, six pages.
Japanese Notice of Allowance dated Jan. 5, 2017 for Japanese Patent Application No. 2015-238784, filed on Dec. 7, 2015, six pages.
Japanese Notice of Allowance dated Nov. 17, 2017 for Japanese Application No. 2016-253736 filed on Dec. 27, 2016, six pages.
Japanese Notice of Allowance dated Nov. 28, 2016 for Japanese Patent Application No. 2015-245598, filed on Mar. 8, 2012, six pages.
Japanese Office Action dated Jan. 10, 2020, for Japanese Patent Application No. 2018-516161, filed Nov. 10, 2016, five pages.
Japanese Office Action dated Apr. 20, 2012 for Japanese Patent Application No. 2011-500921, filed Mar. 18, 2009, four pages.

(56) References Cited

OTHER PUBLICATIONS

Japanese Office Action dated Apr. 3, 2015 for Japanese Patent Application No. 2013-058356, filed Mar. 18, 2009, four pages.
Japanese Office Action dated Dec. 8, 2017 for Japanese Patent Application No. 2017-018858, filed on Feb. 3, 2017, six pages.
Japanese Office Action dated Feb. 17, 2012 for Japanese Application No. 2008-509275, filed on Apr. 27, 2006, six pages.
Japanese Office Action dated Jul. 12, 2019, for Patent Application No. 2018-51661, filed Nov. 10, 2016, twenty-one pages.
Japanese Office Action dated Jul. 22, 2014 for Japanese Patent Application No. 2013-557187 filed Mar. 8, 2012, seven pages.
Japanese Office Action dated Mar. 9, 2015 for Japanese Patent Application No. 2013-557187, filed Mar. 8, 2012, five pages.
Japanese Office Action dated May 26, 2014 in Japanese Patent Application No. 2013-058356, filed on Mar. 18, 2009, w/Concise Explanation of the Relevance, three pages.
Japanese Office Action dated Nov. 11, 2011 for Japanese Application No. 2009-521077, filed on Jul. 30, 2007, four pages.
Japanese Office Action dated Sep. 14, 2012 for Japanese Application No. 2008-509275, filed on Apr. 27, 2006, seven pages.
Japanese Office Action dated Sep. 19, 2014 for Japanese Application No. 2013-246636, filed on Apr. 27, 2006, six pages.
Japanese Office dated Dec. 26, 2012 for Japanese Patent Application No. 2011-500921, filed on Mar. 18, 2009, two pages.
Kolaman, A. et al. (2016). "Amplitude Modulated Video Camera—Light Separation in Dynamic Scenes," IEEE Conference on Computer Vision and Pattern Recognition (CVPR), located at https://www.cv-foundation.org/openaccess/content_cvpr_2016/app/S15-50.pdf last visited on Jun. 8, 2020, nine pages.
Korean Decision on the Trial Against Final Rejection from the Intellectual Property Tribunal (IPT) mailed on Sep. 25, 2017 for Korean Patent Application No. 2013-7026479, filed on Oct. 7, 2013, seventeen pages.
Korean Notice of Allowance dated Dec. 13, 2017 for Korean Patent Application No. 10--2017-7008654, filed on Mar. 29, 2017, three pages.
Korean Notice of Allowance dated Jan. 2, 2017 for Korean Patent Application No. 10-2015-7033310, filed on Nov. 20, 2015, three pages.
Korean Office Action dated Aug. 20, 2015 for Korean Patent Application No. 20137026479 filed on Mar. 8, 2012, three pages.
Korean Office Action dated Aug. 30, 2016 for Korean Patent Application No. 10-2015-7033310 filed on Mar. 8, 2012, seven pages.
Korean Office Action dated Dec. 8, 2015 for Korean Patent Application No. 20157033310 filed on Mar. 8, 2012, seven pages.
Korean Office Action dated Jun. 27, 2017 for Korean Patent Application No. 2017-7008654, filed on Mar. 29, 2017, ten pages.
Lyon, R.E. et al. (2002). "Eyeing the Camera: Into the Next Century," 10 Color and Imaging Conference Final Program & Proceedings 349-355.
Russian Notice of Allowance dated Aug. 19, 2016 for Russian Patent Application No. 2013144845/07, filed on Mar. 8, 2012, thirteen pages.
Sensitization (photography), definition from Wikipedia, original language German, 6 pages.
Török, B. et al. (May 1996). "Simultane digitale Indocyaningrün- und Fluoreszeinangiographie (Simultaneous Digital ICG and Fluorescein Angiography)," Klin Monatsbl Augenheilkd 208(5):333-336.
U.S. Ex Parte Quayle Action mailed on Mar. 23, 2020, for U.S. Appl. No. 15/584,405, filed May 2, 2017, five pages.
U.S. Final Office Action dated Apr. 24, 2015 for U.S. Appl. No. 12/933,512, filed Nov. 24, 2010, nineteen pages.
U.S. Final Office Action dated Aug. 10, 2017 for U.S. Appl. No. 15/343,034, filed Nov. 3, 2016, twelve pages.
U.S. Final Office Action dated Aug. 11, 2017 for U.S. Appl. No. 14/860,687, filed Sep. 21, 2015, seventeen pages.
U.S. Final Office Action dated Aug. 7, 2017 for U.S. Appl. No. 15/343,038, filed Nov. 3, 2016, eleven pages.
U.S. Final Office Action dated Dec. 14, 2018 for U.S. Appl. No. 15/584,405, filed May 2, 2017, seven pages.
U.S. Final Office Action dated Feb. 1, 2018 for U.S. Appl. No. 15/584,405, filed May 2, 2017, ten pages.
U.S. Final Office Action dated Feb. 27, 2017 for U.S. Appl. No. 15/247,419, filed Aug. 25, 2016, ten pages.
U.S. Final Office Action dated Feb. 7, 2020, for U.S. Appl. No. 15/343,038, filed Nov. 3, 2016, sixteen pages.
U.S. Final Office Action dated Jan. 11, 2019 for U.S. Appl. No. 15/343,038, filed Nov. 3, 2016, twelve pages.
U.S. Final Office Action dated Jan. 14, 2019 for U.S. Appl. No. 14/860,687, filed Sep. 21, 2015, sixteen pages.
U.S. Final Office Action dated Jan. 22, 2019 for U.S. Appl. No. 15/343,034, filed Nov. 3, 2016, twelve pages.
U.S. Final Office Action dated Jul. 23, 2008 for U.S. Appl. No. 11/122,267, filed May 4, 2016, six pages.
U.S. Final Office Action dated Jul. 25, 2019 for U.S. Appl. No. 15/416,876, filed Jan. 26, 2017, 13 pages.
U.S. Final Office Action dated Jun. 18, 2015 for U.S. Appl. No. 14/154,177, filed Jan. 13, 2014, eight pages.
U.S. Final Office Action dated Jun. 5, 2014 for U.S. Appl. No. 12/761,462, filed Apr. 16, 2010, fourteen pages.
U.S. Final Office Action dated Mar. 22, 2016 for U.S. Appl. No. 14/873,842, filed Oct. 2, 2015, eighteen pages.
U.S. Final Office Action dated May 11, 2011 for U.S. Appl. No. 11/412,715, filed Apr. 26, 2006, eight pages.
U.S. Final Office Action dated May 21, 2012 for U.S. Appl. No. 11/964,330, filed Dec. 26, 2007, twelve pages.
U.S. Final Office Action dated Nov. 24, 2009 for U.S. Appl. No. 11/009,965, filed Dec. 10, 2004, fourteen pages.
U.S. Non-Final Office Action dated Apr. 3, 2019 for U.S. Appl. No. 15/416,876, filed Jan. 26, 2017, thirteen pages.
U.S. Non-Final Office Action dated Apr. 2, 2009 for U.S. Appl. No. 11/009,965, filed Dec. 10, 2004, thirteen pages.
U.S. Non-Final Office Action dated Apr. 3, 2020, for U.S. Appl. No. 16/746,539, filed Jan. 17, 2020, 15 pages.
U.S. Non-Final Office Action dated Aug. 15, 2018 for U.S. Appl. No. 15/348,664, filed Nov. 10, 2016, eleven pages.
U.S. Non-Final Office Action dated Aug. 16, 2013 for U.S. Appl. No. 12/761,462, filed Apr. 16, 2010, ten pages.
U.S. Non-Final Office Action dated Aug. 16, 2013 for U.S. Appl. No. 12/761,523, filed Apr. 16, 2010, nine pages.
U.S. Non-Final Office Action dated Aug. 2, 2019 for U.S. Appl. No. 15/623,100, filed Jun. 14, 2017, twelve pages.
U.S. Non-Final Office Action dated Aug. 21, 2019 for U.S. Appl. No. 15/584,405, filed May 2, 2017, six pages.
U.S. Non-Final Office Action dated Aug. 23, 2019 for U.S. Appl. No. 14/860,687, filed Sep. 21, 2015, fourteen pages.
U.S. Non-Final Office Action dated Aug. 23, 2019 for U.S. Appl. No. 15/343,034, filed Nov. 3, 2016, eighteen pages.
U.S. Non-Final Office Action dated Aug. 23, 2019 for U.S. Appl. No. 15/343,038, filed Nov. 3, 2016, fourteen pages.
U.S. Non-Final Office Action dated Dec. 10, 2010 for U.S. Appl. No. 11/412,715, filed Apr. 26, 2006, ten pages.
U.S. Non-Final Office Action dated Dec. 14, 2011 for U.S. Appl. No. 11/412,715, filed Apr. 26, 2006, eight pages.
U.S. Non-Final Office Action dated Feb. 5, 2019 for U.S. Appl. No. 15/623,100, filed Jun. 14, 2017, ten pages.
U.S. Non-Final Office Action dated Feb. 1, 2017 for U.S. Appl. No. 14/860,687, filed Sep. 21, 2015, fifteen pages.
U.S. Non-Final Office Action dated Feb. 3, 2010 for U.S. Appl. No. 11/626,308, filed Jan. 23, 2007, eleven pages.
U.S. Non-Final Office Action dated Jan. 16, 2020, for U.S. Appl. No. 15/416,876, filed Jan. 26, 2017, thirteen pages.
U.S. Non-Final Office Action dated Jan. 2, 2008 for U.S. Appl. No. 11/122,267, filed May 4, 2005, five pages.
U.S. Non-Final Office Action dated Jan. 20, 2016 for U.S. Appl. No. 14/629,473, filed Feb. 23, 2015, fifteen pages.
U.S. Non-Final Office Action dated Jan. 26, 2017 for U.S. Appl. No. 15/343,034, filed Nov. 3, 2016, seventeen pages.
U.S. Non-Final Office Action dated Jan. 27, 2017 for U.S. Appl. No. 15/343,038, filed Nov. 3, 2016, fifteen pages.

(56) References Cited

OTHER PUBLICATIONS

U.S. Non-Final Office Action dated Jul. 17, 2003 for U.S. Appl. No. 09/905,642, filed Jul. 13, 2001, six pages.
U.S. Non-Final Office Action dated Jul. 2, 2013 for U.S. Appl. No. 12/933,512, filed Nov. 24, 2010, twelve pages.
U.S. Non-Final Office Action dated Jun. 1, 2007 for U.S. Appl. No. 10/899,648, filed Jul. 26, 2004, seven pages.
U.S. Non-Final Office Action dated Jun. 20, 2008 for U.S. Appl. No. 11/009,398, filed Dec. 10, 2004, fifteen pages.
U.S. Non-Final Office Action dated Jun. 23, 2010 for U.S. Appl. No. 11/009,965, filed Dec. 10, 2004, fifteen pages.
U.S. Non-Final Office Action dated Jun. 27, 2014 for U.S. Appl. No. 13/415,561, filed Mar. 3, 2012, fourteen pages.
U.S. Non-Final Office Action dated Jun. 5, 2018 for U.S. Appl. No. 14/860,687, filed Sep. 21, 2015, eighteen pages.
U.S. Non-Final Office Action dated Jun. 8, 2018 for U.S. Appl. No. 15/343,034, filed Nov. 3, 2016, thirteen pages.
U.S. Non-Final Office Action dated Jun. 8, 2018 for U.S. Appl. No. 15/584,405, filed May 2, 2017, eight pages.
U.S. Non-Final Office Action dated Jun. 9, 2011 for U.S. Appl. No. 11/830,323, filed Jul. 30, 2007, five pages.
U.S. Non-Final Office Action dated May 18, 2004 for U.S. Appl. No. 10/050,601, filed Jan. 15, 2002, eight pages.
U.S. Non-Final Office Action dated May 25, 2018 for U.S. Appl. No. 15/343,038, filed Nov. 3, 2016, eleven pages.
U.S. Non-Final Office Action dated May 5, 2020, for U.S. Appl. No. 15/623,100, filed Jun. 14, 2017, twelve pages.
U.S. Non-Final Office Action dated Nov. 5, 2014 for U.S. Appl. No. 13/930,225, filed Jun. 28, 2013, six pages.
U.S. Non-Final Office Action dated Nov. 23, 2009 for U.S. Appl. No. 11/969,974, filed Jan. 7, 2008, seven pages.
U.S. Non-Final Office Action dated Oct. 23, 2013 for U.S. Appl. No. 13/415,561, filed Mar. 8, 2012, ten pages.
U.S. Non-Final Office Action dated Oct. 5, 2016 for U.S. Appl. No. 15/247,419, filed Aug. 25, 2016, eight pages.
U.S. Non-Final Office Action dated Oct. 7, 2011 for U.S. Appl. No. 11/964,330, filed Dec. 26, 2007; ten pages.
U.S. Non-Final Office Action dated Sep. 12, 2014 for U.S. Appl. No. 14/154,177, filed Jan. 13, 2014, four pages.
U.S. Non-Final Office Action dated Sep. 25, 2017 for U.S. Appl. No. 15/584,405, filed May 2, 2017, eight pages.
U.S. Non-Final Office Action dated Sep. 27, 2019, for U.S. Appl. No. 29/562,795, filed Apr. 28, 2019, 6 pages.
U.S. Non-Final Office Action dated Sep. 6, 2016 for U.S. Appl. No. 14/873,842, filed Oct. 2, 2015, seven pages.
U.S. Non-Final Office Action with Restriction Requirement dated Mar. 4, 2011 for U.S. Appl. No. 11/830,323, filed Jul. 30, 2007, nine pages.
U.S. Notice of Allowance dated Apr. 7, 2004 for U.S. Appl. No. 09/905,642, filed Jul. 13, 2001, six pages.
U.S. Notice of Allowance dated Aug. 26, 2004 for U.S. Appl. No. 10/050,601, filed Jan. 15, 2002, eight pages.
U.S. Notice of Allowance dated Aug. 6, 2015 for U.S. Appl. No. 13/853,656, filed Mar. 29, 2013, seven pages.
U.S. Notice of Allowance dated Dec. 10, 2012 for U.S. Appl. No. 11/964,330, filed Dec. 26, 2007, seven pages.
U.S. Notice of Allowance dated Dec. 30, 2016 for U.S. Appl. No. 14/873,842, filed Oct. 2, 2015, eleven pages.
U.S. Notice of Allowance dated Feb. 14, 2020, for U.S. Appl. No. 14/860,687, filed Sep. 21, 2015, eight pages.
U.S. Notice of Allowance dated Feb. 14, 2020, for U.S. Appl. No. 15/343,034, filed Nov. 3, 2016, seven pages.
U.S. Notice of Allowance dated Feb. 25, 2010 for U.S. Appl. No. 11/969,974, filed Jan. 7, 2008, four pages.
U.S. Notice of Allowance dated Jan. 2, 2008 for U.S. Appl. No. 10/899,648, filed Jul. 26, 2004, three pages.
U.S. Notice of Allowance dated Jul. 10, 2017 for U.S. Appl. No. 15/247,419, filed Aug. 25, 2016, eight pages.
U.S. Notice of Allowance dated Jun. 25, 2015 for U.S. Appl. No. 12/933,512, filed Nov. 24, 2010 fourteen pages.
U.S. Notice of Allowance dated Mar. 10, 2005 for U.S. Appl. No. 10/050,601, filed Jan. 15, 2002, five pages.
U.S. Notice of Allowance dated Mar. 12, 2020, for U.S. Appl. No. 16/441,493, filed Jun. 14, 2019, 8 pages.
U.S. Notice of Allowance dated Mar. 22, 2013 for U.S. Appl. No. 11/964,330, filed Dec. 26, 2007, eight pages.
U.S. Notice of Allowance dated Mar. 28, 2016 for U.S. Appl. No. 13/853,656, filed Mar. 29, 2013, eight pages.
U.S. Notice of Allowance dated May 18, 2015 for U.S. Appl. No. 13/930,225, filed Jun. 28, 2013, nine pages.
U.S. Notice of Allowance dated May 19, 2020, for U.S. Appl. No. 15/584,405, filed May 2, 2017, seven pages.
U.S. Notice of Allowance dated Nov. 23, 2015 for U.S. Appl. No. 13/853,656, filed Mar. 29, 2013, seven pages.
U.S. Notice of Allowance dated Oct. 10, 2014 for U.S. Appl. No. 12/761,462, filed Apr. 16, 2010, ten pages.
U.S. Notice of Allowance dated Oct. 5, 2007 for U.S. Appl. No. 10/899,648, filed Jul. 26, 2004, six pages.
U.S. Notice of Allowance dated Sep. 10, 2013 for U.S. Appl. No. 11/412,715, filed Apr. 26, 2006, eight pages.
U.S. Notice of Allowance dated Sep. 14, 2012 for U.S. Appl. No. 11/830,323, filed Jul. 30, 2007, eight pages.
U.S. Appl. No. 15/810,911, filed Nov. 13, 2017. (A copy of the U.S. Patent Application is not submitted herewith pursuant to the waiver of 37 C.F.R. § 1.98(a)(2)(iii) issued by the Office on Sep. 21, 2004.).
U.S. Restriction Requirement dated Feb. 7, 2019 for U.S. Appl. No. 29/562,795, filed Apr. 28, 2016, seven pages.
Westwick et al., U.S. Office Action dated Aug. 27, 2020, directed to U.S. Appl. No. 15/343,038; 16 pages.
Written Opinion of the International Searching Authority dated Oct. 24, 2017, for Patent Application No. PCT/CA2017/050564, seven pages.
Written Opinion of the International Searching Authority dated Aug. 3, 2006 for International Patent Application No. PCT/CA2006/000669, filed on Apr. 27, 2006, eight pages.
Written Opinion of the International Searching Authority dated Dec. 7, 2007 for International Patent Application No. PCT/CA2007/001335, filed on Jul. 30, 2007, four pages.
Decision to Grant a Patent dated Jun. 29, 2020, directed to JP Application No. 2018-516161; 6 pages.
Decision to Grant dated Jul. 18, 2019, directed to EP Application No. 09819758.5; 2 pages.
Extended European Search Report dated Oct. 14, 2020, directed to EP Application No. 17895908.6; 8 pages.
Fengler et al., U.S. Advisory Action dated Dec. 20, 2019, directed to U.S. Appl. No. 15/416,876; 5 pages.
Fengler et al., U.S. Advisory Action dated Nov. 2, 2020, directed to U.S. Appl. No. 15/416,876; 5 pages.
Fengler et al., U.S. Notice of Allowance and Fee(s) Due dated Aug. 18, 2020, directed to U.S. Appl. No. 15/623,100; 7 pages.
Fengler et al., U.S. Office Action dated Jul. 15, 2020, directed to U.S. Appl. No. 15/416,876; 20 pages.
Murray et al., U.S. Notice of Allowance and Fee(s) due dated Jul. 13, 2020, directed to U.S. Appl. No. 29/562,795; 7 pages.
Office Action dated Jul. 2, 2020, directed to CN Application No. 201680066060.0; 30 pages.
Office Action dated Jul. 6, 2020, directed to CA Application No. 3,009,419; 3 pages.
Office Action dated Nov. 18, 2020, directed to CA Application No. 3,027,592; 3 pages.
Office Action dated Sep. 16, 2020, directed to EP Application No. 16 186 321.2; 4 pages.
U.S. Ex Parte Quayle Action dated Jul. 23, 2020, directed to U.S. Appl. No. 29/724,647; 5 pages.
U.S. Ex Parte Quayle Action dated Jul. 23, 2020, directed to U.S. Appl. No. 29/724,650; 5 pages.
U.S. Ex Parte Quayle Action dated Jul. 23, 2020, directed to U.S. Appl. No. 29/724,651; 5 pages.
Fengler et al., U.S. Notice of Allowance and Fee(s) Due dated Dec. 4, 2020, directed to U.S. Appl. No. 15/416,876; 9 pages.
Moore et al., U.S. Notice of Allowance and Fee(s) due dated Mar. 5, 2019, directed to U.S. Appl. No. 15/348,664; 10 pages.

(56) References Cited

OTHER PUBLICATIONS

Moore et al., U.S. Office Action dated Oct. 17, 2019, directed to U.S. Appl. No. 16/441,493; 8 pages.
Murray et al., U.S. Office Action dated Aug. 31, 2020, directed to U.S. Appl. No. 16/746,539; 16 pages.
Murray et al., U.S. Notice of Allowance and Fee(s) Due dated Dec. 22, 2020, directed to U.S. Appl. No. 16/746,539; 7 pages.
Notice of Reasons for Refusal dated Feb. 12, 2021, directed to JP Application No. 2019-540067; 13 pages.
Notification to Grant Patent Right for Invention dated Mar. 31, 2021, directed to CN Application No. 201680066060.0; 8 pages.
Australian Notice of Allowance dated Jul. 3, 2019 for Australian Patent Application No. 2014408488, filed on Mar. 31, 2017, three pages.
Brazilian Office Action dated May 14, 2019 for Brazilian Application No. PI 0907272-1, filed on Oct. 14, 2010, five pages.
Canadian Office Action dated May 28, 2019 for Canadian Application No. 3,011,310, filed on Jul. 11, 2018, four pages.
Chinese Office Action dated Apr. 26, 2019 for CN Application No. 201580064648.8 filed on May 26, 2017, twenty six pages.
European Notice of Allowance dated Oct. 21, 2015 for EP Application No. 11 826 475.3, filed on Sep. 20, 2010, eight pages.
European Notice of Allowance dated Jul. 16, 2019 for EP Application No. 18166591.0, filed on May 1, 2009, eight pages.
European Notice of Allowance dated Sep. 26, 2019, for Patent Application No. 16163909.1, filed Jan. 25, 2008, 9 pages.
European Summons to Attend the Oral Proceedings mailed on May 31, 2019 for European Application No. 16163909,1 filed on Apr. 5, 2016, two pages.
International Preliminary Report on Patentability completed on Aug. 22, 2019, for PCT/CA2017/050564, filed on May 10, 2017, nine pages.
Japanese Notice of Allowance dated Jun. 7, 2019 for Japanese Patent Application No. 2017-516925 filed on Mar. 28, 2017, six pages.
Japanese Notice of Allowance dated Jun. 21, 2019 for Japanese Patent Application No. 2018-129970, filed on Jul. 9, 2018, six pages.
Japanese Office Action dated Sep. 13, 2019 for Japanese Patent Application No. 2018-153572, filed on Oct. 9, 2014, 7 pages.
Korean Office Action dated Sep. 30, 2019, for Patent Application No. 10-2017-7011565, filed Sep. 28, 2015, 7 pages, including the English translation.
Korean Notice of Allowance dated May 20, 2019 for Korean Patent Application No. 2019-7005800, filed on Feb. 26, 2019, three pages.
Li, X. et al. (May 12, 2004). "Method for Retinal Vessel Detection and Diameter Measurement," Presented at Medical Imaging 2004:Image Processing, San Diego, CA, Proceedings of SPIE 5370:1746-1754.
Martinez-Perez, M.E. et al. (Aug. 2002). "Retinal Vascular Tree Morphology: A Semi-Automatic Quantification," IEEE Transactions of Biomedical Engineering 49(8):912-917.
U.S. Non-Final Office Action dated Jul. 23, 2019, for U.S. Appl. No. 15/517,895, thirteen pages.
U.S. Notice of Allowance dated Jul. 16, 2019, for U.S. Appl. No. 12/776,835, filed May 10, 2010, seven pages.
U.S. Notice of Allowance dated Jul. 10, 2019 for U.S. Appl. No. 15/799,727, filed Oct. 31, 2017, seven pages.
U.S. Appl. No. 16/356,766, filed Mar. 18, 2019, by . (Copy not submitted herewith pursuant to the waiver of 37 C.F.R. §1.98(a)(2)(iii) issued by the Office on Sep. 21, 2004).

\* cited by examiner

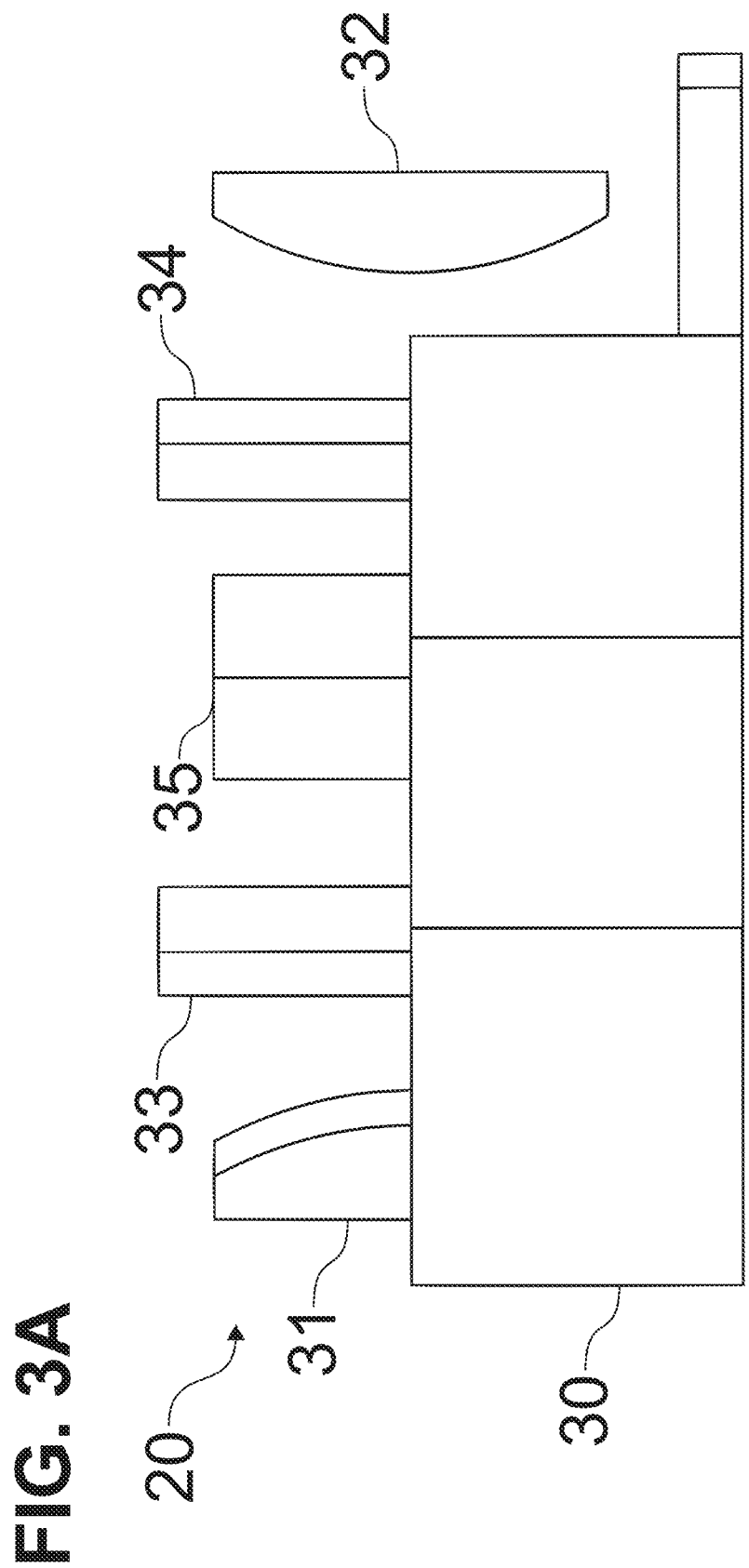

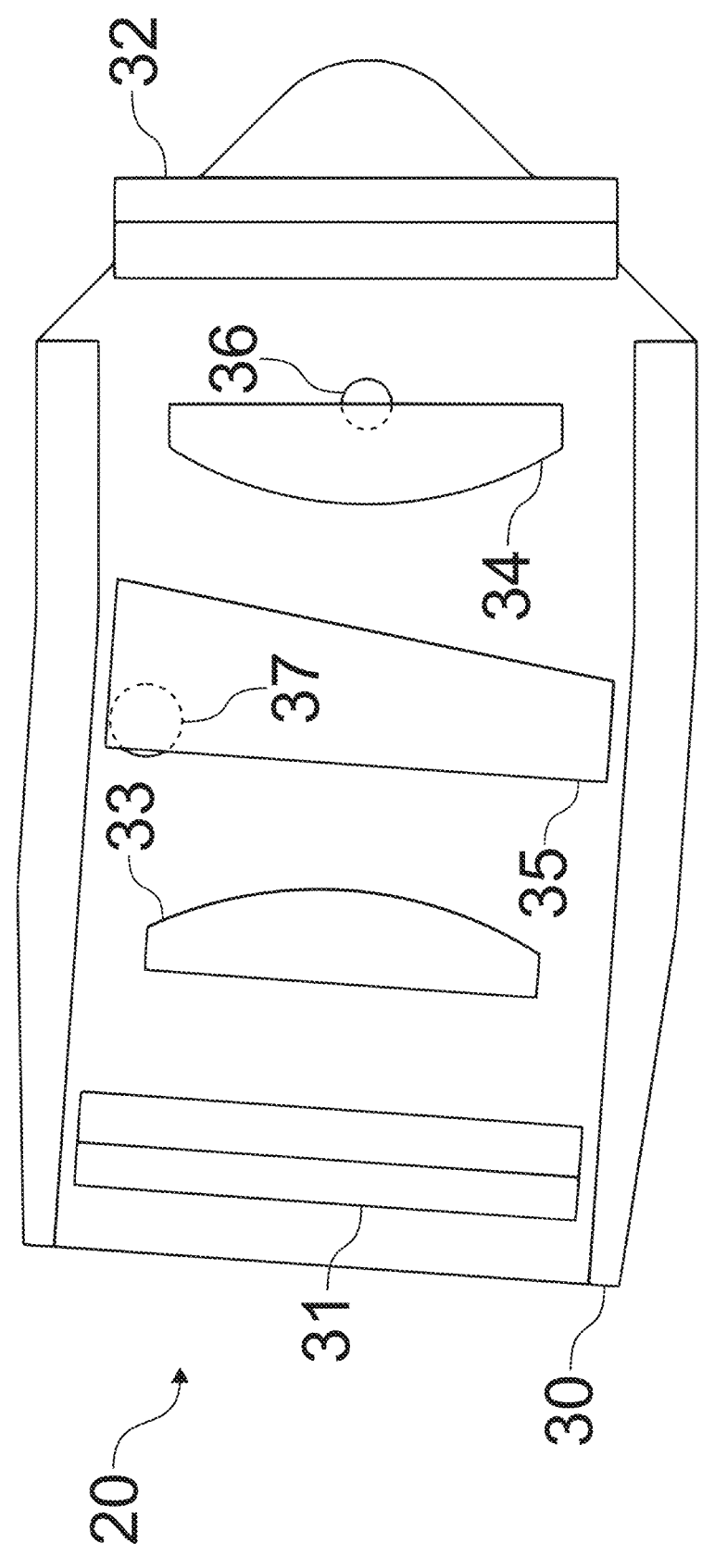

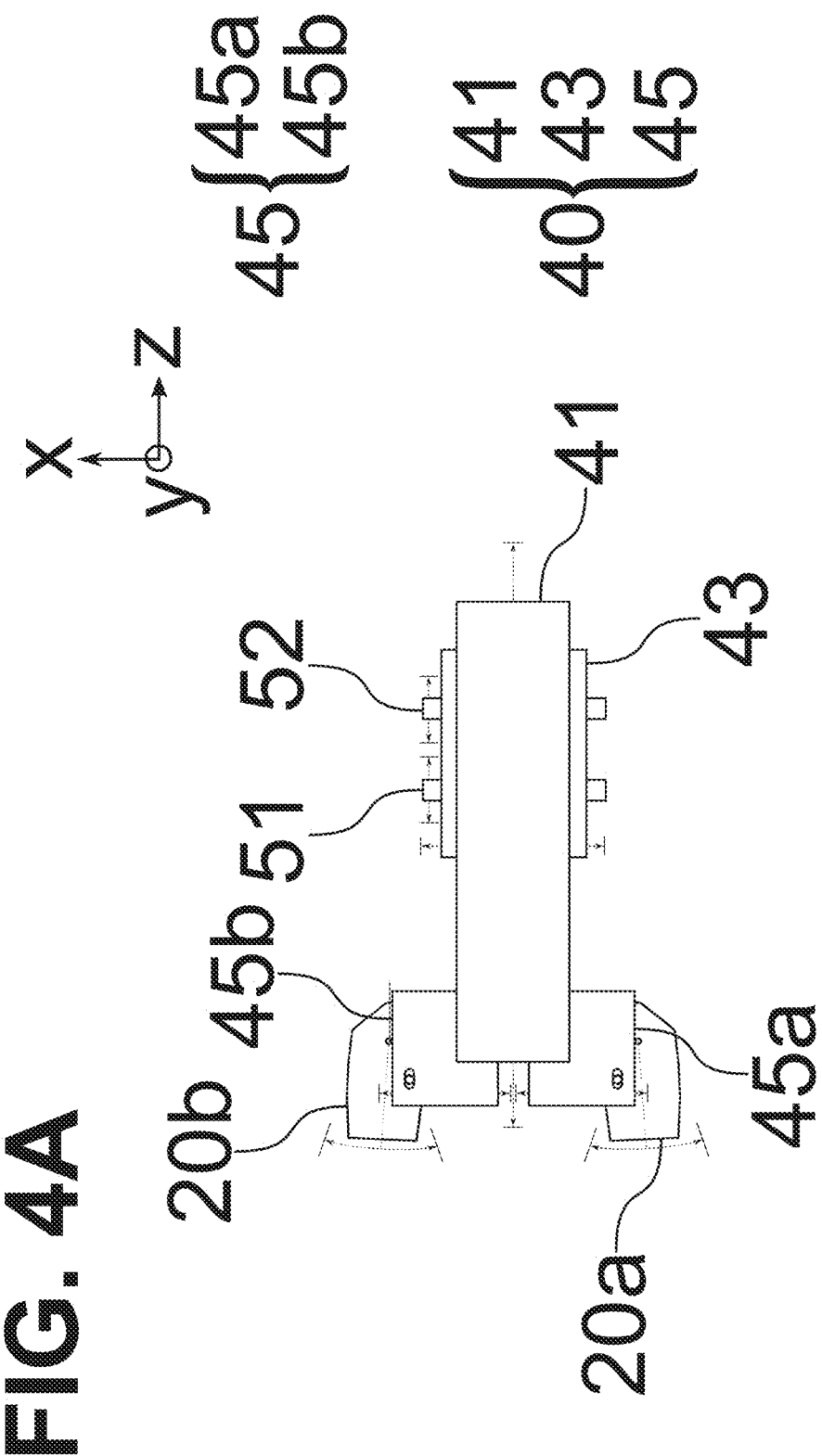

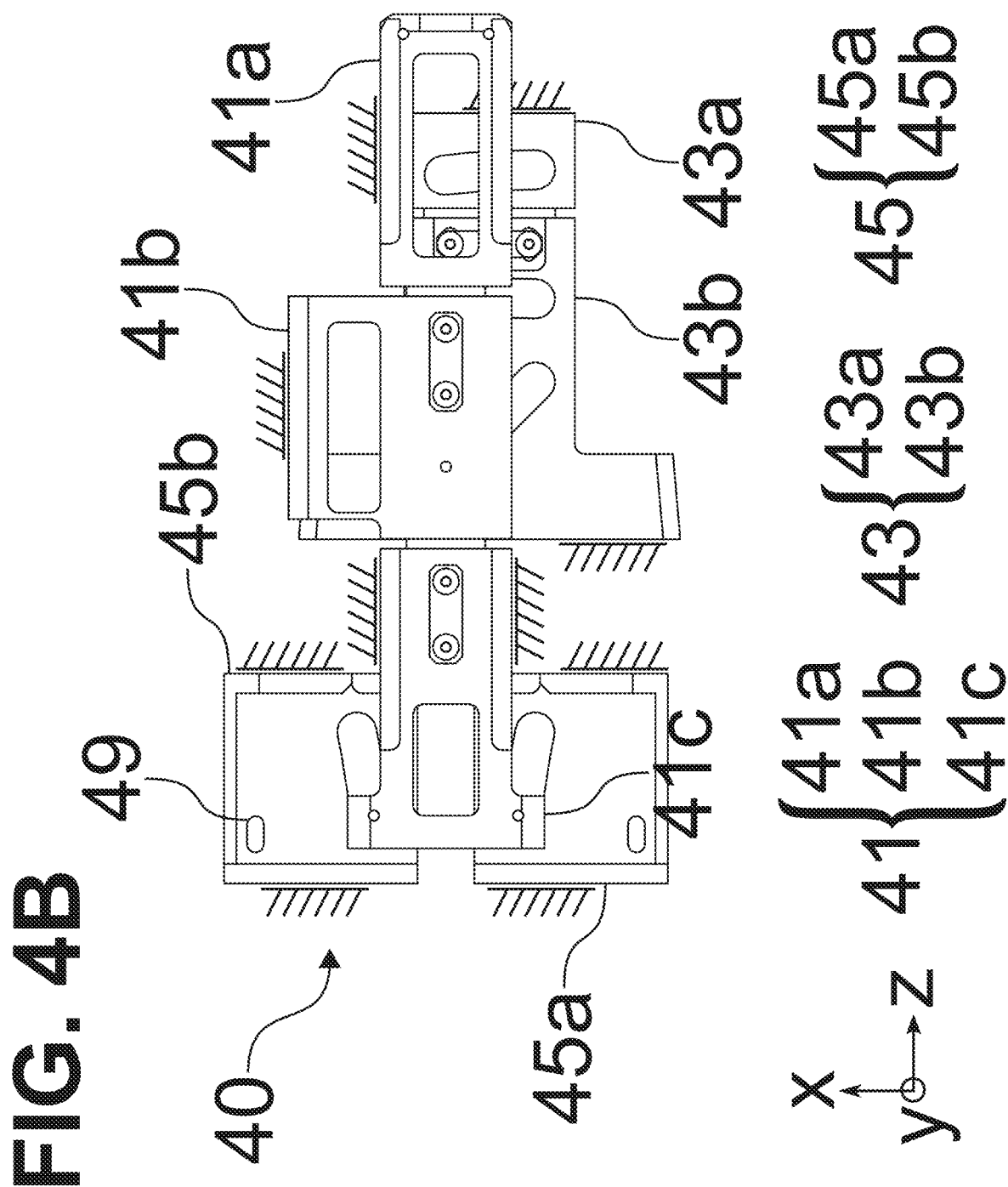

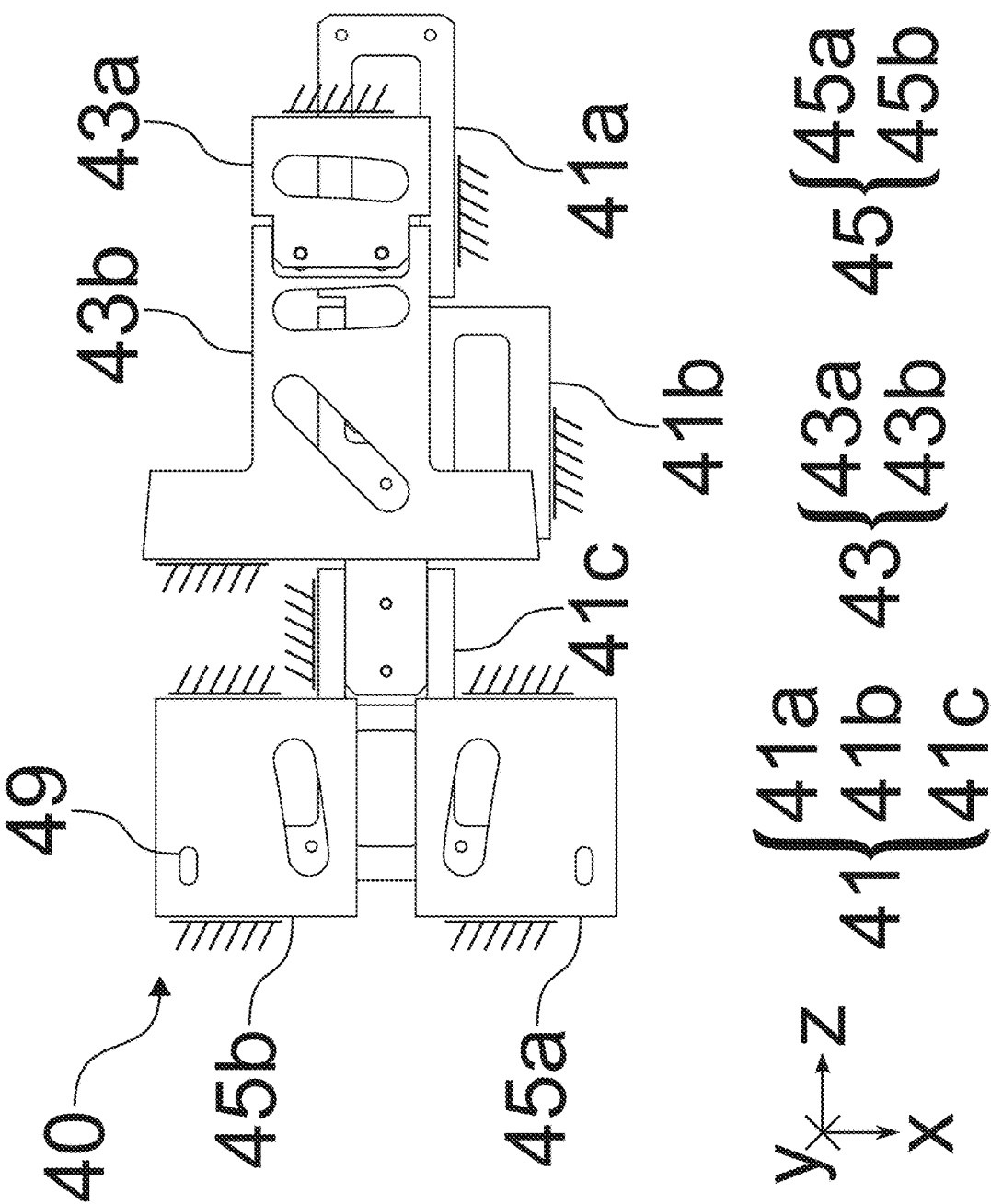

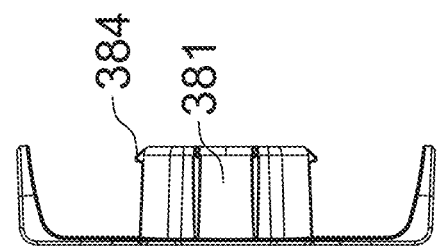
FIG. 9E
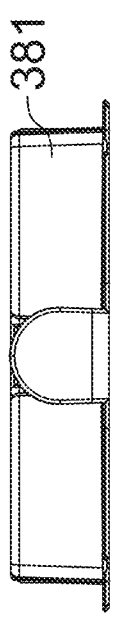
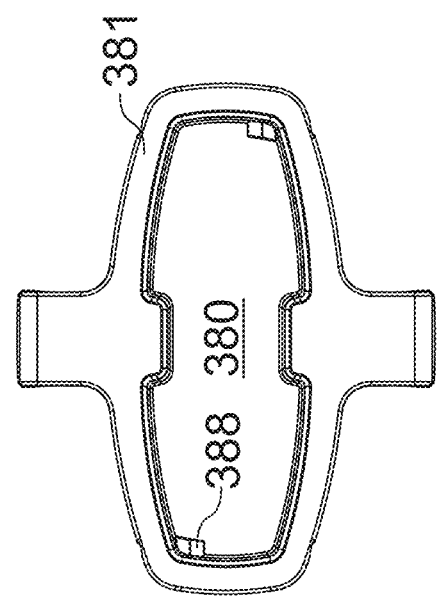
FIG. 9D
FIG. 9C
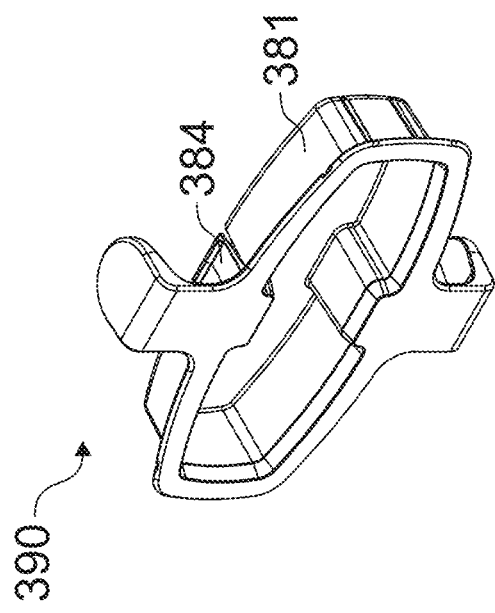
FIG. 9B

SECTION A-A

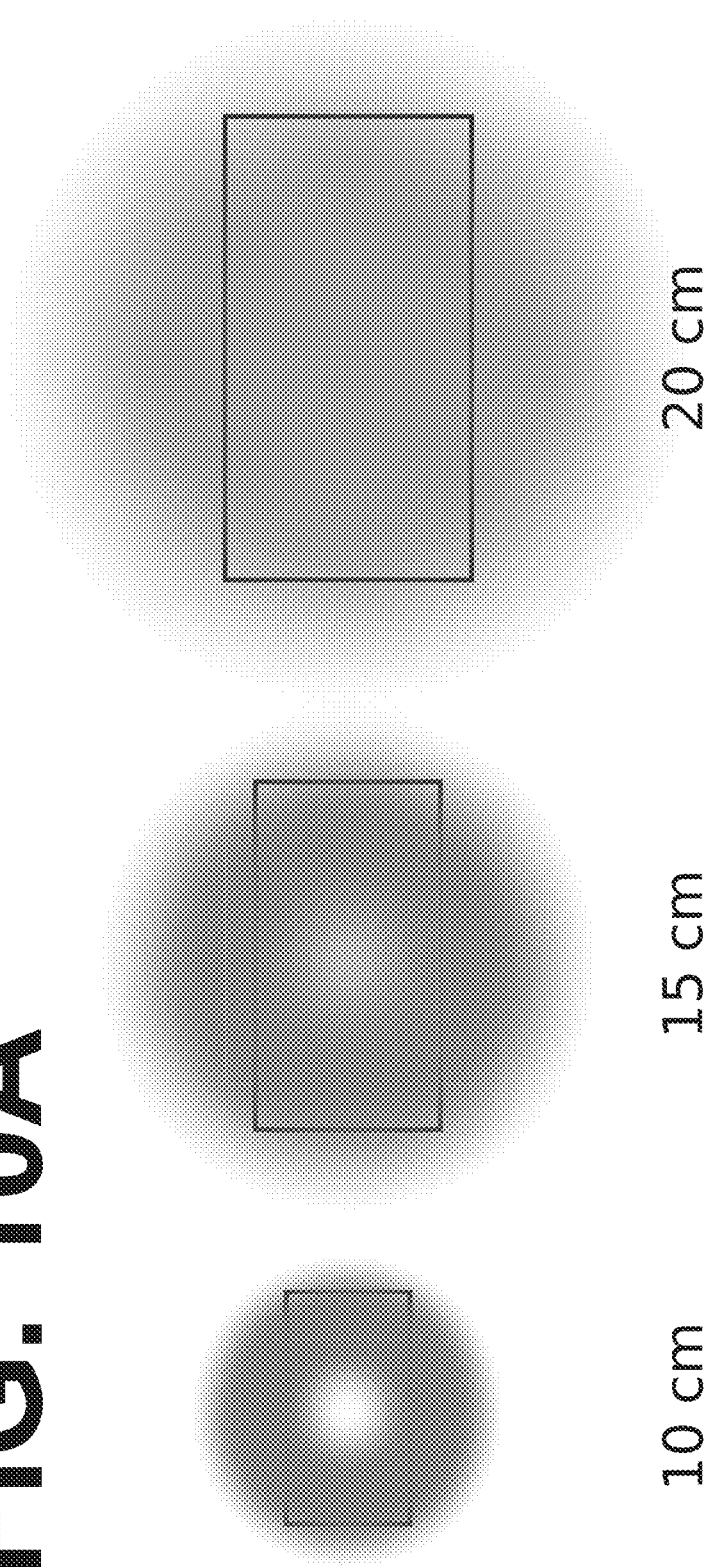

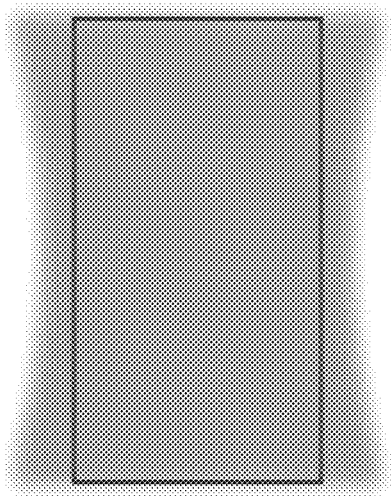
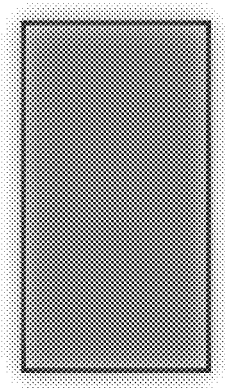
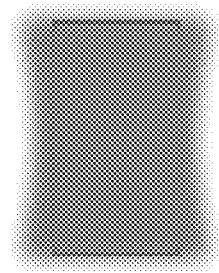
FIG. 10C

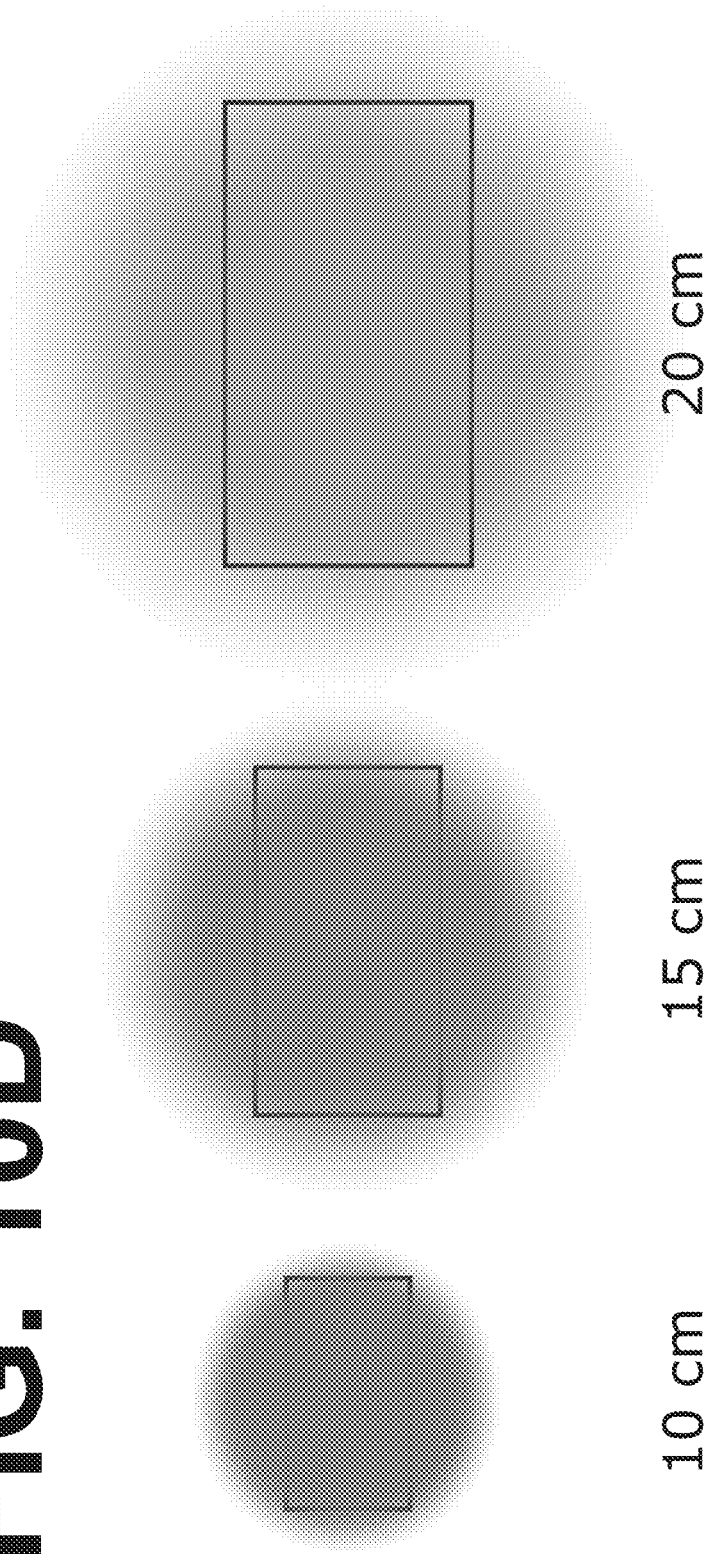

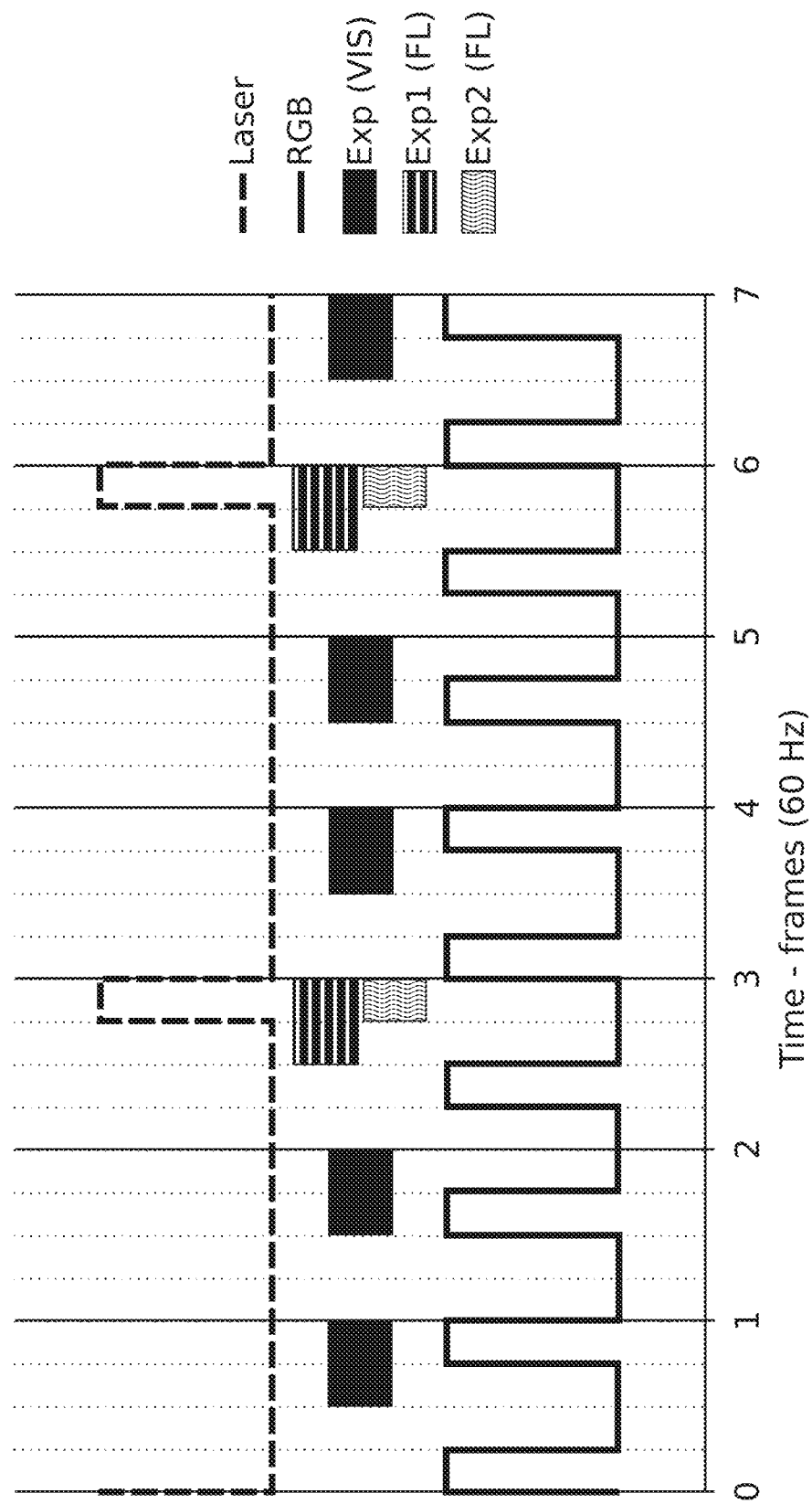

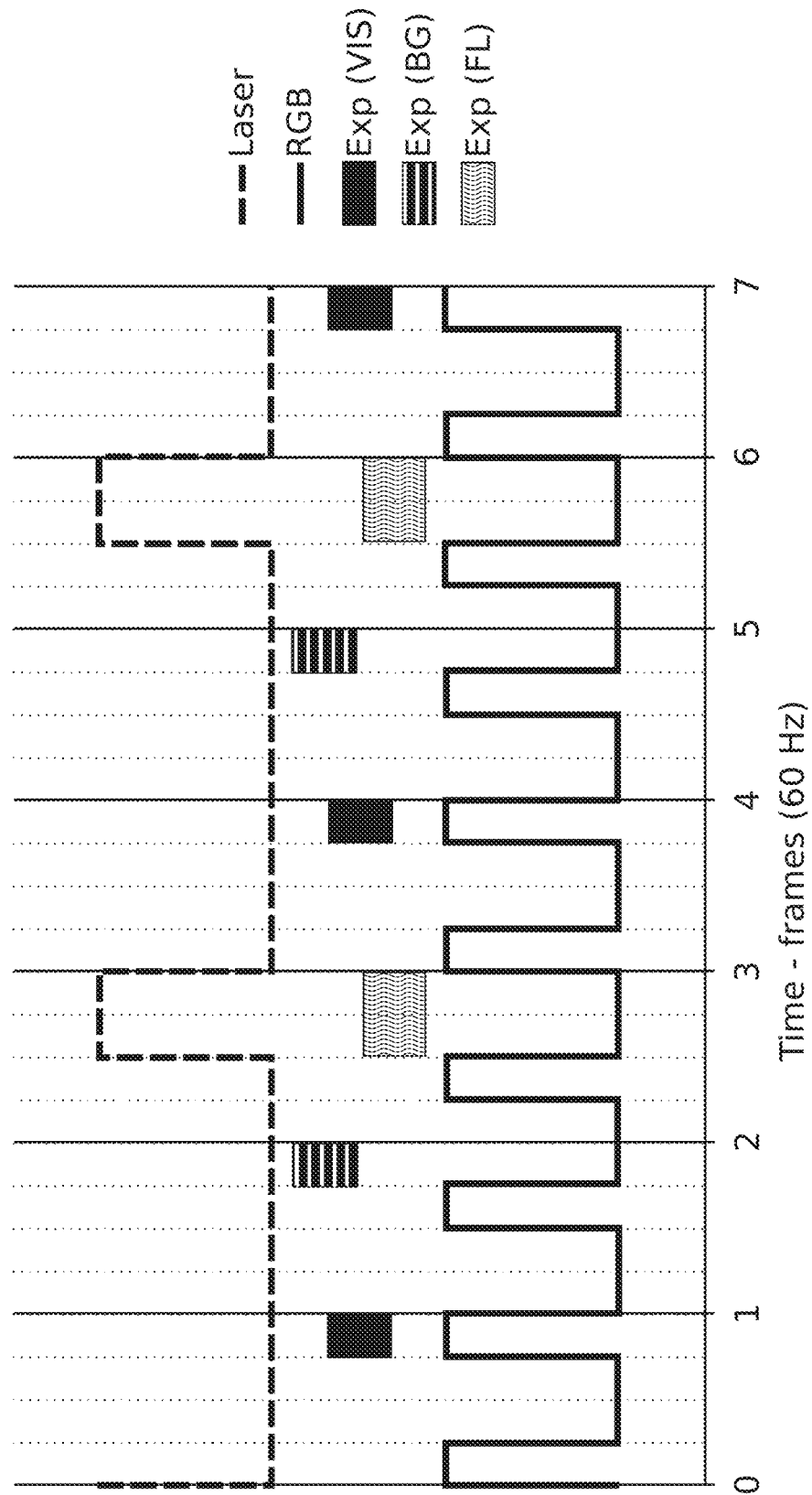

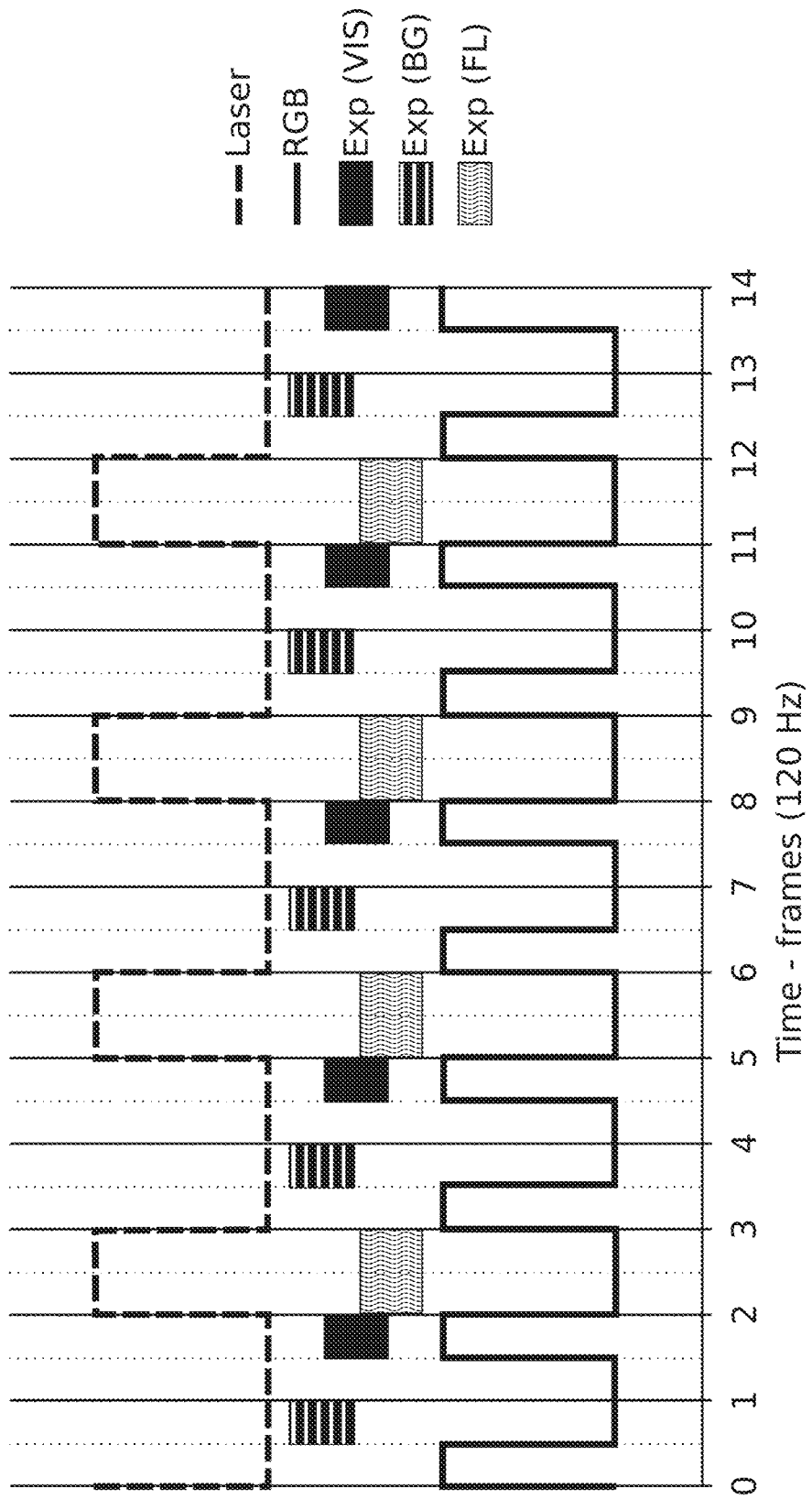

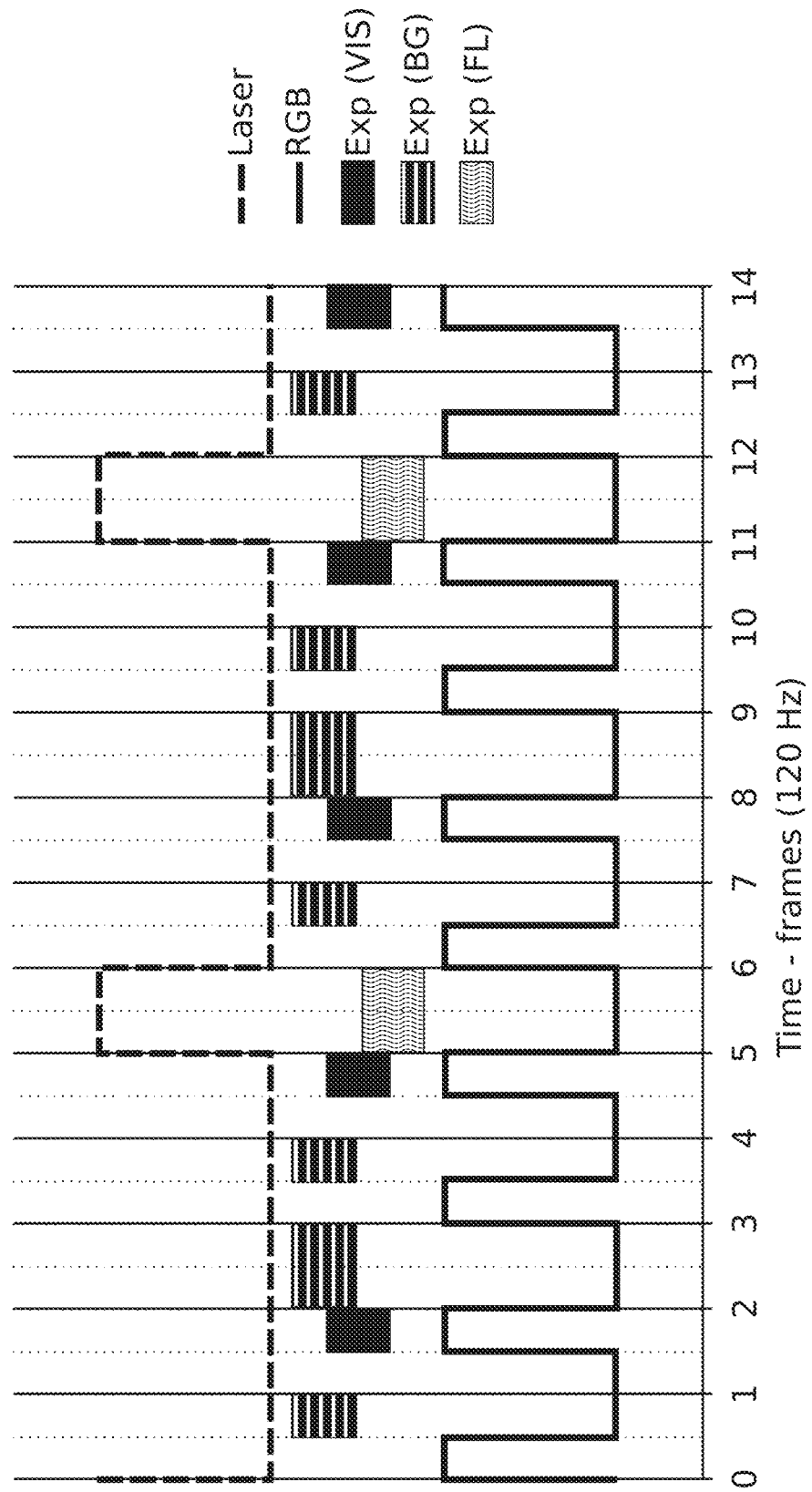

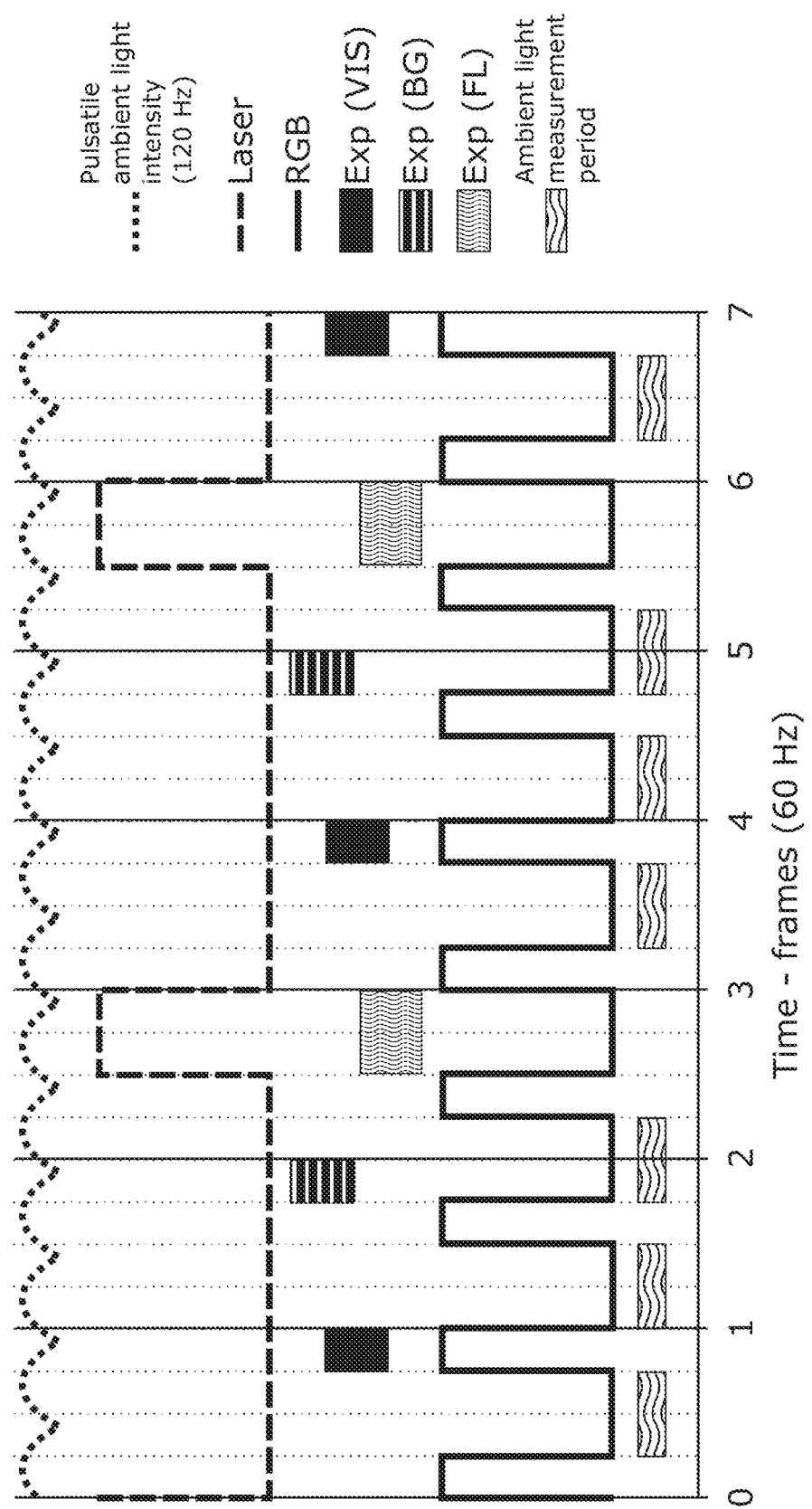

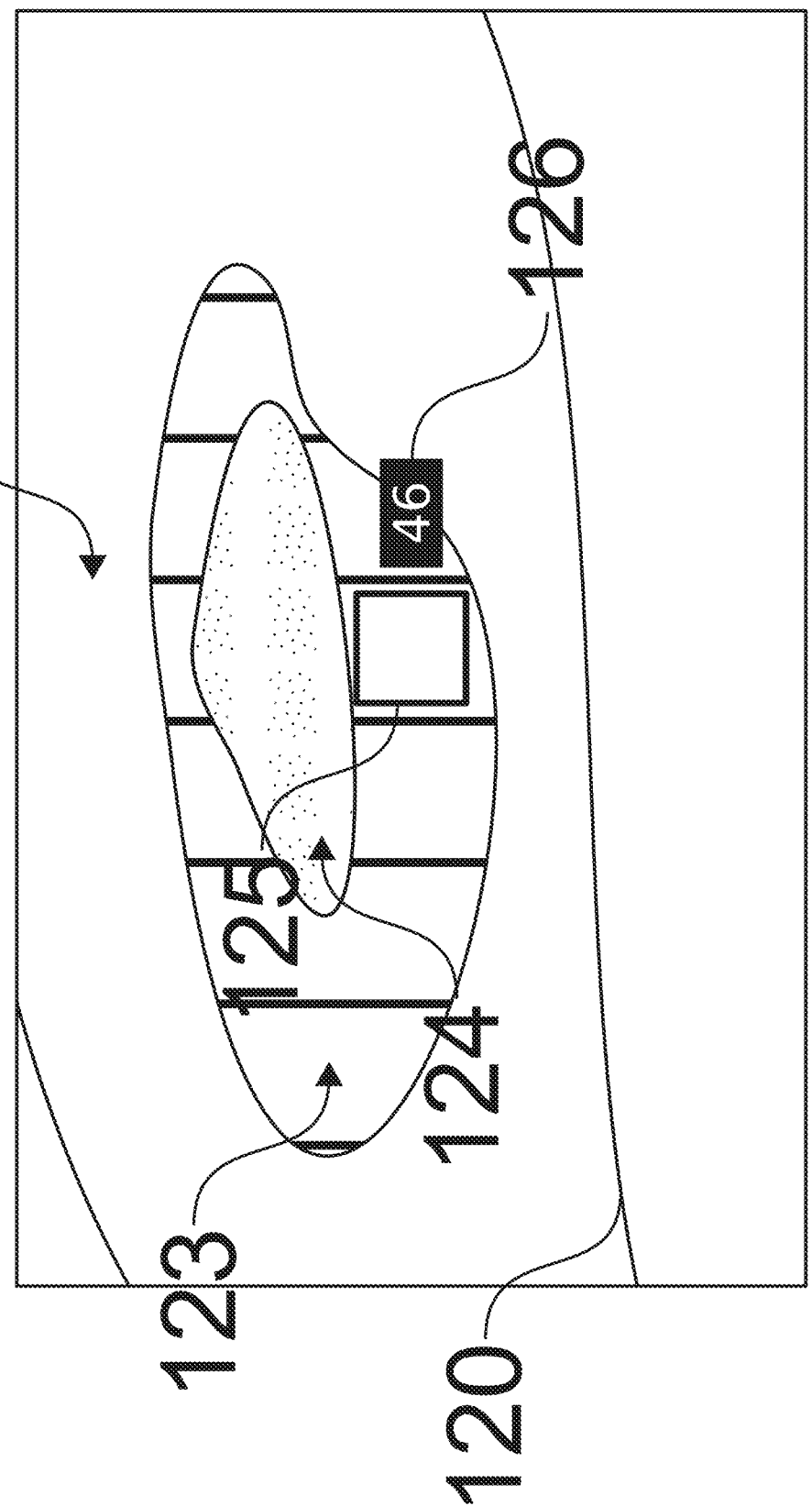

OPEN-FIELD HANDHELD FLUORESCENCE IMAGING SYSTEMS AND METHODS

REFERENCE TO RELATED APPLICATIONS

This application claims priority to U.S. Provisional Application Ser. No. 62/457,690 filed Feb. 10, 2017, titled "OPEN-FIELD HANDHELD FLUORESCENCE IMAGING SYSTEMS AND METHODS," which is hereby incorporated by reference in its entirety.

FIELD OF THE INVENTION

The present disclosure relates generally to medical illumination and imaging. More specifically, the disclosure relates to illumination and imaging of a target material.

BACKGROUND OF THE INVENTION

Illumination is an important component of imaging systems such as, for example, broadband imaging systems with self-contained illumination. In many applications of imaging systems, such as in medical imaging and especially in fluorescence medical imaging, it may be challenging to achieve even, full field illumination of the imaging field of view, and also to provide a sufficient intensity of illumination to yield a sufficiently strong imaging signal. Matching the illumination profile to the imaging field of view is one method of conserving illumination power, while multiple illumination ports may be used to provide even illumination across the field of view. Existing illumination projection in imaging systems may feature anamorphic projection to match the imaging field of view, but typically only feature a single illumination port and are not configured for close working distances. Single port illumination systems result in substantial shadowed regions obscuring vision when illuminating complex topography such as, for example, human anatomical structures or other biological materials. Existing designs for open field surgical imaging and illumination devices may make use of multiple illumination ports to minimize shadowed regions, such as a ring light surrounding the imaging optics, but these designs waste excess illumination that falls outside of the field of view and fail to achieve even illumination of the field of view over a range of working distances.

SUMMARY OF THE INVENTION

According to some embodiments, an imaging device having an imaging field of view may include at least one illumination port configured to output light for illuminating a target; an imaging sensor to detect light traveling along an optical path to the imaging sensor; and a first movable window positioned upstream of the sensor with respect to a direction of travel of light along the optical path, wherein the first movable window is configured to move into the optical path in a deployed position for modifying light received from the target.

In any of these embodiments, the first movable window may be configured to rotate into the optical path in a deployed position.

In any of these embodiments, the first movable window may be configured to translate into the optical path in a deployed position.

In any of these embodiments, the first movable window may extend perpendicularly to an optical axis in the deployed position.

In any of these embodiments, the first movable window may be configured to pivot into the optical path in a deployed position.

In any of these embodiments, the first movable window may be configured to pivot about a first pivot axis extending perpendicularly to an optical axis.

In any of these embodiments, the first movable window may include a filter.

In any of these embodiments, the filter may be configured to filter out visible light.

In any of these embodiments, a second movable window may be positioned upstream of the imaging sensor with respect to the direction of travel of light along the optical path, wherein the second movable window is configured to move into the optical path in a deployed position for modifying light received from the target.

In any of these embodiments, the second movable window may be configured to pivot about a second pivot axis extending perpendicularly to an optical axis.

In any of these embodiments, the first movable window may be configured to pivot about a first pivot axis extending perpendicularly to the optical axis and the first pivot axis and the second pivot axis may be coplanar with a plane extending perpendicularly to the optical axis.

In any of these embodiments, the first movable window and the second movable window may be coupled to a linkage that is configured to simultaneously move the first and second pivoting windows.

In any of these embodiments, when the first movable window is in the deployed position, the second movable window may be moved out of the optical path in a stowed position.

In any of these embodiments, the image sensor may be translatable with respect to the first movable window.

In any of these embodiments, the first movable window may extend perpendicularly to an optical axis in the deployed position and the image sensor may be translatable along the optical axis.

Any of these embodiments may include a first illumination port and a second illumination port, wherein the first illumination port is configured to generate a first illumination distribution at the target, the second illumination port is configured to generate a second illumination distribution at the target, the second illumination port is spaced apart from the first illumination port, the first and second illumination distributions are simultaneously provided to the target and overlap at the target, and the illumination from the first and second ports is matched to a same aspect ratio and field of view coverage as the imaging field of view.

In any of these embodiments, the first and second illumination ports may be fixed with respect to each other.

In any of these embodiments, the at least one illumination port may be configured to output visible light and/or excitation light.

In any of these embodiments, the image sensor may be a single sensor that is configured to detect light from the target resulting from illumination by visible light and excitation light.

In any of these embodiments, the image sensor may comprise separate sensors configured to detect light from the target resulting from illumination by visible light separately from that resulting from illumination by excitation light.

Any of these embodiments may include a wavelength-dependent aperture upstream of the image sensor, wherein the wavelength-dependent aperture is configured to block visible light outside a central region.

Any of these embodiments may include one or more sensors for sensing an amount of light incident on the device.

Any of these embodiments may include a control system configured to adjust at least one image acquisition parameter based on output from the one or more sensors.

In any of these embodiments, the at leak one image acquisition parameter may include an exposure duration, excitation illumination duration, excitation illumination power, or imaging sensor gain.

In any of these embodiments, at least one of the one or more sensors may be configured to sense visible light and near infrared light.

In any of these embodiments, at least one of the one or more sensors may be configured to sense near infrared light.

Any of these embodiments may include one or more drape sensors configured to detect a drape mounted to the device.

Any of these embodiments may include one or more light emitters for emitting light for detection by the one or more drape sensors.

In any of these embodiments, the one or more drape sensors may be configured to detect light emitted from the one or more light emitters after reflection of the emitted light off of one or more reflectors on the drape.

In any of these embodiments, the one or more reflectors may include a prism.

According to some embodiments, an imaging system may include an imaging device according to any one of the above embodiments, an illumination source for providing illumination to the imaging device, and a processor assembly for receiving imaging data generated by the imaging device.

According to some embodiments, a method for imaging a target may include illuminating the target with an illuminator of an imaging device; receiving light from the target at an imaging sensor of the imaging device in a first imaging mode, wherein at least some of the light received at the imaging sensor in the first imaging mode comprises wavelengths in a first band; switching to a second imaging mode; and while in the second imaging mode: blocking light of wavelengths outside of a second band received from the target from reaching the imaging sensor using a first movable filter of the imaging device, wherein at least some of the blocked light comprises wavelengths in the first band, and receiving light of wavelengths within the second band received from the target on the imaging sensor.

In any of these embodiments, the second band may include near infrared wavelengths.

In any of these embodiments, the first band may include visible light wavelengths.

In any of these embodiments, the method may include, while in the second imaging mode, sensing light levels at one or more light level sensors of the imaging device and adjusting one or more of image sensor signal gain, illumination pulse duration, image sensor exposure, and illumination power based on output of the one or more light level sensors.

In any of these embodiments, the method may include, while in the first imaging mode, sensing light levels at one or more light level sensors of the imaging device and adjusting one or more of image sensor signal gain, illumination pulse duration, image sensor exposure, and illumination power based on output of the one or more light level sensors.

In any of these embodiments, switching to the second imaging mode may include moving the first movable filter into an optical path along which light from the target travels to the imaging sensor.

In any of these embodiments, switching to the second imaging mode may include moving a clear window out of the optical path.

In any of these embodiments, switching to the second imaging mode may include moving a second movable filter out of the optical path.

In any of these embodiments, the first imaging mode may be switched to the second imaging mode in response to a user request.

In any of these embodiments, the user request may include a user input to the imaging device.

In any of these embodiments, the method may include, while in the second imaging mode, receiving a request from the user to switch to the first imaging mode; and in response to receiving the request from the user to switch to the first imaging mode, moving the movable filter out of the optical path.

In any of these embodiments, the method may include, while in the second imaging mode, sensing light levels at one or more light level sensors of the imaging device and adjusting one or more of image sensor signal gain, illumination pulse duration, image sensor exposure, and illumination power based on output of the one or more light level sensors; and in response to receiving the request from the user to switch to the first imaging mode, ceasing to adjust one or more of image sensor signal gain, illumination pulse duration, image sensor exposure, and illumination power based on output of the one or more light level sensors.

In any of these embodiments, the method may include detecting an object at least partially blocking an illumination beam of the illuminator, and in response to detecting the object, adjusting an illumination power of the illuminator.

According to some embodiments, a kit for imaging an object may include a fluorescence imaging agent and the device of any one of the above embodiments or the system of any one of the above embodiments.

According to some embodiments, a fluorescence imaging agent may include a fluorescence imaging agent for use with the device of any one of the above embodiments, the system of any one of the above embodiments, the method of any one of the above embodiments, or the kit of any one of the above embodiments.

In any of these embodiments, imaging an object may include imaging an object during blood flow imaging, tissue perfusion imaging, lymphatic imaging, or a combination thereof.

In any of these embodiments, blood flow imaging, tissue perfusion imaging, and/or lymphatic imaging may include blood flow imaging, tissue perfusion imaging, and/or lymphatic imaging during an invasive surgical procedure, a minimally invasive surgical procedure, or during a non-invasive surgical procedure.

In any of these embodiments, the invasive surgical procedure may include a cardiac-related surgical procedure or a reconstructive surgical procedure.

In any of these embodiments, the cardiac-related surgical procedure may include a cardiac coronary artery bypass graft (CABG) procedure.

In any of these embodiments, the CABG procedure may include on pump or off pump.

In any of these embodiments, the non-invasive surgical procedure may include a wound care procedure.

In any of these embodiments, the lymphatic imaging may include identification of a lymph node, lymph node drainage, lymphatic mapping, or a combination thereof.

In any of these embodiments, the lymphatic imaging may relate to the female reproductive system.

According to some embodiments, a system for imaging a target includes one or more processors; memory; and one or more programs, wherein the one or more programs are stored in the memory and configured to be executed by the one or more processors, the one or more programs including instructions for, within a period: activating an excitation light source to generate an excitation pulse to illuminate the target; receiving an ambient light intensity signal from a sensor during a portion of the period in which the excitation light source is not activated; exposing an image sensor for a fluorescent exposure time during the excitation pulse; receiving outputs from the image sensor; compensating for ambient light based on the ambient light intensity signal; and storing a resultant image in the memory.

In any of these embodiments, the one or more programs may include instructions for, within the period: activating a white light source to generate a white light pulse to illuminate the target such that the white light pulse does not overlap the excitation pulse; and exposing the image sensor for a visible exposure time during at least one white light pulse.

In any of these embodiments, the one or more programs may include instructions for exposing the image sensor for a background exposure time when the target is not illuminated.

In any of these embodiments, the one or more programs may include instructions for detecting a periodic frequency of the ambient light intensity.

In any of these embodiments, compensating for ambient light may include setting an image acquisition frame rate equal to a multiple or a factor of the periodic frequency prior to exposing the image sensor for the background exposure time and prior to exposing the image sensor for the fluorescent exposure time during the excitation pulse; and subtracting image sensor output received for the background exposure time from the image sensor output received for the fluorescence exposure time to form the resultant image.

In any of these embodiments, compensating for ambient light may include synthesizing or extracting, from one or more received ambient light intensity signals, a complete periodic cycle of ambient light intensity having the detected periodic frequency; extending the ambient light intensity periodic cycle to a time period corresponding to the fluorescence exposure time; calculating a first accumulated ambient light value corresponding to an area under the curve of ambient light intensity during a background exposure time; calculating a second accumulated ambient light value corresponding to an area under the curve of the ambient light intensity during the fluorescence exposure time; scaling the received image sensor output for the background exposure time and the received image sensor output for the fluorescence exposure time based on a ratio of the first and second accumulated ambient light values; and subtracting the scaled image sensor output for the background exposure time from the scaled image sensor output for the fluorescence exposure time to form the resultant image.

In any of these embodiments, the one or more programs may include instructions for receiving an ambient light intensity signal from the sensor during the background exposure time.

In any of these embodiments, the one or more programs may include instructions for extending the ambient light intensity periodic cycle to the time period corresponding to the fluorescence exposure time.

According to some embodiments, a method for imaging a target includes, at a system having one or more processors and memory, activating an excitation light source to generate an excitation pulse to illuminate the target; receiving an ambient light intensity signal from a sensor during a portion of the period in which the excitation light source is not activated; exposing an image sensor for a fluorescent exposure time during the excitation pulse; receiving outputs from the image sensor; compensating for ambient light based on the ambient light intensity signal; and storing a resultant image in the memory.

In any of these embodiments, the method may include, within the period, activating a white light source to generate a white light pulse to illuminate the target such that the white light pulse does not overlap the excitation pulse; and exposing the image sensor for a visible exposure time during at least one white light pulse.

In any of these embodiments, the method may include exposing the image sensor for a background exposure time when the target is not illuminated.

In any of these embodiments, the method may include detecting a periodic frequency of the ambient light intensity.

In any of these embodiments, compensating for ambient light may include setting an image acquisition frame rate equal to a multiple or a factor of the periodic frequency prior to exposing the image sensor for the background exposure time and prior to exposing the image sensor for the fluorescent exposure time during the excitation pulse; and subtracting image sensor output received for the background exposure time from the image sensor output received for the fluorescence exposure time to form the resultant image.

In any of these embodiments, compensating for ambient light may include synthesizing or extracting, from one or more received ambient light intensity signals, a complete periodic cycle of ambient light intensity having the detected periodic frequency; extending the ambient light intensity periodic cycle to a time period corresponding to the fluorescence exposure time; calculating a first accumulated ambient light value corresponding to an area under the curve of ambient light intensity during a background exposure time; calculating a second accumulated ambient light value corresponding to an area under the curve of the ambient light intensity during the fluorescence exposure time; scaling the received image sensor output for the background exposure time and the received image sensor output for the fluorescence exposure time based on a ratio of the first and second accumulated ambient light values; and subtracting the scaled image sensor output for the background exposure time from the scaled image sensor output for the fluorescence exposure time to form the resultant image.

In any of these embodiments, the method may include receiving an ambient light intensity signal from the sensor during the background exposure time.

In any of these embodiments, the method may include extending the ambient light intensity periodic cycle to the time period corresponding to the fluorescence exposure time.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Features will become apparent to those of ordinary skill in the art by describing in detail exemplary embodiments with reference to the attached drawings in which:

FIGS. 3A and 3B illustrate a schematic side view and plan view, respectively, of an exemplary lens module in a steerable housing according to an embodiment;

FIG. 4A illustrates a schematic view of a linkage for synchronous focusing of the imaging system and steering of the illumination system according to embodiments;

FIGS. 4B and 4C illustrate a bottom view and a top view, respectively, of a linkage for synchronous focusing of the imaging system and steering of the illumination system according to embodiments;

FIGS. 9B to 9E illustrate perspective, front, top, and side views, respectively, of a drape lens and frame for use with the system according to an embodiment.

FIGS. 10A to 10D illustrate illumination distributions for different illumination configurations;

FIG. 11A illustrates a timing diagram for visible and excitation illumination and image sensor exposures according to an embodiment;

FIG. 11B illustrates a timing diagram for visible and excitation illumination and image sensor exposures according to an embodiment;

FIG. 11C illustrates a timing diagram for visible and excitation illumination and image sensor exposures according to an embodiment;

FIG. 11D illustrates a timing diagram for visible and excitation illumination and image sensor exposures according to an embodiment;

FIG. 11E illustrates a timing diagram for visible and excitation illumination, image sensor exposures and ambient light measurement according to an embodiment;

FIGS. 12A to 12C illustrate pixel layout and an interpolation scheme according to an embodiment;

FIGS. 13A to 13C illustrate diagrams of an embodiment of a display method output when a target reticle is placed over regions with no fluorescence intensity, high relative normalized fluorescence intensity, and moderate relative normalized fluorescence intensity, respectively;

DETAILED DESCRIPTION OF THE INVENTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. Various devices, systems, methods, processors, kits and imaging agents are described herein. Although at least two variations of the devices, systems, methods, processors, kits and imaging agents are described, other variations may include aspects of the devices, systems, methods, processors, kits and imaging agents described herein combined in any suitable manner having combinations of all or some of the aspects described.

Generally, corresponding or similar reference numbers will be used, when possible, throughout the drawings to refer to the same or corresponding parts.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Figure 1:
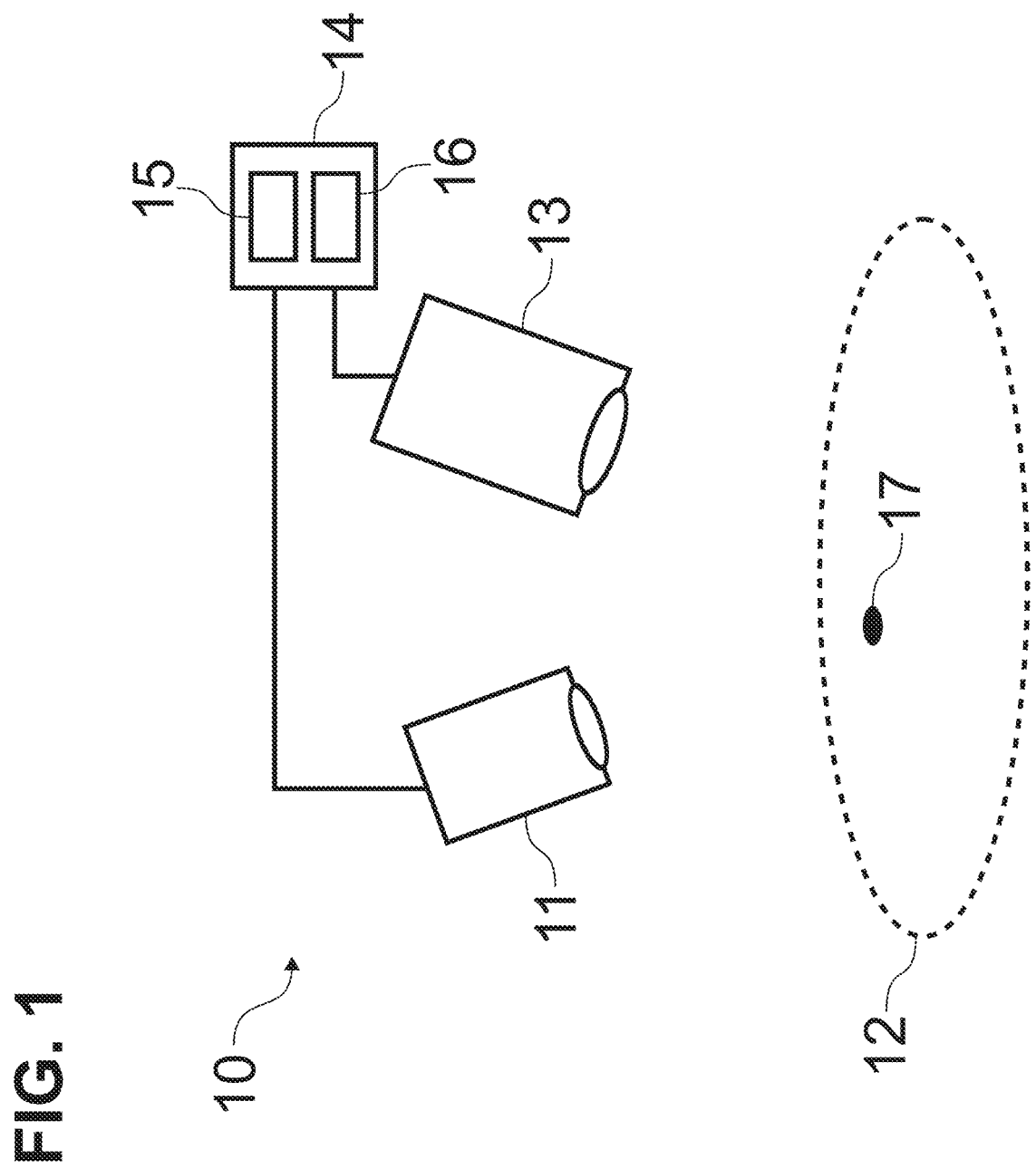
FIG. 1 illustrates a schematic view of a system for illumination and imaging according to an embodiment.

FIG. 1 illustrates a schematic view of an illumination and imaging system 10 according to an embodiment. As may be seen therein, the system 10 may include an illumination module 11, an imaging module 13, and a video processor/illuminator (VPI) 14. The VPI 14 may include an illumination source 15 to provide illumination to the illumination module 11 and a processor assembly 16 to send control signals and to receive data about light detected by the imaging module 13 from a target 12 illuminated by light output by the illumination module 11. In one variation, the video processor/illuminator 14 may comprise a separately housed illumination source 15 and the processor assembly 16. In one variation, the video processor/illuminator 14 may comprise the processor assembly 16 while one or more illumination sources 15 are separately contained within the housing of the illumination module 11. The illumination source 15 may output light at different waveband regions, e.g., white (RGB) light, excitation light to induce fluorescence in the target 12, a combination thereof and so forth, depending on characteristics to be examined and the material of the target 12. Light at different wavebands may be output by the illumination source 15 simultaneously, sequentially, or both. The illumination and imaging system 10 may be used, for example, to facilitate medical (e.g., surgical) decision making e.g., during a surgical procedure. The target 12 may be a topographically complex target, e.g., a biological material including tissue, an anatomical structure, other objects with contours and shapes resulting in shadowing when illuminated, and so forth. The VPI 14 may record, process, display, and so forth, the resulting images and associated information.

Figure 2:
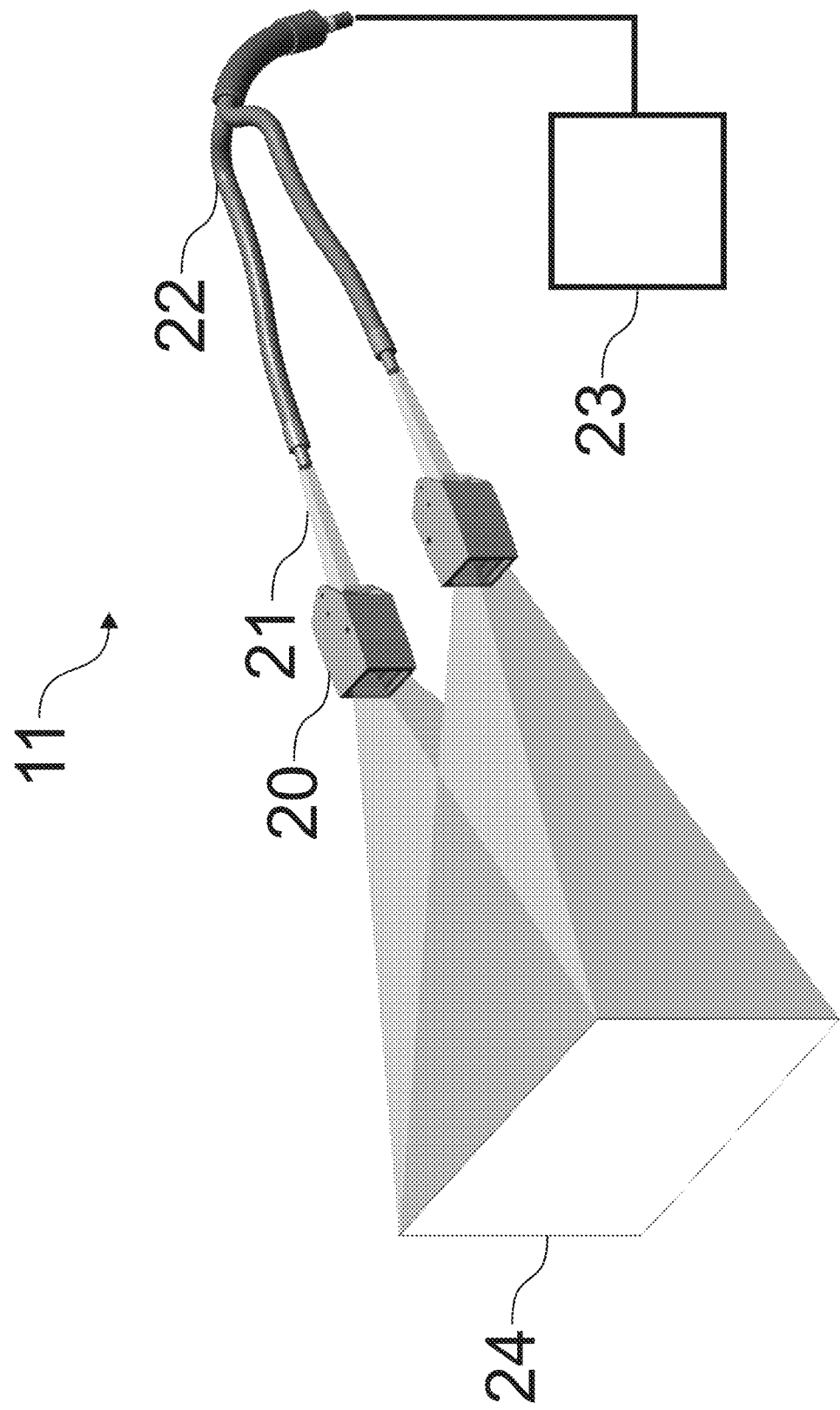
FIG. 2 illustrates a schematic view of an illumination module according to an embodiment.

FIG. 2 illustrates a schematic perspective view of the illumination module 11 of FIG. 1 according to an embodiment. As may be seen therein, the illumination module 11 may include at least two illumination ports directing illumination from an illumination source 23, which may be included in the VPI box 14, to for example a rectangular target field 24. In some variations, the illumination source 23 may be located in a device housing along with the illumination module 11. Each illumination port is to provide illumination over the target field 24, such that the light overlaps, e.g., substantially or completely, at the target material 12 (shown in FIG. 1). More than two illumination ports may be used. The illumination distributions may be substantially similar and overlap (e.g., substantially or completely) at the target 12 to provide uniform illumination of the target 12. The use of at least two illumination ports facilitates reducing the effect of shadowing due to anatomical topography, and aids in providing uniform illumination over the target field 24. Directing illumination from the illumination module 11 to a rectangular target field 24 (which may have a configuration other than rectangular in other embodiments) allows matching the region of illumination to a rectangular imaging field of view (which may have a configuration other than rectangular in other embodiments), which aids in providing uniform illumination and may enhance efficiency of the illumination module by reducing extraneous illumination. Matching the illumination field to the imaging field of view also provides a useful indication of the location and extent of the anatomical region currently being imaged. In some variations, illumination from the illumination module 11 may be directed to provide uniform illumination of the target 12 without matching the region of illumination to a rectangular imaging field of view, and the rectangular target field 24 of FIG. 2 may be replaced by a non-rectangular target field.

In some embodiments, a light pipe may be used to achieve mixing of the illumination light in order to yield a uniform illumination profile. Mixing of the illumination light by a light pipe may remove the influence of the structure of the light source on the illumination profile, which could otherwise adversely affect uniformity of the illumination profile. For example, using a light pipe to mix the illumination light output from a fiber optic light guide may remove images of the structure of the individual optical fibers from the illumination profile. In some embodiments, a rectangular light pipe may be used to efficiently utilize illumination power while matching the illumination profile to a rectangular imaging field of view. In some embodiments, a light pipe material with a high index of refraction for both visible light and near infrared light, such as optical glass material N-SF11, may be used for high efficiency of illumination power transmission.

According to some embodiments, a rectangular light pipe with an aspect ratio matching the aspect ratio of the imaging field of view (e.g., both aspect ratios being 16:9) may be used in conjunction with rotationally symmetric illumination optic elements.

According to some embodiments, a rectangular light pipe with a different aspect ratio than the imaging field of view (e.g., a square light pipe along with a 16:9 imaging field of view aspect ratio) may be used in conjunction with cylindrical illumination optic elements. Cylindrical optic elements may be used to separately conform one or both dimensions of the rectangular illumination profile to match the aspect ratio of the imaging field of view.

Depending on the desired system requirements for range of working distance and illumination uniformity various approaches may be used for matching the illumination to overlap the imaging field of view. For example, applications which require a large range in working distances and high illumination uniformity may necessitate use of illumination optics and/or ports that are steered dynamically to adequately match the illumination to the imaging field of view, while applications with lower requirements may be served with fixed illumination optics and/or ports to match the illumination to the field of view.

In some embodiments, the direction of illumination is adjusted from multiple illumination ports in synchrony with adjustment of the field of view, in order to steer the field of illumination to maintain correspondence to the field of view.

In some embodiments, one or more illumination optic elements may be rotated by a driver in order to steer the illumination.

In some embodiments, one or more illumination optic elements may be translated perpendicular to the imaging optic axis by a driver in order to steer the illumination.

In some embodiments, one or more illumination optic elements may be configured to provide some distortion in the illumination profile, in order to account for distortion inherent to the accompanying imaging system.

In some embodiments, uniform illumination of the imaging field of view over a specified range of working distances may be achieved with a fixed location and orientation of the illumination optics. The offset distance of the illumination optics from the imaging optic axis may be configured, along with the orientation of the of the illumination optics, in order to optimize matching of the illumination profile to the imaging field of view at a working distance within the specified range of working distances while also maintaining substantial matching of the illumination profile to the imaging field of view at other working distances within the specified range.

As is illustrated in FIG. 2, each illumination port may include a lens module 20, a connecting cable 22 connected to the illumination light source 23, and a light pipe 21 adapting a high numerical aperture of the connecting cable 22 to a lower numerical aperture of the lens module 20. The lens module 20 may be steerable, as described in detail below. In some scenarios, acceptable performance may be achievable without steering. In other words, an illumination module, and imaging device having the same, that provides an illumination field having a rectangular form factor (or configuration other than rectangular) that matches the field of view of the imaging system using at least two illumination ports in which each port produces a gradient of illumination such that the sum illumination flux in the object plane is reasonably e same at each point in the illumination field, e.g., provides uniform illumination over the imaging field of view, alone may be sufficient.

In some variations in which the illumination light source 23 may be contained within a device housing along with illumination module 11, the connecting cable 22 from FIG. 2 may be replaced by one or more illumination light sources 23. In some variations, the connecting cable 22 and the light pipes 21 from FIG. 2 may be replaced by one or more illumination light sources 23. In some variations, the lens module 20 from FIG. 2 may contain the illumination light source 23. In some variations, separate variants of the lens module 20 from FIG. 2 may separately contain a white light source and a fluorescence excitation light source of the illumination light source 23. In one embodiment, three or more lens modules 20 may be arranged to comprise a ring of illumination ports, another functionally equivalent configuration of illumination ports, or another configuration including continuous or non-continuous distribution/arrangement of illumination ports, with each lens module 20 oriented to converge on and provide uniform illumination over the imaging field of view. In some variations, the three or more lens modules 20 comprising a ring of illumination ports may not necessarily constrain illumination to a rectangular field, and the rectangular target field 24 of FIG. 2 may be replaced by a non-rectangular target field, such as for example a circular/oval target field.

FIGS. 3A and 3B illustrate a side view and a plan view, respectively, of the lens module 20. The lens module 20 may include lenses mounted in a steerable lens housing 30. As used herein, a lens is any optical element having optical power, whether implemented by a refractive or diffractive element. Other elements not essential to understanding, such as a cover enclosing the lens module (see FIG. 2), are not shown for ease of illustration.

In the particular example shown herein, the lenses may include a pair of horizontal-axis cylindrical lenses 31-32 and a pair of vertical-axis cylindrical lenses 33-34. A prism element 35 is also shown which may align illumination light with the intended outgoing optical axis. In particular, the prism element 35 corrects for an angle introduced by the light pipe 21 for increased device compactness in accordance with an embodiment. The mounting design for each lens element 31-35 may allow for tuning of the magnification and focus of the illumination optical system. In accordance with this embodiment, the steerable lens housing 30 encloses and steers three of the cylindrical lenses 31, 33, 34 and the prism lens element 35, e.g., collectively as a group. This example of lenses is merely illustrative, and the lenses in the lens module 20 may be modified as appropriate.

In this particular embodiment, a base portion of the steerable housing 30 is pinned, e.g., using a pin 46 (see FIG. 6B) inserted into housing hole 37, about a pivot point 36, respectively to a fixed chassis frame 90 (see FIG. 6A) and a mechanical linkage 40 (see FIGS. 4A to 4C) described in detail below, while lens 32 is rigidly connected the chassis 90, i.e. not to the housing 30 (see FIG. 6B).

FIG. 4A illustrates a schematic view showing directions of motion provided by various components of the linkage 40. The linkage 40 may include a drive cam 41, illumination cams 45a, 45b (one for each illumination port), and an imaging cam 43. The drive cam 41 receives an input from a user (see FIG. 7), and translates that to synchronous motion of the lens module 20a, 20b, attached to a corresponding illumination cam 45a, 45b, via a respective housing 30 (see FIG. 3B) and a pin 46 (see FIG. 6B), and an imaging lens 51 and an imaging sensor 52. (see FIGS. 5A and 5B), attached to the imaging cam 43 via cam follower pins. Here, the imaging lens 51 is shown as a single field lens, but additional and/or alternative lenses for focusing light from the target 20 onto the imaging sensor 52 may be employed. Each port has its own associated illumination cam 45A or 45B, here shown as being to a left and right of an input window to receive light from the target 12. Here, drive cam 41 is shown as a plate with a front edge extending beyond the rear of the lens modules 20a, 20b, but the drive cam 41 need not be in the form of a plate and may instead comprise multiple surfaces to interface with and drive three or more lens modules, in which case the front edge of the drive cam 41 and the rear edges of illumination cams 45a, 45b may be set further to the rear in order to accommodate additional lens modules and corresponding illumination cams.

In particular, translation of the drive cam 41 may translate the imaging cam 43 along the x-axis, which, in turn, may result in the imaging cam 43 to translate the imaging lens 51 and the imaging sensor 52 along the z-axis, as well as translate the illumination cams 45a, 45b, which, in turn, simultaneously steer corresponding lens modules 20a, 20b about respective pivot points 36, such that steering of the lens modules 20a, 20b is synchronously performed with the position adjustment of the imaging lens 51 and the imaging sensor 52 to insure proper focus of light from the target onto the sensor 52. Alternatively, the imaging cam 43 may translate only the imaging lens 51 along the z-axis, or any other combination of imaging optical elements in order to insure proper focus of light from the target onto the sensor 52.

FIG. 4B illustrates a bottom view and FIG. 4C illustrates a top view of the linkage 40 according to an embodiment. The drive cam 41 may include two drive parts 41a and 41b, and, if steering is included, a third drive part 41c, all of which are shown here as being rigidly attached to form a rigid drive cam 41. Similarly, the imaging cam 43 may include two imaging parts 43a and 43b. The drive cam 41 receives the input from a user (via control surface 62) via the first drive part 41a and translates the imaging cam 43 via a cam follower pin in drive part 41b, resulting in the imaging cam part 43a translating the sensor 52 and the imaging cam part 43b translating the imaging lens 51. If steering is included in the linkage, the third drive part 41c simultaneously steers (rotates) the lens modules 20a, 20b using the pin 46 (see FIG. 6B) associated with each of the illumination cam parts 45a and 45b, by translating the illumination cam parts 45a and 45b. The pin 46 may be inserted through a through a slot 49 in each of the illumination cams 45a, 45b and the corresponding housing hole 37 in the lens modules 20a, 20b. The drive part 41c steers the lens modules 20a, 20b simultaneously such that they both still illuminate a same field of view as one another at the target field of view of the target 12.

Figure 5A:
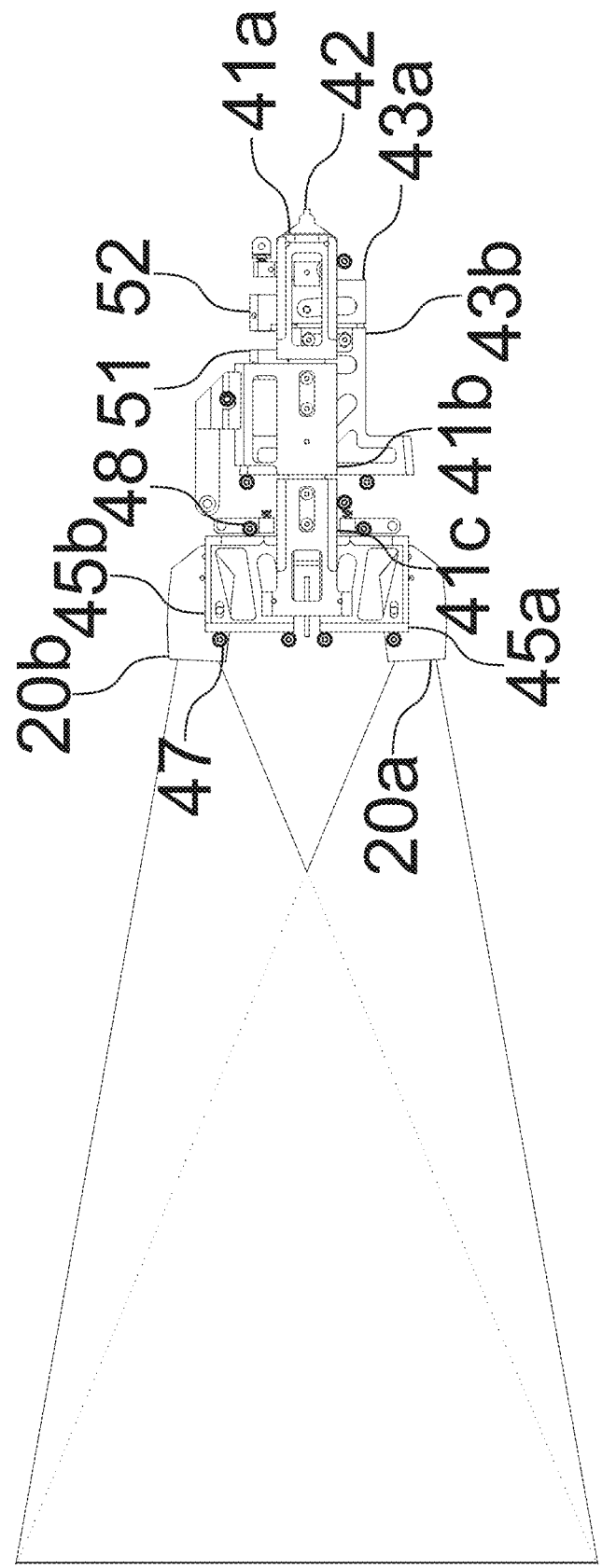
FIGS. 5A and 5B illustrate bottom views of the linkage at a far working distance and a near working distance, respectively, according to an embodiment.
Figure 5B:
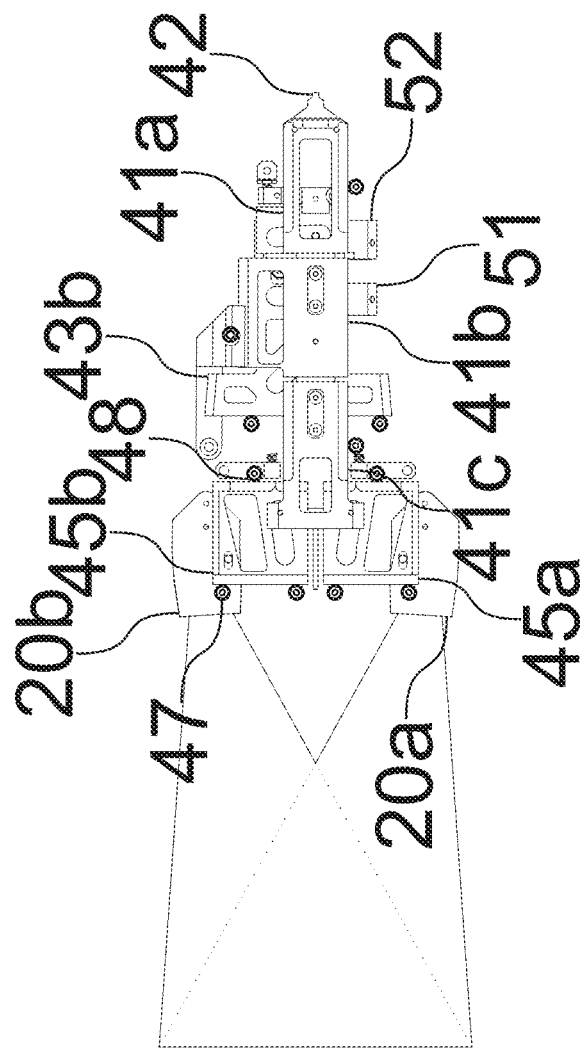

FIGS. 5A and 5B illustrate bottom views of the linkage combined with the lens modules 20a, 20b, the imaging field lens 51, and the sensor 52, at a far working distance and a near working distance, respectively, according to an embodiment. As can be seen therein, the linkage 40 synchronizes steering of the illumination sources with focusing of the imaging system at two sample working distance illumination steering settings. FIGS. 5A-5B show the positions of lens modules 20a, 20b (rotated about the pivot pint 37) and the lens 51 and sensor 52 (translated along an optical axis 55 of the imaging system and along the x-axis) at two focus positions resulting from user input.

As illustrated in FIGS. 5A and 5B, each part that moves axially within the linkage mechanism 40 may be guided by two fixed rolling elements 47, and one spring-loaded rolling element 48, in order to reduce or minimize friction during motion. The linkage 40 also may include a drive cam input connection point 42.

Figure 6A:
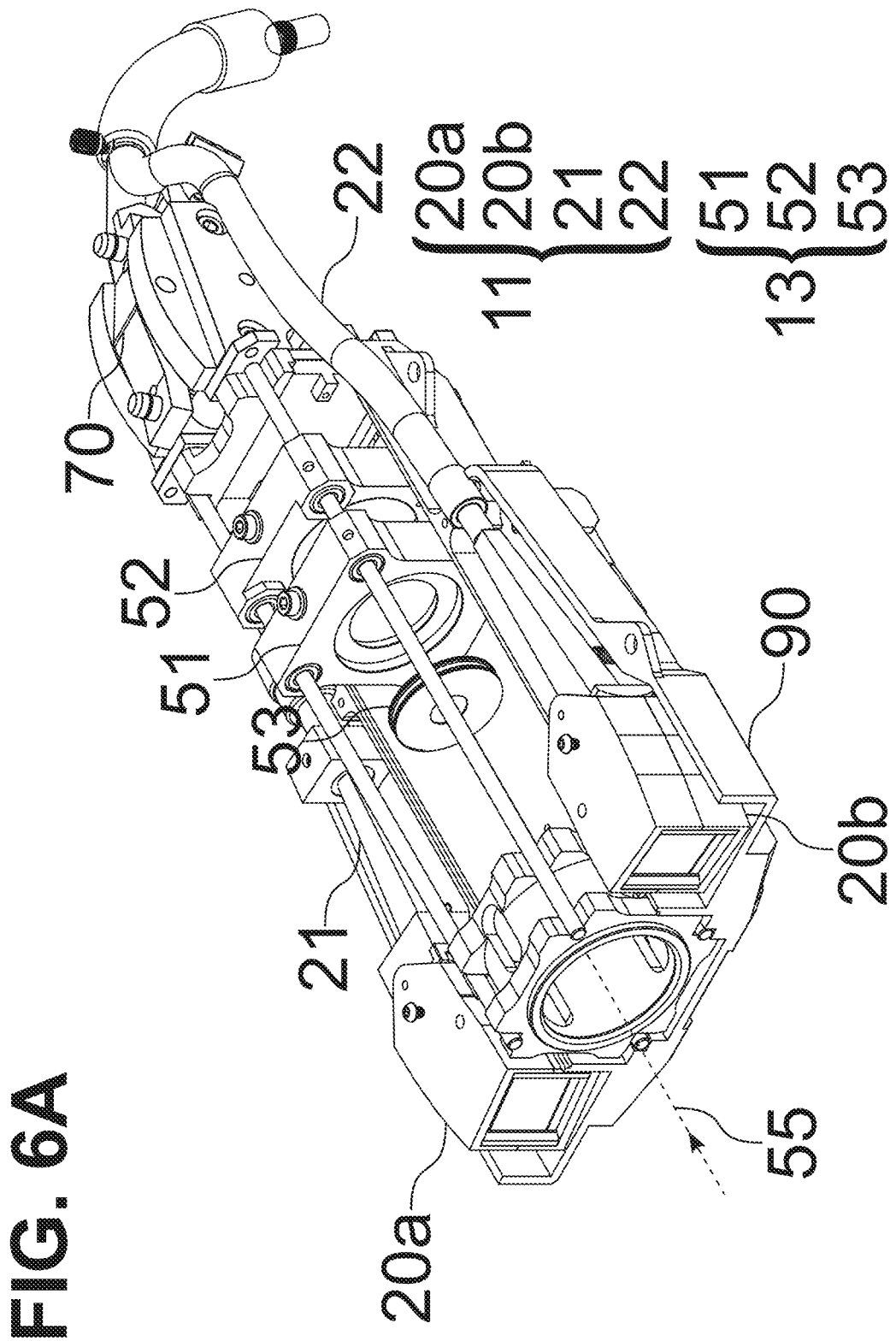
FIGS. 6A and 6B illustrate a perspective top view and a perspective bottom view of an illumination and imaging system according to an embodiment.
Figure 6B:
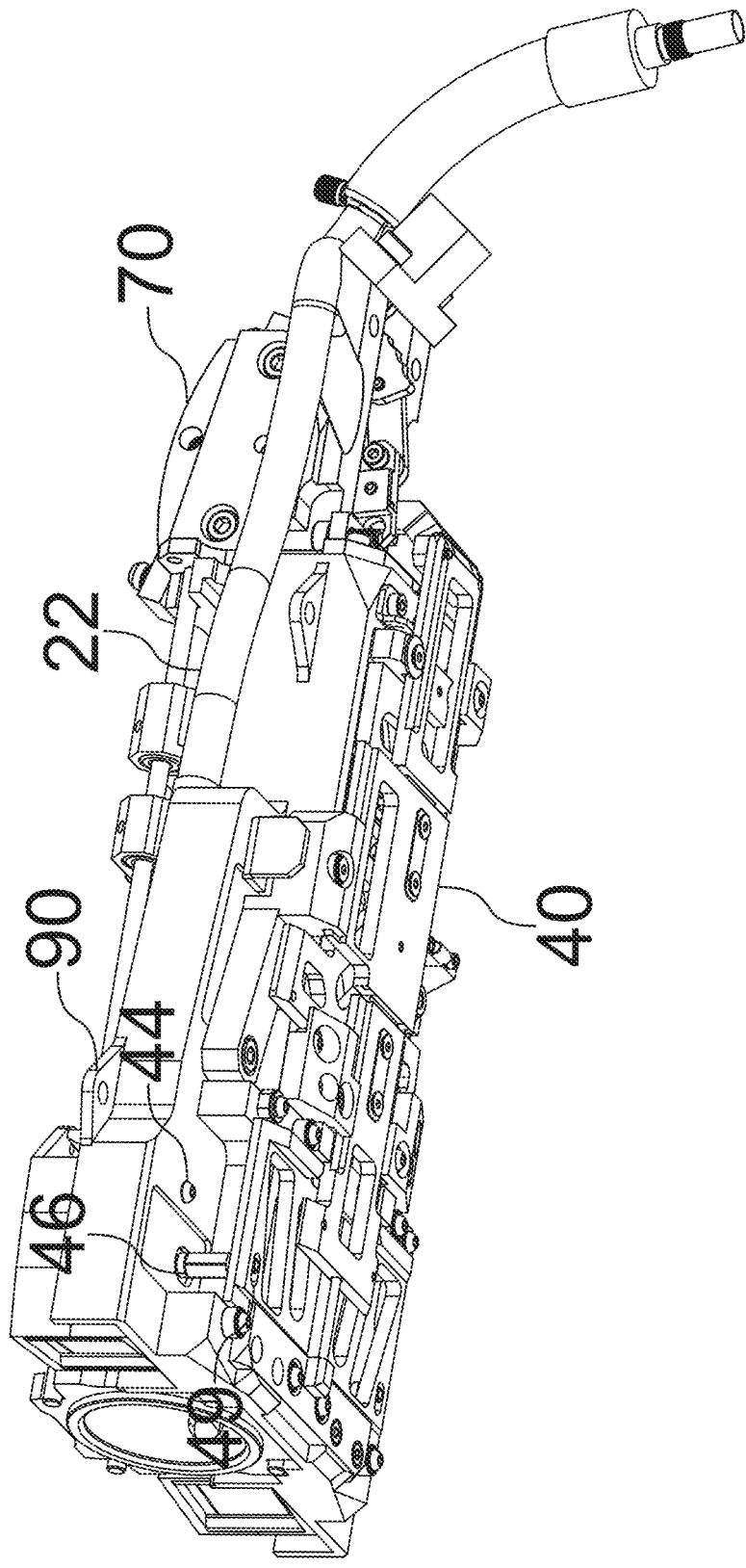

FIGS. 6A and 6B illustrate a perspective top view and a perspective bottom top view of the device 10 in accordance with an embodiment. In FIGS. 6A and 6B, the illumination module 11 and the imaging module 13 are mounted on the chassis 90, the top portion of which is removed in for clarity. Also, a focus actuation mechanism 70 is illustrated, which translates motion from user input to motion of the drive cam 41 via the drive cam input connection point 42.

As can be seen in FIG. 6A, an optical axis 55 of the imaging module 13 runs through a center of the imaging module, with the lens modules 20a, 20b being arranged symmetrically relative to the imaging optical axis 55. The light to be imaged from the target 12 travels along the optical axis 55 to be incident on the lens 51 and sensor 52. A wavelength-dependent aperture 53 that includes a smaller central aperture that permits transmission of all visible and fluoresced light, e.g., near infrared (NIR) light, and a surrounding larger aperture that blocks visible light but permits transmission of fluoresced light, may be provided upstream of the lens 51.

Referring to FIGS. 6B and 4A-4B, the pin 46 connects the lens module 20, via the housing hole 37 in the housing 30, slot 49 of the linkage 40. Also, a pivot point pin 44 connects the lens module 20 to the chassis 90.

Figure 7:
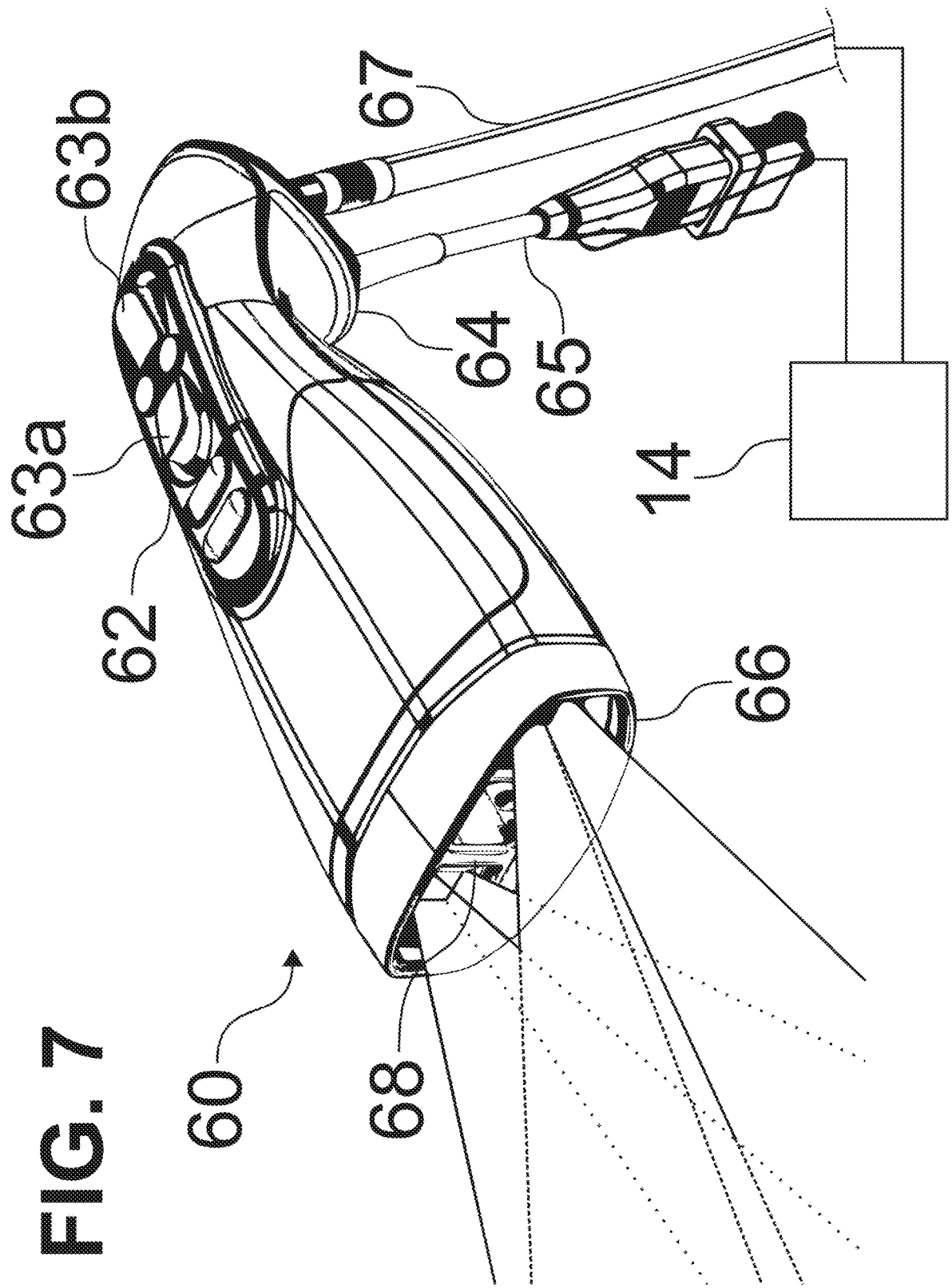
FIG. 7 illustrates an enclosure according to an embodiment.

FIG. 7 illustrates an embodiment of an ergonomic enclosure 60 enclosing the illumination module 11 and the imaging module 13. The ergonomic enclosure 60 is designed to be held in different use-modes/configurations, for example, a pistol-style grip for forward imaging in a scanning-imaging orientation (FIG. 8A), and a vertical-orientation grip for use when imaging downward in an overhead imaging orientation (FIG. 8B). As may be seen in FIG. 7, the enclosure 60 includes a control surface 62, a grip detail 64, a window frame 68 and a nosepiece 66. The ergonomic enclosure 60 is connectable to the VPI box 14 via a light guide cable 67, through which the light is provided to the illumination ports 20a, 20b, and a data cable 65 that transmits power, sensor data, and any other (non-light) connections.

The control surface 62 includes focus buttons 63a (decreasing the working distance) and 63b (increasing the working distance) that control the linkage 40. Other buttons on the control surface 62 may be programmable and may be used for various other functions, e.g., excitation laser power on/off, display mode selection, white light imaging white balance, saving a screenshot, and so forth. Alternatively or additionally to the focus buttons, a proximity sensor may be provided on the enclosure and may be employed to automatically adjust the linkage 40.

Figure 8A:
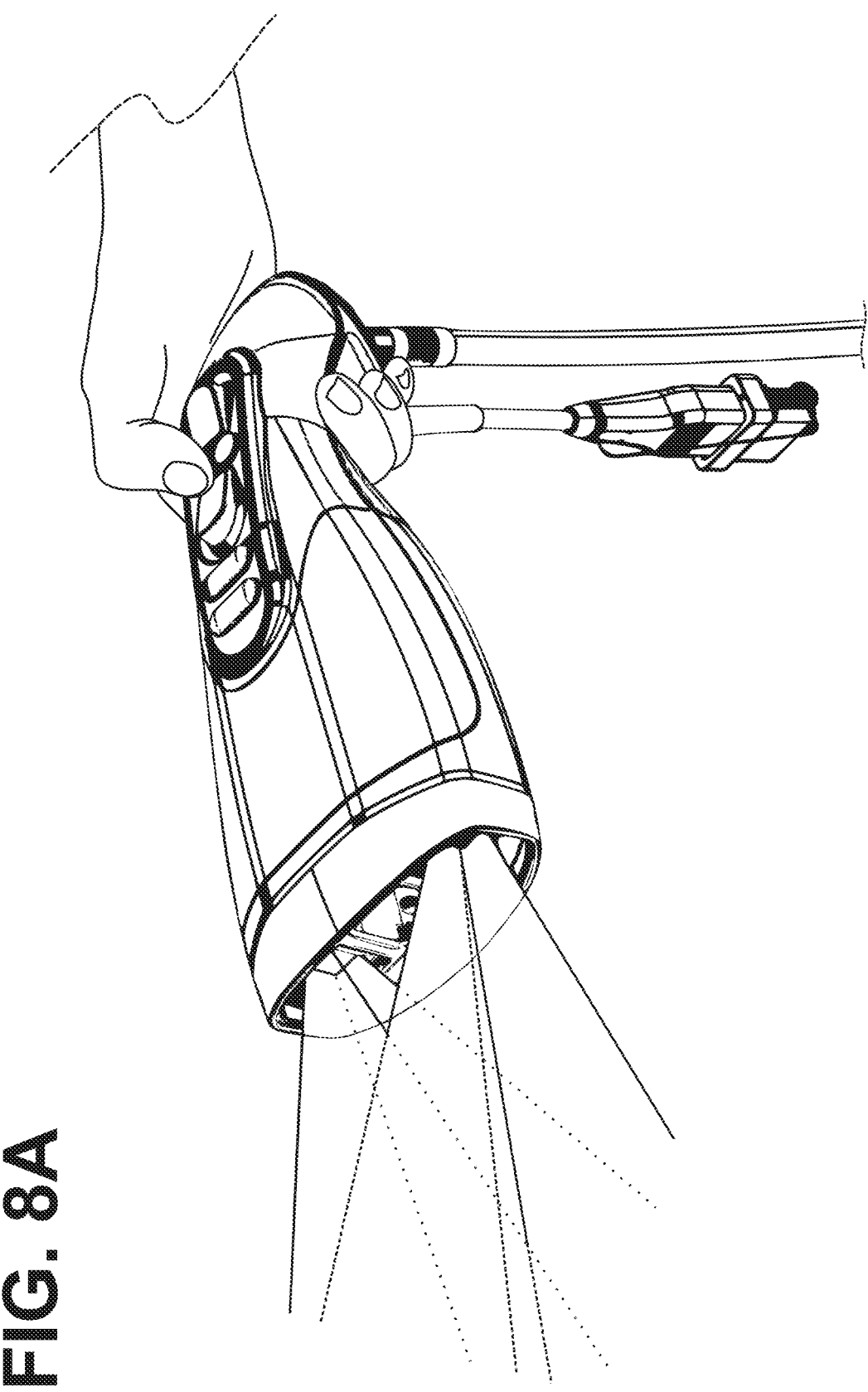
FIGS. 8A and 8B illustrate perspective views of different exemplary positions in which the system may be used.
Figure 8B:
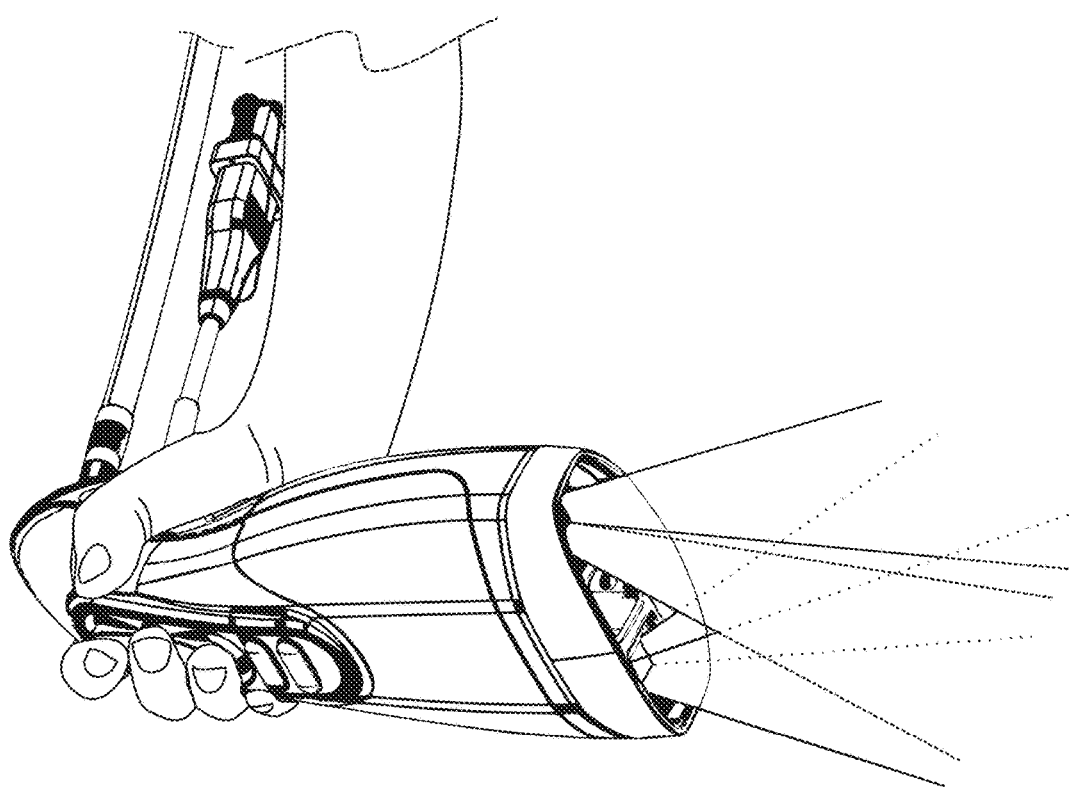

As can be seen in FIG. 8A, when the enclosure 60 is held with the imaging window facing forward, the thumb rests on the control surface 62 while the other fingers on the operator's hand are wrapped loosely around the bottom of the grip detail 64. As can be seen in FIG. 8B, when the enclosure 60 is held with the imaging window facing downward, the grip detail 64 is between the thumb and index finger and the fingers are wrapped around to access the control buttons or switches on the control surface 62. The grip detail 64 is sculpted so as to provide for partial support of the device weight on the top of the wrist in the vertical-orientation grip, such that the enclosure 60 can hang loosely and without the need for a tight grip of the enclosure 60. Thus, the enclosure 60 may be operated by a single hand in multiple orientations. In various other embodiments, the enclosure 60 may be supported on a support (e.g., a movable support).

The window frame 68 (see also FIG. 9A), defines the different windows for the enclosure 60. In other words, the window frame 68 defines windows 68a and 68b, corresponding to the two lens modules 20a and 20b, as well as window 68c, which serves as an input window for light from the target to be incident on the sensor 52.

FIGS. 17A-D illustrate an imaging system 300 in accordance with one embodiment. Imaging system 300 may include one or more components of imaging system 10 of FIG. 1. For example, imaging system 300 may comprise illumination module 11 and imaging module 13 of system 10. System 300 may be used for or with any of the methods and processes described herein with respect to system 10.

Figure 17A:
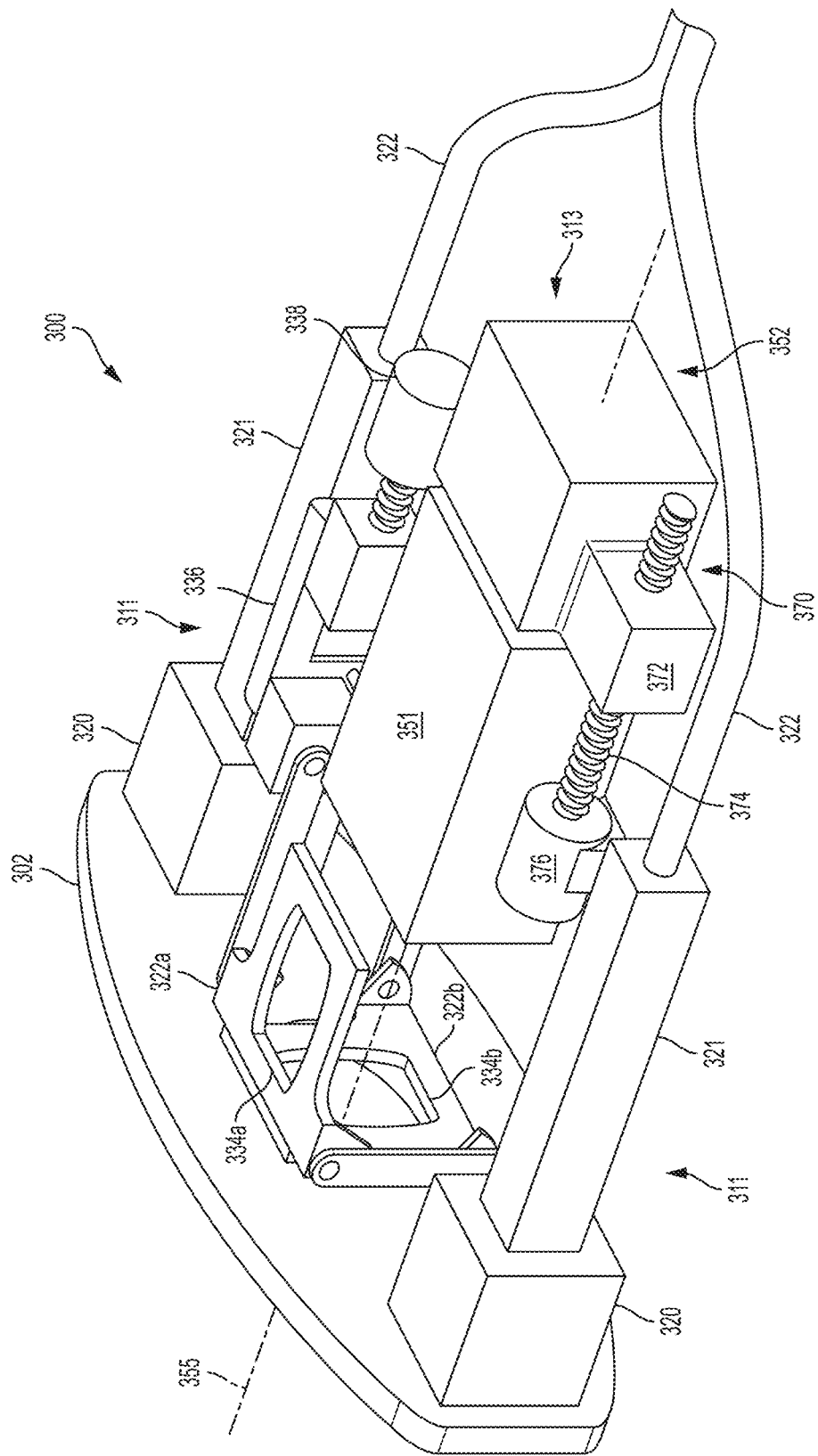
FIG. 17A illustrates a perspective top view of an illumination and imaging system according to an embodiment.

As shown in FIG. 17A, which is a perspective top view, imaging system 300 includes two illumination ports 311, imaging module 313, and plate 302, each of which is mounted to a frame or chassis (not shown). The light to be imaged from target 12, which may include light from illumination ports 311 reflected by target 12 and/or fluorescent light emitted from target 12, travels along the optical axis 355, through plate 302 and into imaging module 313, which houses one or more imaging sensors. As described below, imaging module 313 may include movable filters for filtering light that enters the imaging module. In some embodiments, the imaging module 313 may include one or more wavelength-dependent apertures that includes a smaller central aperture that permits transmission of all visible and fluoresced light, e.g., NIR light, and a surrounding larger aperture that blocks visible light but permits transmission of fluoresced light.

Each illumination port 311 includes a lens module 320, a connecting cable 322 connected to the illumination light source 23, and a light pipe 321 adapting a high numerical aperture of the connecting cable 322 to a lower numerical aperture of the lens module 320. The lens modules 320 may provide illumination having a rectangular form factor that matches the field of view of the imaging system 300. Each illumination port 311 may produce a gradient of illumination such that the sum illumination flux in the object plane is reasonably the same at each point in the illumination field, e.g., providing uniform illumination over the imaging field of view. Lens modules 320 each include one or more lenses and/or prism elements for shaping and orienting illumination to meet application requirements. For example, since the two illumination ports 311 lie horizontally offset from the center of the optical axis 355 of the imaging system 300, prisms may be included in the lens modules 320 to direct the beams towards the center of the field of view. The degree of direction may be tailored to the specific application, or to a set of specific applications. For example, in some variations, the degree of direction is selected such that the beams overlap at a nominal imaging distance of 25 cm. In some variations, the horizontal offset of the illumination ports 311 and the degree of direction are selected such that the beams substantially overlap and substantially cover the field of view over a range of working distances, such as distances from 18-40 cm. In the embodiment illustrated in FIG. 17A, the illumination ports are fixed with respect to the frame. In other embodiments, the illumination ports are steerable, in accordance with the principles described above.

Imaging module 313 includes image sensor assembly 352, optics module 351, and movable filter assembly 330 aligned along an optical axis 355. The image sensor assembly 352, which includes an image sensor and may include one or more lenses, filters, or other optical components, is movable relative to the frame along the optical axis 355 via focus actuation assembly 370. Focus actuation assembly 370 includes lead nut 372 affixed to the housing of the image sensor assembly 352. The lead nut 372 is coupled to lead screw 374, which extends from focus motor 376. Focus motor 376 is fixed to the frame and can be actuated in forward and reverse directions to turn lead screw 374, which causes lead nut 372 to translate along the lead screw axis, moving image sensor assembly 352 forward and backward along the optical axis 355. Lead nut 372 and/or focus actuation assembly 370 may be mounted on shafts that slide within mountings on the frame, for example, using one or more linear ball bearings or bushings to restrain lateral and angular play. In some embodiments, the image sensor assembly 352 may comprise a single image sensor that is configured to detect light from the target resulting from illumination by visible light and excitation light. In other embodiments, the image sensor assembly 352 may comprise multiple image sensors for. For example, the image sensor assembly 352 may comprise separate image sensors configured to detect light from the target resulting from illumination by visible light separately from that resulting from illumination by excitation light.

A controller may be used to control movement of the image sensor assembly 352 for focusing, which may be based on user input. For example, system 300 may be provided with one or more controls such as buttons or touch screen controls to enable the user to adjust the focus. A user may actuate a focus control until the desired focus is achieved or may enter a value associated with a desired focus and the controller may actuate the image sensor assembly 352 until the desired focus is achieved. In some embodiments, a magnetic position sensor mounted on the housing of the image sensor assembly 352 detects the position of the image sensor assembly 352 for closed loop control of focus actuation assembly 370 by the controller. In some embodiments, the controller can use open loop control of focus actuation assembly 370, for example, by using a stepper motor.

Optics module 351, which is located forward of image sensor assembly 352, is fixed relative to the frame and may include one or more optical components (e.g., lenses, apertures, filters, etc.) for adjusting light traveling along the optical path before reaching the image sensor. For example, optics module 351 may include a wavelength-dependent aperture (e.g., similar to aperture 53 of FIG. 6A) that includes a smaller central aperture that permits transmission of all visible and fluoresced light, e.g., NIR light, and a surrounding larger aperture that blocks visible light but permits transmission of fluoresced light.

Movable filter assembly 330 is located forward (upstream with respect to the direction of travel of light from a target to the image sensor) of optics module 351 and includes first window 334a and second window 334b, each of which is housed in a bracket (first window bracket 332a and second window bracket 332b, respectively). First and second windows 334a, 334b can be alternately moved into and out of the optical path. In some embodiments, the first and second windows 334a, 334b can be alternately moved into and out of the optical path via linkage assembly 336, which is actuated by filter motor 338. In some variations, the first and/or second windows can be moved via any combination of motions including rotation (for example on a rotary wheel) and/or translation. One or both of the windows 334a, 334b can include filters for filtering light before it reaches the image sensor. By moving filters into and out of the optical path, imaging system 300 can be operated in different imaging modes. For example, in some embodiments, one of the windows (e.g., first window 334a) includes a filter for blocking visible light while the other window (e.g., second window 334b) includes a clear glass plate that does not block light. With the blocking filter in the optical path, the imaging system can be operated in a first mode and, with the clear glass in the optical path, the imaging system can be operated in a second mode. When switching modes, one window moves into the optical path while the other window moves out of the optical path. In some embodiments, a visible-light rejection filter which only transmits NIR light between 830-900 nm is included in a first window for a fluorescence-only imaging mode and an anti-reflective coated glass plate, which passes all light, is included in the second window for use in a second mode. The glass plate can ensure the same optical path length regardless of mode. In some variations, a controller of system 300 can control movable filter assembly 330 to change modes, for example, in response to a user input.

In the configuration illustrated in FIG. 17A, second window bracket 332b is in a deployed position such that second window 334b is positioned in the optical path and is oriented perpendicularly to the optical axis 355. By actuating filter motor 338, which actuates linkage assembly 336, the second window bracket 332b and second window 334b move out of the optical path by pivoting about a pivot axis that extends perpendicularly to optical axis 355. At the same time, first window bracket 332a and first window 334a move into the optical path by pivoting about a pivot axis that extends perpendicularly to optical axis 355. In some embodiments, the pivot axis of the first window bracket and the pivot axis of the second window bracket are vertically aligned and the first and second window brackets and window are symmetrical to provide matching optical path lengths regardless of mode.

Figure 17B:
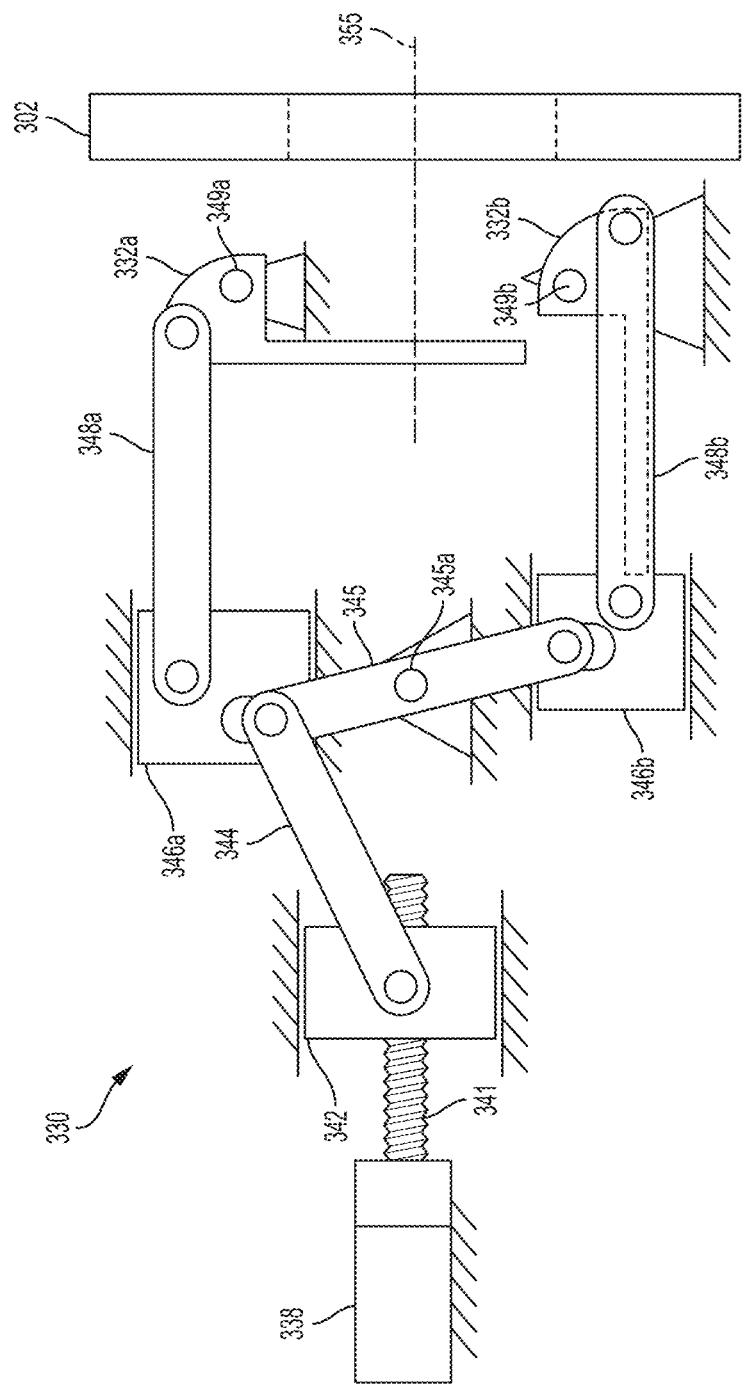
FIG. 17B illustrates a schematic side view of a movable filter assembly for the illumination and imaging system of FIG. 17A, according to an embodiment.

Linkage assembly 336 is actuated by filter motor 338, which may be controlled by a controller of system 300. Filter motor 338 rotates filter lead screw 341, which moves filter lead nut 342 forward and rearward. Linkage 344 is pivotally connected on a first end to filter lead nut 342 and pivotally connected at a second end to slider 346a. A pivot link 348a is pivotally connected at one end to slider 346a and at the other end to first window bracket 332a. As illustrated in FIG. 17B, slider 346b and pivot link 348b (which are not shown in FIG. 17A) are provided below slider 346a and pivot link 348a for actuating second window bracket 332b.

Movable filter assembly 330 is schematically depicted in FIG. 17B. Filter motor 338, which is fixed relative to the frame, rotates the filter lead screw 341 clockwise and counterclockwise, causing filter lead nut 342 to translate forward and rearward along the filter lead screw axis. Translation of filter lead nut 342 causes translation of slider 346a via linkage 344. Translation of slider 346a causes translation of pivot link 348a. Pivot link 348a is pivotally connected to first window bracket 332a at a location off-center from the pivot connection 349a of first window bracket 332a to the frame. Therefore, movement of pivot link 348a causes rotation of first window bracket 332a. For example, from the configuration of FIG. 17B, translation of slider 346a forward (toward plate 302) causes first window bracket 332a to rotate 90 degrees out of the optical path.

Driving linkage 345 is pivotally connected at a first end to linkage 344, pinned to the frame at connection point 345a, and pivotally connected at a second end to slider 346b. Thus, translation of linkage 344 causes rotation of driving linkage 345, which translates slider 346b. Slider 346b is connected to second window bracket 332b via pivot link 348b, which is pivotally connected to second window bracket 332b at a location off-center from the pivot connection 349b of second window bracket 332b to the frame. Thus, translation of slider 346b causes rotation of second window bracket 332b. From the configuration of FIG. 17B, translation of slider 346b rearward (as slider 346a moves forward), causes second window bracket 332b to rotate 90 degrees into the optical path. One or more sensors may be included for sensing the position of one or more of the movable filter assembly 330 components for providing feedback to the controller for closed-loop control.

Plate 302 is a flat plate for sealing the housing and protecting the illumination and imaging optics. In some embodiments, plate 302 is a single plate of glass. One or more optical components such as a lens may be mounted between the glass plate and the movable filter assembly 330. In some variations, one or more sensors are positioned on the rear side of plate 302 to measure light incident on plate 302. One or more of these sensors may detect ambient light, light reflected from the target, light emitted by the target, and/or light reflected from non-target objects. In some embodiments, a drape detector is included to detect the presence of a drape. The drape detector may include, for example, an infrared emitter and a photodetector that detects infrared light reflected by a drape positioned on the imaging system.

Figure 17D:
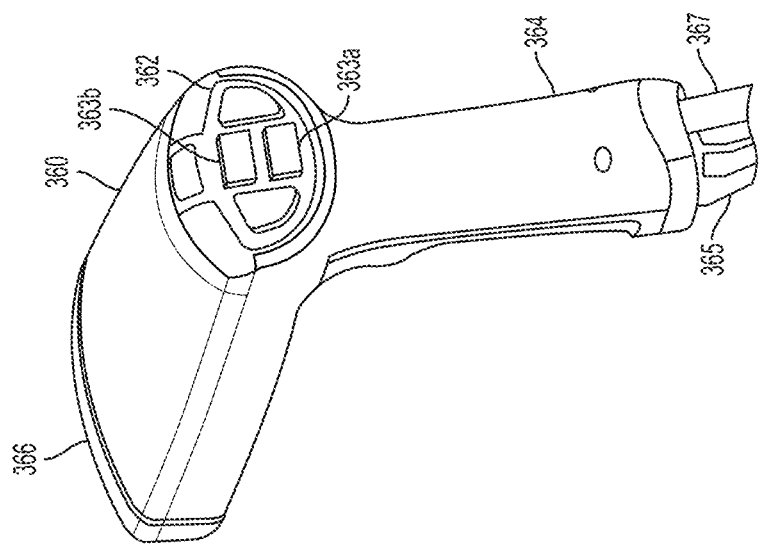
FIGS. 17C to 17D illustrate an enclosure according to an embodiment.
Figure 17C:
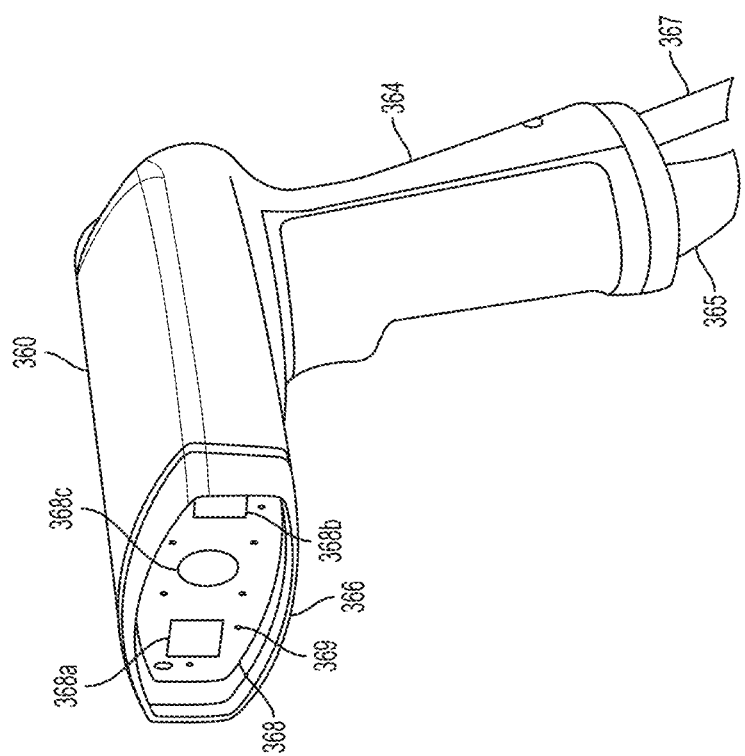

FIGS. 17C-D illustrate an embodiment of an ergonomic enclosure 360 enclosing illumination ports 311 and imaging module 313, according to one variation. The ergonomic enclosure 360 is designed to be held in a pistol-style grip. The enclosure 360 may include a control surface 362, a grip 364, a window frame 368 and a nosepiece 366. The ergonomic enclosure 360 is connectable to the VPI box 14 via a light guide cable 367, through which the light is provided to illumination ports 311, and a data cable 365 that transmits power, sensor data, and any other (non-light) connections.

The control surface 362 includes focus buttons 363a and 363b that control the focus actuation assembly 370. Other buttons on the control surface 362 may be programmable and may be used for various other functions, excitation laser power on/off, display mode selection, white light imaging white balance, saving a screenshot, and so forth. Alternatively or additionally to the focus buttons, a proximity sensor may be provided on the enclosure and may be employed to automatically adjust the focus actuation assembly 370.

Enclosure 360 may be operated by a single hand in a pistol-grip style orientation. In various other embodiments, the enclosure 360 may be supported on a support (e.g., a movable support). In some embodiments, enclosure 360 may be used in concert with a drape, such as drape 80 of FIG. 9A or drape 390 of FIG. 9B.

In some embodiments, a window frame 368 is provided on the forward portion of enclosure 360 in front of plate 302. In other embodiments, the window frame 368 is provided on the forward portion of enclosure 360 behind plate 302, and plate 302 provides the outer surface of the enclosure. In other embodiments, no frame is provided and plate 302 provides the outer surface of the enclosure. Window frame 368 may include windows 368a and 368b, corresponding to the two lens modules 320, as well as window 368c, which serves as an input window for light from the target to be incident on the image sensor. Window frame 368 may also include one or more windows 369 for sensors provided behind plate 302.

Figure 17E:
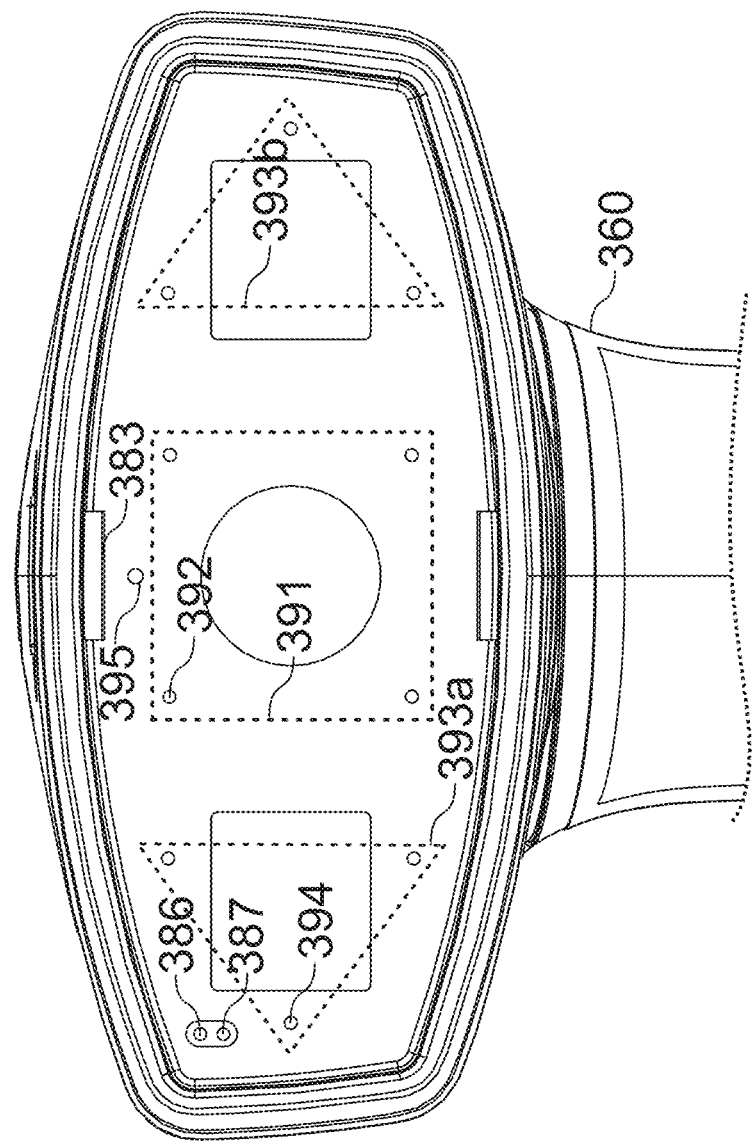
FIG. 17E illustrates a sensor and light source arrangement in a forward portion of an enclosure according to an embodiment.

FIG. 17E illustrates an embodiment of a sensor arrangement provided behind plate 302 on the forward portion of enclosure 360, according to one variation. In this embodiment, a central sensor group 391 comprising one or more sensors 392 is provided in order to detect reflected illumination light for input to an automatic gain control function, as described below. Also in this embodiment, peripheral sensor groups 393a and 393b, each comprising one or more sensors 394, are provided in order to detect reflected illumination light for purposes of proximity detection to the imaging target or to detect any objects near to the forward portion of the enclosure 360, as described below. The source of the illumination light for proximity detection may be either the main illumination beam or may be one or more dedicated emitters for proximity detection. Also in this embodiment, one or more sensors 387 and one or more light sources 386 are provided in order to detect the presence of an installed drape lens, as described below. Also in this embodiment, one or more sensors 395 may be provided in order to detect ambient room light intensity to facilitate correction of image intensity artifacts arising from pulsating room light components, as described herein.

Figure 18:
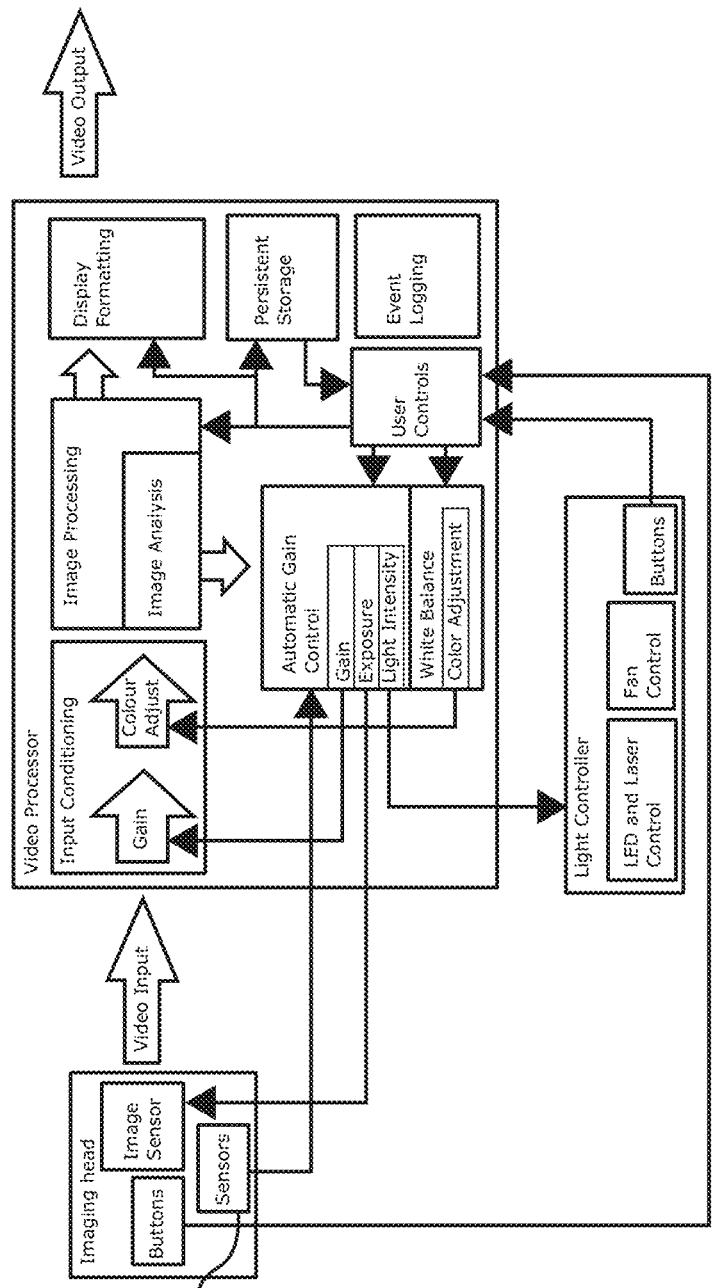
FIG. 18 illustrates a schematic diagram of components of an illumination and imaging system according to an embodiment.

The sensors 392 may be used to detect reflected light levels in order to provide input for an automatic gain control (AGC) function (see FIG. 18) that may be used to facilitate optimizing illumination and imaging parameters and providing a consistent and/or smoothly varying image brightness, even when varying the working distance. AGC may also be used to facilitate optimizing or maximizing the image signal to noise ratio, or to minimize the illumination intensity to facilitate minimizing photo-bleaching. For example, the AGC may be used to dynamically adjust image signal gain, illumination pulse duration, exposure, and/or illumination power. The reflected illumination light detected by the sensors 392 may include visible light and/or fluorescence excitation light, such as NIR light. In one embodiment, sensors 392 are sensitive to NIR light but not to visible light, such that ambient visible light and white light illumination do not contribute to the light level signal from sensors 392. In some variations, sensors 392 are comprised of photodiodes.

The reflected light level sensors 392 may be used as input to AGC in any imaging mode, including a white light imaging mode and/or a multiplexed combined white light and fluorescence imaging mode, and may be particularly important in a fluorescence-only imaging mode. When operating in a fluorescence-only imaging mode, for example with filter 334a blocking visible light from reaching the image sensor, no reflected white light luminance image is recorded, which could otherwise be used as an input to AGC, while the recorded fluorescence image necessarily excludes reflected fluorescence excitation light (which would otherwise overpower the fluorescence signal) through use of a notch filter in the imaging optics. Therefore, the sensors 392 may provide the only measure of reflected light. In one variation, the operation of AGC in a fluorescence-only imaging mode prioritizes maximizing the exposure duration and minimizing the gain.

In some embodiments, for which the sensors 392 are sensitive to the excitation light, the gain, excitation period (which may, for example, be the same as the image sensor exposure time) and instantaneous excitation power can be adjusted as follows in order to achieve a constant image brightness for a given fluorescence sample regardless of working distance. Based on the reflected excitation light E, as measured by sensors 392, the AGC may adjust the excitation period, T, instantaneous excitation power, P, and image sensor gain, G, such that E*T*G=K, where K is a constant based on the desired target brightness. The priorities of adjusting T, G and P can be optimized to minimize noise while limiting maximum exposure of tissue to excitation light.

In one embodiment, as shown in FIG. 17E, the sensors 392 are arranged such that their detection cones approximately cover the imaging field of view. For example, in this embodiment, a sensor group 391 is comprised of four sensors 392 arranged in a rectangular pattern surrounding the imaging port.

According to one embodiment, AGC operates by starting with settings for an initial gain $g_0$, initial exposure $e_0$, and initial illumination power $p_0$. User defined brightness parameters may prescribe target values, such as for example, a target peak brightness $P_t$ and a target mean brightness $M_t$, as well as a choice of AGC mode to be based on the peak values, mean values, or a balanced combination of both peak and mean values.

During each image acquisition frame, a peak sensor brightness $P_s$ may be calculated based on a peak signal from among sensors 392 during the acquisition duration, and a mean sensor brightness $M_s$ may be calculated based on a mean of the signals from sensors 392 during the duration. An adjustment factor F is then calculated based on these values and used to calculate a target exposure value $e_t$ and a target gain value $g_t$. For example, in peak mode $F=P_t/P_s$, in mean mode $F=M_t/M_s$, and in balanced mode $F=(\frac{1}{2})(P_t/P_s+M_t/M_s)$. In one variation, a balanced mode may be a weighted combination of sensor signal values, such as a weighted average of $P_s$ and $M_s$ as in $F=(k1*P_s+k2*M_s)$, where k1 and k2 are constants. In one variation, the constants k1 and k2 may satisfy the constraints k1+k2=1 and 0<=k1<=1. The target exposure is calculated as $e_t=Fe_0$, and the target gain is calculated as $g_t=Fg_0$.

According to an embodiment, AGC adjusts the exposure duration (and the corresponding excitation illumination duration) by a step equal to one-half of the value between the current exposure $e_0$ and the target exposure $e_t$, such that the new exposure $e_1=e_0+(e_t-e_0)/2$. In this manner, the exposure cannot be increased above a maximum exposure $e_{max}$ or decreased below a minimum exposure $e_{min}$.

According to an embodiment, if the current exposure $e_0$ is at the maximum exposure $e_{max}$ and the adjustment factor F is greater than unity, then AGC adjusts the gain to a new gain $g_1=g_0+(g_t-g_0)/4$. If the current gain is greater than unity and F is less than unity, then the gain is instead adjusted to a new gain $g_1=g_0-(g_0-g_0(e_{max}/e_0))/4$. Otherwise, the new gain instead remains unchanged as $g_1=g_0$.

According to an embodiment, the excitation power may be adjusted as a lowest adjustment priority.

Following each AGC cycle, the new values for exposure, gain, and power are treated as the current values for the next AGC cycle.

The sensors 394 may be used to detect reflected illumination light that is reflected off of objects entering into the periphery of the illumination beams and located near to the front of the enclosure 360. For example, detection of such near objects may be used to trigger switching to a reduced illumination power setting in order to reduce a possible safety risk from high illumination power being delivered to a nearby object. The reflected illumination light detected by sensors 394 may include visible light and/or fluorescence excitation light, such as NIR light. In one embodiment, sensors 394 are sensitive to NIR light but not to visible light, such that ambient visible light and white light illumination do not contribute to the detection signal from sensors 394. In some variations, sensors 394 are comprised of photodiodes or of time-of-flight sensors. In one variation, the sensors 394 are arranged such that they may detect objects entering the illumination beams which are not within the imaging field of view.

In some embodiments, a method for imaging a target includes illuminating the target with an illuminator of an imaging system, such as illumination ports 311 of imaging system 300, and receiving light from the target at an imaging sensor of the imaging system in an unrestricted imaging mode. In some embodiments the light received from the target include light reflected by the target and light emitted by the target. In some embodiments, the reflected light includes visible light and the emitted light includes fluorescent light from the target. The imaging mode is switched from the unrestricted imaging mode to a restricted imaging mode in which light of wavelengths outside of a desired wavelength band or bands is blocked from reaching the imaging sensor. The light is blocked using a movable filter of the imaging device. The light that is passed by the filter is received by the imaging sensor. The imaging mode can be switched back to the unrestricted imaging mode in which the filter is moved out of the optical path so that it no longer blocks light in the optical path.

For example, system 300 can be operated in an unrestricted imaging mode in which first window 334a is in a deployed position in the optical path. First window 334a may include a clear plate that permits all light to pass through it. In this unrestricted imaging mode, the image sensor may receive all or most of the light that reaches first window 334a. System 300 can be switched to a restricted imaging mode in which the first window 334a is in a stowed position out of the optical path and the second window 334b is in a deployed position in the optical path, according to the principles described above. The second window 334b may include a filter that filters out light that is not in a desired wavelength band or set of wavelength bands. For example, the filter may filter out all visible light but pass infrared light (e.g., NIR light). Thus, during the restricted imaging mode, the imaging sensor provides imaging data of only the light passed by the filter.

System 300 may be switched to the restricted imaging mode in response to a request that may be received from a user (e.g., via actuation of one or more buttons on the control surface 362) or that may be received from an external control system. Although the above description refers to restricted and unrestricted modes, the same principles can be used to switch between two restricted modes (i.e., some light is blocked in both modes). For example, the system can switch between two restricted imaging modes by including a first filter configured to block a first wavelength band or set of wavelength bands and a second filter, different from the first, that is configured to block a different wavelength band or set of wavelength bands from the first.

In some embodiments, the automatic gain control process described above can be started upon switching to the restricted imaging mode and may be stopped upon switching to the unrestricted imaging mode (e.g., AGC can be automatically started and stopped by a controller of the system 300). In other embodiments, AGC is performed during both the restricted and unrestricted imaging modes.

Figure 9A:
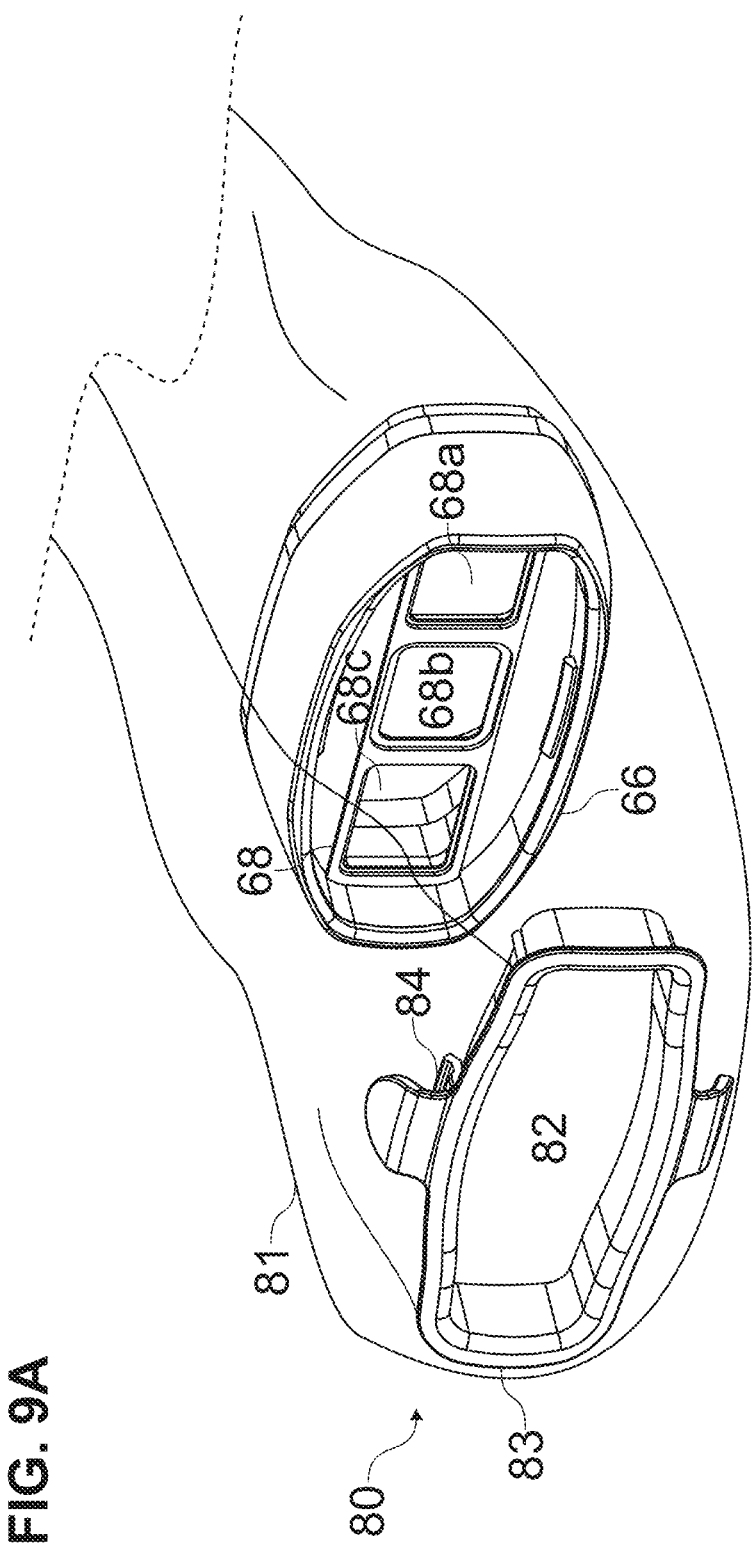
FIG. 9A illustrates a drape for use with the system according to an embodiment.
Figure 9G:
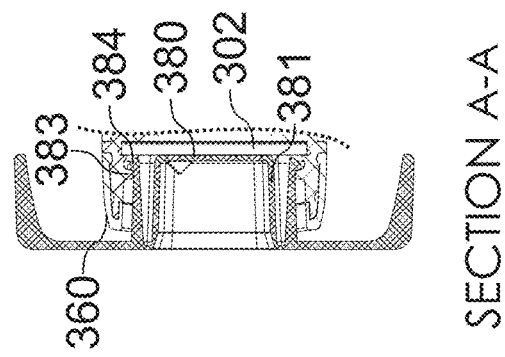
FIG. 9G illustrates a section view of the installed drape lens and frame on the enclosure of the system of FIG. 9F.
Figure 9F:
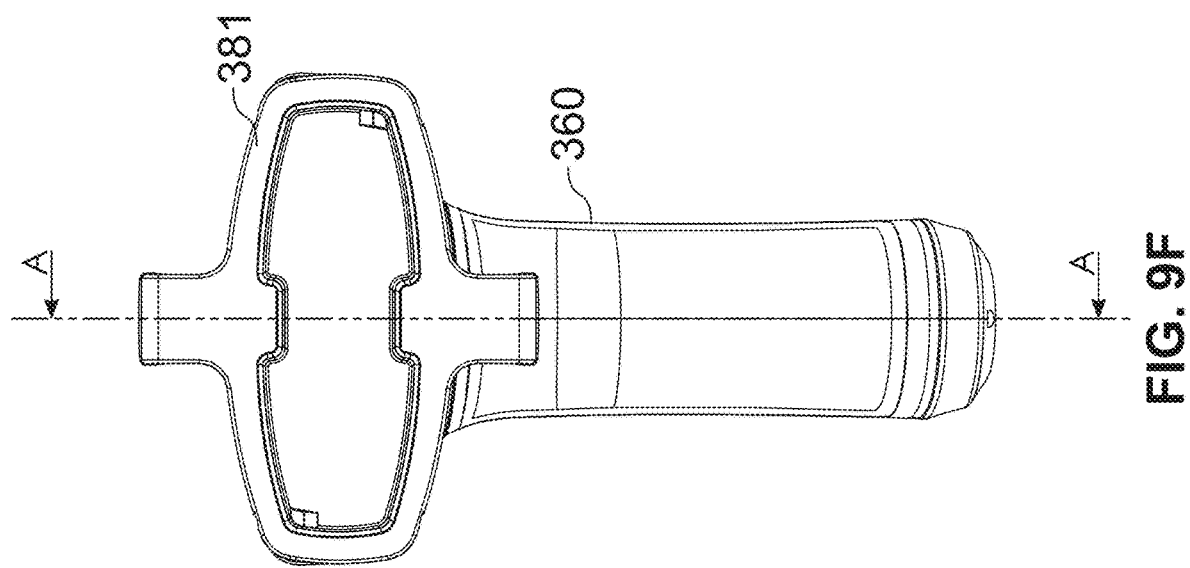
FIG. 9F illustrates a drape lens and frame installed on an enclosure of the system, according to an embodiment.

As illustrated in FIG. 9A, the enclosure 60 of FIG. 7 may be used in concert with a drape 80. The drape 80 may be a surgical drape suitable for use during a surgical procedure. The drape includes drape material 81, a drape lens 82, a drape window frame 83 surrounding the drape lens, and an interlock interface 84 that is integral with the drape window frame 83. The drape material 81 is to envelope the device in the enclosure 60, as well as to cover anything else as required. The drape window frame 83 may follow a shape of the enclosure nosepiece 66 such that the drape window frame 83 may be inserted therein without obstructing the windows 68a to 68c. The drape 80 is designed to minimize reflections and imaging ghosting by ensuring the drape lens 82 is flush, e.g., to within 0.5 mm, with the imaging and illumination window frame 68. The drape 80 may use the interlock interface 84, which may fit over a ridge on the inner surface of the enclosure nosepiece 66, to be secured flush thereto. In one variation, the interlock interface 84 may fit into a recess on the inner surface of the enclosure nosepiece 66.

One or more interlock interfaces 84 may be used on the inner or outer surface of the enclosure nosepiece 66, in order to ensure a secure and close fit of the drape lens 82 against the window frame 68. In the particular embodiment shown, two interfaces 84, here one on the top and one on the bottom of the drape window frame 83 to engage with an inner surface of the enclosure nosepiece 66, are used.

According to some variations, feedback may be provided to the user to indicate when the drape lens has been installed correctly onto the enclosure nosepiece. In one variation, a raised ridge around at least a portion of the drape window frame may provide tactile and/or aural feedback when pushed over one or more detent features on the interior surface of the enclosure nosepiece. In another variation, a raised ridge around at least a portion of the drape window frame may provide tactile and/or aural feedback when pushed over one or more detent features on the exterior surface of the enclosure nosepiece. In another variation, one or more interlock interfaces may provide tactile and/or aural feedback when pushed into place to engage with an inner surface of the enclosure nosepiece. In another variation, one or more interlock interfaces may provide tactile and/or aural feedback when pushed into place to engage with an outer surface of the enclosure nosepiece. Additionally or alternatively, a drape detection module, as described below, may provide feedback to indicate when the drape lens has been installed correctly.

According to an embodiment, the drape may be symmetrical such that it may be rotated by 180 degrees about its central axis (e.g., the axis aligned with the imaging optical axis) and may be installed correctly onto the enclosure nosepiece both before and after such a rotation.

The drape lens material may comprise a transparent polymer material such as, for example, polymethyl methacrylate (PMMA), polycarbonate, polyvinyl chloride, or polyethylene terephthalate glycol-modified. In one embodiment, the drape lens material may be chosen based in part on having a relatively low refractive index and high light transmission in the visible and NIR bands compared to other candidate materials, so as to minimize artifacts caused by reflections at the drape lens and to maximise illumination and imaging transmission. For example, the drape lens material, such as PMMA, may have an index of refraction of less than about 1.5 and light transmission greater than about 92% in the visible and NIR bands. The drape lens and/or the drape window frame may be manufactured by injection molding.

In one variation, the drape lens may be coated with an anti-reflection coating to reduce imaging and illumination artifacts from reflection at the window.

FIGS. 9B-G illustrate an embodiment of a drape 390 comprising drape lens 380 and drape window frame 381 to be used in combination with drape material (not shown), such as drape material 81 (see FIG. 9A), to cover the enclosure 360 of FIG. 17C-D. The drape 390 may be a surgical drape suitable for use during a surgical procedure. The drape includes drape material (not shown), a drape lens 380, a drape window frame 381 surrounding the drape lens, an interlock interface 384 that is integral with the drape window frame 381, and a reflective feature 388. The drape material is to envelope the device in the enclosure 360, as well as to cover anything else as required. The drape window frame 381 may follow a shape of a forward portion of the enclosure 360 such that the drape window frame 381 may be inserted thereon. The drape 390 is designed to minimize reflections and imaging ghosting by ensuring the drape lens 380 is flush, e.g., to within 0.5 mm, with the front surface of the enclosure 360, such as plate 302 of FIGS. 17A-B. The drape 390 may use the interlock interface 384, which may fit into over a ridge 383 on the inner surface of the front portion of the enclosure 360, to be secured flush thereto.

Figure 19:
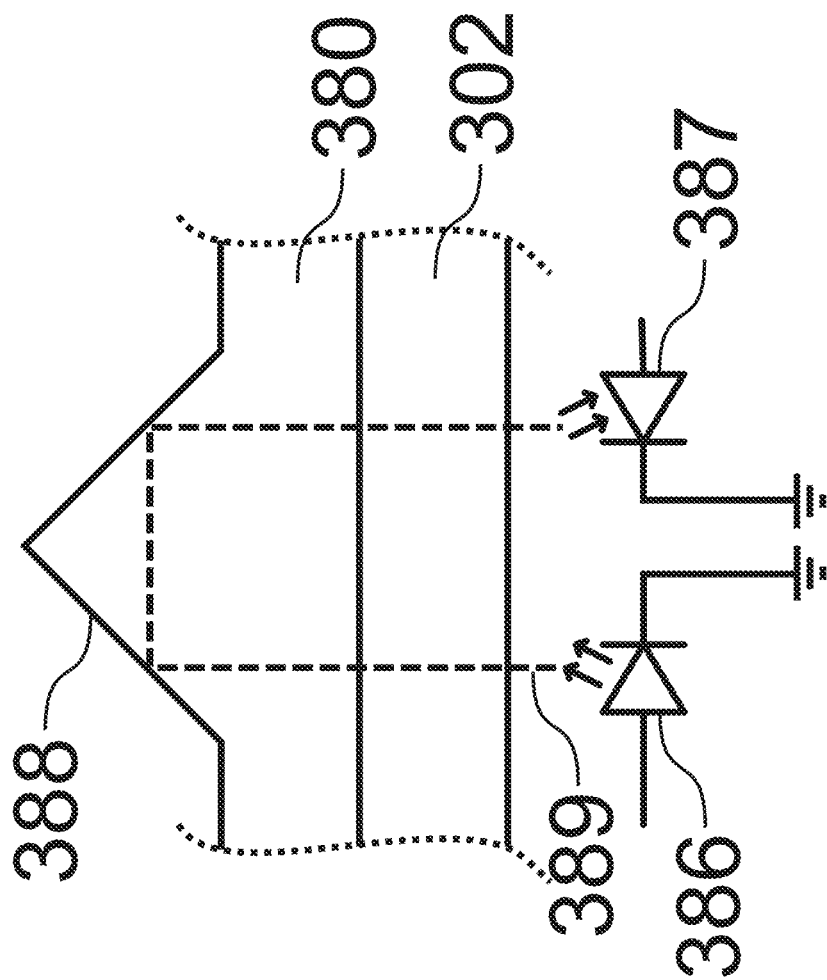
FIG. 19 illustrates a schematic diagram of a drape detection module according to an embodiment.

In one embodiment, a drape detection module may be provided to detect the installation of the drape lens onto the enclosure nosepiece. For example, the drape detection module may use any combination of one or more ultrasonic sensor, inductive sensor, capacitive sensor, optical sensor, light emitter, radio frequency identification chip and antenna, hall effect sensor, proximity sensor, or electrical contacts in order to detect the installation of the drape lens onto the enclosure. In one embodiment, a drape detection light source 386 (see FIG. 17E), such as an LED, may be used to transmit light that is detected by a corresponding sensor 387, such as a photodiode, only when reflected off of an installed drape lens. For example, according to an embodiment, the light source 386 may have a narrow emission wavelength band centered around about 905 nm and the sensor 387 may have a narrow wavelength detection band that includes wavelengths of about 905 nm. In one embodiment, the light source 386 and the sensor 387 are located near the forward portion of the enclosure 360 behind the plate 302. In one embodiment, as shown in FIG. 9C, a reflective feature 388 is located on the drape lens 380 in a position aligned with the light source 386 and the sensor 387, such that light from the light source 386 is reflected off of one or more interfaces of the reflective feature 388 and onto the sensor 387. For example, according to one embodiment of a drape detection module 385 as shown in FIG. 19, the reflective feature 388 may comprise a triangular prism protruding from the surface of the drape lens 380, which may reflect detection light 389 from light source 386 onto sensor 387. For example, the reflective feature 388 may reflect detection light 389 using total internal reflection. In one variation, the output from the sensor 387 may be fed to a transimpedance amplifier in order to amplify the drape detection signal. In one variation, the light source 386 and the sensor 387 may be located on the enclosure nosepiece. In one variation, the intensity of the reflected light signal detected at the sensor 387 may be used as feedback to assess and adjust the installation positioning of the drape lens 380, in order to minimize artifacts caused by misalignment of the drape lens. In one variation, detection of the installation of the drape lens 380 as indicated by the drape detection module 385 may trigger automatic adjustment of illumination and/or imaging parameters or automated changes to the image processing performed by the processor assembly. For example, the imaging and illumination system may be calibrated and/or configured to correct for distortion, attenuation, or other effects on illumination and/or imaging caused by the installation of the drape lens 380.

According to an embodiment, the process for installation of the drape onto the enclosure includes unpacking the drape, installing the drape lens onto the enclosure nosepiece by pushing the drape lens into place until an audible and/or tactile click is sensed by the user (indicating the interlock interfaces have engaged with the corresponding ridges in the enclosure nosepiece), rolling the drape bag back over the camera, and securing as needed the drape bag at the front and rear of the enclosure and along the enclosure cables. To remove the drape from the enclosure, the clips on the drape interlock interfaces may be pressed inwards in order to disengage from the ridges and then pulled away from the enclosure. In accordance with the above processes, both the installation and removal of the drape lens may be performed with one hand in contact with the drape lens.

Figure 10B:
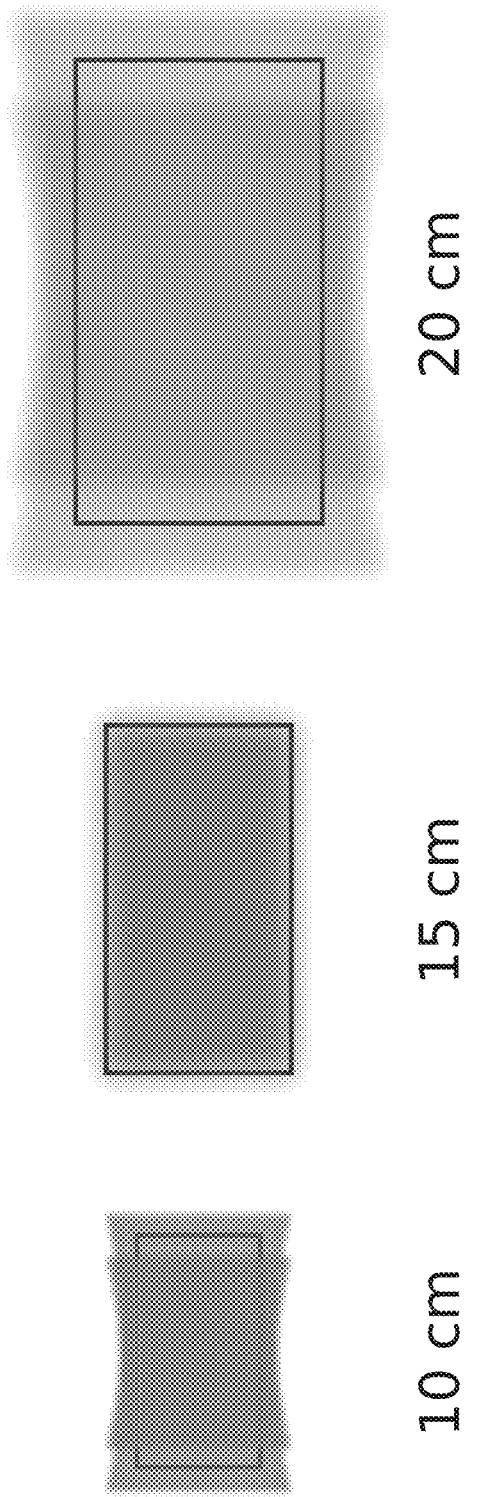

FIGS. 10A to 10C illustrate typical illumination distributions (fill) relative to a rectangular imaging field of view (outline) for an illumination ring (FIG. 10A), a pair of fixed anamorphic projection illumination sources (FIG. 10B), a pair of steered anamorphic projection illumination sources in accordance with an embodiment (FIG. 10C), and a steered illumination ring (FIG. 10D) at working distances of 10 cm (left column), 15 cm (center column), and 20 cm (right column). FIG. 10A illustrates use of a ring of illumination ports to minimize shadowing, but does not match illumination to the imaging field of view and may not provide even illumination at all working distances (e.g. varied distributions in accordance with distance). FIG. 10D illustrates use of a steered ring of three or more illumination ports to facilitate minimizing shadowing and providing even illumination when changing working distance in accordance with an embodiment, but does not constrain illumination to the imaging field of view. FIG. 10B illustrates anamorphic projection from two illumination sources using, e.g., an illumination lens arrangement featuring cylindrical lenses or an engineered diffuser) that are fixed, thus they are well calibrated for even illumination that matches the imaging field of view at a fixed working distance, e.g., 15 cm, but not as even or well matched at other distances, whether smaller or greater. As noted above, such illumination is often acceptable on its own. FIG. 10C illustrates the ability to better maintain even illumination and constrain illumination to the field of view by steering illumination when changing the working distance and imaging focus in accordance with an embodiment.

As noted above, the illumination used may include both white light and fluorescence excitation illumination, e.g., from a laser, to excite NIR light from the target. However, ambient light may interfere with the light from the target.

FIG. 11A illustrates a timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor. As used herein, a white pulse will indicate that the white light (RGB) is illuminating the target and an excitation pulse will indicate that the laser is illuminating the target.

Exposures of even (Exp 1) and odd (Exp 2) sensor pixel rows are shown interleaved with differing exposure times to facilitate isolation of an estimate of the ambient room light signal component. Such an interleaved exposure read-out mode is offered on some imaging sensors, such as the 'High Dynamic Range Interleaved Read-out' mode offered on the CMOSIS CMV2000 sensor.

Pulsing the white light illumination at 80 Hz brings the frequency of the flashing light above that which is perceptible by the human eye or which may trigger epileptic seizures. The visible light image exposure may be longer than, e.g., twice, the RGB illumination to ensure overlap between the 60 Hz exposure frame rate and the 80 Hz RGB illumination pulse. Extra ambient light captured during the visible exposure may be ignored, due to the much greater intensity of the RGB illumination pulse and signal from the target 12.

By setting the NIR fluorescence image exposure times Exp 1 and Exp 2 to acquire for one-half frame and one quarter frame periods, respectively, while running the excitation laser only in the last one quarter of every third frame, the even rows (Exp 1) record one-half frame of ambient room light in addition to one quarter frame of NIR fluorescence, while the odd rows (Exp 2) record one quarter frame of ambient room light plus one quarter frame of NIR fluorescence. Performing these fractional exposures within each visible or NIR fluorescence frame minimizes motion artifacts which would otherwise be caused by inserting additional exposure frames into the frame sequence for the purpose of ambient room light subtraction.

With such an acquisition design, an estimate of the ambient room light contribution to the image signals can be isolated by subtracting the Exp 2 sensor rows of the NIR fluorescence image from the Exp 1 sensor rows (interpolated to match Exp 2 pixel positions), yielding an estimate of one quarter frame of ambient room light signal. The estimate of one quarter frame of ambient room light signal can then be subtracted from the Exp 2 sensor rows of the NIR fluorescence image to yield an estimate of the NIR fluorescence signal with the one quarter frame of ambient room light removed. The control of the illumination and the exposure may be performed by the VPI box 14.

Figures 12A, 12B, 12C:
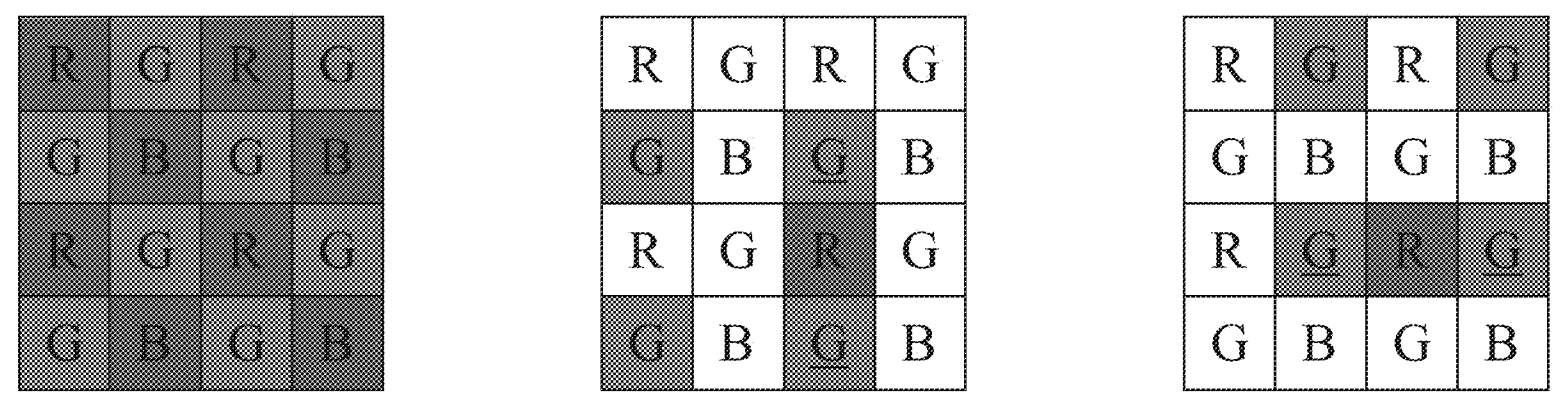

In one embodiment, the above room light subtraction method may be altered in order to accommodate use of a Bayer-pattern color sensor. FIG. 12A illustrates a Bayer pattern arrangement of colored sensor pixels, wherein the even sensor rows and odd sensor rows have different filter arrangements (e.g., no red pixels in the even sensor rows and no blue pixels in the odd sensor rows), so the ambient light recorded on even rows will not be a good estimate of what reached the odd rows over the same period. However, every row does include green pixel signals, which are also sensitive to NIR fluorescence. Using only the green pixels, and performing a two-dimensional interpolation from the green pixel signals to the other pixel locations can yield an estimate of the ambient light signal component, and thus also of the NIR fluorescence or visible light components for the NIR and visible light images, respectively.

In order to calculate the NIR signal value at a given location, calculate the Exp 1 (even row) and Exp 2 (odd row) green pixel values near that location, with one or both of those values needing to be interpolated. FIG. 12B demonstrates an example wherein at a red pixel location, the best estimate of the Exp 1 (even row) green value is the average of the immediately neighboring green values above and below, while the best estimate of the Exp 2 (odd row) green value is the average of the immediately neighboring green values to the left and right.

The following mathematical example serves to illustrate an embodiment of the ambient room light subtraction method. If A=ambient light incident in one quarter frame period, and F=fluorescence incident in one quarter frame period, then:

$$Exp\ 1 = 2A + F$$

$$Exp\ 2 = A + F$$

Solving for yields:

$$F = *Exp\ 2 - Exp\ 1$$

In the particular example illustrated in FIG. 11A, a period for the sensing is three frames, the white light pulse and the excitation pulse have a same duration or width, but different frequencies, the visible light is sensed during two frames, e.g., the first two frames, and the fluorescence is sensed for during one frame, e.g., the third or final frame, for two different exposure times. As shown therein, the visible exposure time may be twice the duration of the white light pulse, a first fluorescent exposure times may be equal to the duration of the excitation pulse, and a second fluorescent exposure time may be pulse longer, e.g., twice, than the excitation pulse. Further, the visible exposure may have a different frequency than the white light pulse, e.g., visible exposure does not occur with every white light pulse, while the fluorescent exposure may have a same frequency as the excitation pulse.

Alternative timing and exposure diagrams are discussed below, in which a sensor having rows that are all active for a common exposure duration may be used while still compensating for ambient light using a single sensor. For example, background light may be directly detected by the sensor when the target is not illuminated. Other variations on pulsing, exposing, and sensing may be apparent to those of skill in the art.

FIG. 11B illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor. Exposures for visible light and for fluorescence are shown in sequence along with an exposure to capture the background (BG) image signal due to ambient light. The white light illumination may be pulsed at 80 Hz as described above. The fluorescence excitation illumination may be pulsed at 20 Hz and the pulse duration or width may be increased, e.g., up to double the white light pulse duration, to enable a longer corresponding fluorescence exposure. If using an imaging sensor with a global shutter, each sensor exposure must terminate with the read-out period at the end of an imaging frame. An exposure to capture the ambient light background image signal may be performed at the end portion of a frame in the absence of any pulsed white light or excitation light. In the case of acquiring video at a frame rate of 60 Hz, as shown in the example in FIG. 11B, a white light illumination pulse width of one quarter frame duration may be used, along with a one quarter frame duration visible light exposure occurring in frames when the end of a white light illumination pulse is aligned with the end of the frame.

A scaled image signal recorded during one or more background exposures can be subtracted from each fluorescence exposure image to remove the contribution of ambient light from the fluorescence image. For example, the image signal from a one quarter frame duration background exposure may be scaled up by two times and subtracted from a subsequent image signal from a one-half frame duration fluorescence exposure. As another example, a one quarter frame duration background exposure image signal prior to a one-half frame duration fluorescence exposure image signal, and a second one quarter frame background image signal subsequent to the fluorescence exposure, may both be subtracted from the fluorescence image signal. Scaling of the image signals from a first and a second background exposure can include interpolation of pixel values from the first exposure time point and the second exposure time point to estimate pixel values corresponding to an intermediate time point.

Use of an imaging sensor with high speed read-out that enables higher video frame acquisition rates may allow for additional exposure periods to be allocated within an illumination and exposure timing scheme for a given white light pulse frequency. For example, maintaining an 80 Hz white light illumination pulse as above and using a sensor with a higher video frame acquisition rate such as 120 Hz may allow additional white light, ambient background, or fluorescence exposures within a given time period, compared to when using a slower video frame acquisition rate such as 60 Hz.

In the particular example illustrated in FIG. 11B, a period for the sensing is three frames, the excitation pulse has twice the width of the white light pulse, the visible light is sensed during one frame, e.g., the first frame, the background light is sensed during one frame, e.g., the second frame, and the fluorescence is sensed during one frame, e.g., the third or final frame. Here, a visible exposure time may be equal to the duration of the white light pulse, the background exposure time may be equal to the duration of the white light pulse, and the fluorescence exposure time may be equal to the duration of the excitation pulse. Further, the visible exposure may have a different frequency than the white light pulse, e.g., visible exposure does not occur with every white light pulse, while the fluorescent exposure may have a same frequency as the excitation pulse. Finally, the background exposure may occur only once within the period.

FIG. 11C illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor with a 120 Hz video frame acquisition rate. A white light pulse frequency of 80 Hz is used, and a white light illumination pulse width of one-half frame duration may be used, along with a one-half frame duration visible light exposure occurring in frames when the end of a white light illumination puke is aligned with the end of the frame. The fluorescence excitation illumination is shown pulsed at 40 Hz with a pulse duration of one frame, to enable a higher frequency of corresponding fluorescence exposures. An exposure to capture the ambient light background image signal may be performed at the end portion of a frame in the absence of any pulsed white light or excitation light, such as an exposure of one-half frame duration occurring in the frame between a fluorescence exposure and a successive white light exposure as shown in this example embodiment.

In the particular example illustrated in FIG. 11C, a period for the sensing is three frames, the excitation pulse has twice the width of the white light pulse, the visible light is sensed during one frame, e.g., the second frame, the background light is sensed during one frame, e.g., the first frame, and the fluorescence is sensed during one frame, e.g., the third or final frame. Here, a visible exposure time may be equal to the duration of the white light pulse, the background exposure time may be equal to the duration of the white light pulse, and the fluorescence exposure time may be equal to the duration of the excitation pulse. Further, the visible exposure may have a different frequency than the white light pulse, e.g., visible exposure does not occur with every white light pulse, while the fluorescent exposure may have a same frequency as the excitation pulse. Finally, the background exposure may occur only once within the period.

Depending on the intensity of the fluorescence excitation light used, there may be safety considerations limiting the duration and frequency of excitation light pulses. One approach to reduce the excitation light intensity applied is to reduce the duration of the excitation light pulses and the corresponding fluorescence exposures. Additionally or alternatively, the frequency of excitation light pulses (and corresponding fluorescence exposures) may be reduced, and the read-out periods which could otherwise be used for fluorescence exposures may instead be used for background exposures to improve measurement of the ambient light.

FIG. 11D illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor with a 120 Hz video frame acquisition rate. A white light pulse frequency of 80 Hz is used, and a white light illumination pulse width of one-half frame duration may be used, along with a one-half frame duration visible light exposure occurring in frames when the end of a white light illumination pulse is aligned with the end of the frame. The fluorescence excitation illumination is shown pulsed at 20 Hz with a pulse duration of one frame. An exposure to capture the ambient light background image signal may be performed at the end portion of a frame in the absence of any pulsed white light or excitation light, such as a background exposure of one-half frame duration occurring in the frame between a fluorescence exposure and a successive first white light exposure, and a first background exposure of one frame duration and a second background exposure of one-half frame duration both occurring in the frames between the first white light exposure and a successive second white light exposure, as shown in this example embodiment.

In the particular example illustrated in FIG. 11D, a period for the sensing is six frames, the excitation pulse has twice the width of the white light pulse, the visible light is sensed during two frames, e.g., the second and fifth frames, the background light is sensed during three frames, the first, third, and fourth frames, and the fluorescence is sensed for during one frame, e.g., the sixth or final frame. Here, a visible exposure time may be equal to the duration of the white light pulse, the background exposure time may be equal to or twice the duration of the white light pulse, and the fluorescence exposure time may be equal to the duration of the excitation pulse. Further, the visible exposure may have a different frequency than the white light pulse, e.g., visible exposure does not occur with every white light pulse, e.g., only twice within the period, while the fluorescence exposure may have a same frequency as the excitation pulse. Finally, the background exposure may occur three times within the period for a total duration equal to four times the duration of the white light pulse.

In some use environments for an open field imaging device, such as the device according to the various embodiments described herein, the ambient room lighting may comprise light that is pulsating, or periodic, rather than continuous. Such pulsating light components may, for example, be due to the interaction between some room light sources and an AC frequency of their power source. For example, incandescent lights, some LED lights, some fluorescent lights including fluorescent lights with low frequency ballasts, or arc lamps may emit pulsating light when connected to common 50 Hz or 60 Hz AC mains power or other AC power sources. The presence of pulsating light components in the background light signal may introduce distracting image intensity artifacts during acquisition of sequential images, due to sequential exposures receiving different accumulated light intensity contributions from the pulsating light components in the background light, therefore it may be useful to correct acquired images to reduce or remove such artifacts. Such correction may be useful both with or without also using a room light subtraction technique, and may include one or more exemplary techniques such as: detecting the AC frequency of the power source for the pulsating light components; modifying the image acquisition frame rate; modifying the exposure durations for fluorescence and/or background light exposures; measuring the pulsating light intensity during a period in which the device illumination is turned off; synthesizing a complete periodic cycle of the pulsating light intensity; identifying the portion of the periodic cycle of the pulsating light intensity coinciding with the fluorescence and/or background light exposures; calculating a fluorescence accumulated ambient light value, $FL_{acc}$, corresponding to the accumulated ambient light intensity during a fluorescence exposure; calculating a background accumulated ambient light value, $BG_{acc}$, corresponding to the accumulated ambient light intensity during a background exposure; and scaling the image intensity of a fluorescence image or a background image based on a ratio of the respective accumulated light values, $FL_{acc}$ and $BG_{acc}$, and, subtracting the background image from the fluorescence image to output a resultant image.

In some embodiments, the AC frequency, $F_{AC}$, of the power source for a pulsating light component of the ambient room lighting may be retrieved from the device memory, for example due to a user setting a known frequency value during device calibration in a use environment, or may be detected based on measurements by the imaging device. For example, one or more sensors 395 (see FIG. 17E) may be used to measure the ambient light intensity during one or more periods when the device white light illumination is turned off and the fluorescence excitation illumination is turned off. In one embodiment, the one or more sensors 395 may be photodiodes and may have similar responsivity to the sensor used for fluorescence imaging, such as responsivity to visible and NIR light, with input cones approximating the field of view of the imaging device. As another example, in one variation in which an image sensor responsive only to NIR light, or an image sensor with separate filters provided forward of the image sensor that block visible or other non-NIR light from reaching the sensor, is used for fluorescence imaging, the one or more sensors 395 may be photodiodes with responsivity only to NIR light.

The periods of measurement by sensors 395 should be of sufficient duration and number such that they capture, in combination of successive measurement periods captured over, at maximum, about the time between successive fluorescence exposures, portions of the pulsating ambient light intensity constituting a complete periodic cycle, and such that there is at least partial overlap of cycle coverage for successive measurement periods in order to assist with synthesizing the periodic cycle of the pulsating ambient light, which may constrain the lower limit of frequencies $F_{AC}$ which may be supported. However, frequency values for $F_{AC}$ that are below 30 Hz may not be practical for use with room lighting as they may induce noticeable and distracting visible light flicker in general use. The frequency of the pulsating light intensity is typically twice that of the corresponding value of $F_{AC}$, since room light sources typically have equivalent response for each of the positive and negative voltage halves of an AC cycle.

FIG. 11E illustrates an exemplary timing diagram for white light (RGB) and fluorescence excitation (Laser) illumination, periods of ambient light measurement by sensors 395, and visible (VIS) and fluorescence (FL) imaging sensor exposures configured to allow ambient room light subtraction from the fluorescence signal and correction for pulsatile ambient light intensity with a single sensor, according to an embodiment. In this embodiment, the frequency of fluorescence excitation illumination and corresponding fluorescence exposures is 20 Hz, the frequency of white light illumination is 80 Hz, and ambient light measurement periods are all those periods in which both the white light illumination and fluorescence excitation illumination are turned off. The timing scheme shown may allow for pulsating ambient light intensity signals corresponding to all practical frequency values for $F_{AC}$ of 30 Hz or greater to be detected based on measurements within the time between successive fluorescence exposures, by capturing, in combination of multiple measurement periods, portions of the pulsating ambient light intensity constituting a complete periodic cycle, with at least partial overlap of cycle coverage for the multiple measurement periods. While a simplified pulsatile ambient light intensity profile with a frequency of 120 Hz, corresponding to a $F_{AC}$ of 60 Hz, is shown here for reference, the pulsatile ambient light correction technique as described herein may be used for any arbitrary pulsatile, or periodic, ambient light intensity profile. As seen here, the sample pulsatile ambient light intensity profile would yield different contributions of accumulated ambient light intensity for a fluorescence exposure and a background exposure, wherein those differences are not accounted for simply by a difference in exposure duration, because of those exposures capturing different portions of the pulsatile ambient light intensity profile. Other pulsatile ambient light intensity profiles, such as those with a frequency that is not a multiple or a factor of the fluorescence exposure frequency, may generally also yield different contributions of accumulated ambient light intensity from one fluorescence exposure to the next.

In some embodiments, a minimum sampling rate within each measurement period for sensors 395 may be set to at least four times the quotient of the anticipated maximum frequency $F_{AC}$ and the measurement period duty cycle in order to allow accurate synthesis of a complete pulsating ambient light intensity cycle with periodic frequency twice that of $F_{AC}$. In some variations, a higher sensor sampling rate may be used to provide more measurement points in partial overlap regions and/or to support higher possible $F_{AC}$ values. For example, as shown in FIG. 11E, with a measurement period duty cycle of 50%, a sensor sampling rate of at least 480 Hz may be used within the ambient light intensity measurement periods to support frequency values for $F_{AC}$ of up to 60 Hz and corresponding pulsatile ambient light intensity frequencies of up to 120 Hz. Partial overlap of cycle coverage allows comparison of measurements taken from multiple measurement periods in order to detect the frequency $F_{AC}$ (or the corresponding frequency of the pulsatile ambient light intensity), for example by calculating the frequency $F_{AC}$ (or the corresponding frequency of the pulsatile ambient light intensity) corresponding with the best temporal alignment, such as by minimizing a measure of average error between corresponding measurement points in candidate temporal alignments, of the portions of the periodic cycle captured by the multiple measurement periods. Arranging the portions of the periodic cycle captured by the multiple measurement periods according to the best temporal alignment may then yield the synthesis of a complete periodic cycle of duration $1/(2F_{AC})$. In some variations, a complete periodic cycle may be extracted directly from a single measurement period which is longer in duration than the complete periodic cycle. Synthesis or extraction of the complete periodic cycle permits extending/extrapolating the pulsatile ambient light signal beyond periods in which measurement by the sensors 395 was performed.

In some embodiments, the imaging device image acquisition frame rate may be set to match the known or detected AC frequency, or a multiple thereof, of the power source for a pulsating light component of the ambient room lighting such that equivalent contributions from the pulsating light component are present in each fluorescence exposure of a given duration. To accommodate such a setting of the image acquisition frame rate, corresponding scaling may be performed of the frequency of a pulsed white light source, the frequency of a pulsed fluorescence excitation light source, and the frequencies of image exposures. In embodiments also using a room light subtraction technique that includes taking a background light exposure, exposure durations for the background light exposure and the fluorescence light exposure may be set to be equal such that equivalent contributions from the pulsating light component are present in both exposures.

In some embodiments using a room light subtraction technique that includes taking a background light exposure, a background exposure image intensity and/or a fluorescence exposure image intensity may be scaled based on measurements of the pulsating room light intensity, in order that the scaled image intensities correspond to equivalent contributions from the pulsating room light. After measuring the pulsating light intensity and synthesizing a complete periodic cycle of the pulsating light intensity, as described herein, identification of the portion of the periodic cycle of the pulsating light intensity coinciding with a fluorescence exposure and a background light exposure may be performed by repeating/extrapolating the periodic cycle as necessary to find the portion that coincided with the time spanned by each respective exposure. Calculating a fluorescence accumulated ambient light value, $FL_{acc}$, corresponding to the accumulated ambient light intensity during a fluorescence exposure may then be performed by calculating the area under the curve marked by the portion of the periodic cycle of pulsating light intensity for that exposure, and calculating a background accumulated ambient light value, $BG_{acc}$, corresponding to the accumulated ambient light intensity during a background exposure may be performed by calculating the area under the curve for the portion of the periodic pulsating light intensity coinciding with that exposure. Scaling the image intensity of a fluorescence image or a background image may then be performed based on a ratio of the respective accumulated light values, $FL_{acc}$ and $BG_{acc}$, in order to normalize the scaled images such that they reflect equivalent contributions of accumulated ambient light. Subsequent to scaling, the scaled background image may be subtracted from the scaled fluorescence image to yield a corrected fluorescence image that removes the ambient light signal and includes correction for pulsatile ambient light contributions. In one embodiment, one or the other of the fluorescence image or the background image is scaled by a factor of 1.

In embodiments where room light subtraction is not employed, the fluorescence exposure image intensity may be scaled based on measurements of the pulsating room light intensity, in order to facilitate reducing image intensity artifacts resulting from the pulsating room light. For example, the scaling may be performed based on a ratio of measured intensities for successive fluorescence images.

To improve performance of ambient room light compensation methods described herein, a wavelength-dependent aperture (e.g., element 55 in FIG. 6A) may be used that includes a smaller central aperture that permits transmission of all visible and NIR light, and a surrounding larger aperture that blocks visible light but permits transmission of NIR light. Use of such a wavelength-dependent aperture allows a larger proportion of NIR signal to be collected relative to the visible light signal, which improves performance of the image signal subtraction for estimation and removal of the ambient room light component. A wavelength-dependent aperture may also feature a third, larger aperture, surrounding the other smaller apertures, that blocks both visible and NIR light. As an example, a wavelength-dependent aperture may comprise a film aperture, wherein a film (e.g., a plastic or glass film) of material that blocks transmission of visible light but permits transmission of NIR light has a central opening (e.g., a hole) that permits transmission of both visible and NIR light. Such a film aperture may comprise material that blocks transmission of visible light through reflection and/or material that blocks transmission of visible light through absorption. As another example, a wavelength-dependent aperture may comprise a dichroic aperture which is formed by masked thin-film deposition on a single substrate, wherein a thin-film that permits transmission of visible and NIR light is deposited on a smaller central aperture, and a second thin-film that blocks transmission of visible light but permits transmission of NIR light is deposited on a surrounding larger aperture. The respective aperture sizes of the smaller central aperture and the surrounding larger aperture of a wavelength-dependent aperture may be set in order to make the depth of field for visible light and for NIR light appear substantially similar when imaged by the imaging system. One or more wavelength-dependent filters may be placed in different positions throughout the device, where rejection of the visible and passage of the NIR signal may be optimized. For example, such a wavelength-dependent filter may be positioned just before the lens 51. As another example, one or more wavelength-dependent filters may be placed in a pupil plane of the imaging lens.

It may be useful, e.g., to facilitate comparison of the fluorescence signal of different regions, to display a target reticle around a region within the imaged field of view, and to calculate and display the normalized fluorescence intensity within that region. Normalization of the measured fluorescence intensity values may allow for meaningful comparison of multiple images and corresponding values. To correct for the variation of measured fluorescence intensity with working distance (e.g., distance of the imaging system to the imaged anatomy), normalized fluorescence intensity values may be based on a ratio between the measured fluorescence intensity values and a reflected light value within the target reticle region.

A numerical representation of the normalized fluorescence intensity value within the target reticle region may be displayed on or near the image frame, to facilitate comparing values when aiming the target reticle at different locations on the imaged anatomy. For example, the numerical representation may be the mean value of the normalized fluorescence intensity values for all of the image pixels in the target reticle region.

Additionally or alternatively, a time history plot of the numerical representation of the normalized fluorescence intensity value within the target reticle region may be displayed on or near the image frame, to facilitate comparing values when aiming the target reticle at different locations on the imaged anatomy or at the same location over a series of time points. Such a time history plot may further assist the user in assessing the fluorescence profile in the imaged tissue surface by scanning across the anatomy region of interest and viewing the relative normalized fluorescence intensity profile plot.

Figure 13A:
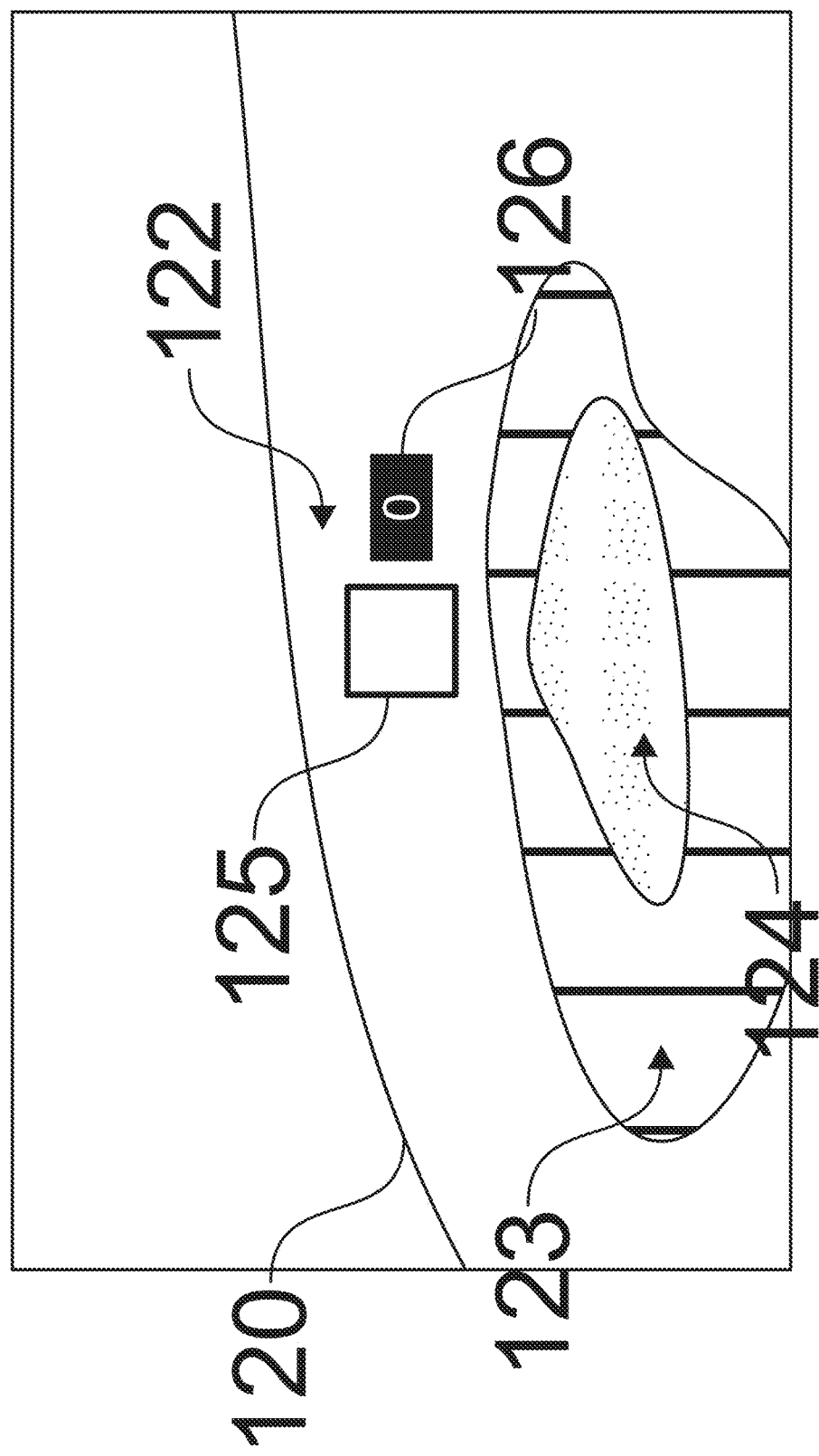
Figure 13B:
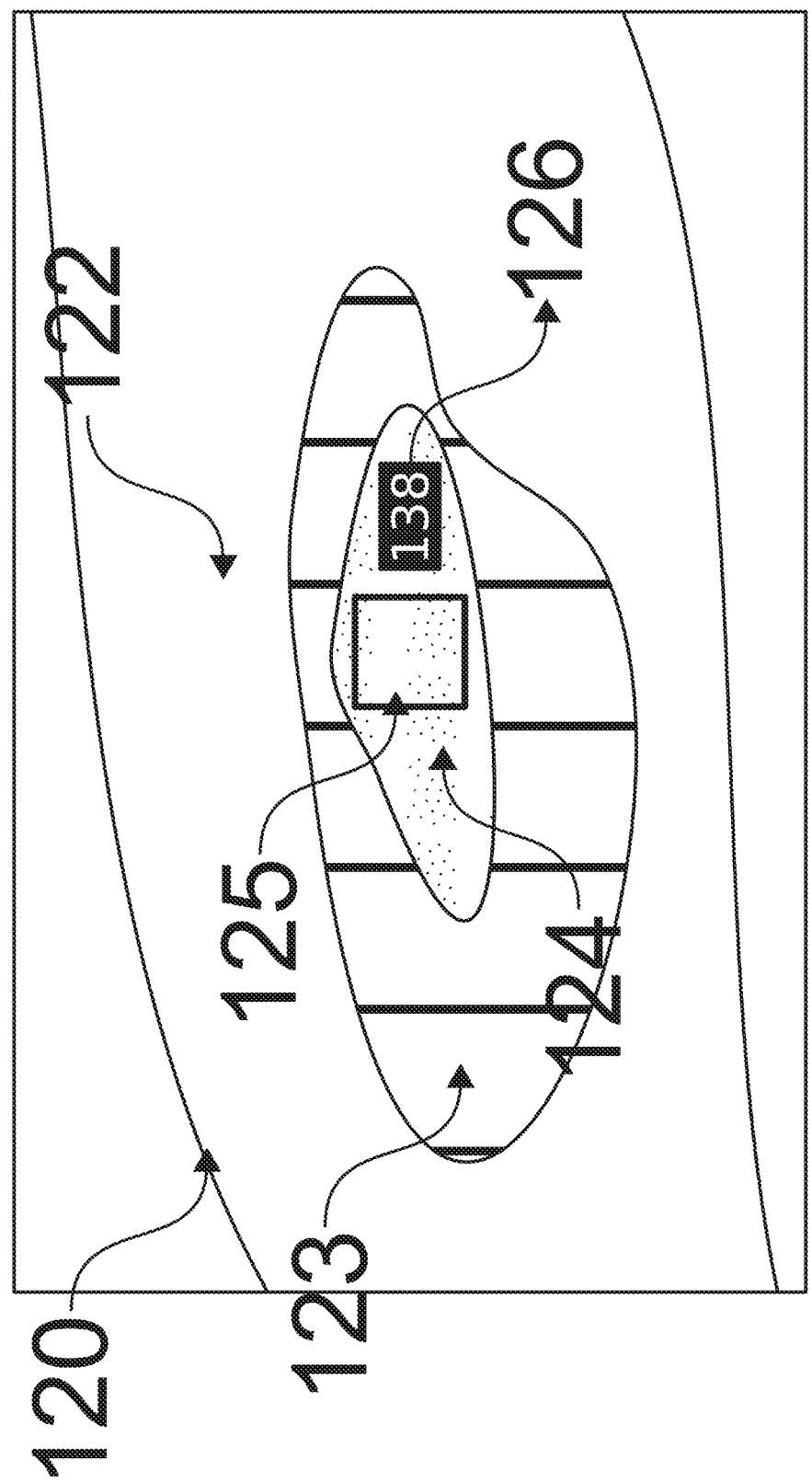
Figure 13D:
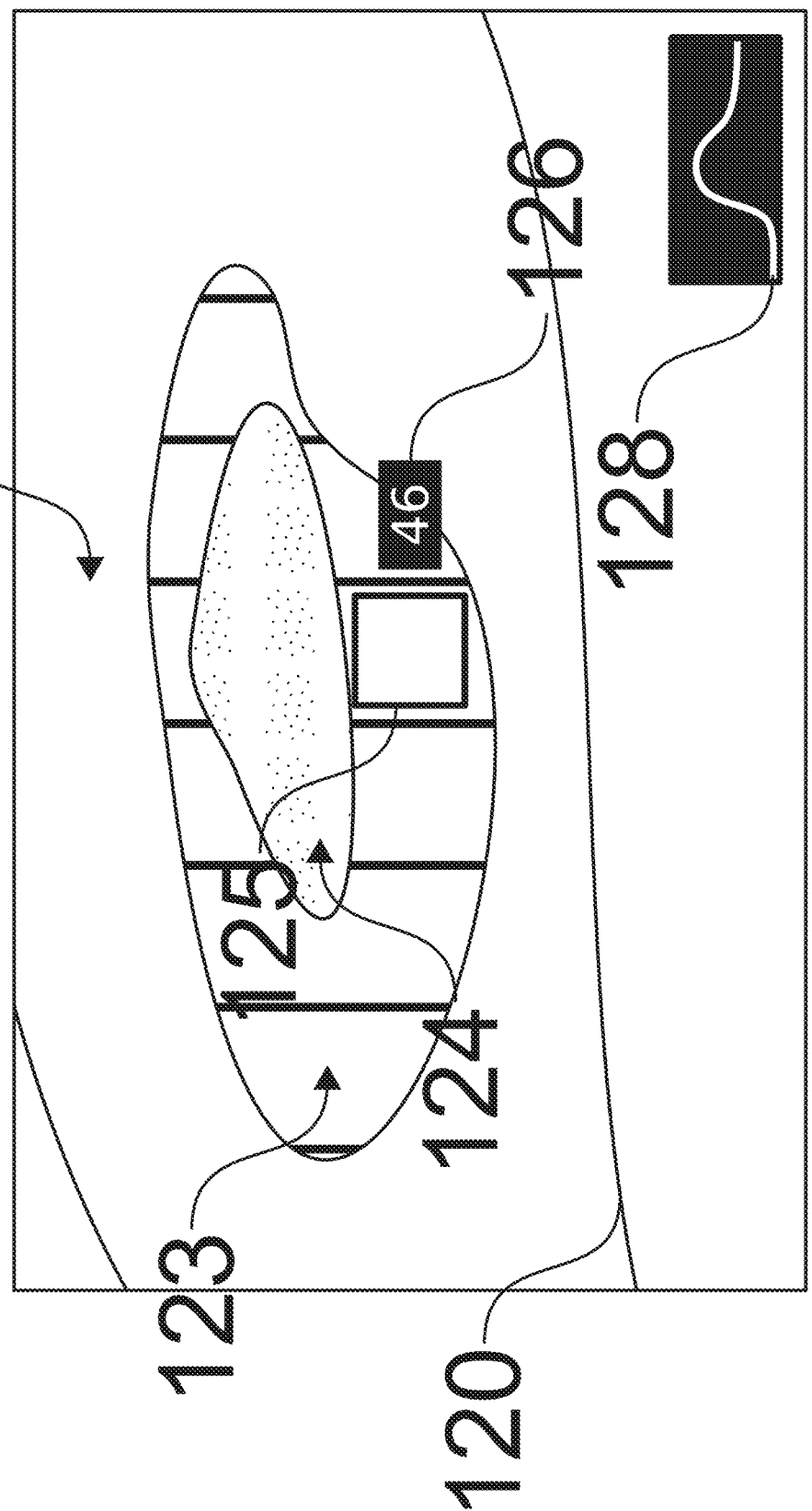
FIG. 13D illustrates a diagram of an embodiment of a display method output that includes a signal time history plot of normalized fluorescence intensity values on the display.

FIG. 13A illustrates a diagram of a sample display output from an embodiment of the display method, wherein the target reticle 125 is positioned over a region of no fluorescence intensity 122 on the imaged anatomy 120, and the numerical representation of the fluorescence intensity 126 is displayed near the target reticle 125. FIG. 13B illustrates a diagram of another sample display output, wherein the target reticle 125 is positioned over a region of high relative normalized fluorescence intensity 124, and showing a corresponding numerical representation 126 of relatively high fluorescence intensity. FIG. 13C illustrates a diagram of another sample display output, wherein the target reticle 125 is positioned over a region of moderate relative normalized fluorescence intensity 124, and showing a corresponding numerical representation 126 of relatively moderate fluorescence intensity. FIG. 13D illustrates a diagram of a sample display output, wherein the target reticle 125 is positioned over a region of moderate relative normalized fluorescence intensity 124, and showing a time history plot 128 of the numerical representation of normalized fluorescence intensity that would be consistent with sequential imaging of regions of zero, high, and moderate relative normalized fluorescence intensity. Alternatively or additionally to displaying the numerical representation and/or historical plot on the target, a display region associated with the target reticle, e.g., on the device itself or some other display, may display this information.

Figure 14:
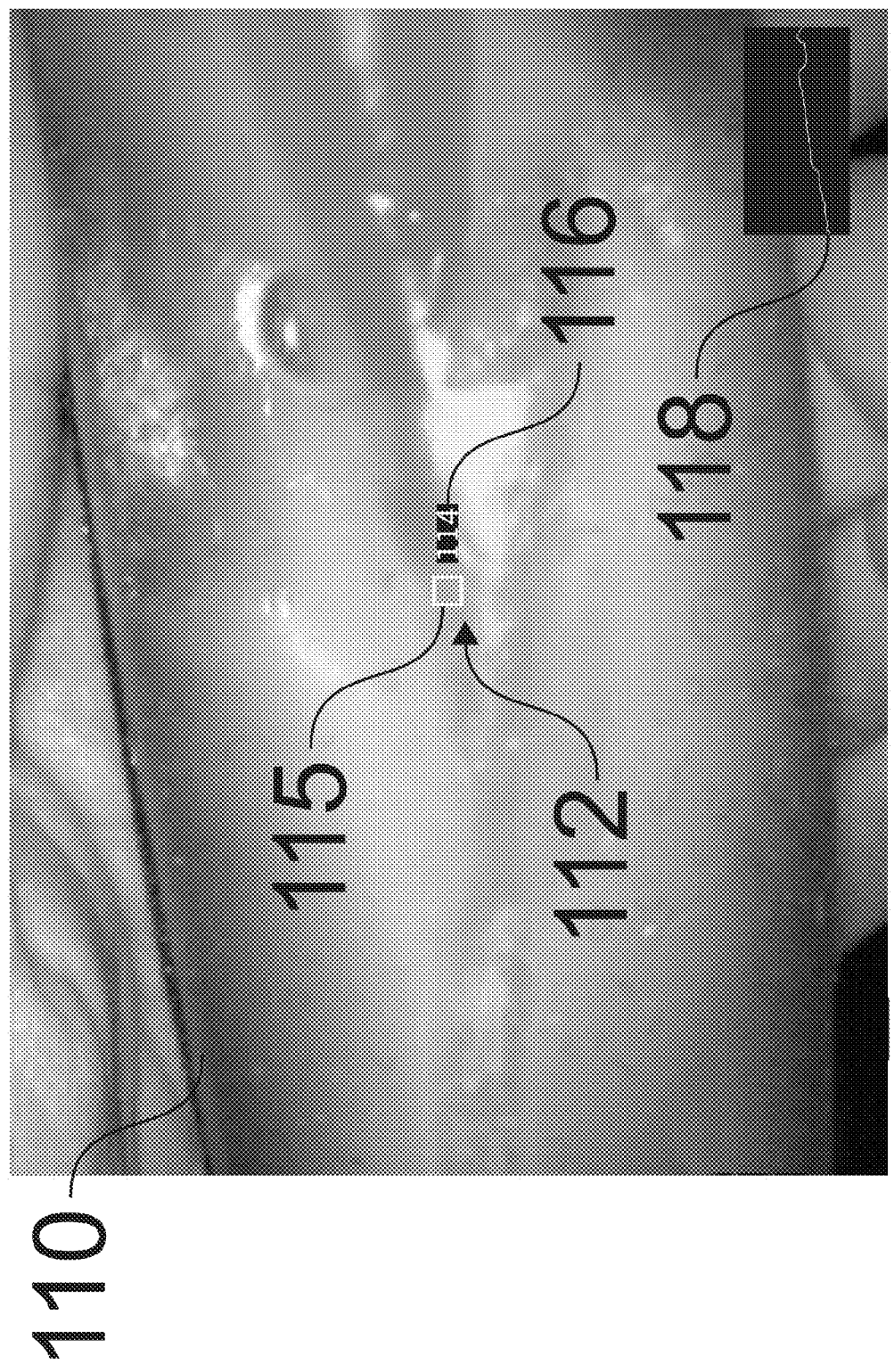
FIG. 14 illustrates a recorded image of an anatomical fluorescence imaging phantom, featuring an embodiment of a display method output that displays normalized fluorescence intensity.

FIG. 14 illustrates a recorded image of an anatomical fluorescence imaging phantom, featuring an embodiment of a display method output that displays normalized fluorescence intensity. In particular, a target 110 is illuminated by excitation light in accordance with an embodiment and a target reticle 115 is positioned over a region of fluorescence intensity 112. A numerical representation of the target reticle 115 is displayed in a region 116 associated with the target reticle 115. A time history plot 118 of the numerical representation of normalized fluorescence intensity due to imaging of different positions of the reticle 115 may be displayed.

Normalization of the measured fluorescence intensity values may additionally or alternatively be performed on a pixel basis for an entire acquired fluorescence image or series of images, which may facilitate providing a consistent and/or smoothly varying image brightness, even when varying the working distance. To correct for the variation of measured fluorescence intensity with working distance (e.g., distance of the imaging system to the imaged anatomy), normalized fluorescence intensity values for each pixel in an acquired fluorescence image may be based on a ratio between the measured fluorescence intensity value of that pixel and a reflected light value or component of a reflected light value for the same pixel in an acquired reflected light image. In one embodiment, the reflected light image used for such normalization is a white light image formed from reflection of visible white light illumination. For example, in embodiments in which a color image sensor is used to acquire the reflected light image, an overall luminance value, or a combination of one or more color channel intensities detected for each pixel from the color image sensor may be used.

Such a display method and/or technique for normalization of the measured intensity values, as any one of those described herein, may be useful for a variety of fluorescence imaging systems, including an endoscopic or laparoscopic fluorescence imaging system, an open field fluorescence imaging system, or a combination thereof. Such normalization and display of the fluorescence intensity values can allow useful quantitative comparisons of relative fluorescence intensity between image data from various time points within an imaging session. Combined with appropriate standardized fluorescent agent administration and imaging protocols, and standardized calibration of imaging devices, such normalization and display of the fluorescence intensity values can further allow useful quantitative comparisons of relative fluorescence intensity between image data from different imaging sessions.

EXAMPLES

A Fluorescence Medical Imaging System for Acquisition of Image Data

In some embodiments, a system (also referred in some embodiments as a device) for illumination and imaging of a subject may be used with or as a component of a medical imaging system such as, for example, a fluorescence medical imaging system for acquiring fluorescence medical image data. An example of such a fluorescence medical imaging system is the fluorescence imaging system 10 schematically illustrated in FIG. 1. In this embodiment, the fluorescence imaging system 10 is configured to acquire a time series of fluorescence signal intensity data (e.g., images, video) capturing the transit of a fluorescence imaging agent through the tissue.

The fluorescence imaging system 10 (FIG. 1) comprises an illumination source 15 and illumination module 11 to illuminate the tissue of the subject to induce fluorescence emission from a fluorescence imaging agent 17 in the tissue of the subject (e.g., in blood), an imaging module 13 configured to acquire the time series of fluorescence images from the fluorescence emission, and a processor assembly 16 configured to utilize the acquired time series of fluorescence images (fluorescence signal intensity data) according to the various embodiments described herein.

In various embodiments, the illumination source 15 (FIG. 1) comprises, for example, a light source 200 (FIG. 15) comprising a fluorescence excitation source configured to generate an excitation light having a suitable intensity and a suitable wavelength for exciting the fluorescence imaging agent 17. The light source 200 in FIG. 15 comprises a laser diode 202 (e.g., which may comprise, for example, one or more fiber-coupled diode lasers) configured to provide excitation light to excite the fluorescence imaging agent 17 (not shown). Examples of other sources of the excitation light which may be used in various embodiments include one or more LEDs, arc lamps, or other illuminant technologies of sufficient intensity and appropriate wavelength to excite the fluorescence imaging agent 17 in the tissue (e.g., in blood). For example, excitation of the fluorescence imaging agent 17 in blood, wherein the fluorescence imaging agent 17 is a fluorescent dye with near infra-red excitation characteristics, may be performed using one or more 793 nm, conduction-cooled, single bar, fiber-coupled laser diode modules from DILAS Diode Laser Co, Germany.

Figure 15:
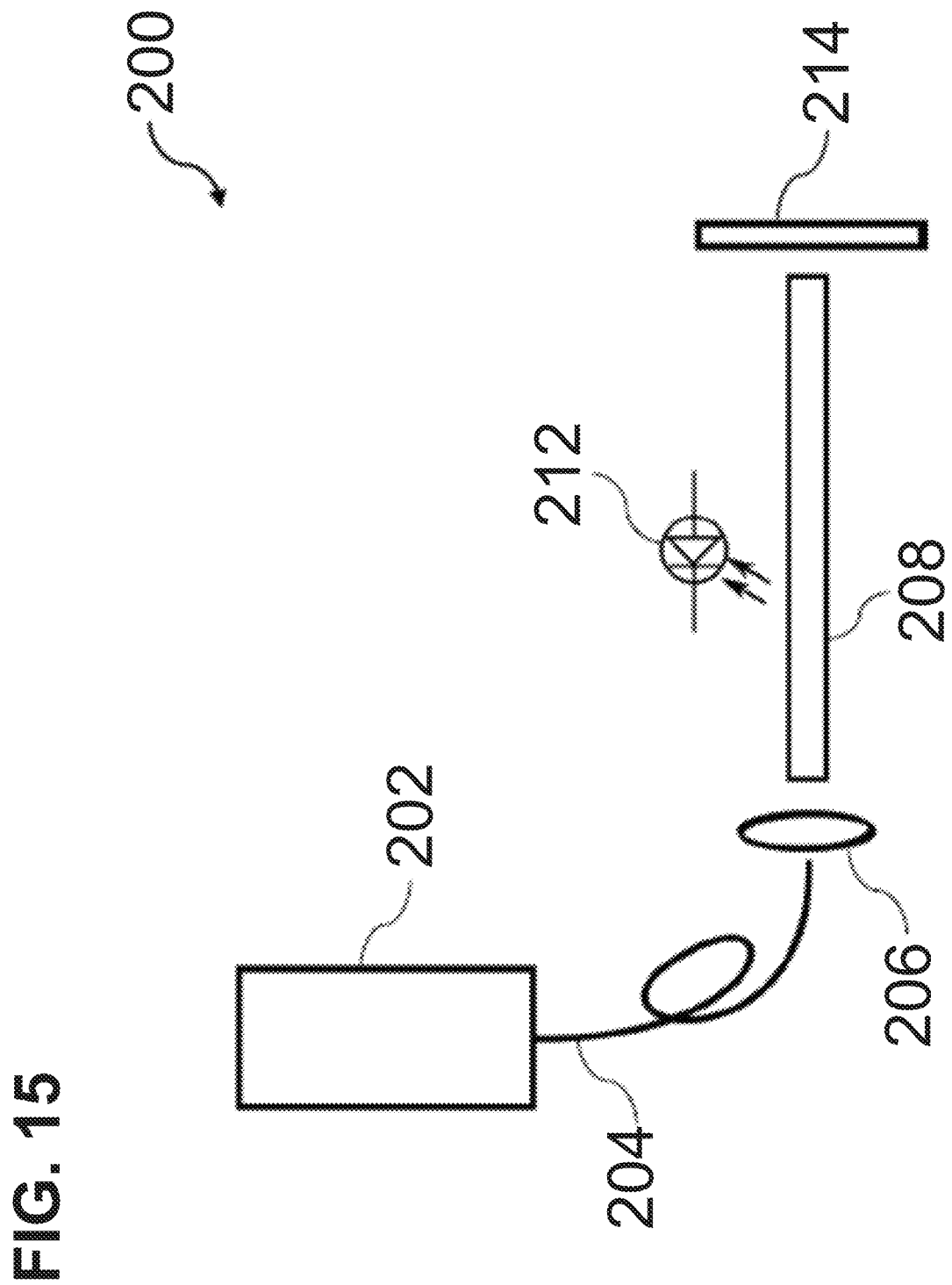
FIG. 15 illustrates an exemplary light source of an exemplary illumination source of the system for illumination shown in FIG. 1.

In various embodiments, the light output from the light source 200 in FIG. 15 may be projected through an optical element (e.g., one or more optical elements) to shape and guide the output being used to illuminate the tissue area of interest. The shaping optics may consist of one or more lenses, light guides, and/or diffractive elements so as to ensure a flat field over substantially the entire field of view of the imaging module 13. In particular embodiments, the fluorescence excitation source is selected to emit at a wavelength close to the absorption maximum of the fluorescence imaging agent 17 (e.g., ICG). For example, referring to the embodiment of the light source 200 in FIG. 15, the output 204 from the laser diode 202 is passed through one or more focusing lenses 206, and then through a homogenizing light pipe 208 such as, for example, light pipes commonly available from Newport Corporation, USA. Finally, the light is passed through an optical diffractive element 214 (e.g., one or more optical diffusers) such as, for example, ground glass diffractive elements also available from Newport Corporation, USA. Power to the laser diode 202 itself is provided by, for example, a high-current laser driver such as those available from Lumina Power Inc. USA. The laser may optionally be operated in a pulsed mode during the image acquisition process. In this embodiment, an optical sensor such as a solid state photodiode 212 is incorporated into the light source 200 and samples the illumination intensity produced by the light source 200 via scattered or diffuse reflections from the various optical elements. In various embodiments, additional illumination sources may be used to provide guidance when aligning and positioning the module over the area of interest. In various embodiments, at least one of the components of light source 200 depicted in FIG. 15 may be components comprising the illumination source 15 and/or comprising the illumination module 11.

Figure 16:
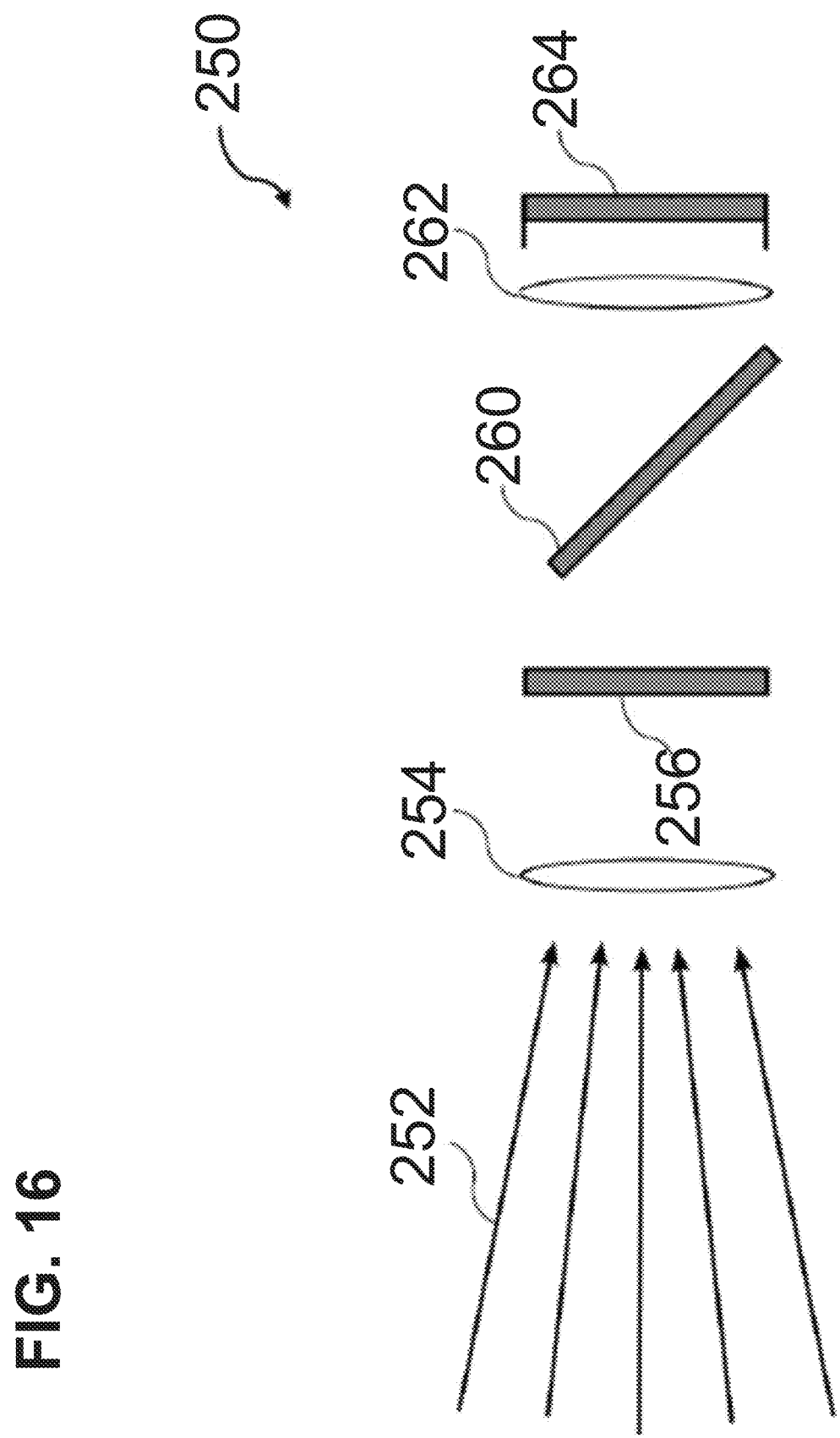
FIG. 16 illustrates an exemplary imaging module of the fluorescence imaging system in FIG. 1, the imaging module comprising a camera module.

Referring back to FIG. 1, in various embodiments, the imaging module 13 may be a component of, for example, the fluorescence imaging system 10 configured to acquire the time series of fluorescence images (e.g., video) from the fluorescence emission from the fluorescence imaging agent 17. Referring to FIG. 16, there is shown an exemplary embodiment of an imaging module 13 comprising a camera module 250. As is shown in FIG. 16, the camera module 250 acquires images of the fluorescence emission 252 from the fluorescence imaging agent 17 in the tissue (e.g., in blood) (not shown) by using a system of imaging optics (e.g., front element 254, rejection filter 256, dichroic 260 and rear element 262) to collect and focus the fluorescence emission onto an image sensor assembly 264 comprising at least one 2D solid state image sensor. A rejection filter 256 may be, for example, a notch filter used to reject a band of wavelengths corresponding to the excitation light. A dichroic 260 may be, for example, a dichroic mirror used to selectively pass one subset of the incoming light wavelength spectrum and redirect remaining wavelengths off of the optical path for rejection or towards a separate image sensor. The solid state image sensor may be a charge coupled device (CCD), a CMOS sensor, a CID or similar 2D sensor technology. The charge that results from the optical signal transduced by the image sensor assembly 264 is converted to an electrical video signal, which includes both digital and analog video signals, by the appropriate read-out and amplification electronics in the camera module 250.

According to some embodiments, excitation wavelength of about 800 nm+/−10 nm and emission wavelengths of >820 nm are used along with NIR compatible optics for ICG fluorescence imaging. A skilled person will appreciate that other excitation and emission wavelengths may be used for other imaging agents.

Referring back to FIG. 1, in various embodiments, the processor assembly 16 comprises, for example,

- a processor module (not shown) configured to perform various processing operations, including executing instructions stored on computer-readable medium, wherein the instructions cause one or more of the systems described herein to execute the methods and techniques described herein, and
- a data storage module (not shown) to record and store the data from the operations, as well as to store, in some embodiments, instructions executable by the processor module to implement the methods and techniques disclosed herein.

In various embodiments, the processor module comprises any computer or computing means such as, for example, a tablet, laptop, desktop, networked computer, or dedicated standalone microprocessor. Inputs are taken, for example, from the image sensor 264 of the camera module 250 shown in FIG. 16, from the solid state photodiode in the light source 200 in FIG. 15, and from any external control hardware such as a footswitch or remote-control. Output is provided to the laser diode driver, and optical alignment aids. In various embodiments, the processor assembly 16 (FIG. 1) may have a data storage module with the capability to save the time series of input data (e.g., image data) to a tangible non-transitory computer readable medium such as, for example, internal memory (e.g. a hard disk or flash memory), so as to enable recording and processing of data. In various embodiments, the processor module may have an internal clock to enable control of the various elements and ensure correct timing of illumination and sensor shutters. In various other embodiments, the processor module may also provide user input and graphical display of outputs. The fluorescence imaging system may optionally be configured with a video display (not shown) to display the images as they are being acquired or played back after recording, or further to visualize the data generated at various stages of the method as was described above.

In operation, and with continuing reference to the exemplary embodiments in FIGS. 1, 15 and 16, the subject is in a position for imaging where the anatomical area of interest of the subject is located beneath both the illumination module 11 and the imaging module 13 such that a substantially uniform field of illumination is produced across substantially the entire area of interest. In various embodiments, prior to the administration of the fluorescence imaging agent 17 to the subject, an image may be acquired of the area of interest for the purposes of background deduction. For example, in order to do this, the operator of the fluorescence imaging system 10 in FIG. 1 may initiate the acquisition of the time series of fluorescence images (e.g., video) by depressing a remote switch or foot-control, or via a keyboard (not shown) connected to the processor assembly 16. As a result, the illumination source 15 is turned on and the processor assembly 16 begins recording the fluorescence image data provided by the image acquisition assembly 13. In lieu of the pulsed mode discussed above, it will be understood that, in some embodiments, the illumination source 15 can comprise an emission source which is continuously on during the image acquisition sequence. When operating in the pulsed mode of the embodiment, the image sensor 264 in the camera module 250 (FIG. 16) is synchronized to collect fluorescence emission following the laser pulse produced by the diode laser 202. In the light source 200 (FIG. 15). In this way, maximum fluorescence emission intensity is recorded, and signal-to-noise ratio is optimized. In this embodiment, the fluorescence imaging agent 17 is administered to the subject and delivered to the area of interest via arterial flow. Acquisition of the time series of fluorescence images is initiated, for example, shortly after administration of the fluorescence imaging agent 17, and the time series of fluorescence images from substantially the entire area of interest are acquired throughout the ingress of the fluorescence imaging agent 17. The fluorescence emission from the region of interest is collected by the collection optics of the camera module 250. Residual ambient and reflected excitation light is attenuated by subsequent optical elements (e.g., optical element 256 in FIG. 16 which may be a filter) in the camera module 250 so that the fluorescence emission can be acquired by the image sensor assembly 264 with minimal interference by light from other sources.

In various embodiments, the processor is in communication with the imaging system or is a component of the imaging system. The program code or other computer-readable instructions, according to the various embodiments, can be written and/or stored in any appropriate programming language and delivered to the processor in various forms, including, for example, but not limited to information permanently stored on non-writeable storage media (e.g., read-only memory devices such as ROMs or CD-ROM disks), information alterably stored on writeable storage media (e.g., hard drives), information conveyed to the processor via transitory mediums (e.g., signals), information conveyed to the processor through communication media, such as a local area network, a public network such as the Internet, or any type of media suitable for storing electronic instruction. In various embodiments, the tangible non-transitory computer readable medium comprises all computer-readable media. In some embodiments, computer-readable instructions for performing one or more of the methods or techniques discussed herein may be stored solely on non-transitory computer readable media.

In some embodiments, the illumination and imaging system may be a component of a medical imaging system such as the fluorescence medical imaging system 10, which acquires medical image data. In embodiments where the illumination and imaging system is a component of the imaging system, such as the fluorescence imaging system described above, the light source, illumination module, imaging module and the processor of the medical imaging system may function as the camera assembly and the processor of the illumination and imaging system. A skilled person will appreciate that imaging systems other than fluorescence imaging systems may be employed for use with illumination and/or imaging systems such as those described herein, depending on the type of imaging being performed.

Example Imaging Agents for Use in Generating Image Data

According to some embodiments, in fluorescence medical imaging applications, the imaging agent is a fluorescence imaging agent such as, for example, indocyanine green (ICG) dye. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 µM to about 10 µM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue large vessels and microvasculature, and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. A fluorescence dye includes any non-toxic fluorescence dye. In certain embodiments, the fluorescence dye optimally emits fluorescence in the near-infrared spectrum. In certain embodiments, the fluorescence dye is or comprises a tricarbocyanine dye. In certain embodiments, the fluorescence dye is or comprises indocyanine green (ICG), methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality.

In some variations, the fluorescence imaging agent used in combination with the methods, systems and kits described herein may be used for blood flow imaging, tissue perfusion imaging, lymphatic imaging, or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

In variations relating to cardiac applications or any vascular applications, the imaging agent(s) (e.g., ICG alone or in combination with another imaging agent) may be injected intravenously. For example, the imaging agent may be injected intravenously through the central venous line, bypass pump and/or cardioplegia line and/or other vasculature to flow and/or perfuse the coronary vasculature, microvasculature and/or grafts. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes require involvement of a nuclear physician and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticarial and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various embodiments for use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue for comparison). One 25 mg vial of ICG may be reconstituted with 10 ml sterile water for injection to yield a 2.5 mg/ml solution immediately prior to ICG administration. Using a TB syringe and a 30 G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast, ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to highlight/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN, ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages:high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, fluorescence is easier to detect intraoperatively than blue staining (isosulfan blue) of lymph nodes. In other variations, the methods, dosages or a combination thereof as described herein in connection with lymphatic imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through microvasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

By way of summation and review, one or more embodiments may accommodate varied working distances while providing a flat illumination field and matching an illumination field to a target imaging field, thus allowing accurate quantitative imaging applications. An imaging element that focuses light from a target onto a sensor may be moved in synchrony with steering of the illumination field. Additionally or alternatively, a drape may be used that insures a close fit between a drape lens and a window frame of the device. Additionally or alternatively, one or more embodiments may allow ambient light to be subtracted from light to be imaged using a single sensor and controlled timing of illumination and exposure or detection. Additionally or alternatively, one or more embodiments may allow the display of a normalized fluorescence intensity measured within a target reticle region of an image frame.

In contrast, when illumination and imaging devices do not conform illumination to the target imaging field of view or provide a flat, i.e., even or substantially uniform, illumination field, illumination and image quality may suffer. An uneven illumination field can cause distracting and inaccurate imaging artifacts, especially for hand held imaging devices and when used at varied working distances, while excess light outside the imaging field of view reduces device efficiency and can distract the user when positioning the device.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method embodiments described herein.

One or more embodiments are directed to an illumination module for use in an imaging system having an imaging field of view for imaging a target, the illumination module including a first illumination port to output a first light beam having a first illumination distribution at the target to illuminate the target and a second illumination part to output a second light beam having a second illumination distribution at the target to illuminate the target. The second illumination distribution may be substantially similar to the first illumination distribution at the target, the second illumination port being spaced apart from the first illumination port, the first and second illumination distributions being simultaneously provided to the target and overlapping at the target, wherein the illumination from the first and second ports is matched to a same aspect ratio and field of view coverage as the imaging field of view.

Light from the first and second illumination ports may respectively overlap to provide uniform illumination over a target field of view.

The illumination module may include a steering driver to simultaneously steer the first and second illumination ports through different fields of view.

Each of the first and second illumination ports may include a lens module having at least one fixed lens, a steerable housing, and at least one lens mounted in the steerable housing, the steerable housing being in communication with the steering driver.

The illumination module may include an enclosure, the enclosure housing the first and second illumination ports and the steering driver.

The enclosure may be a hand held enclosure and may include a control surface including activation devices to control the steering driver.

Each of the first and second illumination distributions may be a rectangular illumination distribution.

Each of the first and second illumination ports may include a lens module having two pairs of cylindrical lenses.

The first and second illumination ports may be symmetrically offset from a long dimension midline of the rectangular illumination distribution.

One or more embodiments are directed to an imaging device having an imaging field of view, the imaging device including a first illumination port to output first light having a first illumination distribution at a target to illuminate the target, a second illumination port to output second light having a second illumination distribution at the target to illuminate the target, the second illumination distribution being substantially similar to the first illumination distribution at the target, the second illumination port being spaced apart from the first illumination port, the first and second illumination distributions being simultaneously provided to the target and overlapping at the target, wherein the illumination from the first and second ports is matched to a same aspect ratio and field of view coverage as the imaging field of view, and a sensor to detect light from the target.

The imaging device may include an enclosure, the enclosure housing the first and second illumination ports, and the sensor.

The imaging device may include a steering driver to simultaneously steer the first and second illumination ports through different fields of view.

The imaging device may include an imaging element to focus light onto the sensor, wherein the steering driver is to move the imaging element in synchrony with steering of the first and second illumination ports.

The steering driver may be in the enclosure and the enclosure may include a control surface including activation devices to control the steering driver.

The enclosure may have a hand held enclosure having a form factor that allows a single hand to control the control surface and illumination of the target from multiple orientations.

The imaging device may include an illumination source to output light to the first and second illumination ports, the illumination source being outside the enclosure.

The illumination source may output visible light and/or excitation light to the first and second illumination ports.

The sensor may be a single sensor that is to detect light from the target resulting from illumination by visible light and excitation light.

The imaging device may include a wavelength-dependent aperture upstream of the sensor, the wavelength-dependent aperture to block visible light outside a central region.

The imaging device may include a video processor box, the video processor box being outside the enclosure.

The illumination source may be integral with the video processor box.

One or more embodiments are directed to a method of examining a target, the method including simultaneously illuminating the target with a first light output having a first illumination distribution at the target and with a second light output having a second illumination distribution at the target, the second illumination distribution being substantially similar to the first illumination distribution, the first and second illumination distributions overlapping at the target, wherein the illumination on the target is matched to the same aspect ratio and field of view coverage as an imaging field of view.

The method may include simultaneously steering the first and second light outputs through different fields of view.

The method may include receiving light from the target and focusing light onto a sensor using an imaging element, the imaging element being moved in synchrony with simultaneous steering of the first and second light outputs.

One or more embodiments are directed to a drape for use with an imaging device, the drape including a barrier material enveloping the imaging device, a drape window frame defining an opening in the barrier material, a drape lens in the opening in the barrier material, and an interface integral with the drape window frame to secure the drape lens to a window frame of the imaging device.

The drape may be insertable into the window frame of the imaging device.

The interface may include two clamps integrated symmetrically on respective opposing sides of the drape window frame.

The two clamps are on a top and a bottom of the drape window frame.

One or more embodiments are directed to a processor to image a target, the processor to, within a period, turn on an excitation light source to generate an excitation pulse to illuminate the target, turn on a white light source to generate a white pulse to illuminate the target such that the white pulse does not overlap the excitation pulse and the white pulse is generated at least twice within the period, expose an image sensor for a fluorescent exposure time during the excitation pulse, expose the image sensor for a visible exposure time during at least one white pulse, detect outputs from the image sensor, compensate for ambient light, and output a resultant image.

To compensate for ambient light, the processor may expose a first set of sensor pixel rows of the image sensor for a fraction of the fluorescent exposure time for a first set of sensor pixel rows; and expose a second set of sensor pixel rows of the image sensor for all of the fluorescent exposure time, the first and second sets to detect at least one different color from the other.

The fraction may be ½.

The processor may determine the fluorescent signal F using the following equation:

$$F = 2 \ast \text{Exp } 2 - \text{Exp } 1,$$

where Exp1 is a signal output during the fraction of fluorescent exposure time and Exp2 is a signal output during all of the fluorescent exposure time.

The fraction of the exposure time may equal a width of the excitation pulse.

The visible exposure time may be longer than a width of the at least one white pulse.

The visible exposure time may be for one white pulse within the period.

The visible exposure time may be for two white pulses within the period.

To compensate for ambient light, the processor may expose the image sensor for a background exposure time when target is not illuminated at least once within the period.

One or more embodiments are directed a method for imaging a target, within a period, the method including generating an excitation pulse to illuminate the target, generating a white pulse to illuminate the target such that the white pulse does not overlap the excitation pulse and the white pulse is generated at least twice within the period, exposing an image sensor for a fluorescent exposure time during the excitation pulse, exposing the image sensor for a visible exposure time during at least one white pulse, detecting outputs from the image sensor, compensating for ambient light, and outputting a resultant image.

Compensating for ambient light may include exposing a first set of sensor pixel rows of the image sensor for a fraction of the fluorescent exposure time and exposing a second set of sensor pixel rows of the image sensor for all of the fluorescent exposure time, the first and second sets to detect at least one different color from the other.

Compensating for ambient light may include exposing the image sensor for a background exposure time when target is not illuminated at least once within the period.

Generating the excitation pulse may include providing uniform, anamorphic illumination to the target.

Providing uniform, anamorphic illumination to the target includes overlapping illumination from at least two illumination ports.

One or more embodiments are directed to a method of displaying fluorescence intensity in an image, the method including displaying a target reticle covering a region of the image, calculating a normalized fluorescence intensity within the target reticle, and displaying the normalized fluorescence intensity in a display region associated with the target.

The display region may be projected onto the target.

The normalized fluorescence intensity may include a single numerical value and/or a historical plot of normalized fluorescence intensities.

One or more embodiments are directed to a kit, including an illumination module including at least two illumination ports spaced apart from one another, first and second illumination distributions to being simultaneously provided to a target and to overlap at the target, and an imaging module including a sensor to detect light from the target.

The kit may include an enclosure to enclose the illumination module and the imaging module.

One or more embodiments are directed to a fluorescence imaging agent for use in the imaging device and methods as described herein. In one or more embodiments, the use may comprise blood flow imaging, tissue perfusion imaging, lymphatic imaging, or a combination thereof, which may occur during an invasive surgical procedure, a minimally invasive surgical procedure, a non-invasive surgical procedure, or a combination thereof. The fluorescence agent may be included in the kit described herein.

In one or more embodiments, the invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

In one or more embodiments, the minimally invasive or the non-invasive surgical procedure may comprise a wound care procedure.

In one or more embodiments, the lymphatic imaging may comprise identification of a lymph node, lymph node drainage, lymphatic mapping, or a combination thereof. The lymphatic imaging may relate to the female reproductive system.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A system for imaging a target, the system comprising:
   one or more processors;
   memory; and
   one or more programs, wherein the one or more programs are stored in the memory and configured to be executed by the one or more processors, the one or more programs including instructions for, within a period:
   activating an excitation light source to generate an excitation pulse to illuminate the target;
   receiving an ambient light intensity signal from a non-imaging sensor during a portion of the period in which the excitation light source is not activated;
   exposing an image sensor for a fluorescent exposure time during the excitation pulse;
   receiving outputs from the image sensor;
   compensating for ambient light based on the ambient light intensity signal; and
   storing a resultant image in the memory,
   wherein the one or more programs include instructions for determining a periodic frequency of the ambient light intensity,
   wherein compensating for ambient light comprises:
   synthesizing or extracting, from one or more received ambient light intensity signals, a complete periodic cycle of ambient light intensity having the determined periodic frequency,
   extending the ambient light intensity periodic cycle to a time period corresponding to the fluorescence exposure time,
   calculating a first accumulated ambient light value corresponding to an area under the curve of ambient light intensity during a background exposure time,
   calculating a second accumulated ambient light value corresponding to an area under the curve of the ambient light intensity during the fluorescence exposure time,
   scaling the received image sensor output for the background exposure time and the received image sensor output for the fluorescence exposure time based on a ratio of the first and second accumulated ambient light values, and
   subtracting the scaled image sensor output for the background exposure time from the scaled image sensor output for the fluorescence exposure time to form the resultant image.

2. The system of claim 1, wherein the one or more programs include instructions for, within the period:
   activating a white light source to generate a white light pulse to illuminate the target such that the white light pulse does not overlap the excitation pulse; and
   exposing the image sensor for a visible exposure time during at least one white light pulse.

3. The system of claim 1, wherein the one or more programs include instructions for exposing the image sensor for a background exposure time when the target is not illuminated.

4. The system of claim 1, wherein the one or more programs include instructions for receiving an ambient light intensity signal from the non-imaging sensor during the background exposure time.

5. The system of claim 1, wherein the one or more programs include instructions for extending the ambient light intensity periodic cycle to the time period corresponding to the fluorescence exposure time.

6. A method for imaging a target, the method comprising:
   at a system having one or more processors and memory:
   activating an excitation light source to generate an excitation pulse to illuminate the target;
   receiving an ambient light intensity signal from a non-imaging sensor during a portion of the period in which the excitation light source is not activated;
   exposing an image sensor for a fluorescent exposure time during the excitation pulse;
   receiving outputs from the image sensor;
   determining a periodic frequency of the ambient light intensity;
   compensating for ambient light based on the ambient light intensity signal, wherein compensating for ambient light comprises:
   synthesizing or extracting, from one or more received ambient light intensity signals, a complete periodic cycle of ambient light intensity having the determined periodic frequency,
   extending the ambient light intensity periodic cycle to a time period corresponding to the fluorescence exposure time, calculating a first accumulated ambient light value corresponding to an area under the curve of ambient light intensity during a background exposure time, calculating a second accumulated ambient light value corresponding to an area under the curve of the ambient light intensity during the fluorescence exposure time, scaling the received image sensor output for the background exposure time and the received image sensor output for the fluorescence exposure time based on a ratio of the first and second accumulated ambient light values, and subtracting the scaled image sensor output for the background exposure time from the scaled image sensor output for the fluorescence exposure time to form the resultant image; and storing a resultant image in the memory.

7. The method of claim 6, further comprising, within the period:

activating a white light source to generate a white light pulse to illuminate the target such that the white light pulse does not overlap the excitation pulse; and exposing the image sensor for a visible exposure time during at least one white light pulse.

8. The method of claim 6, further comprising exposing the image sensor for a background exposure time when the target is not illuminated.

9. The method of claim 6, further comprising receiving an ambient light intensity signal from the non-imaging sensor during the background exposure time.

10. The method of claim 6, further comprising extending the ambient light intensity periodic cycle to the time period corresponding to the fluorescence exposure time.

11. The method of claim 6, wherein the non-imaging sensor is configured to detect a periodic frequency of the ambient light intensity that results from a frequency of an ambient light power source.

12. The system of claim 1, wherein the non-imaging sensor is configured to detect a periodic frequency of the ambient light intensity that results from a frequency of an ambient light power source.

* * * * *